US012673945B2

(12) United States Patent
Lee et al.

(10) Patent No.: US 12,673,945 B2
(45) Date of Patent: Jul. 7, 2026

(54) 3-((8-((1H-PYRAZOL-4-YL)AMINO) IMIDAZO[1,2-A]PYRIDIN-3-YL)ETHINYL)-N-PHENYLBENZAMIDE DERIVATIVE, METHOD FOR PREPARING SAME, AND PHARMACEUTICAL COMPOSITION CONTAINING SAME AS ACTIVE INGREDIENT FOR PREVENTION OR TREATMENT OF CANCER

(71) Applicants: DAEGU-GYEONGBUK MEDICAL INNOVATION FOUNDATION, Daegu (KR); IMMUNOFORGE CO., LTD., Seoul (KR)

(72) Inventors: Doohyun Lee, Daegu (KR); Seungyeon Lee, Daegu (KR); Ye Ri Han, Daegu (KR); Chun Young Im, Daegu (KR); So Young Kim, Daegu (KR); Nam Hui Kim, Daegu (KR); Hwan Geun Choi, Seoul (KR); Eunhwa Ko, Incheon (KR); Heegyum Moon, Daegu (KR); Sun Joo Lee, Daegu (KR); Sang Bum Kim, Daegu (KR); Hyo-Ji Kim, Daegu (KR); Sion Lee, Daegu (KR); Sung-Min Ahn, Seoul (KR); Kiho Chang, Seoul (KR); Eunkyu Lee, Seoul (KR); Hyun Jin Kwon, Seoul (KR); Myeong-Sook Jeong, Seoul (KR); Ji Young Kim, Seoul (KR)

(73) Assignees: Daegu-Gyeongbuk Medical Innovation Foundation, Daegu (KR); Immunoforge Co., Ltd., Seoul (KR)

( * ) Notice: Subject to any disclaimer, the term of this patent is extended or adjusted under 35 U.S.C. 154(b) by 759 days.

(21) Appl. No.: 17/801,757

(22) PCT Filed: Feb. 26, 2021

(86) PCT No.: PCT/KR2021/002452

§ 371 (c)(1),
(2) Date: Aug. 23, 2022

(87) PCT Pub. No.: WO2021/172931

PCT Pub. Date: Sep. 2, 2021

(65) Prior Publication Data

US 2023/0295153 A1 Sep. 21, 2023

(30) Foreign Application Priority Data

Feb. 28, 2020 (KR) ........................ 10-2020-0025409
Feb. 23, 2021 (KR) ........................ 10-2021-0024063

(51) Int. Cl.

| | |
|---|---|
| ***C07D 471/04*** | (2006.01) |
| ***A61K 31/437*** | (2006.01) |
| ***A61K 31/444*** | (2006.01) |
| ***A61K 31/496*** | (2006.01) |
| ***A61P 35/00*** | (2006.01) |
| ***C07D 471/10*** | (2006.01) |

(52) U.S. Cl.
CPC ............ *C07D 471/04* (2013.01); *A61P 35/00* (2018.01)

(58) Field of Classification Search
CPC .. C07D 471/04; C07D 471/10; A61K 31/437; A61K 31/444; A61K 31/496; A61P 35/00
See application file for complete search history.

(56) References Cited

U.S. PATENT DOCUMENTS

2019/0315738 A1 10/2019 Choi et al.

FOREIGN PATENT DOCUMENTS

| | | | |
|---|---|---|---|
| EP | 3473624 | A1 | 4/2019 |
| KR | 10-2013-0084083 | A | 7/2013 |
| KR | 10-2014-0016889 | A | 2/2014 |
| KR | 10-2017-0143456 | A | 12/2017 |
| KR | 102550999 | B1 | 7/2023 |
| WO | WO 2005/060969 | A1 | 7/2005 |
| WO | WO 2012/098416 | A1 | 7/2012 |
| WO | WO 2013/101281 | A1 | 7/2013 |
| WO | WO 2013/162727 | A1 | 10/2013 |
| WO | WO 2013/170774 | A1 | 11/2013 |

OTHER PUBLICATIONS

International Search Report and Written Opinion in PCT/KR2021/002452, issued by the Korean Search Authority of the Korean Intellectual Property Office, mailed on Jun. 14, 2021, 8 pages (with English translation of the International Search Report, 4 pages).

Gozit, Joseph M. et al., "Ponatinib (AP24534), A Multitargeted Pan-FGFR Inhibitor with Active in Multiple FGRF-Amplified or Mutated Cancer Models," *Molecular Cancer Therapeutics*, 11(3):690-699 (Mar. 1, 2012).

Gozgit, Joseph M. et al., "RET fusions observed in lung and colorectal cancers are sensitive to ponatinib," *Oncotarget*, 9(51):29654-29664 (Jul. 3, 2018).

(Continued)

*Primary Examiner* — Bruck Kifle
(74) *Attorney, Agent, or Firm* — Klarquist Sparkman, LLP

(57) ABSTRACT

The present invention relates to a 3-((8-((1H-pyrazol-4-yl)amino)imidazo[1,2-a]pyridin-3-yl)ethynyl)-N-phenylbenzamide derivative, a method for preparing the same, and a pharmaceutical composition comprising the same as an active ingredient for preventing or treating cancer. The derivative can significantly inhibit the proliferation of cancer cells by inhibiting kinases, particularly Bcr-Abl kinase or Bcr-Abl (T315I) kinase. Therefore, the derivative can be effectively used as a pharmaceutical composition for the prevention or treatment of cancer.

10 Claims, 4 Drawing Sheets

(56) References Cited

OTHER PUBLICATIONS

Melo, Junia V., et al., "Expression of the ABL-BCR Fusion Gene in Philadelphia- Positive Acute Lymphoblastic Leukemia," *Blood*, 81(10):2488-2491 (May 15, 1993).

Watanabe, Keisuke et al., "T315I Mutation in Ph-positive Acute Lymphoblastic Leukemia is Associated with a Highly Aggressive Disease Phenotype: Three Case Reports," *Anticancer Research*, 32(5):1779-1783 (May 15, 2012).

3-((8-((1H-PYRAZOL-4-YL)AMINO)IMIDAZO[1,2-A]PYRIDIN-3-YL)ETHINYL)-N-PHENYLBENZAMIDE DERIVATIVE, METHOD FOR PREPARING SAME, AND PHARMACEUTICAL COMPOSITION CONTAINING SAME AS ACTIVE INGREDIENT FOR PREVENTION OR TREATMENT OF CANCER

CROSS REFERENCE TO RELATED APPLICATIONS

This is the U.S. National Stage of International Application No. PCT/KR2021/002452, filed Feb. 26, 2021, which in turn claims the benefit of priority under 35 U.S.C. § 119 from Korean Patent Application No. 10-2021-0024063, filed Feb. 23, 2021, and Korean Patent Application No. 10-2020-0025409, filed Feb. 28, 2020. The Korean patent applications are incorporated herein by reference in their entirety.

BACKGROUND OF THE INVENTION

1. Field of the Invention

The present invention relates to a 3-((8-((1H-pyrazol-4-yl)amino)imidazo[1,2-a]pyridin-3-yl)ethynyl)-N-phenylbenzamide derivative, a method for preparing the same, and a pharmaceutical composition comprising the same as an active ingredient for preventing or treating cancer.

2. Description of the Related Art

Protein Tyrosine Kinase (PTK) is an important target molecule in drug development for the treatment of various diseases, in particular for the treatment of proliferative diseases. Dysregulation of tyrosine kinase activity is known as a major mechanism by which cancer cells avoid normal physiological constraints in growth, proliferation and survival.

Tyrosine kinase (TK) is an enzyme that catalyzes the transfer of phosphate from ATP to a tyrosine residue in a polypeptide. The human genome contains about 90 TK and 43 TK-like genes, and the products of the genes control a variety of cellular functions including cell proliferation, survival, differentiation, function and mobility.

Dysregulation of TK activity resulting from mutation, overexpression, or dysfunctional self-regulatory mechanism has been implicated in many diseases, including cancer. A common mechanism of TK activation in hematological cancers is the fusion of a receptor or non-receptor TK with a partner protein, usually as a result of balanced chromosomal translocation. A basic example of this mechanism is Bcr-Abl, a non-receptor fusion TK in chronic myelogenous leukemia (CML). At this time, the tetrameric domain in Bcr overcomes auto-repression of Abl catalytic activity through oligomerization and autophosphorylation. For some receptor TKs, the absence of a near-membrane inhibitory domain in the fusion protein contributes to the activation.

A second important mechanism of TK dysregulation is a mutation that disrupts the self-regulation of a kinase. Mutations in the Fms-like tyrosine kinase 3 (FLT3) receptor in acute myeloid leukemia (AML) render the TK active in the absence of a ligand. A third mechanism of TK dysregulation is increased or aberrant expression of the receptor TK, its ligand, or both. Finally, the increased TK activity may result from the decreased factors limiting TK activity, such as impaired tyrosine phosphatase activity or decreased expression of TK inhibitor proteins. Abnormal TK activation can increase survival, proliferation and cytotoxic drug resistance of malignant cells, and can increase angiogenesis, permeability and metastasis potential in tumors.

The TK family of enzymes has emerged as an important target class for therapeutic intervention, and TK can be pharmacologically inhibited through multiple mechanisms. One of the important focuses in anti-TK drug screening is the design and development of small molecules that can directly inhibit the catalytic activity of kinases by interfering with the binding of ATP or substrates. An important advantage of TK-associated therapies is the ability to conduct pharmacodynamic studies correlating inhibition of targeted TK in cancer cells with clinical response to drugs (Korean Patent Publication No. 10-2014-0016889).

In particular, Bcr-Abl is a critical cause in the pathogenesis of 95% of chronic myelogenous leukemia (CML) and 10% of acute lymphocytic leukemia (AML). Therefore, a Bcr-Abl kinase inhibitor can be effectively used as a targeted therapeutic agent for chronic myeloid leukemia, and a targeted anticancer drug has been released based on many studies, a representative example of which is Gleevec.

Gleevec is effective by blocking the activity of Bcr-Abl that prevents the proliferation of blood cells, but recently, Gleevec resistance due to Bcr-Abl mutation has been reported. Some patients in the blastic crisis phase of CML are caused by mutations in Bcr-Abl kinase, and to date, more than 22 kinds of mutations have been reported. Among them, the T315I (gate keeper residue mutation) is emerging as the biggest problem.

Tasigna and Sprycell, the second-generation drugs that improved Gleevec, have been developed, but they do not effectively act on mutant Abl such as T315I so far, and no drug has been reported that can be used for this mutation. Therefore, there is an urgent need to develop a drug capable of simultaneously inhibiting wild-type Abl kinase as well as mutant Abl kinase such as T315I (Korean Patent Publication No. 10-2013-0084083).

SUMMARY OF THE INVENTION

It is an object of the present invention to provide a 3-((8-((1H-pyrazol-4-yl)amino)imidazo[1,2-a]pyridin-3-yl)ethynyl)-N-phenylbenzamide derivative, a solvate thereof, or a pharmaceutically acceptable salt thereof.

It is another object of the present invention to provide a method for preparing a 3-((8-((1H-pyrazol-4-yl)amino)imidazo[1,2-a]pyridin-3-yl)ethynyl)-N-phenylbenzamide derivative.

It is another object of the present invention to provide a pharmaceutical composition for preventing or treating kinase-related disease containing a 3-((8-((1H-pyrazol-4-yl)amino)imidazo[1,2-a]pyridin-3-yl)ethynyl)-N-phenylbenzamide derivative, a solvate thereof, or a pharmaceutically acceptable salt thereof as an active ingredient.

It is another object of the present invention to provide a pharmaceutical composition for preventing or treating cancer containing a 3-((8-((1H-pyrazol-4-yl)amino)imidazo[1,2-a]pyridin-3-yl)ethynyl)-N-phenylbenzamide derivative, a solvate thereof, or a pharmaceutically acceptable salt thereof as an active ingredient.

It is another object of the present invention to provide a health functional food composition for preventing or ameliorating kinase-related disease containing a 3-((8-((1H-pyrazol-4-yl)amino)imidazo[1,2-a]pyridin-3-yl)ethynyl)-N-phenylbenzamide derivative, a solvate thereof, or a pharmaceutically acceptable salt thereof as an active ingredient.

It is another object of the present invention to provide a health functional food composition for preventing or ameliorating cancer containing a 3-((8-((1H-pyrazol-4-yl)amino)imidazo[1,2-a]pyridin-3-yl)ethynyl)-N-phenylbenzamide derivative, a solvate thereof, or a pharmaceutically acceptable salt thereof as an active ingredient.

It is another object of the present invention to provide a method for treating kinase-related disease or cancer, comprising a step of administering a 3-((8-((1H-pyrazol-4-yl)amino)imidazo[1,2-a]pyridin-3-yl)ethynyl)-N-phenylbenzamide derivative, a solvate thereof, or a pharmaceutically acceptable salt thereof to an individual or subject in need thereof.

It is another object of the present invention to provide a use of a 3-((8-((1H-pyrazol-4-yl)amino)imidazo[1,2-a]pyridin-3-yl)ethynyl)-N-phenylbenzamide derivative, a solvate thereof, or a pharmaceutically acceptable salt thereof for the preparation of a medicament for the treatment of kinase-related disease or cancer.

To achieve the above objects, in one aspect of the present invention, the present invention provides a compound represented by formula 1, a solvate thereof, or a pharmaceutically acceptable salt thereof:

[Formula 1]

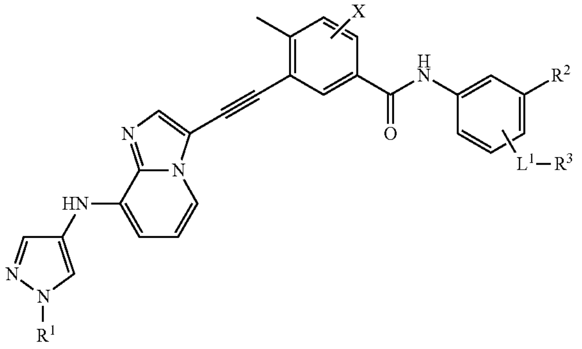

In formula 1 above, $R^1$ is hydrogen or $C_{1-10}$ alkyl;

X is halogen;

$R^2$ is

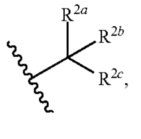

wherein, $R^{2a}$, $R^{2b}$ and $R^{2c}$ are independently hydrogen, halogen, cyano or $C_{1-10}$ alkyl;

$L^1$ is single bond, —O— or $C_{1-10}$ alkylene;

$R^3$ is 5-8 membered nonsubstituted or substituted heteroaryl containing one or more heteroatoms selected from the group consisting of N, O and S, 4-8 membered nonsubstituted or substituted heterocycloalkyl containing one or more heteroatoms selected from the group consisting of N, O and S, nonsubstituted or substituted $C_{1-10}$ alkyl or $NR^{3a}R^{3b}$, wherein, $R^{3a}$ and $R^{3b}$ are independently hydrogen or nonsubstituted or substituted $C_{1-10}$ alkyl, wherein, the substituted heteroaryl, substituted heterocycloalkyl and substituted alkyl are substituted with one or more substituents selected from the group consisting of $C_{1-10}$ alkyl nonsubstituted or substituted with one or more halogens, $C_{1-10}$ alkylalcohol, $C_{1-10}$ alkylsulfonyl, $C_{1-10}$ alkoxy, oxo, $NR^{3c}R^{3d}$ and heterocycloalkyl substituted with 5-8 membered $C_{1-10}$ alkyl containing one or more heteroatoms selected from the group consisting of N, O and S, wherein, $R^{3c}$ and $R^{3d}$ are independently hydrogen or $C_{1-10}$ alkyl.

In another aspect of the present invention, the present invention provides a method for preparing the compound represented by formula 1 of claim 1, comprising a step of preparing a compound represented by formula 1 by reacting a compound represented by formula 2 with a compound represented by formula 3, as shown in reaction formula 1 below:

[Reaction Formula 1]

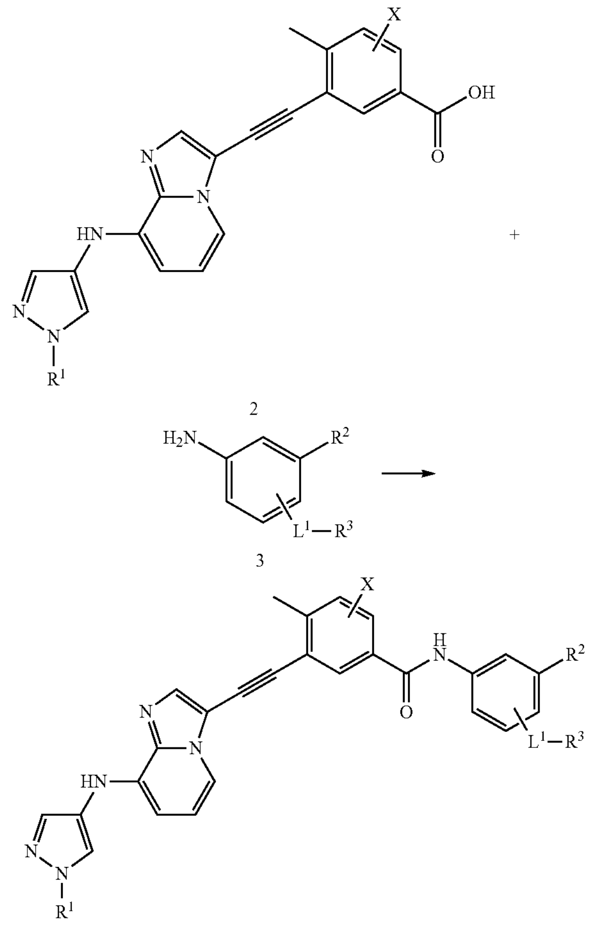

2

3

1

In reaction formula 1 above, $L^1$, $R^1$, $R^2$, $R^3$ and X are as defined in formula 1 of claim 1.

In another aspect of the present invention, the present invention provides a pharmaceutical composition containing a compound represented by formula 1, a solvate thereof, or a pharmaceutically acceptable salt thereof as an active ingredient for preventing or treating diseases related to one or more protein kinases selected from the group consisting of ABL1(E255K)-phosphorylated, ABL1(F317I)-nonphosphorylated, ABL1(F317I)-phosphorylated, ABL1(F317L)-nonphosphorylated, ABL1(F317L)-phosphorylated, ABL1

(H396P)-nonphosphorylated, ABL1(H396P)-phosphorylated, ABL1(M351T)-phosphorylated, ABL1 (Q252H)-nonphosphorylated, ABL1(Q252H)-phosphorylated, ABL1(T315I)-nonphosphorylated, ABL1 (T315I)-phosphorylated, ABL1(Y253F)-phosphorylated, ABL1-nonphosphorylated, ABL1-phosphorylated, ABL2, AURKB, AURKC, AXL, BLK, BMX, BRAF, BRAF (V600E), BRK, BTK, CDC2L1, CDC2L2, CDC2L5, CDK11, CDK7, CDKL2, CIT, CSF1R, CSK, DDR1, DDR2, DLK, EGFR, EGFR(E746-A750del), EGFR(G719C), EGFR(G719S), EGFR(L747-E749del, A750P), EGFR (L747-S752del, P753S), EGFR(L747-T751del, Sins), EGFR(L858R), EGFR(L861Q), EGFR(S752-I759del), EPHA1, EPHA3, EPHA4, EPHA5, EPHA6, EPHA7, EPHA8, EPHB1, EPHB2, EPHB6, ERBB2, ERBB4, ERK8, FER, FES, FGFR1, FGFR2, FGFR3, FGFR3(G697C), FGFR4, FGR, FLT1, FLT3, FLT3(D835H), FLT3(D835V), FLT3(D835Y), FLT3(ITD), FLT3(ITD, F691L), FLT3 (K663Q), FLT3(N841I), FLT3(R834Q), FLT4, FRK, FYN, GAK, GCN2(Kin.Dom.2, S808G), HCK, HPK1, IKK-alpha, IKK-beta, IRAK1, IRAK4, JNK2, KIT, KIT(A829P), KIT(D816H), KIT(D816V), KIT(L576P), KIT(V559D), KIT(V559D,T670I), KIT(V559D, V654A), LCK, LIMK1, LOK, LRRK2, LTK, LYN, MAP3K2, MAP3K3, MAP4K2, MAP4K3, MAP4K4, MAP4K5, MEK5, MERTK, MET (Y1235D), MINK, MKNK1, MKNK2, MLK1, MLK3, MST3, MUSK, NEK1, NEK4, NLK, p38-alpha, p38-beta, p38-delta, p38-gamma, PAK3, PCTK2, PDGFRA, PDGFRB, PFCDPK1(P.falciparum), PFTAIRE2, PFTK1, RET, RET(M918T), RET(V804L), RET(V804M), RIOK3, RIPK1, RIPK2, SIK, SLK, SRC, SRMS, STK33, STK35, STK36, TAK1, TAOK1, TAOK2, TAOK3, TEC, TESK1, TIE1, TIE2, TNIK, TNK1, TNK2, TNNI3K, TRKA, TRKB, TRKC, TXK, TYK2(JH1domain-catalytic), VEGFR2, YES, YSK4 and ZAK.

In another aspect of the present invention, the present invention provides a pharmaceutical composition for preventing or treating cancer containing a compound represented by formula 1, a solvate thereof, or a pharmaceutically acceptable salt thereof as an active ingredient.

In another aspect of the present invention, the present invention provides a health functional food composition for preventing or ameliorating kinase-related disease containing a compound represented by formula 1, a solvate thereof, or a pharmaceutically acceptable salt thereof as an active ingredient.

In another aspect of the present invention, the present invention provides a health functional food composition for preventing or ameliorating cancer containing a compound represented by formula 1, a solvate thereof, or a pharmaceutically acceptable salt thereof as an active ingredient.

In another aspect of the present invention, the present invention provides a method for treating kinase-related disease or cancer, comprising a step of administering the compound, the solvate thereof, or the pharmaceutically acceptable salt thereof to an individual or subject in need thereof.

In addition, the present invention provides a use of the compound, the solvate thereof, or the pharmaceutically acceptable salt thereof for the preparation of a medicament for the treatment of kinase-related disease or cancer.

ADVANTAGEOUS EFFECT

The 3-((8-((1H-pyrazole-4-yl)amino)imidazo[1,2-a]pyridin-3-yl)ethynyl)-N-phenylbenzamide derivative according to the present invention can significantly inhibit the proliferation of cancer cells by inhibiting kinases, particularly Bcr-Abl kinase or Bcr-Abl (T315I) kinase. Therefore, the derivative can be effectively used as a pharmaceutical composition for the prevention or treatment of cancer.

DESCRIPTION OF THE PREFERRED EMBODIMENTS

Figure 1:
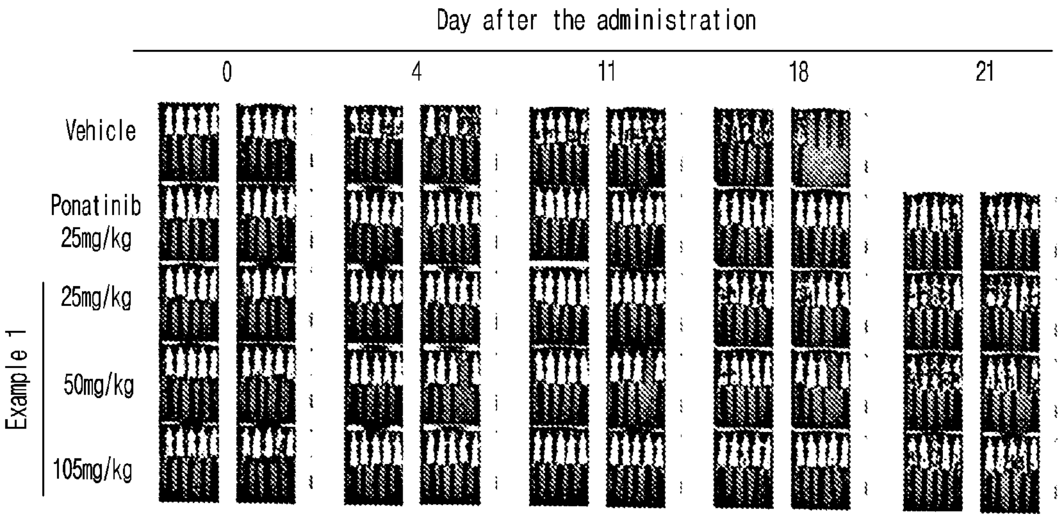
FIG. 1 is a diagram showing the optical images according to the course of vehicle or drug treatment in each of 5 groups in a blood cancer animal model.

Hereinafter, the present invention is described in detail.

The present invention provides a compound represented by formula 1, a solvate thereof, or a pharmaceutically acceptable salt thereof:

[Formula 1]

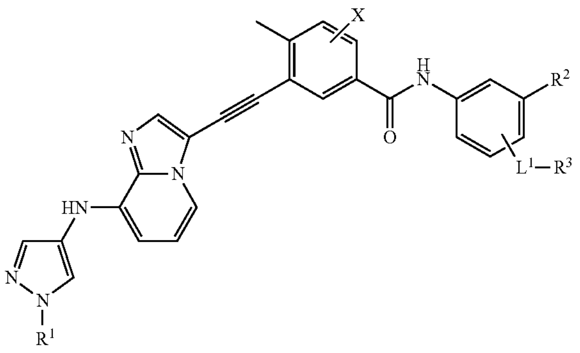

In formula 1 above, $R^1$ is hydrogen or $C_{1-10}$ alkyl;

X is halogen;

$R^2$ is

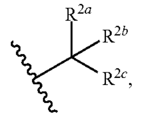

where, $R^{2a}$, $R^{2b}$ and $R^{2c}$ are independently hydrogen, halogen, cyano or $C_{1-10}$ alkyl;

$L^1$ is single bond, —O— or $C_{1-10}$ alkylene;

$R^3$ is 5-8 membered nonsubstituted or substituted heteroaryl containing one or more heteroatoms selected from the group consisting of N, O and S, 4-8 membered nonsubstituted or substituted heterocycloalkyl containing one or more heteroatoms selected from the group consisting of N, O and S, nonsubstituted or substituted $C_{1-10}$ alkyl or $NR^{3a}R^{3b}$, wherein, $R^{3a}$ and $R^{3b}$ are independently hydrogen or nonsubstituted or substituted $C_{1-10}$ alkyl, wherein, the substituted heteroaryl, substituted heterocycloalkyl and substituted alkyl are substituted with one or more substituents selected from the group consisting of $C_{1-10}$ alkyl nonsubstituted or substituted with one or more halogens, $C_{1-10}$ alkylalcohol, $C_{1-10}$ alkylsulfonyl, $C_{1-10}$ alkoxy, oxo, $NR^{3c}R^{3d}$ and heterocycloalkyl substituted with 5-8 membered $C_{1-10}$ alkyl containing one or more heteroatoms selected from the group consisting of N, O and S, wherein, $R^{3c}$ and $R^{3d}$ are independently hydrogen or $C_{1-10}$ alkyl.

In formula 1 above, $R^1$ is hydrogen or $C_{1-6}$ alkyl;

X is halogen;

$R^2$ is

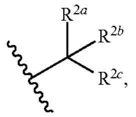

where, $R^{2a}$, $R^{2b}$ and $R^{2c}$ are independently hydrogen, halogen, cyano or $C_{1-6}$ alkyl;

$L^1$ is single bond, —O— or $C_{1-6}$ alkylene;

$R^3$ is 5-6 membered nonsubstituted or substituted heteroaryl containing one or more heteroatoms selected from the group consisting of N and O, 4-7 membered nonsubstituted or substituted heterocycloalkyl containing one or more heteroatoms selected from the group consisting of N and O, nonsubstituted or substituted $C_{1-6}$alkyl or $NR^{3a}R^{3b}$, wherein, $R^{3a}$ and $R^{3b}$ are independently hydrogen or nonsubstituted or substituted $C_{1-6}$ alkyl, wherein, the substituted heteroaryl, substituted heterocycloalkyl and substituted alkyl are substituted with one or more substituents selected from the group consisting of $C_{1-6}$ alkyl nonsubstituted or substituted with one or more halogens, $C_{1-6}$ alkylalcohol, $C_{1-6}$ alkylsulfonyl, $C_{1-6}$ alkoxy, oxo, $NR^{3c}R^{3d}$ and heterocycloalkyl substituted with 5-6 membered $C_{1-6}$ alkyl containing one or more heteroatoms selected from the group consisting of N and O, wherein, $R^{3c}$ and $R^{3d}$ are independently hydrogen or $C_{1-6}$ alkyl.

In formula 1 above, $R^1$ is hydrogen or methyl;

X is fluorine or chlorine;

$R^2$ is

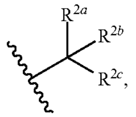

where, $R^{2a}$, $R^{2b}$ and $R^{2c}$ are independently fluorine, cyano or methyl;

$L^1$ is single bond, —O— or methylene;

$R^3$ is nonsubstituted or substituted imidazolyl, pyridinyl, pyrimidinyl, substituted piperazinyl, substituted pyrazolyl, substituted diazepanyl, substituted piperidinyl, morpholinyl, substituted pyrrolidinyl, substituted azetidinyl, triazolyl, substituted ethyl, substituted propyl or $NR^{3a}R^{3b}$, wherein $R^{3a}$ and $R^{3b}$ are independently methyl, substituted ethyl or substituted propyl, wherein the substituted imidazolyl, substituted piperazinyl, substituted pyrazolyl, substituted diazepanyl, substituted piperidinyl, substituted pyrrolidinyl, substituted azetidinyl, substituted ethyl and substituted propyl are substituted with one or more substituents selected from the group consisting of methyl, $CF_3$, $CH_2CF_3$, isopropyl, methylsulfonyl, isopropylalkoxy, ethyl alcohol, piperazine substituted with methyl, piperidine substituted with methyl, oxo and $NR^{3c}R^{3d}$, wherein, $R^{3c}$ and $R^{3d}$ can be methyl.

The compound represented by formula 1 may be a compound represented by formula 2 below.

[Formula 2]

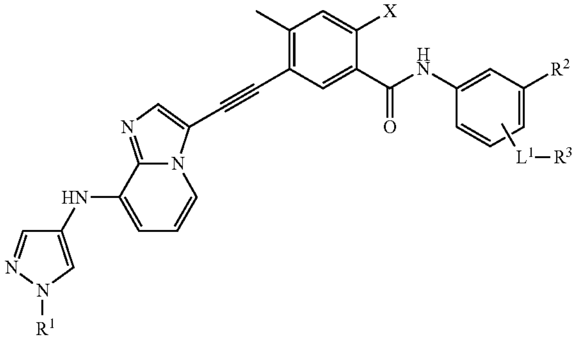

In formula 1 above, $R^1$ is hydrogen or methyl;

X is fluorine or chlorine;

$R^2$ is

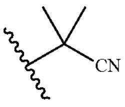 or 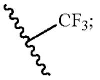

$L^1$-$R^3$ is

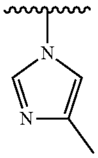, 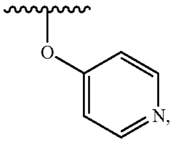

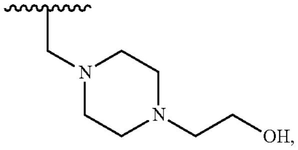 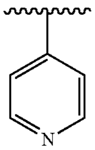, 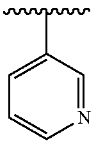,

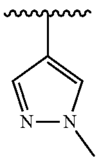, 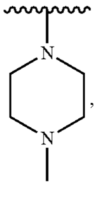, 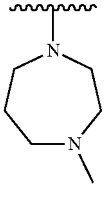,

-continued

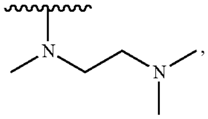,
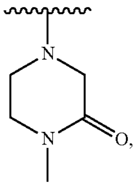,
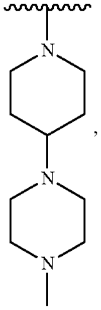,
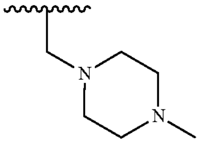,
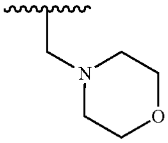,
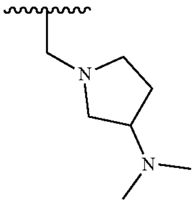,
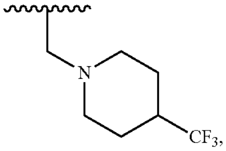,
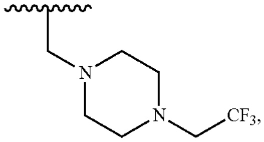,
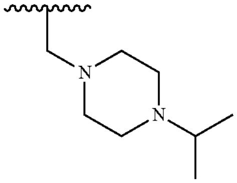,
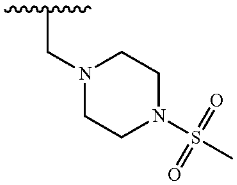,
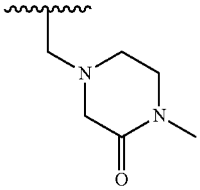,
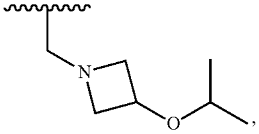,
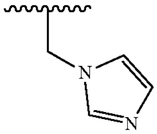,
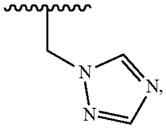,
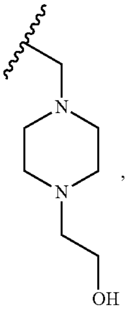,
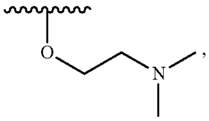, -continued

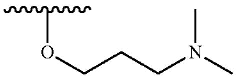, or 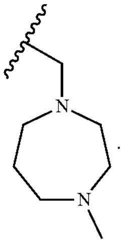.

Examples of the compound represented by formula 1 according to the present invention include the following compounds:

<1> N-(3-(2-cyanopropan-2-yl)-5-(4-methyl-1H-imidazol-1-yl)phenyl)-2-fluoro-4-methyl-5-((8-((1-methyl-1H-pyrazol-4-yl)amino)imidazo[1,2-a]pyridin-3-yl)ethynyl)benzamide;

<2> 3-fluoro-4-methyl-N-(3-(4-methyl-1H-imidazol-1-yl)-5-(trifluoromethyl)phenyl)-5-((8-((1-methyl-1H-pyrazol-4-yl)amino)imidazo[1,2-a]pyridin-3-yl)ethynyl)benzamide;

<3> N-(3-(2-cyanopropan-2-yl)-5-(4-methyl-1H-imidazol-1-yl)phenyl)-2-fluoro-4-methyl-3-((8-((1-methyl-1H-pyrazol-4-yl)amino)imidazo[1,2-a]pyridin-3-yl)ethynyl)benzamide;

<4> 2-fluoro-4-methyl-N-(3-(4-methyl-1H-imidazol-1-yl)-5-(trifluoromethyl)phenyl)-5-((8-((1-methyl-1H-pyrazol-4-yl)amino)imidazo[1,2-a]pyridin-3-yl)ethynyl)benzamide;

<5> 3-fluoro-4-methyl-N-(3-(4-methyl-1H-imidazol-1-yl)-5-(trifluoromethyl)phenyl)-5-((8-((1-methyl-1H-pyrazol-4-yl)amino)imidazo[1,2-a]pyridin-3-yl)ethynyl)benzamide;

<6> 2-fluoro-4-methyl-N-(3-(4-methyl-1H-imidazol-1-yl)-5-(trifluoromethyl)phenyl)-3-((8-((1-methyl-1H-pyrazol-4-yl)amino)imidazo[1,2-a]pyridin-3-yl)ethynyl)benzamide;

<7> 2-fluoro-4-methyl-5-((8-((1-methyl-1H-pyrazol-4-yl)amino)imidazo[1,2-a]pyridin-3-yl)ethynyl)-N-(3-(pyridin-4-yloxy)-5-(trifluoromethyl)phenyl)benzamide;

<8> 3-fluoro-4-methyl-5-((8-((1-methyl-1H-pyrazol-4-yl)amino)imidazo[1,2-a]pyridin-3-yl)ethynyl)-N-(3-(pyridin-4-yloxy)-5-(trifluoromethyl)phenyl)benzamide;

<9> 2-fluoro-4-methyl-3-((8-((1-methyl-1H-pyrazol-4-yl)amino)imidazo[1,2-a]pyridin-3-yl)ethynyl)-N-(3-(pyridin-4-yloxy)-5-(trifluoromethyl)phenyl)benzamide;

<10> N-(3-(2-cyanopropan-2-yl)-5-((4-(2-hydroxyethyl)piperazin-1-yl)methyl)phenyl)-2-fluoro-4-methyl-5-((8-((1-methyl-1H-pyrazol-4-yl)amino)imidazo[1,2-a]pyridin-3-yl)ethynyl)benzamide;

<11> N-(3-(2-cyanopropan-2-yl)-5-((4-(2-hydroxyethyl)piperazin-1-yl)methyl)phenyl)-3-fluoro-4-methyl-5-((8-((1-methyl-1H-pyrazol-4-yl)amino)imidazo[1,2-a]pyridin-3-yl)ethynyl)benzamide;

<12> N-(3-(2-cyanopropan-2-yl)-5-((4-(2-hydroxyethyl)piperazin-1-yl)methyl)phenyl)-2-fluoro-4-methyl-3-((8-((1-methyl-1H-pyrazol-4-yl)amino)imidazo[1,2-a]pyridin-3-yl)ethynyl)benzamide;

<13> 2-chloro-N-(3-(2-cyanopropan-2-yl)-5-(4-methyl-1H-imidazol-1-yl)phenyl)-4-methyl-5-((8-((1-methyl-1H-pyrazol-4-yl)amino)imidazo[1,2-a]pyridin-3-yl)ethynyl)benzamide;

<14> 2-chloro-4-methyl-N-(3-(4-methyl-1H-imidazol-1-yl)-5-(trifluoromethyl)phenyl)-5-((8-((1-methyl-1H-pyrazol-4-yl)amino)imidazo[1,2-a]pyridin-3-yl)ethynyl)benzamide;

<15> 2-chloro-4-methyl-5-((8-((1-methyl-1H-pyrazol-4-yl)amino)imidazo[1,2-a]pyridin-3-yl)ethynyl)-N-(3-(pyridin-4-yloxy)-5-(trifluoromethyl)phenyl)benzamide;

<16> 2-chloro-N-(3-(2-cyanopropan-2-yl)-5-((4-(2-hydroxyethyl)piperazin-1-yl)methyl)phenyl)-4-methyl-5-((8-((1-methyl-1H-pyrazol-4-yl)amino)imidazo[1,2-a]pyridin-3-yl)ethynyl)benzamide;

<17> N-(3-(2-cyanopropan-2-yl)-5-(pyridin-4-yl)phenyl)-2-fluoro-4-methyl-5-((8-((1-methyl-1H-pyrazol-4-yl)amino)imidazo[1,2-a]pyridin-3-yl)ethynyl)benzamide;

<18> N-(3-(2-cyanopropan-2-yl)-5-(pyridin-3-yl)phenyl)-2-fluoro-4-methyl-5-((8-((1-methyl-1H-pyrazol-4-yl)amino)imidazo[1,2-a]pyridin-3-yl)ethynyl)benzamide;

<19> N-(3-(2-cyanopropan-2-yl)-5-(1-methyl-1H-pyrazol-4-yl)phenyl)-2-fluoro-4-methyl-5-((8-((1-methyl-1H-pyrazol-4-yl)amino)imidazo[1,2-a]pyridin-3-yl)ethynyl)benzamide;

<20> N-(3-(2-cyanopropan-2-yl)-5-(4-methylpiperazin-1-yl)phenyl)-2-fluoro-4-methyl-5-((8-((1-methyl-1H-pyrazol-4-yl)amino)imidazo[1,2-a]pyridin-3-yl)ethynyl)benzamide;

<21> N-(3-(2-cyanopropan-2-yl)-5-(4-methyl-1,4-diazepan-1-yl)phenyl)-2-fluoro-4-methyl-5-((8-((1-methyl-1H-pyrazol-4-yl)amino)imidazo[1,2-a]pyridin-3-yl)ethynyl)benzamide;

<22> N-(3-(2-cyanopropan-2-yl)-5-((2-(dimethylamino)ethyl)(methyl)amino)phenyl)-2-fluoro-4-methyl-5-((8-((1-methyl-1H-pyrazol-4-yl)amino)imidazo[1,2-a]pyridin-3-yl)ethynyl)benzamide;

<23> N-(3-(2-cyanopropan-2-yl)-5-((3-(dimethylamino)propyl)(methyl)amino)phenyl)-2-fluoro-4-methyl-5-((8-((1-methyl-1H-pyrazol-4-yl)amino)imidazo[1,2-a]pyridin-3-yl)ethynyl)benzamide;

<24> N-(3-(2-cyanopropan-2-yl)-5-(4-methyl-3-oxopiperazin-1-yl)phenyl)-2-fluoro-4-methyl-5-((8-((1-methyl-1H-pyrazol-4-yl)amino)imidazo[1,2-a]pyridin-3-yl)ethynyl)benzamide;

<25> N-(3-(2-cyanopropan-2-yl)-5-(4-(4-methylpiperazin-1-yl)piperidin-1-yl)phenyl)-2-fluoro-4-methyl-5-((8-((1-methyl-1H-pyrazol-4-yl)amino)imidazo[1,2-a]pyridin-3-yl)ethynyl)benzamide;

<26> N-(3-(2-cyanopropan-2-yl)-5-(pyridin-4-yloxy)phenyl)-2-fluoro-4-methyl-5-((8-((1-methyl-1H-pyrazol-4-yl)amino)imidazo[1,2-a]pyridin-3-yl)ethynyl)benzamide;

<27> N-(3-(2-cyanopropan-2-yl)-5-((4-methylpiperazin-1-yl)methyl)phenyl)-2-fluoro-4-methyl-5-((8-((1-methyl-1H-pyrazol-4-yl)amino)imidazo[1,2-a]pyridin-3-yl)ethynyl)benzamide;

<28> N-(3-(2-cyanopropan-2-yl)-5-(morpholinomethyl)phenyl)-2-fluoro-4-methyl-5-((8-((1-methyl-1H-pyrazol-4-yl)amino)imidazo[1,2-a]pyridin-3-yl)ethynyl)benzamide;

<29> N-(3-(2-cyanopropan-2-yl)-5-((3-(dimethylamino)pyrrolidin-1-yl)methyl)phenyl)-2-fluoro-4-methyl-5-((8-((1-methyl-1H-pyrazol-4-yl)amino)imidazo[1,2-a]pyridin-3-yl)ethynyl)benzamide;

<30> N-(3-(2-cyanopropan-2-yl)-5-((4-methyl-1,4-diazepan-1-yl)methyl)phenyl)-2-fluoro-4-methyl-5-((8-((1-methyl-1H-pyrazol-4-yl)amino)imidazo[1,2-a]pyridin-3-yl)ethynyl)benzamide;

<31> N-(3-(2-cyanopropan-2-yl)-5-((4-(trifluoromethyl)piperidin-1-yl)methyl)phenyl)-2-fluoro-4-methyl-5-((8-((1-methyl-1H-pyrazol-4-yl)amino)imidazo[1,2-a]pyridin-3-yl)ethynyl)benzamide;

<32> N-(3-(2-cyanopropan-2-yl)-5-((4-(2,2,2-trifluoroethyl)piperazin-1-yl)methyl)phenyl)-2-fluoro-4-methyl-5-((8-((1-methyl-1H-pyrazol-4-yl)amino)imidazo[1,2-a]pyridin-3-yl)ethynyl)benzamide;

<33> N-(3-(2-cyanopropan-2-yl)-5-((4-isopropylpiperazin-1-yl)methyl)phenyl)-2-fluoro-4-methyl-5-((8-((1-methyl-1H-pyrazol-4-yl)amino)imidazo[1,2-a]pyridin-3-yl)ethynyl)benzamide;

<34> N-(3-(2-cyanopropan-2-yl)-5-((4-(methylsulfonyl)piperazin-1-yl)methyl)phenyl)-2-fluoro-4-methyl-5-((8-((1-methyl-1H-pyrazol-4-yl)amino)imidazo[1,2-a]pyridin-3-yl)ethynyl)benzamide;

<35> N-(3-(2-cyanopropan-2-yl)-5-((4-methyl-3-oxopiperazin-1-yl)methyl)phenyl)-2-fluoro-4-methyl-5-((8-((1-methyl-1H-pyrazol-4-yl)amino)imidazo[1,2-a]pyridin-3-yl)ethynyl)benzamide;

<36> N-(3-(2-cyanopropan-2-yl)-5-((3-isopropoxyazetidin-1-yl)methyl)phenyl)-2-fluoro-4-methyl-5-((8-((1-methyl-1H-pyrazol-4-yl)amino)imidazo[1,2-a]pyridin-3-yl)ethynyl)benzamide;

<37> N-(3-((1H-imidazol-1-yl)methyl)-5-(2-cyanopropan-2-yl)phenyl)-2-fluoro-4-methyl-5-((8-((1-methyl-1H-pyrazol-4-yl)amino)imidazo[1,2-a]pyridin-3-yl)ethynyl)benzamide;

<38> N-(3-((1H-1,2,4-triazol-1-yl)methyl)-5-(2-cyanopropan-2-yl)phenyl)-2-fluoro-4-methyl-5-((8-((1-methyl-1H-pyrazol-4-yl)amino)imidazo[1,2-a]pyridin-3-yl)ethynyl)benzamide;

<39> N-(3-(2-cyanopropan-2-yl)-4-((4-methylpiperazin-1-yl)methyl)phenyl)-2-fluoro-4-methyl-5-((8-((1-methyl-1H-pyrazol-4-yl)amino)imidazo[1,2-a]pyridin-3-yl)ethynyl)benzamide;

<40> N-(3-(2-cyanopropan-2-yl)-4-(morpholinomethyl)phenyl)-2-fluoro-4-methyl-5-((8-((1-methyl-1H-pyrazol-4-yl)amino)imidazo[1,2-a]pyridin-3-yl)ethynyl)benzamide;

<41> N-(3-(2-cyanopropan-2-yl)-4-((3-(dimethylamino)pyrrolidin-1-yl)methyl)phenyl)-2-fluoro-4-methyl-5-((8-((1-methyl-1H-pyrazol-4-yl)amino)imidazo[1,2-a]pyridin-3-yl)ethynyl)benzamide;

<42> N-(3-(2-cyanopropan-2-yl)-4-((4-methyl-1,4-diazepan-1-yl)methyl)phenyl)-2-fluoro-4-methyl-5-((8-((1-methyl-1H-pyrazol-4-yl)amino)imidazo[1,2-a]pyridin-3-yl)ethynyl)benzamide;

<43> N-(3-(2-cyanopropan-2-yl)-4-((4-(2-hydroxyethyl)piperazin-1-yl)methyl)phenyl)-2-fluoro-4-methyl-5-((8-((1-methyl-1H-pyrazol-4-yl)amino)imidazo[1,2-a]pyridin-3-yl)ethynyl)benzamide;

<44> N-(3-(2-cyanopropan-2-yl)-4-((4-methyl-3-oxopiperazin-1-yl)methyl)phenyl)-2-fluoro-4-methyl-5-((8-((1-methyl-1H-pyrazol-4-yl)amino)imidazo[1,2-a]pyridin-3-yl)ethynyl)benzamide;

<45> N-(3-(2-cyanopropan-2-yl)-4-((4-(methylsulfonyl)piperazin-1-yl)methyl)phenyl)-2-fluoro-4-methyl-5-((8-((1-methyl-1H-pyrazol-4-yl)amino)imidazo[1,2-a]pyridin-3-yl)ethynyl)benzamide;

<46> N-(4-((1H-imidazol-1-yl)methyl)-3-(2-cyanopropan-2-yl)phenyl)-2-fluoro-4-methyl-5-((8-((1-methyl-1H-pyrazol-4-yl)amino)imidazo[1,2-a]pyridin-3-yl)ethynyl)benzamide;

<47> 2-fluoro-4-methyl-5-((8-((1-methyl-1H-pyrazol-4-yl)amino)imidazo[1,2-a]pyridin-3-yl)ethynyl)-N-(3-(4-methylpiperazin-1-yl)-5-(trifluoromethyl)phenyl)benzamide;

<48> N-(3-((2-(dimethylamino)ethyl)(methyl)amino)-5-(trifluoromethyl)phenyl)-2-fluoro-4-methyl-5-((8-((1-methyl-1H-pyrazol-4-yl)amino)imidazo[1,2-a]pyridin-3-yl)ethynyl)benzamide;

<49> 2-fluoro-4-methyl-5-((8-((1-methyl-1H-pyrazol-4-yl)amino)imidazo[1,2-a]pyridin-3-yl)ethynyl)-N-(3-(4-methyl-3-oxopiperazin-1-yl)-5-(trifluoromethyl)phenyl)benzamide;

<50> N-(3-(2-(dimethylamino)ethoxy)-5-(trifluoromethyl)phenyl)-2-fluoro-4-methyl-5-((8-((1-methyl-1H-pyrazol-4-yl)amino)imidazo[1,2-a]pyridin-3-yl)ethynyl)benzamide;

<51> N-(3-(3-(dimethylamino)propoxy)-5-(trifluoromethyl)phenyl)-2-fluoro-4-methyl-5-((8-((1-methyl-1H-pyrazol-4-yl)amino)imidazo[1,2-a]pyridin-3-yl)ethynyl)benzamide;

<52> 2-fluoro-4-methyl-5-((8-((1-methyl-1H-pyrazol-4-yl)amino)imidazo[1,2-a]pyridin-3-yl)ethynyl)-N-(3-(pyridin-4-yl)-5-(trifluoromethyl)phenyl)benzamide;

<53> 2-fluoro-4-methyl-5-((8-((1-methyl-1H-pyrazol-4-yl)amino)imidazo[1,2-a]pyridin-3-yl)ethynyl)-N-(3-(pyridin-3-yl)-5-(trifluoromethyl)phenyl)benzamide;

<54> 2-fluoro-4-methyl-N-(3-(1-methyl-1H-pyrazol-4-yl)-5-(trifluoromethyl)phenyl)-5-((8-((1-methyl-1H-pyrazol-4-yl)amino)imidazo[1,2-a]pyridin-3-yl)ethynyl)benzamide;

<55> 2-fluoro-4-methyl-5-((8-((1-methyl-1H-pyrazol-4-yl)amino)imidazo[1,2-a]pyridin-3-yl)ethynyl)-N-(4-((4-methylpiperazin-1-yl)methyl)-3-(trifluoromethyl)phenyl)benzamide;

<56> 2-fluoro-N-(4-((4-(2-hydroxyethyl)piperazin-1-yl)methyl)-3-(trifluoromethyl)phenyl)-4-methyl-5-((8-((1-methyl-1H-pyrazol-4-yl)amino)imidazo[1,2-a]pyridin-3-yl)ethynyl)benzamide;

<57> 2-fluoro-4-methyl-5-((8-((1-methyl-1H-pyrazol-4-yl)amino)imidazo[1,2-a]pyridin-3-yl)ethynyl)-N-(4-(morpholinomethyl)-3-(trifluoromethyl)phenyl)benzamide;

<58> 2-fluoro-4-methyl-5-((8-((1-methyl-1H-pyrazol-4-yl)amino)imidazo[1,2-a]pyridin-3-yl)ethynyl)-N-(4-((4-methyl-3-oxopiperazin-1-yl)methyl)-3-(trifluoromethyl)phenyl)benzamide;

<59> N-(4-((3-(dimethylamino)pyrrolidine-1-yl)methyl)-3-(trifluoromethyl)phenyl)-2-fluoro-4-methyl-5-((8-((1-methyl-1H-pyrazol-4-yl)amino)imidazo[1,2-a]pyridin-3-yl)ethynyl)benzamide;

<60> 2-fluoro-4-methyl-5-((8-((1-methyl-1H-pyrazol-4-yl)amino)imidazo[1,2-a]pyridin-3-yl)ethynyl)-N-(4-((4-(methylsulfonyl)piperazin-1-yl)methyl)-3-(trifluoromethyl)phenyl)benzamide;

<61> 2-fluoro-4-methyl-N-(4-((4-methyl-1,4-diazepan-1-yl)methyl)-3-(trifluoromethyl)phenyl)-5-((8-((1-methyl-1H-pyrazol-4-yl)amino)imidazo[1,2-a]pyridin-3-yl)ethynyl)benzamide;

<62> 2-fluoro-N-(4-((3-isopropoxyazetidin-1-yl)methyl)-3-(trifluoromethyl)phenyl)-4-methyl-5-((8-((1-methyl-1H-pyrazol-4-yl)amino)imidazo[1,2-a]pyridin-3-yl)ethynyl)benzamide;

<63> N-(4-((1H-imidazol-1-yl)methyl)-3-(trifluoromethyl)phenyl)-2-fluoro-4-methyl-5-((8-((1-methyl-1H-pyrazol-4-yl)amino)imidazo[1,2-a]pyridin-3-yl)ethynyl)benzamide;

<64> N-(4-((1H-1,2,4-triazol-1-yl)methyl)-3-(trifluoromethyl)phenyl)-2-fluoro-4-methyl-5-((8-((1-methyl-1H-pyrazol-4-yl)amino)imidazo[1,2-a]pyridin-3-yl)ethynyl)benzamide;

<65> 2-fluoro-4-methyl-5-((8-((1-methyl-1H-pyrazol-4-yl)amino)imidazo[1,2-a]pyridin-3-yl)ethynyl)-N-(4-(pyridin-4-yloxy)-3-(trifluoromethyl)phenyl)benzamide;

<66> 2-fluoro-4-methyl-5-((8-((1-methyl-1H-pyrazol-4-yl)amino)imidazo[1,2-a]pyridin-3-yl)ethynyl)-N-(3-(morpholinomethyl)-5-(trifluoromethyl)phenyl)benzamide;

<67> 2-fluoro-4-methyl-N-(3-((4-methyl-1,4-diazepan-1-yl)methyl)-5-(trifluoromethyl)phenyl)-5-((8-((1-methyl-1H-pyrazol-4-yl)amino)imidazo[1,2-a]pyridin-3-yl)ethynyl)benzamide;

<68> N-(3-((3-(dimethylamino)pyrrolidin-1-yl)methyl)-5-(trifluoromethyl)phenyl)-2-fluoro-4-methyl-5-((8-((1-methyl-1H-pyrazol-4-yl)amino)imidazo[1,2-a]pyridin-3-yl)ethynyl)benzamide;

<69> 2-fluoro-N-(3-((4-(2-hydroxyethyl)piperazin-1-yl)methyl)-5-(trifluoromethyl)phenyl)-4-methyl-5-((8-((1-methyl-1H-pyrazol-4-yl)amino)imidazo[1,2-a]pyridin-3-yl)ethynyl)benzamide;

<70> 2-fluoro-4-methyl-5-((8-((1-methyl-1H-pyrazol-4-yl)amino)imidazo[1,2-a]pyridin-3-yl)ethynyl)-N-(3-((4-(methylsulfonyl)piperazin-1-yl)methyl)-5-(trifluoromethyl)phenyl)benzamide;

<71> 2-fluoro-4-methyl-5-((8-((1-methyl-1H-pyrazol-4-yl)amino)imidazo[1,2-a]pyridin-3-yl)ethynyl)-N-(3-((4-methyl-3-oxopiperazin-1-yl)methyl)-5-(trifluoromethyl)phenyl)benzamide;

<72> 2-fluoro-N-(3-((3-isopropoxyazetidin-1-yl)methyl)-5-(trifluoromethyl)phenyl)-4-methyl-5-((8-((1-methyl-1H-pyrazol-4-yl)amino)imidazo[1,2-a]pyridin-3-yl)ethynyl)benzamide;

<73> N-(3-((1H-imidazol-1-yl)methyl)-5-(trifluoromethyl)phenyl)-2-fluoro-4-methyl-5-((8-((1-methyl-1H-pyrazol-4-yl)amino)imidazo[1,2-a]pyridin-3-yl)ethynyl)benzamide;

<74> N-(3-((1H-1,2,4-triazol-1-yl)methyl)-5-(trifluoromethyl)phenyl)-2-fluoro-4-methyl-5-((8-((1-methyl-1H-pyrazol-4-yl)amino)imidazo[1,2-a]pyridin-3-yl)ethynyl)benzamide;

<75> 5-((8-((1H-pyrazol-4-yl)amino)imidazo[1,2-a]pyridin-3-yl)ethynyl)-N-(3-(2-cyanopropan-2-yl)-5-(4-methyl-1H-imidazol-1-yl)phenyl)-2-fluoro-4-methylbenzamide;

<76> 5-((8-((1H-pyrazol-4-yl)amino)imidazo[1,2-a]pyridin-3-yl)ethynyl)-2-chloro-N-(3-(2-cyanopropan-2-yl)-5-(4-methyl-1H-imidazol-1-yl)phenyl)-4-methylbenzamide;

<77> 5-((8-((1H-pyrazol-4-yl)amino)imidazo[1,2-a]pyridin-3-yl)ethynyl)-N-(3-(2-cyanopropan-2-yl)-5-(1-methyl-1H-pyrazol-4-yl)phenyl)-2-fluoro-4-methylbenzamide;

<78> 5-((8-((1H-pyrazol-4-yl)amino)imidazo[1,2-a]pyridin-3-yl)ethynyl)-N-(3-(2-cyanopropan-2-yl)-5-(pyridin-4-yl)phenyl)-2-fluoro-4-methylbenzamide;

<79> 5-((8-((1H-pyrazol-4-yl)amino)imidazo[1,2-a]pyridin-3-yl)ethynyl)-N-(3-(2-cyanopropan-2-yl)-5-(pyridin-3-yl)phenyl)-2-fluoro-4-methylbenzamide;

<80> 5-((8-((1H-pyrazol-4-yl)amino)imidazo[1,2-a]pyridin-3-yl)ethynyl)-N-(3-(2-cyanopropan-2-yl)-5-(4-methylpiperazin-1-yl)phenyl)-2-fluoro-4-methylbenzamide;

<81> 5-((8-((1H-pyrazol-4-yl)amino)imidazo[1,2-a]pyridin-3-yl)ethynyl)-N-(3-(2-cyanopropan-2-yl)-5-((2-(dimethylamino)ethyl)(methyl)amino)phenyl)-2-fluoro-4-methylbenzamide;

<82> 5-((8-((1H-pyrazol-4-yl)amino)imidazo[1,2-a]pyridin-3-yl)ethynyl)-N-(3-(2-cyanopropan-2-yl)-5-(4-methyl-3-oxopiperazin-1-yl)phenyl)-2-fluoro-4-methylbenzamide;

<83> 5-((8-((1H-pyrazol-4-yl)amino)imidazo[1,2-a]pyridin-3-yl)ethynyl)-N-(3-(2-cyanopropan-2-yl)-5-(pyridin-4-yloxy)phenyl)-2-fluoro-4-methylbenzamide;

<84> 5-((8-((1H-pyrazol-4-yl)amino)imidazo[1,2-a]pyridin-3-yl)ethynyl)-N-(3-(2-cyanopropan-2-yl)-5-((4-methylpiperazin-1-yl)methyl)phenyl)-2-fluoro-4-methylbenzamide;

<85> 5-((8-((1H-pyrazol-4-yl)amino)imidazo[1,2-a]pyridin-3-yl)ethynyl)-N-(3-(2-cyanopropan-2-yl)-5-((3-(dimethylamino)pyrrolidin-1-yl)methyl)phenyl)-2-fluoro-4-methylbenzamide;

<86> 5-((8-((1H-pyrazol-4-yl)amino)imidazo[1,2-a]pyridin-3-yl)ethynyl)-N-(3-(2-cyanopropan-2-yl)-5-((4-(2-hydroxyethyl)piperazin-1-yl)methyl)phenyl)-2-fluoro-4-methylbenzamide;

<87> 5-((8-((1H-pyrazol-4-yl)amino)imidazo[1,2-a]pyridin-3-yl)ethynyl)-N-(3-(2-cyanopropan-2-yl)-5-((4-(methylsulfonyl)piperazin-1-yl)methyl)phenyl)-2-fluoro-4-methylbenzamide;

<88> 5-((8-((1H-pyrazol-4-yl)amino)imidazo[1,2-a]pyridin-3-yl)ethynyl)-N-(3-(2-cyanopropan-2-yl)-5-((4-methyl-3-oxopiperazin-1-yl)methyl)phenyl)-2-fluoro-4-methylbenzamide;

<89> N-(3-((1H-1,2,4-triazol-1-yl)methyl)-5-(2-cyanopropan-2-yl)phenyl)-5-((8-((1H-pyrazol-4-yl)amino)imidazo[1,2-a]pyridin-3-yl)ethynyl)-2-fluoro-4-methylbenzamide;

<90> 5-((8-((1H-pyrazol-4-yl)amino)imidazo[1,2-a]pyridin-3-yl)ethynyl)-N-(3-(2-cyanopropan-2-yl)-4-((4-methylpiperazin-1-yl)methyl)phenyl)-2-fluoro-4-methylbenzamide;

<91> 5-((8-((1H-pyrazol-4-yl)amino)imidazo[1,2-a]pyridin-3-yl)ethynyl)-N-(3-(2-cyanopropan-2-yl)-4-((3-(dimethylamino)pyrrolidin-1-yl)methyl)phenyl)-2-fluoro-4-methylbenzamide;

<92> 5-((8-((1H-pyrazol-4-yl)amino)imidazo[1,2-a]pyridin-3-yl)ethynyl)-N-(3-(2-cyanopropan-2-yl)-4-((4-(2-hydroxyethyl)piperazin-1-yl)methyl)phenyl)-2-fluoro-4-methylbenzamide;

<93> 5-((8-((1H-pyrazol-4-yl)amino)imidazo[1,2-a]pyridin-3-yl)ethynyl)-N-(3-(2-cyanopropan-2-yl)-4-((4-methyl-3-oxopiperazin-1-yl)methyl)phenyl)-2-fluoro-4-methylbenzamide;

<94> 5-((8-((1H-pyrazol-4-yl)amino)imidazo[1,2-a]pyridin-3-yl)ethynyl)-N-(3-(2-cyanopropan-2-yl)-4-((4-(methylsulfonyl)piperazin-1-yl)methyl)phenyl)-2-fluoro-4-methylbenzamide;

<95> 5-((8-((1H-pyrazol-4-yl)amino)imidazo[1,2-a]pyridin-3-yl)ethynyl)-2-fluoro-4-methyl-N-(3-(4-methyl-1H-imidazol-1-yl)-5-(trifluoromethyl)phenyl)benzamide;

<96> 5-((8-((1H-pyrazol-4-yl)amino)imidazo[1,2-a]pyridin-3-yl)ethynyl)-2-fluoro-4-methyl-N-(3-(1-methyl-1H-pyrazol-4-yl)-5-(trifluoromethyl)phenyl)benzamide;

<97> 5-((8-((1H-pyrazol-4-yl)amino)imidazo[1,2-a]pyridin-3-yl)ethynyl)-2-fluoro-4-methyl-N-(3-(pyridin-4-yl)-5-(trifluoromethyl)phenyl)benzamide;

<98> 5-((8-((1H-pyrazol-4-yl)amino)imidazo[1,2-a]pyridin-3-yl)ethynyl)-2-fluoro-4-methyl-N-(3-(pyridin-3-yl)-5-(trifluoromethyl)phenyl)benzamide;

<99> 5-((8-((1H-pyrazol-4-yl)amino)imidazo[1,2-a]pyridin-3-yl)ethynyl)-2-fluoro-4-methyl-N-(3-(4-methylpiperazin-1-yl)-5-(trifluoromethyl)phenyl)benzamide;

<100> 5-((8-((1H-pyrazol-4-yl)amino)imidazo[1,2-a]pyridin-3-yl)ethynyl)-2-fluoro-4-methyl-N-(3-(4-methyl-3-oxopiperazin-1-yl)-5-(trifluoromethyl)phenyl)benzamide;

<101> 5-((8-((1H-pyrazol-4-yl)amino)imidazo[1,2-a]pyridin-3-yl)ethynyl)-2-fluoro-4-methyl-N-(3-(pyridin-4-yloxy)-5-(trifluoromethyl)phenyl)benzamide;

<102> 5-((8-((1H-pyrazol-4-yl)amino)imidazo[1,2-a]pyridin-3-yl)ethynyl)-N-(3-(2-(dimethylamino)ethoxy)-5-(trifluoromethyl)phenyl)-2-fluoro-4-methylbenzamide;

<103> 5-((8-((1H-pyrazol-4-yl)amino)imidazo[1,2-a]pyridin-3-yl)ethynyl)-N-(3-(3-(dimethylamino)propoxy)-5-(trifluoromethyl)phenyl)-2-fluoro-4-methylbenzamide;

<104> 5-((8-((1H-pyrazol-4-yl)amino)imidazo[1,2-a]pyridin-3-yl)ethynyl)-2-fluoro-4-methyl-N-(3-((4-methylpiperazin-1-yl)methyl)-5-(trifluoromethyl)phenyl)benzamide;

<105> 5-((8-((1H-pyrazol-4-yl)amino)imidazo[1,2-a]pyridin-3-yl)ethynyl)-N-(3-((3-(dimethylamino)pyrrolidin-1-yl)methyl)-5-(trifluoromethyl)phenyl)-2-fluoro-4-methylbenzamide;

<106> 5-((8-((1H-pyrazol-4-yl)amino)imidazo[1,2-a]pyridin-3-yl)ethynyl)-2-fluoro-N-(3-((4-(2-hydroxyethyl)piperazin-1-yl)methyl)-5-(trifluoromethyl)phenyl)-4-methylbenzamide;

<107> 5-((8-((1H-pyrazol-4-yl)amino)imidazo[1,2-a]pyridin-3-yl)ethynyl)-2-fluoro-4-methyl-N-(3-((4-methyl-3-oxopiperazin-1-yl)methyl)-5-(trifluoromethyl)phenyl)benzamide;

<108> N-(3-((1H-1,2,4-triazol-1-yl)methyl)-5-(trifluoromethyl)phenyl)-5-((8-((1H-pyrazol-4-yl)amino)imidazo[1,2-a]pyridin-3-yl)ethynyl)-2-fluoro-4-methylbenzamide;

<109> 5-((8-((1H-pyrazol-4-yl)amino)imidazo[1,2-a]pyridin-3-yl)ethynyl)-2-fluoro-4-methyl-N-(4-((4-methylpiperazin-1-yl)methyl)-3-(trifluoromethyl)phenyl)benzamide;

<110> 5-((8-((1H-pyrazol-4-yl)amino)imidazo[1,2-a]pyridin-3-yl)ethynyl)-N-(4-((3-(dimethylamino)pyrrolidin-1-yl)methyl)-3-(trifluoromethyl)phenyl)-2-fluoro-4-methylbenzamide;

<111> 5-((8-((1H-pyrazol-4-yl)amino)imidazo[1,2-a]pyridin-3-yl)ethynyl)-2-fluoro-N-(4-((4-(2-hydroxyethyl)piperazin-1-yl)methyl)-3-(trifluoromethyl)phenyl)-4-methylbenzamide;

<112> 5-((8-((1H-pyrazol-4-yl)amino)imidazo[1,2-a]pyridin-3-yl)ethynyl)-2-fluoro-4-methyl-N-(4-((4-methyl-3-oxopiperazin-1-yl)methyl)-3-(trifluoromethyl)phenyl)benzamide;

<113> 5-((8-((1H-pyrazol-4-yl)amino)imidazo[1,2-a]pyridin-3-yl)ethynyl)-2-fluoro-4-methyl-N-(4-((4-(methylsulfonyl)piperazin-1-yl)methyl)-3-(trifluoromethyl)phenyl)benzamide;

<114> N-(4-((1H-1,2,4-triazol-1-yl)methyl)-3-(trifluoromethyl)phenyl)-5-((8-((1H-pyrazol-4-yl)amino)imidazo[1,2-a]pyridin-3-yl)ethynyl)-2-fluoro-4-methylbenzamide.

The compound represented by formula 1 of the present invention can be used as a form of a pharmaceutically acceptable salt, in which the salt is preferably acid addition salt formed by pharmaceutically acceptable free acids. The acid addition salt herein can be obtained from inorganic acids such as hydrochloric acid, nitric acid, phosphoric acid, sulfuric acid, hydrobromic acid, hydroiodic acid, nitrous acid, and phosphorous acid; non-toxic organic acids such as aliphatic mono/dicarboxylate, phenyl-substituted alkanoate, hydroxy alkanoate, alkandioate, aromatic acids, and aliphatic/aromatic sulfonic acids; or organic acids such as acetic acid, benzoic acid, citric acid, lactic acid, maleic acid, gluconic acid, methanesulfonic acid, 4-toluenesulfonic acid, tartaric acid, and fumaric acid. The pharmaceutically non-toxic salts are exemplified by sulfate, pyrosulfate, bisulfate, sulphite, bisulphite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutylate, caprate, heptanoate, propiolate, oxalate, malonate, succinate, suberate, cabacate, fumarate, maliate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutylate, citrate, lactate, hydroxybutylate, glycolate, malate, tartrate, methanesulfonate, propanesulfonate, naphthalene-1-sulfonate, naphthalene-2-sulfonate, and mandelate.

The acid addition salt according to the present invention can be prepared by the conventional method known to those in the art. For example, the derivative represented by formula 1 is dissolved in an organic solvent such as methanol, ethanol, acetone, methylenechloride, and acetonitrile, to which organic acid or inorganic acid is added to induce precipitation. Then, the precipitate is filtered and dried to give the salt. Or the solvent and the excessive acid are distillated under reduced pressure, and dried. Then, the precipitate is crystallized in an organic solvent to give the same.

A pharmaceutically acceptable metal salt can be prepared by using a base. Alkali metal or alkali earth metal salt is obtained by the following processes: dissolving the compound in excessive alkali metal hydroxide or alkali earth metal hydroxide solution; filtering non-soluble compound salt; evaporating the remaining solution and drying thereof. At this time, the metal salt is preferably prepared in the pharmaceutically suitable form of sodium, potassium, or calcium salt. And the corresponding salt is prepared by the reaction of alkali metal or alkali earth metal salt with proper silver salt (ex; silver nitrate).

In addition, the present invention includes not only the compound represented by formula 1 but also a pharmaceutically acceptable salt thereof, and a solvate, an isomer, and a hydrate possibly produced from the same.

The term "solvate" refers to a compound or a salt thereof of the present invention containing a stoichiometric or non-stoichiometric amount of solvent bound by a non-covalent intermolecular force. Preferred solvents therefor include volatile, non-toxic, and/or solvents suitable for administration to human. In this case, when the solvent is water, it is referred to as "hydrate".

The term "isomer" refers to a compound or a salt thereof of the present invention having the same chemical formula or molecular formula, but structurally or sterically different. Such isomers include structural isomers such as tautomers, R or S isomers having an asymmetric carbon center, stereoisomers such as geometric isomers (trans, cis), and optical isomers (enantiomers). All these isomers and mixtures thereof are also included in the scope of the present invention.

In another aspect of the present invention, the present invention provides a method for preparing the compound represented by formula 1 of claim 1, comprising a step of preparing a compound represented by formula 1 by reacting a compound represented by formula 2 with a compound represented by formula 3, as shown in reaction formula 1 below:

[Reaction Formula 1]

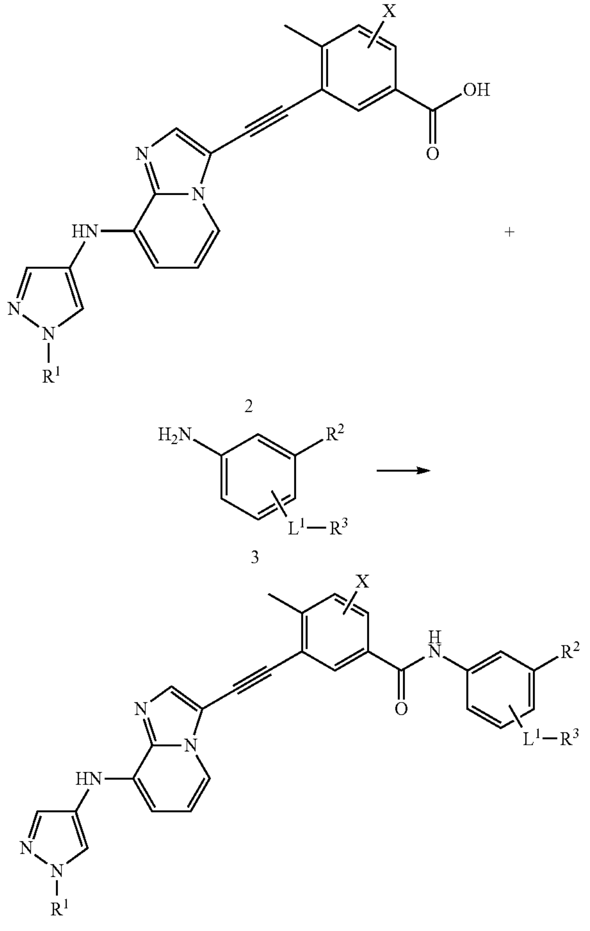
2
3
1

In reaction formula 1 above, $L^1$, $R^1$, $R^2$, $R^3$ and X are as defined in formula 1 of claim 1.

Hereinafter, the preparation method shown in the reaction formula 1 above is described in more detail.

In the method for preparing a compound represented by formula 1 according to the present invention, the step of reaction formula 1 is a step of preparing a compound represented by formula 1 by reacting a compound represented by formula 2 with a compound represented by formula 3. Specifically, it is a step in which the carboxyl of the compound represented by formula 2 and the amine of the compound represented by formula 3 react to form the compound represented by formula 1.

At this time, as long as it is a method for preparing a 3-((8-((1H-pyrazol-4-yl)amino)imidazo[1,2-a]pyridin-3-yl)

ethynyl)-N-phenylbenzamide derivative represented by formula 1, it is not particularly limited, and is included in the scope of the present invention. The compound represented by formula 2 can be understood as a compound having the carboxyl capable of reacting with the amine to form an amide, and the compound represented by formula 3 can be understood as an amine capable of amide-forming reaction. However, this is only an example and is not limited thereto. The 3-((8-((1H-pyrazol-4-yl)amino)imidazo[1,2-a]pyridin-3-yl)ethynyl)-N-phenylbenzamide derivative of the present invention, the final compound, is prepared by the amide-forming reaction of the carboxyl and the amine.

In more detail, it can be understood with reference to the preparation methods of the example compounds of the present invention below. Each reaction condition (reaction conditions conceivable by a person skilled in the art of organic synthesis, such as reaction temperature, time, atmospheric conditions, pressure conditions, etc.) can be changed, and it can be understood that the present invention is not limited thereto. In addition, it can be understood that the compounds and the derivatives thereof used in each step include the derivatives other than those disclosed herein that can be modified by simple modification, alteration or removal of substituents, and the modified derivatives are included in the present invention.

Preferred embodiments of the preparation method include the preparation methods disclosed in Examples 1 to 114 below, but the present invention is not limited thereto.

In another aspect of the present invention, the present invention provides a pharmaceutical composition containing a compound represented by formula 1, a solvate thereof, or a pharmaceutically acceptable salt thereof as an active ingredient for preventing or treating diseases related to one or more protein kinases selected from the group consisting of ABL1(E255K)-phosphorylated, ABL1(F317I)-nonphosphorylated, ABL1(F317I)-phosphorylated, ABL1(F317L)-nonphosphorylated, ABL1(F317L)-phosphorylated, ABL1 (H396P)-nonphosphorylated, ABL1(H396P)-phosphorylated, ABL1(M351T)-phosphorylated, ABL1 (Q252H)-nonphosphorylated, ABL1(Q252H)-phosphorylated, ABL1(T315I)-nonphosphorylated, ABL1 (T315I)-phosphorylated, ABL1(Y253F)-phosphorylated, ABL1-nonphosphorylated, ABL1-phosphorylated, ABL2, AURKB, AURKC, AXL, BLK, BMX, BRAF, BRAF (V600E), BRK, BTK, CDC2L1, CDC2L2, CDC2L5, CDK11, CDK7, CDKL2, CIT, CSF1R, CSK, DDR1, DDR2, DLK, EGFR, EGFR(E746-A750del), EGFR(G719C), EGFR(G719S), EGFR(L747-E749del, A750P), EGFR (L747-S752del, P753S), EGFR(L747-T751del,Sins), EGFR (L858R), EGFR(L861Q), EGFR(S752-I759del), EPHA1, EPHA3, EPHA4, EPHA5, EPHA6, EPHA7, EPHA8, EPHB1, EPHB2, EPHB6, ERBB2, ERBB4, ERK8, FER, FES, FGFR1, FGFR2, FGFR3, FGFR3(G697C), FGFR4, FGR, FLT1, FLT3, FLT3(D835H), FLT3(D835V), FLT3 (D835Y), FLT3(ITD), FLT3(ITD,F691L), FLT3(K663Q), FLT3(N841I), FLT3(R834Q), FLT4, FRK, FYN, GAK, GCN2(Kin.Dom.2,S808G), HCK, HPK1, IKK-alpha, IKK-beta, IRAK1, IRAK4, JNK2, KIT, KIT(A829P), KIT (D816H), KIT(D816V), KIT(L576P), KIT(V559D), KIT (V559D,T670I), KIT(V559D, V654A), LCK, LIMK1, LOK, LRRK2, LTK, LYN, MAP3K2, MAP3K3, MAP4K2, MAP4K3, MAP4K4, MAP4K5, MEK5, MERTK, MET (Y1235D), MINK, MKNK1, MKNK2, MLK1, MLK3, MST3, MUSK, NEK1, NEK4, NLK, p38-alpha, p38-beta, p38-delta, p38-gamma, PAK3, PCTK2, PDGFRA, PDGFRB, PFCDPK1(P.falciparum), PFTAIRE2, PFTK1, RET, RET(M918T), RET(V804L), RET(V804M), RIOK3, RIPK1, RIPK2, SIK, SLK, SRC, SRMS, STK33, STK35, STK36, TAK1, TAOK1, TAOK2, TAOK3, TEC, TESK1, TIE1, TIE2, TNIK, TNK1, TNK2, TNNI3K, TRKA, TRKB, TRKC, TXK, TYK2(JH1domain-catalytic), VEGFR2, YES, YSK4 and ZAK.

In another aspect of the present invention, the present invention provides a pharmaceutical composition for preventing or treating cancer containing a compound represented by formula 1, a solvate thereof, or a pharmaceutically acceptable salt thereof as an active ingredient.

At this time, the compound can prevent or treat cancer by exhibiting an inhibitory activity against Bcr-Abl kinase or Bcr-Abl (T315I) kinase.

The cancer is not limited as long as it is a known cancer, but for example, it can be one or more selected from the group consisting of pseudomyxoma, intrahepatic biliary tract cancer, hepatoblastoma, liver cancer, thyroid cancer, colon cancer, testicular cancer, myelodysplastic syndrome, glioblastoma, oral cancer, labial cancer, mycosis fungoides, acute myeloid leukemia, acute lymphocytic leukemia, basal cell carcinoma, ovarian epithelial cancer, ovarian germ cell cancer, male breast cancer, brain cancer, pituitary adenoma, multiple myeloma, gallbladder cancer, biliary tract cancer, colorectal cancer, chronic myelogenous leukemia, chronic lymphocytic leukemia, retinoblastoma, choroidal melanoma, ampulla Barter cancer, bladder cancer, peritoneal cancer, parathyroid cancer, adrenal cancer, nasal cavity cancer, non-small cell lung cancer, tongue cancer, astrocytoma, small cell lung cancer, childhood brain cancer, childhood lymphoma, childhood leukemia, small intestine cancer, meningioma, esophageal cancer, glioma, renal pelvic cancer, kidney cancer, heart cancer, duodenal cancer, malignant soft tissue cancer, malignant bone cancer, malignant lymphoma, malignant mesothelioma, malignant melanoma, eye cancer, vulvar cancer, ureter cancer, urethral cancer, cancer of unknown primary site, gastric lymphoma, gastric cancer, gastric carcinoma, gastrointestinal stromal cancer, Wilms cancer, breast cancer, triple-negative breast cancer, sarcoma, penile cancer, pharyngeal cancer, pregnancy chorionic disease, cervical cancer, endometrial cancer, uterine sarcoma, prostate cancer, metastatic bone cancer, metastatic brain cancer, mediastinal cancer, rectal cancer, rectal carcinoma, vaginal cancer, spinal cancer, acoustic schwannoma, pancreatic cancer, salivary gland cancer, Kaposi's sarcoma, Paget's disease, tonsil cancer, squamous cell carcinoma, lung adenocarcinoma, lung cancer, lung squamous cell carcinoma, skin cancer, anal cancer, rhabdomyosarcoma, laryngeal cancer, pleural cancer, blood cancer and thymus cancer.

The compound represented by formula 1 of the present invention or the pharmaceutically acceptable salt thereof can be administered orally or parenterally and be used in general forms of pharmaceutical formulation. That is, the compound or the pharmaceutically acceptable salt thereof can be prepared for oral or parenteral administration by mixing with generally used diluents or excipients such as fillers, extenders, binders, wetting agents, disintegrating agents and surfactants. Solid formulations for oral administration are tablets, pills, powders, granules and capsules. These solid formulations are prepared by mixing one or more compounds with one or more suitable excipients such as starch, calcium carbonate, sucrose or lactose, gelatin, etc.

Except for the simple excipients, lubricants, for example magnesium stearate, talc, etc, can be used. Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin.

Parenteral administration is conducted by subcutaneous injection, intravenous injection, intramuscular injection or intrathoracic injection. Formulations for parenteral administration are sterilized aqueous solutions, water-insoluble excipients, suspensions and emulsions. Water insoluble excipients and suspensions can contain, in addition to the active compound or compounds, propylene glycol, polyethylene glycol, vegetable oil like olive oil, injectable ester like ethylolate, etc.

In another aspect of the present invention, the present invention provides a health functional food composition containing a compound represented by formula 1, a solvate thereof, or a pharmaceutically acceptable salt thereof as an active ingredient for preventing or ameliorating diseases related to one or more protein kinases selected from the group consisting of ABL1(E255K)-phosphorylated, ABL1 (F317I)-nonphosphorylated, ABL1(F317I)-phosphorylated, ABL1(F317L)-nonphosphorylated, ABL1(F317L)-phosphorylated, ABL1(H396P)-nonphosphorylated, ABL1 (H396P)-phosphorylated, ABL1(M351T)-phosphorylated, ABL1(Q252H)-nonphosphorylated, ABL1(Q252H)-phosphorylated, ABL1(T315I)-nonphosphorylated, ABL1 (T315I)-phosphorylated, ABL1(Y253F)-phosphorylated, ABL1-nonphosphorylated, ABL1-phosphorylated, ABL2, AURKB, AURKC, AXL, BLK, BMX, BRAF, BRAF (V600E), BRK, BTK, CDC2L1, CDC2L2, CDC2L5, CDK11, CDK7, CDKL2, CIT, CSF1R, CSK, DDR1, DDR2, DLK, EGFR, EGFR(E746-A750del), EGFR(G719C), EGFR(G719S), EGFR(L747-E749del, A750P), EGFR (L747-S752del, P753S), EGFR(L747-T751del,Sins), EGFR (L858R), EGFR(L861Q), EGFR(S752-I759del), EPHA1, EPHA3, EPHA4, EPHA5, EPHA6, EPHA7, EPHA8, EPHB1, EPHB2, EPHB6, ERBB2, ERBB4, ERK8, FER, FES, FGFR1, FGFR2, FGFR3, FGFR3(G697C), FGFR4, FGR, FLT1, FLT3, FLT3(D835H), FLT3(D835V), FLT3 (D835Y), FLT3(ITD), FLT3(ITD,F691L), FLT3(K663Q), FLT3(N841I), FLT3(R834Q), FLT4, FRK, FYN, GAK, GCN2(Kin.Dom.2,S808G), HCK, HPK1, IKK-alpha, IKK-beta, IRAK1, IRAK4, JNK2, KIT, KIT(A829P), KIT (D816H), KIT(D816V), KIT(L576P), KIT(V559D), KIT (V559D,T670I), KIT(V559D, V654A), LCK, LIMK1, LOK, LRRK2, LTK, LYN, MAP3K2, MAP3K3, MAP4K2, MAP4K3, MAP4K4, MAP4K5, MEK5, MERTK, MET (Y1235D), MINK, MKNK1, MKNK2, MLK1, MLK3, MST3, MUSK, NEK1, NEK4, NLK, p38-alpha, p38-beta, p38-delta, p38-gamma, PAK3, PCTK2, PDGFRA, PDGFRB, PFCDPK1(P.falciparum), PFTAIRE2, PFTK1, RET, RET(M918T), RET(V804L), RET(V804M), RIOK3, RIPK1, RIPK2, SIK, SLK, SRC, SRMS, STK33, STK35, STK36, TAK1, TAOK1, TAOK2, TAOK3, TEC, TESK1, TIE1, TIE2, TNIK, TNK1, TNK2, TNNI3K, TRKA, TRKB, TRKC, TXK, TYK2(JH1domain-catalytic), VEGFR2, YES, YSK4 and ZAK.

In another aspect of the present invention, the present invention provides a health functional food composition for preventing or ameliorating cancer containing a compound represented by formula 1, a solvate thereof, or a pharmaceutically acceptable salt thereof as an active ingredient.

At this time, the compound can prevent or ameliorate cancer by exhibiting an inhibitory activity against Bcr-Abl kinase or Bcr-Abl (T315I) kinase.

The cancer is not limited as long as it is a known cancer, but for example, it can be one or more selected from the group consisting of pseudomyxoma, intrahepatic biliary tract cancer, hepatoblastoma, liver cancer, thyroid cancer, colon cancer, testicular cancer, myelodysplastic syndrome, glioblastoma, oral cancer, labial cancer, mycosis fungoides, acute myeloid leukemia, acute lymphocytic leukemia, basal cell carcinoma, ovarian epithelial cancer, ovarian germ cell cancer, male breast cancer, brain cancer, pituitary adenoma, multiple myeloma, gallbladder cancer, biliary tract cancer, colorectal cancer, chronic myelogenous leukemia, chronic lymphocytic leukemia, retinoblastoma, choroidal melanoma, ampulla Barter cancer, bladder cancer, peritoneal cancer, parathyroid cancer, adrenal cancer, nasal cavity cancer, non-small cell lung cancer, tongue cancer, astrocytoma, small cell lung cancer, childhood brain cancer, childhood lymphoma, childhood leukemia, small intestine cancer, meningioma, esophageal cancer, glioma, renal pelvic cancer, kidney cancer, heart cancer, duodenal cancer, malignant soft tissue cancer, malignant bone cancer, malignant lymphoma, malignant mesothelioma, malignant melanoma, eye cancer, vulvar cancer, ureter cancer, urethral cancer, cancer of unknown primary site, gastric lymphoma, gastric cancer, gastric carcinoma, gastrointestinal stromal cancer, Wilms cancer, breast cancer, triple-negative breast cancer, sarcoma, penile cancer, pharyngeal cancer, pregnancy chorionic disease, cervical cancer, endometrial cancer, uterine sarcoma, prostate cancer, metastatic bone cancer, metastatic brain cancer, mediastinal cancer, rectal cancer, rectal carcinoma, vaginal cancer, spinal cancer, acoustic schwannoma, pancreatic cancer, salivary gland cancer, Kaposi's sarcoma, Paget's disease, tonsil cancer, squamous cell carcinoma, lung adenocarcinoma, lung cancer, lung squamous cell carcinoma, skin cancer, anal cancer, rhabdomyosarcoma, laryngeal cancer, pleural cancer, blood cancer and thymus cancer.

At this time, the health functional food can include the compound represented by formula 1 of the present invention, the solvate thereof, or the pharmaceutically acceptable salt thereof as an active ingredient, and can be prepared and used as a general health functional food. In addition, the health functional food is included within the scope of the present invention as long as it is a formulation, food form, or administration form known to those skilled in the art, and if it is within a range that can be recognized as a health functional food, it is included in the health functional food of the present invention.

Hereinafter, the present invention will be described in detail by the following preparative examples, examples and experimental examples.

However, the following preparative examples, examples and experimental examples are only for illustrating the present invention, and the contents of the present invention are not limited thereto.

<Analysis and Purification Conditions>

The compounds synthesized in examples of the present invention were purified by the following methods or subjected to structural analysis.

1. LC-MS Analysis Condition
   Device name: Shimadzu LCMS-2020
   Column: ACE Excel2 C18, 75×2.1 mm
   Mobile phase: acetonitrile/$H_2O$+0.1% TFA
   Flow rate: 0.5 mL/min
   UV detector: 254 nm
2. MPLC Purification Condition (A)
   Device name: CombiFlash®
   UV detector: 254 nm
3. Prep-HPLC Purification Condition (B)
   Device name: Gilson GX-281, 321 pump, UV/VIS-155
   Column: Luna® 10 vÅmm
   Mobile phase: acetonitrile/0.1% TFA $H_2O$
   Flow rate: 18 mL/min
   UV detector: 254 nm
4. $^1H$ NMR
   Device name: Bruker Avance (400 MHz)

scheme-1
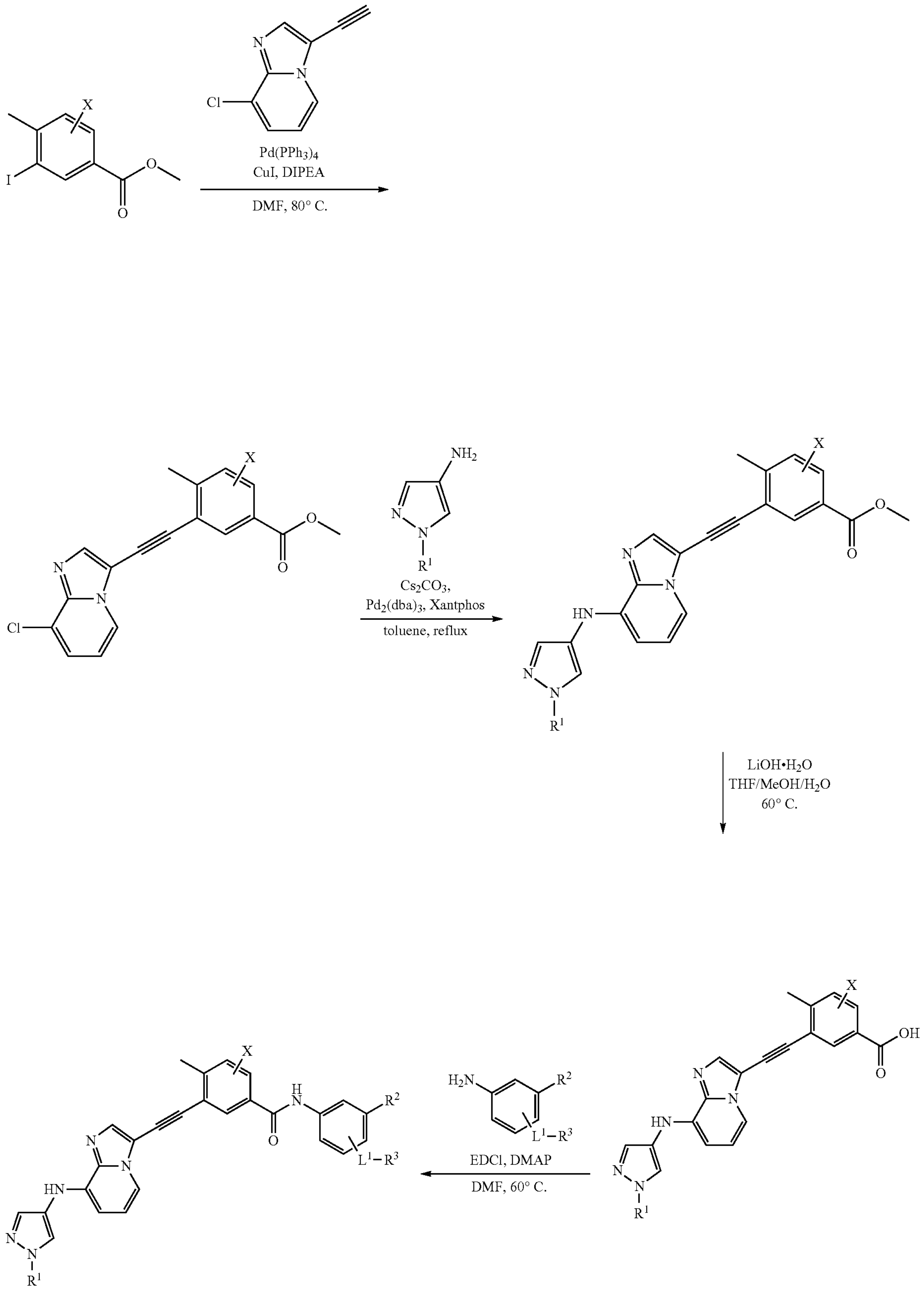

<Example 1> Preparation of N-(3-(2-cyanopropane-2-yl)-5-(4-methyl-1H-imidazol-1-yl)phenyl)-2-fluoro-4-methyl-5-((8-((1-methyl-1H-pyrazol-4-yl)amino)imidazo[1,2-a]pyridin-3-yl)ethynyl)benzamide

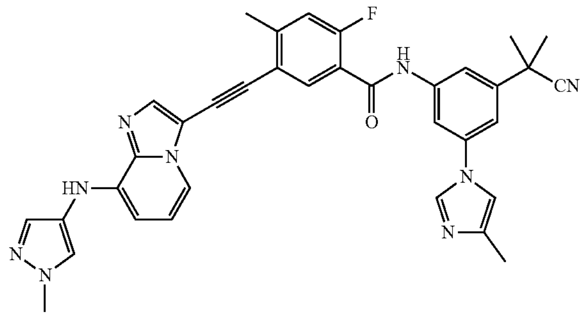 [SMILES: Cc1cn(-c2cc(NC(=O)c3cc(C#Cc4cnc5c(Nc6cnn(C)c6)cccn45)c(C)cc3F)cc(C(C)(C)C#N)c2)cn1]

Step 1: Preparation of methyl 5-((8-chloroimidazo[1,2-a]pyridin-3-yl)ethynyl)-2-fluoro-4-methylbenzoate

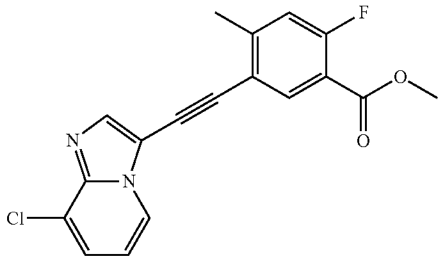 [SMILES: COC(=O)c1cc(C#Cc2cnc3c(Cl)cccn23)c(C)cc1F]

Methyl 2-fluoro-5-iodo-4-methylbenzoate (12.1 g, 35.0 mmol) was dissolved in DMF(80 mL), to which 8-chloro-3-ethynylimidazo[1,2-a]pyridine (6.18 g, 35.0 mmol), $Pd(PPh_3)_4$(2.02 g, 1.75 mmol), CuI (0.666 g, 3.50 mmol) and DIPEA (9.14 mL, 52.5 mmol) were added at room temperature. The reaction mixture was degassed using a nitrogen balloon, followed by stirring at room temperature for 30 minutes. Then, the reaction mixture was heated to 80° C., and stirred with heat for 1 hour. Upon completion of the reaction, the mixture was cooled to room temperature, filtered through celite, and then concentrated under reduced pressure. The obtained residue was purified by silica gel chromatography to give a target compound (8.0 g, 67%) as a yellow solid.

$^1$H NMR (400 MHz, $CDCl_3$) δ 8.28 (dd, J=6.8, 0.9 Hz, 1H), 8.13 (d, J=7.3 Hz, 1H), 7.97 (s, 1H), 7.38 (dd, J=7.4, 0.9 Hz, 1H), 7.08 (d, J=11.2 Hz, 1H), 6.94 (t, J=7.1 Hz, 1H), 3.95 (s, 3H), 2.58 (s, 3H); LC-MS (ESI) m/z: 343$[M+H]^+$

Step 2: Preparation of methyl 2-fluoro-4-methyl-5-((8-((1-methyl-1H-pyrazol-4-yl)amino)imidazo[1,2-a]pyridin-3-yl)ethynyl)benzoate

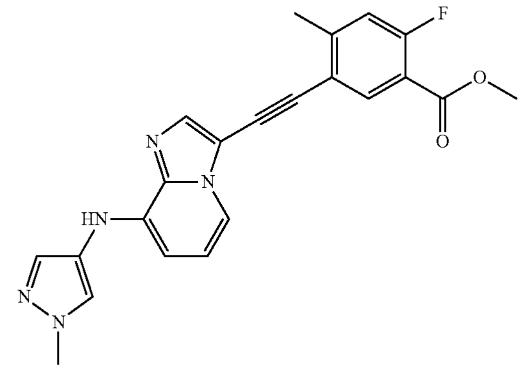 [SMILES: COC(=O)c1cc(C#Cc2cnc3c(Nc4cnn(C)c4)cccn23)c(C)cc1F]

The methyl 5-((8-chloroimidazo[1,2-a]pyridin-3-yl)ethynyl)-2-fluoro-4-methylbenzoate (2.00 g, 5.84 mmol) prepared in step 1 was dissolved in toluene (10 mL), and 1-methyl-1H-pyrazol-4-amine (0.623 g, 6.42 mmol) and $Cs_2CO_3$ (3.80 g, 11.7 mmol) were added thereto at room temperature. The mixture was gradually heated and degassed at 70° C. for 5 minutes, and then $Pd_2(dba)_3$ (0.267 g, 0.292 mmol) and Xantphos (0.338 g, 0.584 mmol) were added. The reaction mixture was gradually heated and reflux-stirred for 24 hours. Upon completion of the reaction, the mixture was filtered with celite and then concentrated under reduced pressure. The obtained residue was purified by silica gel chromatography and then washed with acetonitrile to give a target compound (1.3 g, 55%) as a yellow solid.

$^1$H NMR (400 MHz, $CDCl_3$) δ 8.13 (d, J=7.3 Hz, 1H), 7.80 (s, 1H), 7.79 (dd, J=6.7, 0.9 Hz, 1H), 7.53 (s, 1H), 7.43 (s, 1H), 7.07 (d, J=11.3 Hz, 1H), 6.81 (t, J=7.1 Hz, 1H), 6.59 (s, 1H), 6.48 (dd, J=7.5, 0.8 Hz, 1H), 3.95 (s, 3H), 3.93 (s, 3H), 2.59 (s, 3H); LC-MS (ESI) m/z: 404$[M+H]^+$

Step 3: Preparation of 2-fluoro-4-methyl-5-((8-((1-methyl-1H-pyrazol-4-yl)amino)imidazo[1,2-a]pyridin-3-yl)ethynyl)benzoic acid

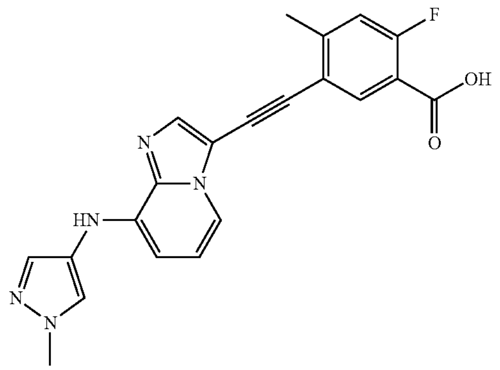 [SMILES: Cc1cc(F)c(C(=O)O)cc1C#Cc1cnc2c(Nc3cnn(C)c3)cccn12]

The methyl 2-fluoro-4-methyl-5-((8-((1-methyl-1H-pyrazol-4-yl)amino)imidazo[1,2-a]pyridin-3-yl)ethynyl)benzoate (1.30 g, 3.22 mmol) prepared in step 2 was dissolved in THF/MeOH/$H_2O$ (4/2/2 mL each), and then LiOH·$H_2O$ (0.193 g, 8.06 mmol) was added thereto at room temperature, followed by stirring for 20 minutes. Then, the reaction mixture was gradually heated and stirred with heating at 60° C. for 2 hours. Upon completion of the reaction, the mixture was cooled to room temperature, and then 1 N hydrochloric acid aqueous solution was slowly added dropwise to adjust pH 3. The resulting solid was filtered and dried under vacuum to give 2-fluoro-4-methyl-5-((8-((1-methyl-1H-pyrazol-4-yl)amino)imidazo[1,2-a]pyridin-3-yl)ethynyl) benzoate (1.2 g, 96%) as a pale yellow solid.

$^1$H NMR (400 MHz, DMSO-$d_6$,) δ 13.35 (s, 1H), 8.27 (s, 1H), 8.08 (d, J=7.5 Hz, 1H), 8.03 (s, 1H), 7.99 (d, J=6.3 Hz, 1H), 7.83 (s, 1H), 7.52 (s, 1H), 7.39 (d, J=11.7 Hz, 1H), 7.03-6.94 (m, 1H), 6.63 (d, J=7.5 Hz, 1H), 3.83 (s, 3H), 2.57 (s, 3H).; LC-MS (ESI) m/z: 390[M+H]$^+$

Step 4: Preparation of N-(3-(2-cyanopropan-2-yl)-5-(4-methyl-1H-imidazol-1-yl)phenyl)-2-fluoro-4-methyl-5-((8-((1-methyl-1H-pyrazol-4-yl)amino) imidazo[1,2-a]pyridin-3-yl)ethynyl)benzamide

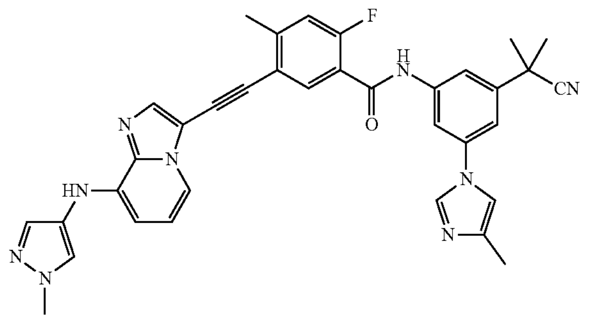 [SMILES: Cc1cn(-c2cc(NC(=O)c3cc(C#Cc4cnc5c(Nc6cnn(C)c6)cccn45)c(C)cc3F)cc(C(C)(C)C#N)c2)cn1]

The 2-fluoro-4-methyl-5-((8-((1-methyl-1H-pyrazol-4-yl)amino)imidazo[1,2-a]pyridin-3-yl)ethynyl)benzoic acid (25 mg, 0.064 mmol) prepared in step 3 was dissolved in DMF (1 mL), and EDCI (19.9 mg, 0.128 mmol), DMAP (15.7 mg, 0.128 mmol) and 2-(3-amino-5-(4-methyl-1H-imidazol-1-yl)phenyl)-2-methylpropanenitrile (16.2 mg, 0.067 mmol) were added thereto at room temperature. The reaction mixture was heated gradually and stirred at 60° C. for 16 hours. Upon completion of the reaction, the mixture was cooled to room temperature, washed with brine, and extracted with dichloromethane. The extracted organic layer was dried over anhydrous sodium sulfate, filtered, and then concentrated under reduced pressure. The obtained residue was purified by silica gel chromatography to give the compound of Example 1 (12.3 mg, 31%) as an ivory solid.

$^1$H NMR (400 MHz, DMSO-$d_6$) δ 9.00 (d, J=2.2 Hz, 1H), 8.57 (d, J=2.2 Hz, 1H), 8.27 (d, J=3.0 Hz, 1H), 8.17 (d, J=6.5 Hz, 1H), 7.76 (s, 1H), 7.54 (s, 1H), 7.47-7.43 (m, 1H), 7.28 (td, J=7.9, 2.6 Hz, 1H), 7.21 (s, 1H), 7.02 (dd, J=7.7, 3.9 Hz, 1H), 6.77 (s, 1H), 3.92 (s, 3H), 3.77 (t, J=7.1 Hz, 2H), 3.40 (t, J=7.0 Hz, 2H), 3.05 (s, 3H), 2.99 (s, 6H), 2.87 (s, 3H), 1.74 (s, 6H); LC-MS (ESI) m/z: 615[M+H]$^+$

The compounds of Examples 2 to 74 were prepared in a method similar to the method described in Example 1, and the structures and analysis results of the compounds are summarized in Table 1 below.

TABLE 1

| Example | Structure / Name | $^1$H NMR/LC-MS | Purification condition |
|---|---|---|---|
| 2 | 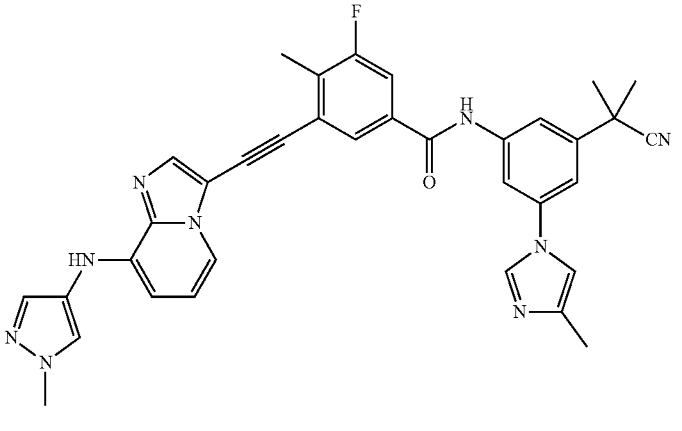 [SMILES: Cc1cn(-c2cc(NC(=O)c3cc(F)c(C)c(C#Cc4cnc5c(Nc6cnn(C)c6)cccn45)c3)cc(C(C)(C)C#N)c2)cn1] N-(3-(2-cyanopropan-2-yl)-5-(4-methyl-1H-imidazol-1-yl)phenyl)-3-fluoro-4-methyl-5-((8-((1-methyl-1H-pyrazol-4-yl) amino)imidazo [1,2-a]pyridin-3-yl)ethynyl)benzamide | $^1$H NMR (400 MHz, TFA salt, MeOD-$d_4$) δ9.40 (d, J = 1.6, 1H), 8.30 (t, J = 1.88 Hz, 1H), 8.23 (s, 1H), 8.14-8.10 (m, 2H), 8.05 (t, J = 1.68 Hz, 1H), 7.83 (s, 1H), 7.79 (dd, J = 9.92, 1.28 Hz, 1H), 7.75 (s, 1H), 7.59 (t, J = 1.8 Hz, 1H), 7.53 (s, 1H), 7.27 (dd, J = 7.82, 6.68 Hz, 1H), 7.00 (d, J = 7.64 Hz, 1H), 3.92 (s, 3H), 2.55 (s, 3H), 2.46 (s, 3H), 1.82 (s, 6H); LC-MS (ESI) m/z: 612 [M + H]$^+$ | B |

TABLE 1-continued

| Example | Structure / Name | $^1$H NMR/LC-MS | Purification condition |
|---|---|---|---|
| 3 | 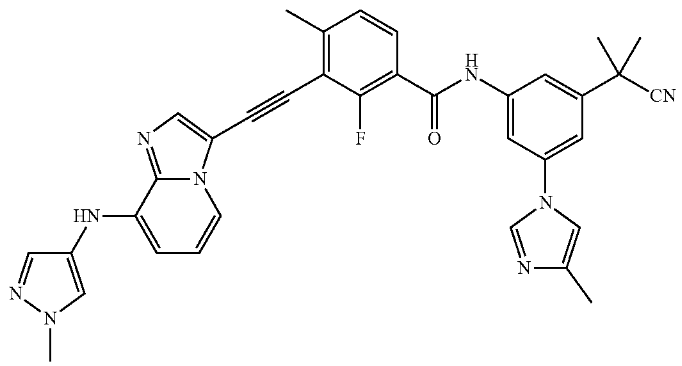 [SMILES: Cc1cn(-c2cc(NC(=O)c3ccc(C)c(C#Cc4cnc5c(Nc6cnn(C)c6)cccn45)c3F)cc(C(C)(C)C#N)c2)cn1] N-(3-(2-cyanopropan-2-yl)-5-(4-methyl-1H-imidazol-1-yl)phenyl)-2-fluoro-4-methyl-3-((8-((1-methyl-1H-pyrazol-4-yl)amino)imidazo[1,2-a]pyridin-3-yl)ethynyl)benzamide | $^1$H NMR (400 MHz, DMSO-$d_6$) δ10.80 (s, 1H), 8.26 (s, 1H), 8.13 (s, 1H), 8.05-7.97 (m, 2H), 7.90-7.80 (m, 3H), 7.66 (t, J = 7.6 Hz, 1H), 7.52 (s, 1H), 7.44 (d, J = 6.7 Hz, 1H), 7.37 (d, J = 8.1 Hz, 1H), 7.00 (t, J = 7.1 Hz, 1H), 6.61 (d, J = 7.6 Hz, 1H), 3.83 (s, 3H), 2.62 (s, 3H), 2.18 (s, 3H), 1.75 (s, 6H) .; LC-MS (ESI) m/z: 612 $[M + H]^+$ | A |
| 4 | 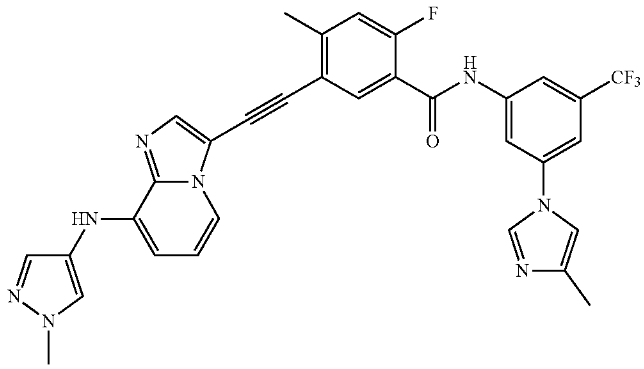 [SMILES: Cc1cn(-c2cc(NC(=O)c3cc(C#Cc4cnc5c(Nc6cnn(C)c6)cccn45)c(C)cc3F)cc(C(F)(F)F)c2)cn1] 2-fluoro-4-methyl-N-(3-(4-methyl-1H-imidazol-1-yl)-5-(trifluoromethyl)phenyl)-5-((8-((1-methyl-1H-pyrazol-4-yl)amino)imidazo [1,2-a]pyridin-3-yl)ethynyl)benzamide | $^1$H NMR (400 MHz, TFA salt, DMSO-$d_6$) δ11.12 (s, 1H), 9.54 (s, 1H), 8.45 (s, 1H), 8.23 (s, 1H), 8.16 (s, 1H), 8.07-7.93 (m, 5H), 7.82 (s, 1H), 7.52 (s, 1H), 7.49 (d, J = 11.2 Hz, 1H), 7.02-6.94 (m, 1H), 6.61 (d, J = 7.5 Hz, 1H), 3.83 (s, 3H), 2.60 (s, 3H), 2.35 (s, 3H); LC-MS (ESI) m/z: 613 $[M + H]^+$ | B |

TABLE 1-continued

| Example | Structure / Name | $^1$H NMR/LC-MS | Purification condition |
|---|---|---|---|
| 5 | 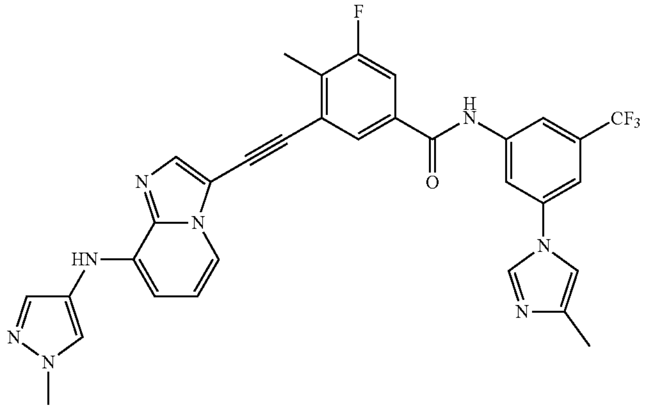 [SMILES: Cc1cn(-c2cc(NC(=O)c3cc(F)c(C)c(C#Cc4cnc5c(Nc6cnn(C)c6)cccn45)c3)cc(C(F)(F)F)c2)cn1] 3-fluoro-4-methyl-N-(3-(4-methyl-1H-imidazol-1-yl)-5-(trifluoromethyl)phenyl)-5-((8-((1-methyl-1H-pyrazol-4-yl)amino)imidazo[1,2-a]pyridin-3-yl)ethynyl)benzamide | $^1$H NMR (400 MHz, TFA salt, MeOD-$d_4$) δ9.41 (d, J = 1.32 Hz, 1H), 8.51 (s, 1H), 8.19 (s, 1H), 8.06-8.04 (m, 2H), 8.00 (d, J = 6.48 Hz, 1H), 7.84 (s, 1H), 7.81 (s, 1H), 7.76-7.73 (m, 2H), 7.51 (s, 1H), 7.12 (dd, J = 7.66, 6.8 Hz, 1H), 6.82 (d, J = 7.68 Hz, 1H), 3.90 (s, 3H), 2.52 (d, J = 1.64 Hz, 3H), 2.45 (s, 3H); LC-MS (ESI) m/z: 613 [M + H]$^+$ | B |
| 6 | 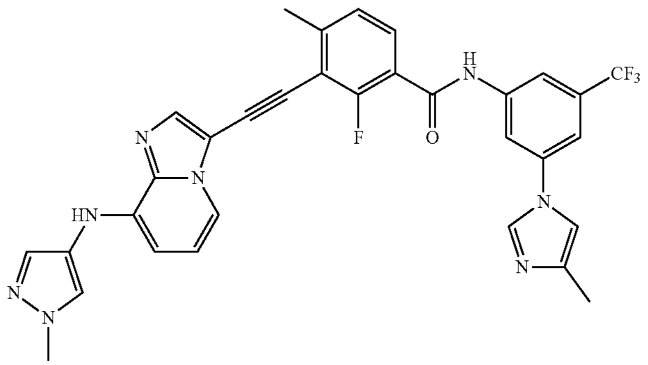 [SMILES: Cc1cn(-c2cc(NC(=O)c3ccc(C)c(C#Cc4cnc5c(Nc6cnn(C)c6)cccn45)c3F)cc(C(F)(F)F)c2)cn1] 2-fluoro-4-methyl-N-(3-(4-methyl-1H-imidazol-1-yl)-5-(trifluoromethyl)phenyl)-3-((8-((1-methyl-1H-pyrazol-4-yl)amino)imidazo[1,2-a]pyridin-3-yl)ethynyl)benzamide | $^1$H NMR (400 MHz, TFA salt, DMSO-$d_6$) δ11.11 (s, 1H), 9.51 (s, 1H), 8.45 (s, 1H), 8.28 (s, 1H), 8.16 (s, 1H), 8.05-8.00 (m, 2H), 7.95 (s, 1H), 7.86 (d, J = 6.1 Hz, 1H), 7.83 (s, 1H), 7.72-7.66 (m, 1H), 7.52 (s, 1H), 7.41 (d, J = 8.1 Hz, 1H), 7.04-6.99 (m, 1H), 6.62 (d, J = 7.6 Hz, 1H), 3.83 (s, 2H), 2.63 (s, 2H), 2.34 (s, 2H); LC-MS (ESI) m/z: 613 [M + H]$^+$ | B |

TABLE 1-continued

| Example | Structure / Name | $^1$H NMR/LC-MS | Purification condition |
| --- | --- | --- | --- |
| 7 | 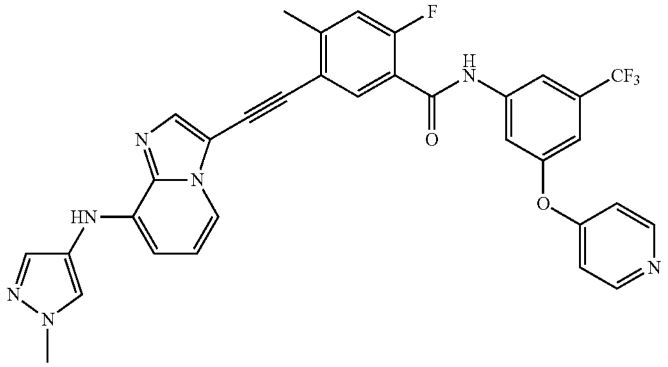 [SMILES: Cc1cc(F)c(C(=O)Nc2cc(Oc3ccncc3)cc(C(F)(F)F)c2)cc1C#Cc1cnc2c(Nc3cnn(C)c3)cccn12] 2-fluoro-4-methyl-5-((8-((1-methyl-1H-pyrazol-4-yl)amino)imidazo[1,2-a]pyridin-3-yl)ethynyl)-N-(3-(pyridin-4-yloxy)-5-(trifluoromethyl)phenyl)benzamide | $^1$H NMR (400 MHz, TFA salt, DMSO-$d_6$) δ11.10 (s, 1H), 8.52 (d, J = 7.5 Hz, 2H), 8.30 (s, 1H), 8.23 (s, 2H), 8.07-8.01 (m, 2H), 7.99 (d, J = 6.5 Hz, 1H), 7.90 (s, 1H), 7.83 (s, 1H), 7.52 (s, 1H), 7.49 (d, J = 11.2 Hz, 1H), 6.99 (t, J = 7.1 Hz, 1H), 6.85 (d, J = 7.4 Hz, 2H), 6.63 (d, J = 7.5 Hz, 1H), 3.83 (s, 3H), 2.60 (s, 3H); LC-MS (ESI) m/z: 626 $[M + H]^+$ | B |
| 8 | 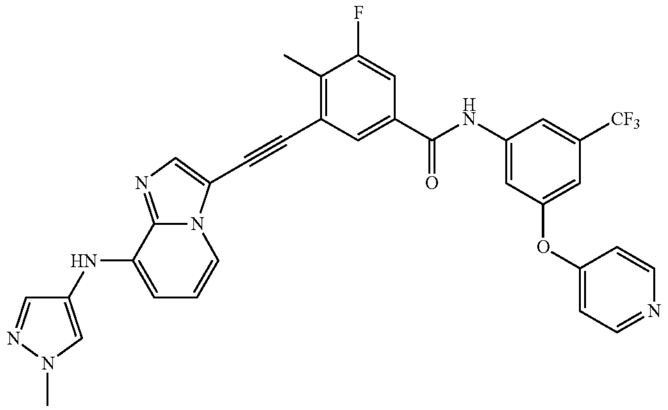 [SMILES: Cc1c(F)cc(C(=O)Nc2cc(Oc3ccncc3)cc(C(F)(F)F)c2)cc1C#Cc1cnc2c(Nc3cnn(C)c3)cccn12] 3-fluoro-4-methyl-5-((8-((1-methyl-1H-pyrazol-4-yl)amino)imidazo[1,2-a]pyridin-3-yl)ethynyl)-N-(3-(pyridin-4-yloxy)-5-(trifluoromethyl)phenyl)benzamide | $^1$H NMR (400 MHz, TFA salt, MeOD-$d_4$) δ8.53 (d, J = 7.48 Hz, 2H), 8.43 (s, 1H), 8.25 (s, 1H), 8.20 (br s, 1H), 8.14-8.12 (m, 2H), 7.81-7.76 (m, 3H), 7.54 (s, 1H), 7.24 (t, J = 7.72 Hz, 1H), 7.04 (d, J = 7.52 Hz, 2H), 6.97 (d, J = 7.8 Hz, 1H), 3.92 (s, 3H), 2.57 (d, J = 1.64 Hz, 3H); LC-MS (ESI) m/z: 626 $[M + H]^+$ | B |

TABLE 1-continued

| Example | Structure / Name | $^1$H NMR/LC-MS | Purification condition |
|---|---|---|---|
| 9 | 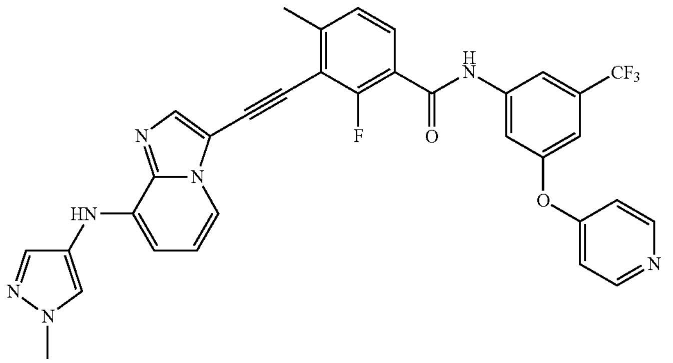 [SMILES: Cc1ccc(C(=O)Nc2cc(Oc3ccncc3)cc(C(F)(F)F)c2)c(F)c1C#Cc1cnc2c(Nc3cnn(C)c3)cccn12] 2-fluoro-4-methyl-3-((8-((1-methyl-1H-pyrazol-4-yl)amino)imidazo[1,2-a]pyridin-3-yl)ethynyl)-N-(3-(pyridin-4-yloxy)-5-(trifluoromethyl)phenyl)benzamide | $^1$H NMR (400 MHz, TFA salt, DMSO-$d_6$) δ11.11 (s, 1H), 8.56-8.47 (m, 2H), 8.34-8.25 (m, 2H), 8.22 (s, 1H), 8.06 (s, 1H), 7.89 (br s, 1H), 7.87 (d, J = 6.5 Hz, 1H), 7.83 (s, 1H), 7.69 (t, J = 7.6 Hz, 1H), 7.52 (s, 1H), 7.41 (d, J = 8.1 Hz, 1H), 7.07-6.99 (m, 1H), 6.88-6.79 (m, 2H), 6.64 (d, J = 7.6 Hz, 1H), 3.83 (s, 3H), 2.62 (s, 3H); LC-MS (ESI) m/z: 626 [M + H]$^+$ | B |
| 10 | 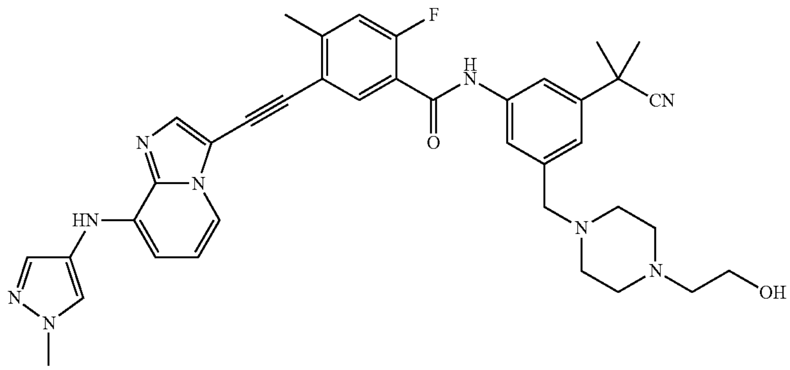 [SMILES: Cc1cc(F)c(C(=O)Nc2cc(CN3CCN(CCO)CC3)cc(C(C)(C)C#N)c2)cc1C#Cc1cnc2c(Nc3cnn(C)c3)cccn12] N-(3-(2-cyanopropan-2-yl)-5-((4-(2-hydroxyethyl)piperazin-1-yl)methyl)phenyl)-2-fluoro-4-methyl-5-((8-((1-methyl-1H-pyrazol-4-yl)amino)imidazo[1,2-a]pyridin-3-yl)ethynyl)benzamide | $^1$H NMR (400 MHz, TFA salt, MeOD-$d_4$) δ8.24 (s, 1H), 8.17 (d, J = 6.6 Hz, 1H), 8.03 (d, J = 7.1 Hz, 1H), 7.86 (s, 1H), 7.77 (s, 1H), 7.55 (s, 1H), 7.38 (s,1H), 7.34-7.25 (m, 2H), 7.03 (d, J = 8.1 Hz, 1H), 3.93 (s, 3H), 3.90-3.85 (m, 2H), 3.83 (s, 2H), 3.48-3.32 (m, 4H), 3.28-3.23 (m, 2H), 3.02-2.82 (m, 4H), 2.66 (s, 3H), 1.76 (s, 6H); LC-MS (ESI) m/z: 674 [M + H]$^+$ | B |

TABLE 1-continued

| Example | Structure / Name | $^1$H NMR/LC-MS | Purification condition |
| --- | --- | --- | --- |
| 11 | 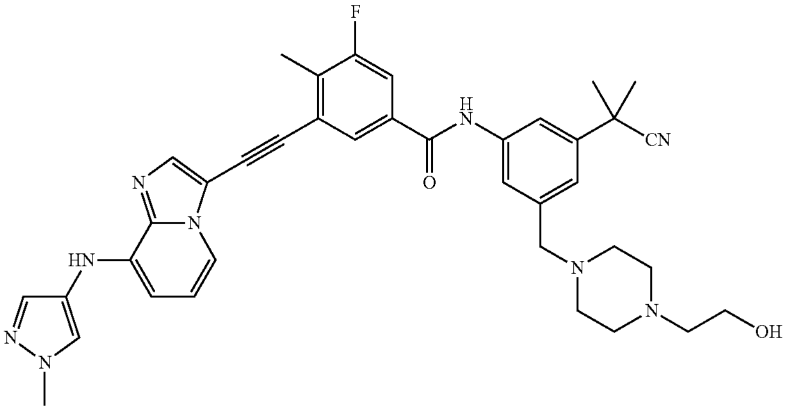 [SMILES: Cc1c(F)cc(C(=O)Nc2cc(CN3CCN(CCO)CC3)cc(C(C)(C)C#N)c2)cc1C#Cc1cnc2c(Nc3cnn(C)c3)cccn12] N-(3-(2-cyanopropan-2-yl)-5-((4-(2-hydroxyethyl)piperazin-1-yl)methyl)phenyl)-3-fluoro-4-methyl-5-((8-((1-methyl-1H-pyrazol-4-yl)amino)imidazo[1,2-a]pyridin-3-yl)ethynyl)benzamide | $^1$H NMR (400 MHz, TFA salt, MeOD-$d_4$) δ8.18 (s, 1H), 8.11 (d, J = 6.52 Hz, 1H), 8.07 (d, J = 1.16 Hz, 1H), 7.87 (s, 1H), 7.83 (s, 1H), 7.76-7.74 (m, 2H), 7.53 (s, 1H), 7.37 (s, 1H), 7.23 (dd, J = 7.78, 6.72 Hz, 1H), 6.95 (d, J = 7.84 Hz, 1H), 3.92 (s, 3H), 3.87 (t, J = 5.32 Hz, 4H), 3.43 (br s, 4H), 3.26 (t, J = 5.24 Hz, 2H), 2.98 (br s, 4H), 2.55 (d, J = 1.6 Hz, 3H), 1.75 (s, 6H); LC-MS (ESI) m/z: 674 [M + H]$^+$ | B |
| 12 | 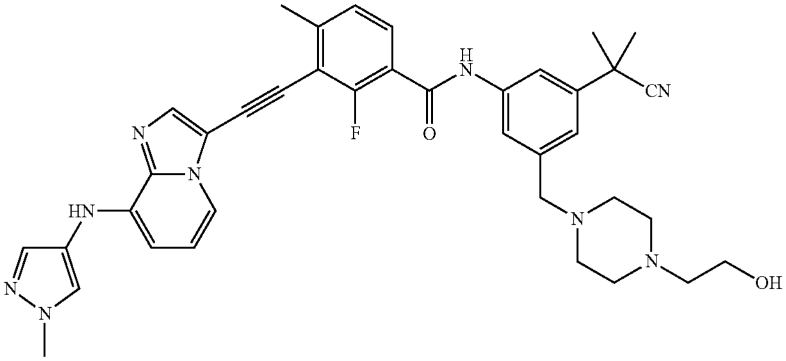 [SMILES: Cc1ccc(C(=O)Nc2cc(CN3CCN(CCO)CC3)cc(C(C)(C)C#N)c2)c(F)c1C#Cc1cnc2c(Nc3cnn(C)c3)cccn12] N-(3-(2-cyanopropan-2-yl)-5-((4-(2-hydroxyethyl)piperazin-1-yl)methyl)phenyl)-2-fluoro-4-methyl-3-((8-((1-methyl-1H-pyrazol-4-yl)amino)imidazo[1,2-a]pyridin-3-yl)ethynyl)benzamide | $^1$H NMR (400 MHz, TFA salt, MeOD-$d_4$) δ8.21 (s, 1H), 8.10 (d, J = 6.4 Hz, 1H), 7.89 (s, 1H), 7.77 (s, 1H), 7.76-7.67 (m, 2H), 7.55 (s, 1H), 7.38 (s, 1H), 7.34 (d, J = 8.0 Hz, 1H), 7.28-7.18 (m, 1H), 6.97 (d, J = 7.3 Hz, 1H), 3.93 (s, 3H), 3.89-3.80 (m, 2H), 3.81 (s, 2H), 3.49-3.33 (m, 4H), 3.27-3.23 (m, 2H), 3.03-2.80 (m, 4H), 2.66 (s, 3H), 1.76 (s, 6H); LC-MS (ESI) m/z: 674 [M + H]$^+$ | B |

TABLE 1-continued

| Example | Structure / Name | $^1$H NMR/LC-MS | Purification condition |
|---|---|---|---|
| 13 | 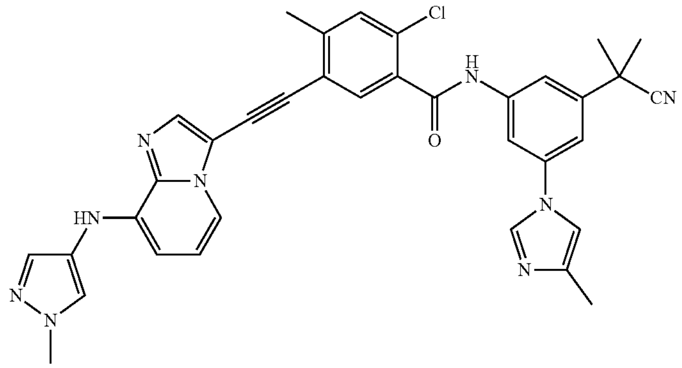 [SMILES: Cc1cn(-c2cc(NC(=O)c3cc(C#Cc4cnc5c(Nc6cnn(C)c6)cccn45)c(C)cc3Cl)cc(C(C)(C)C#N)c2)cn1] 2-chloro-N-(3-(2-cyanopropan-2-yl)-5-(4-methyl-1H-imidazol-1-yl)phenyl)-4-methyl-5-((8-((1-methyl-1H-pyrazol-4-yl)amino)imidazo[1,2-a]pyridin-3-yl)ethynyl)benzamide | LC-MS (ESI) m/z: 628 $[M + H]^+$ | A |
| 14 | 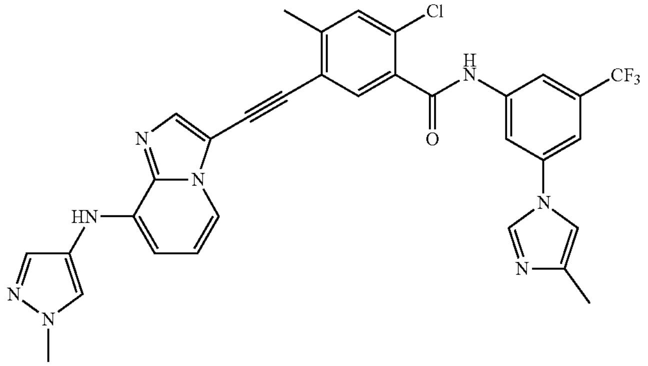 2-chloro-4-methyl-N-(3-(4-methyl-1H-imidazol-1-yl)-5-(trifluoromethyl)phenyl)-5-((8-((1-methyl-1H-pyrazol-4-yl)amino)imidazo[1,2-a]pyridin-3-yl)ethynyl)benzamide | LC-MS (ESI) m/z: 629 $[M + H]^+$ | A |
| 15 | 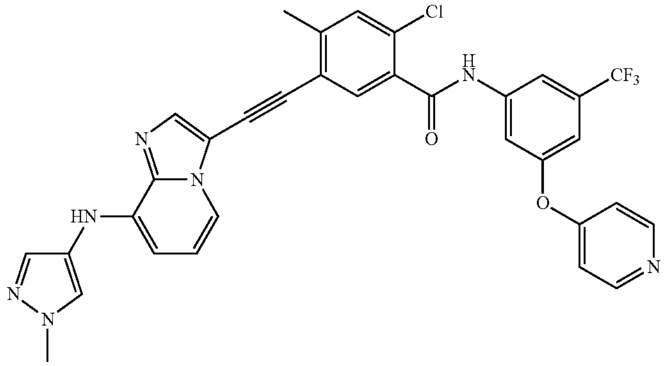 [SMILES: Cc1cc(Cl)c(C(=O)Nc2cc(Oc3ccncc3)cc(C(F)(F)F)c2)cc1C#Cc1cnc2c(Nc3cnn(C)c3)cccn12] 2-chloro-4-methyl-5-((8-((1-methyl-1H-pyrazol-4-yl)amino)imidazo[1,2-a]pyridin-3-yl)ethynyl)-N-(3-(pyridin-4-yloxy)-5-(trifluoromethyl)phenyl)benzamide | LC-MS (ESI) m/z: 642 $[M + H]^+$ | B |

TABLE 1-continued

| Example | Structure / Name | $^1H$ NMR/LC-MS | Purification condition |
|---|---|---|---|
| 16 | 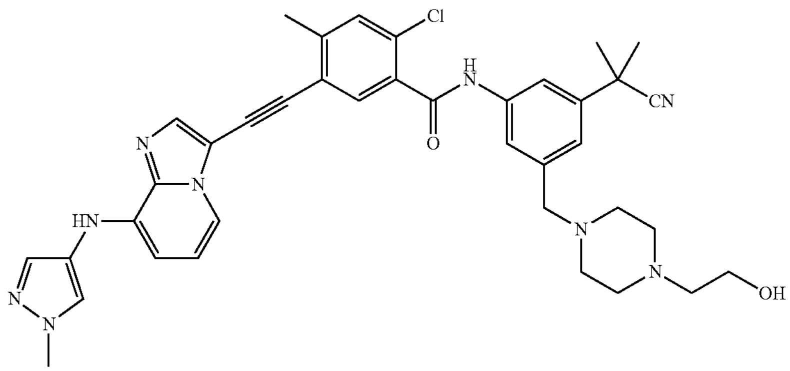 [SMILES: Cc1cc(Cl)c(C(=O)Nc2cc(CN3CCN(CCO)CC3)cc(C(C)(C)C#N)c2)cc1C#Cc1cnc2c(Nc3cnn(C)c3)cccn12] 2-chloro-N-(3-(2-cyanopropan-2-yl)-5-((4-(2-hydroxyethyl)piperazin-1-yl)methyl)phenyl)-4-methyl-5-((8-((1-methyl-1H-pyrazol-4-yl)amino)imidazo[1,2-a]pyridin-3-yl)ethynyl)benzamide | LC-MS (ESI) m/z: 690 $[M + H]^+$ | B |
| 17 | 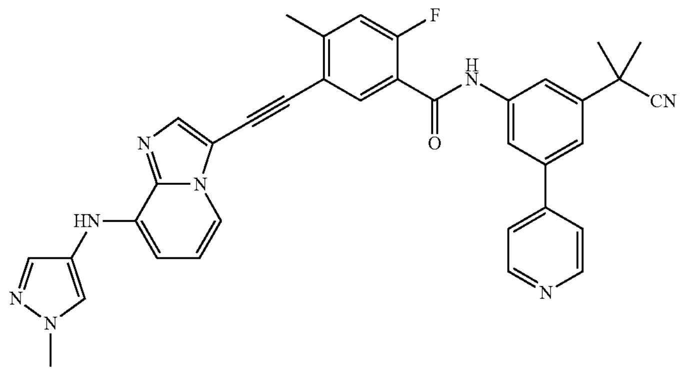 [SMILES: Cc1cc(F)c(C(=O)Nc2cc(-c3ccncc3)cc(C(C)(C)C#N)c2)cc1C#Cc1cnc2c(Nc3cnn(C)c3)cccn12] N-(3-(2-cyanopropan-2-yl)-5-(pyridin-4-yl)phenyl)-2-fluoro-4-methyl-5-((8-((1-methyl-1H-pyrazol-4-yl)amino)imidazo[1,2-a]pyridin-3-yl)ethynyl)benzamide | $^1H$ NMR (400 MHz, TFA salt, DMSO-$d_6$) δ10.83 (s, 1H), 8.89 (d, J = 5.4 Hz, 2H), 8.34 (s, 1H), 8.22 (br s, 1H), 8.12 (d, J = 5.0 Hz, 2H), 8.08 (s, 1H), 8.05-7.96 (m, 3H), 7.82 (s, 1H), 7.76 (s, 1H), 7.52 (s, 1H), 7.47 (d, J = 11.1 Hz, 1H), 6.99 (t, J = 7.1 Hz, 1H), 6.63 (d, J = 7.6 Hz, 1H), 3.84 (s, 3H), 2.60 (s, 3H), 1.79 (s, 6H); LC-MS (ESI) m/z: 609 $[M + H]^+$ | B |

TABLE 1-continued

| Example | Structure / Name | $^1$H NMR/LC-MS | Purification condition |
| --- | --- | --- | --- |
| 18 | 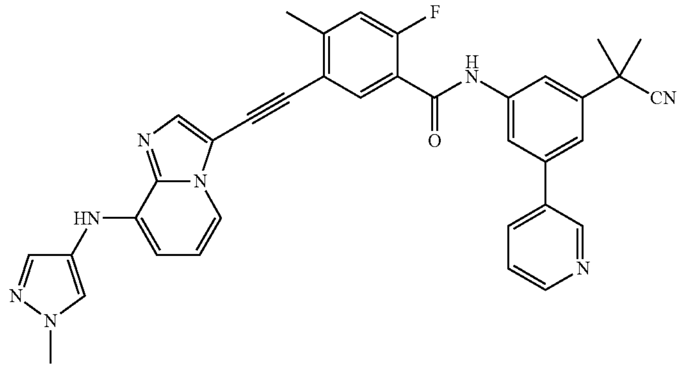 [SMILES: Cc1cc(F)c(C(=O)Nc2cc(-c3cccnc3)cc(C(C)(C)C#N)c2)cc1C#Cc1cnc2c(Nc3cnn(C)c3)cccn12] N-(3-(2-cyanopropan-2-yl)-5-(pyridin-3-yl)phenyl)-2-fluoro-4-methyl-5-((8-((1-methyl-1H-pyrazol-4-yl)amino)imidazo[1,2-a]pyridin-3-yl)ethynyl)benzamide | $^1$H NMR (400 MHz, TFA salt, DMSO-$d_6$) δ10.78 (s, 1H), 9.07 (s, 1H), 8.77 (d, J = 5.0 Hz, 1H), 8.43 (d, J = 7.9 Hz, 1H), 8.30-8.15 (m, 2H), 8.10-7.99 (m, 4H), 7.88-7.76 (m, 2H), 7.64 (s, 1H), 7.52 (s, 1H), 7.46 (d, J = 11.1 Hz, 1H), 7.01 (t, J = 7.2 Hz, 1H), 6.66 (d, J = 7.6 Hz, 1H), 3.84 (s, 3H), 2.60 (s, 3H), 1.78 (s, 6H); LC-MS (ESI) m/z: 609 $[M + H]^+$ | B |
| 19 | 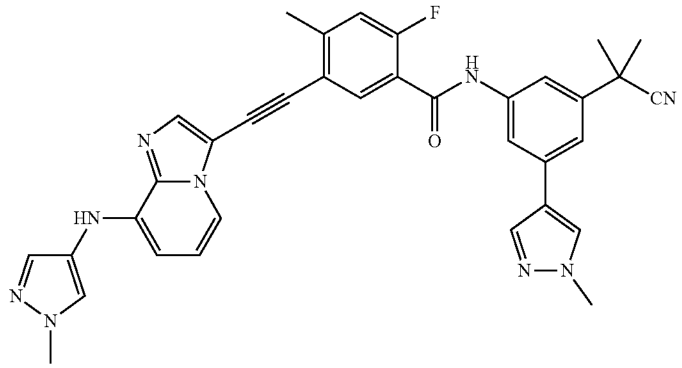 [SMILES: Cc1cc(F)c(C(=O)Nc2cc(-c3cnn(C)c3)cc(C(C)(C)C#N)c2)cc1C#Cc1cnc2c(Nc3cnn(C)c3)cccn12] N-(3-(2-cyanopropan-2-yl)-5-(1-methyl-1H-pyrazol-4-yl)phenyl)-2-fluoro-4-methyl-5-((8-((1-methyl-1H-pyrazol-4-yl)amino)imidazo[1,2-a]pyridin-3-yl)ethynyl)benzamide | $^1$H NMR (400 MHz, TFA salt, $CDCl_3$) δ8.50 (d, J = 15.6 Hz, 1H), 8.43 (d, J = 7.9 Hz, 1H), 7.98 (s, 1H), 7.98-7.93 (m, 1H), 7.86-7.80 (m, 2H), 7.73 (s, 1H), 7.63-7.61 (m, 1H), 7.52 (s, 1H), 7.39 (t, J = 1.6 Hz, 1H), 7.25-7.17 (m, 2H), 7.09 (d, J = 7.4 Hz, 1H), 3.99 (s, 3H), 3.95 (s, 3H), 2.64 (s, 3H), 1.79 (s, 6H); LC-MS (ESI) m/z: 612 $[M + H]^+$ | B |

TABLE 1-continued

| Example | Structure / Name | $^1$H NMR/LC-MS | Purification condition |
|---|---|---|---|
| 20 | 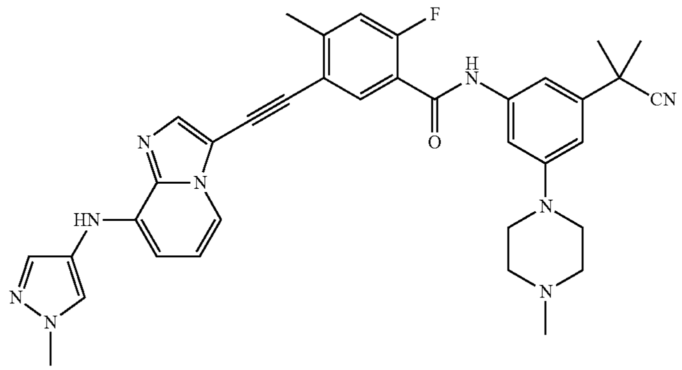 [SMILES: Cc1cc(F)c(C(=O)Nc2cc(N3CCN(C)CC3)cc(C(C)(C)C#N)c2)cc1C#Cc1cnc2c(Nc3cnn(C)c3)cccn12] N-(3-(2-cyanopropan-2-yl)-5-(4-methylpiperazin-1-yl)phenyl)-2-fluoro-4-methyl-5-((8-((1-methyl-1H-pyrazol-4-yl)amino)imidazo[1,2-a]pyridin-3-yl)ethynyl)benzamide | $^1$H NMR (400 MHz, TFA salt, MeOD-$d_4$) δ 8.10-8.08 (m, 2H), 8.00 (d, J = 7.16 Hz, 1H), 7.848-7.843 (m, 1H), 7.76 (s, 1H), 7.73 (dd, J = 8.4, 2.0 Hz, 1H), 7.63 (d, J = 8.44 Hz, 1H), 7.54 (s, 1H), 7.30 (d, J = 11.28 Hz, 1H), 7.15 (dd, J = 7.74, 6.68 Hz, 1H), 6.89 (d, J = 7.32 Hz, 1H), 4.00 (s, 2H), 3.92 (s, 3H), 3.51-3.43 (m, 4H), 3.21-3.08 (m, 4H), 2.91 (s, 3H), 2.65 (s, 3H), 1.85 (s, 6H); LC-MS (ESI) m/z: 630 $[M + H]^+$ | B |
| 21 | 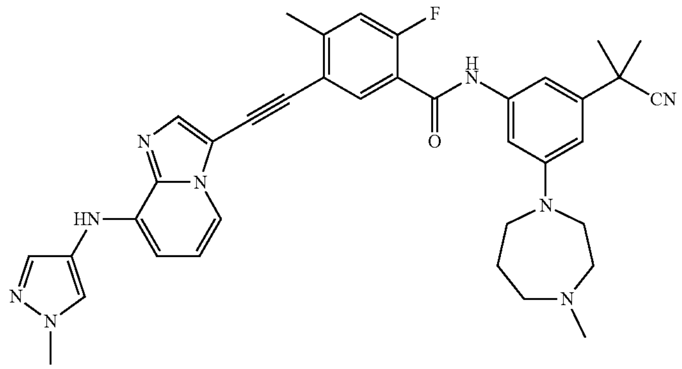 [SMILES: Cc1cc(F)c(C(=O)Nc2cc(N3CCCN(C)CC3)cc(C(C)(C)C#N)c2)cc1C#Cc1cnc2c(Nc3cnn(C)c3)cccn12] N-(3-(2-cyanopropan-2-yl)-5-(4-methyl-1,4-diazepan-1-yl)phenyl)-2-fluoro-4-methyl-5-((8-((1-methyl-1H-pyrazol-4-yl)amino)imidazo[1,2-a]pyridin-3-yl)ethynyl)benzamide | $^1$H NMR (400 MHz, TFA salt, DMSO-$d_6$) δ10.40 (s, 1H), 9.56 (br s, 1H), 8.20 (s, 1H), 7.96 (dd, J = 19.7, 7.7 Hz, 3H), 7.82 (s, 1H), 7.51 (d, J = 0.6 Hz, 1H), 7.42 (d, J = 11.1 Hz, 1H), 7.26 (s, 2H), 7.00-6.93 (m, 1H), 6.61 (d, J = 7.6 Hz, 1H), 6.58 (s, 1H), 3.88-3.70 (m, 5H), 3.70-3.63 (m, 2H), 3.44-3.39 (m, 2H), 3.30-3.14 (m, 2H), 2.87 (d, J = 4.7 Hz, 3H), 2.59 (s, 3H), 2.27-2.09 (m, 2H), 1.69 (s, 6H); LC-MS (ESI) m/z: 644 $[M + H]^+$ | B |

TABLE 1-continued

| Example | Structure / Name | $^1$H NMR/LC-MS | Purification condition |
|---|---|---|---|
| 22 | 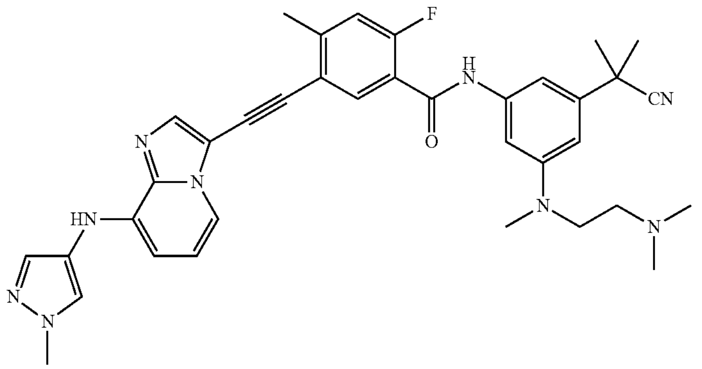 [SMILES: Cc1cc(F)c(C(=O)Nc2cc(N(C)CCN(C)C)cc(C(C)(C)C#N)c2)cc1C#Cc1cnc2c(Nc3cnn(C)c3)cccn12] N-(3-(2-cyanopropan-2-yl)-5-((2-(dimethylamino)ethyl)(methyl)amino)phenyl)-2-fluoro-4-methyl-5-((8-((1-methyl-1H-pyrazol-4-yl)amino)imidazo[1,2-a]pyridin-3-yl)ethynyl)benzamide | $^1$H NMR (400 MHz, TFA salt, $CDCl_3$) δ9.13 (br s, 1H), 8.60 (d, J = 12.8 Hz, 1H), 8.31 (d, J = 7.8 Hz, 1H), 8.02-7.91 (m, 2H), 7.61 (s, 1H), 7.52 (s, 1H), 7.27-7.14 (m, 4H), 7.08 (d, J = 7.7 Hz, 1H), 6.67 (s, 1H), 3.95 (s, 3H), 3.89-3.79 (m, 2H), 3.31-3.19 (m, 2H), 3.06 (s, 3H), 2.93 (s, 6H), 2.62 (s, 3H), 1.75 (s, 6H); LC-MS (ESI) m/z: 632 $[M + H]^+$ | B |
| 23 | 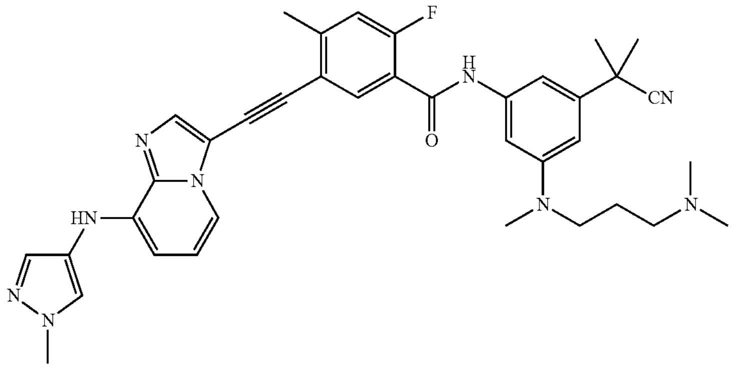 [SMILES: Cc1cc(F)c(C(=O)Nc2cc(N(C)CCCN(C)C)cc(C(C)(C)C#N)c2)cc1C#Cc1cnc2c(Nc3cnn(C)c3)cccn12] N-(3-(2-cyanopropan-2-yl)-5-((3-(dimethylamino)propyl)(methyl)amino)phenyl)-2-fluoro-4-methyl-5-((8-((1-methyl-1H-pyrazol-4-yl)amino)imidazo[1,2-a]pyridin-3-yl)ethynyl)benzamide | $^1$H NMR (400 MHz, TFA salt, DMSO-$d_6$) δ10.38 (s, 1H), 9.38 (br s, 1H), 8.20 (s, 1H), 8.00 (s, 1H), 7.99-7.89 (m, 2H), 7.82 (s, 1H), 7.51 (d, J = 0.6 Hz, 1H), 7.42 (d, J = 11.1 Hz, 1H), 7.26 (s, 1H), 7.18 (s, 1H), 7.03-6.94 (m, 1H), 6.62 (d, J = 7.0 Hz, 1H), 6.54 (s, 1H), 3.84 (s, 3H), 3.45-3.36 (m, 4H), 3.13-3.06 (m, 2H), 2.93 (s, 3H), 2.78 (d, J = 4.9 Hz, 6H), 2.59 (s, 3H), 1.96-1.82 (m, 2H), 1.68 (s, 6H); LC-MS (ESI) m/z: 646 $[M + H]^+$ | B |

TABLE 1-continued

| Example | Structure / Name | $^1$H NMR/LC-MS | Purification condition |
|---|---|---|---|
| 24 | 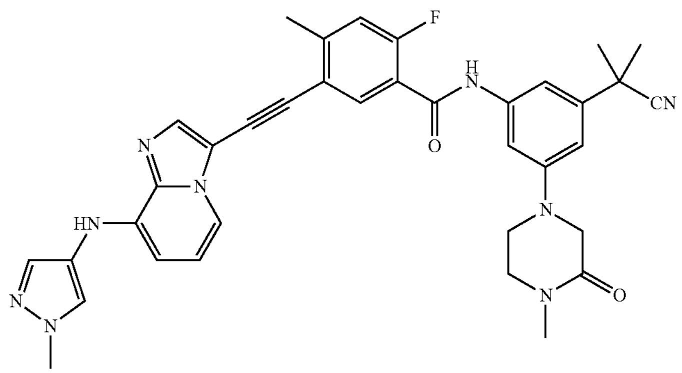 [SMILES: Cc1cc(F)c(C(=O)Nc2cc(N3CCN(C)C(=O)C3)cc(C(C)(C)C#N)c2)cc1C#Cc1cnc2c(Nc3cnn(C)c3)cccn12] N-(3-(2-cyanopropan-2-yl)-5-(4-methyl-3-oxopiperazin-1-yl)phenyl)-2-fluoro-4-methyl-5-((8-((1-methyl-1H-pyrazol-4-yl)amino)imidazo[1,2-a]pyridin-3-yl)ethynyl)benzamide | $^1$H NMR (400 MHz, $CDCl_3$) δ8.43 (d, J = 15.9 Hz, 1H), 8.33 (d, J = 8.1 Hz, 1H), 7.86-7.77 (m, 2H), 7.54 (s, 1H), 7.44 (s, 1H), 7.38 (s, 1H), 7.14 (t, J = 6.4 Hz, 1H), 6.85-6.79 (m, 1H), 6.78 (s, 1H), 6.58 (s, 1H), 6.49 (d, J = 6.8 Hz, 1H), 3.94 (d, J = 5.1 Hz, 4H), 3.73 (d, J = 6.8 Hz, 1H), 3.64-3.56 (m, 2H), 3.56-3.46 (m, 2H), 3.17 (d, J = 6.8 Hz, 1H), 3.06 (s, 2H), 2.62 (s, 2H), 1.75 (s, 4H), 1.52-1.38 (m, 4H); LC-MS (ESI) m/z: 644 $[M + H]^+$ | A |
| 25 | 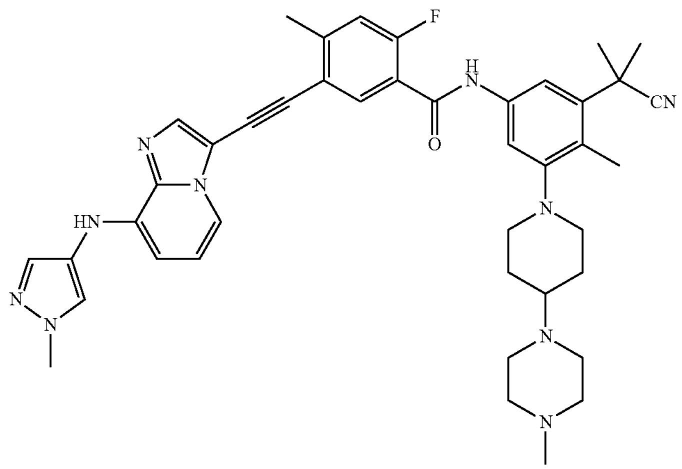 N-(3-(2-cyanopropan-2-yl)-5-(4-(4-methylpiperazin-1-yl)piperidin-1-yl)phenyl)-2-fluoro-4-methyl-5-((8-((1-methyl-1H-pyrazol-4-yl)amino)imidazo [1,2-a]pyridin-3-yl)ethynyl)benzamide | $^1$H NMR (400 MHz, TFA salt, MeOD-$d_4$) δ 8.15 (s, 1H), 8.13 (d, J = 6.52 Hz, 1H), 8.00 (d, J = 7.16 Hz, 1H), 7.76 (s, 1H), 7.54 (d, J = 0.64 Hz, 2H), 7.32-7.29 (m, 2H), 7.22 (t, J = 6.72 Hz, 1H), 6.97-6.93 (m, 2H), 3.98 (s, 3H), 3.86 (d, J = 12.04 Hz, 2H), 3.23-3.19 (m, 4H), 3.06-3.01 (m, 2H), 2.94-2.88 (m, 4H), 2.81 (s, 3H), 2.65 (s, 3H), 2.08 (d, J = 11 Hz, 2H), 1.78-1.77 (m, 3H), 1.73 (s, 6H); LC-MS (ESI) m/z: 713 $[M + H]^+$ | B |

TABLE 1-continued

| Example | Structure / Name | $^1$H NMR/LC-MS | Purification condition |
|---|---|---|---|
| 26 | 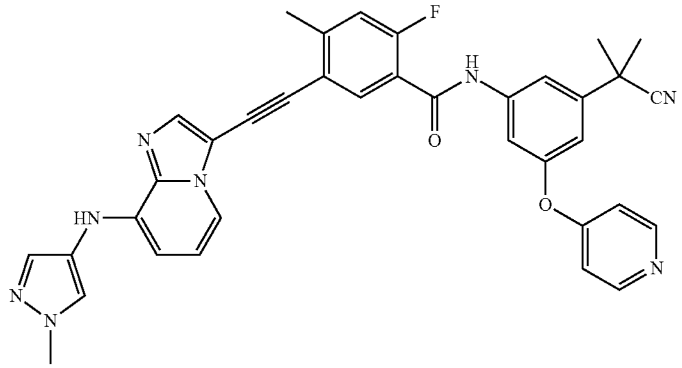 [SMILES: Cc1cc(F)c(C(=O)Nc2cc(Oc3ccncc3)cc(C(C)(C)C#N)c2)cc1C#Cc1cnc2c(Nc3cnn(C)c3)cccn12] N-(3-(2-cyanopropan-2-yl)-5-(pyridin-4-yloxy)phenyl)-2-fluoro-4-methyl-5-((8-((1-methyl-1H-pyrazol-4-yl)amino)imidazo[1,2-a]pyridin-3-yl)ethynyl)benzamide | $^1$H NMR (400 MHz, TFA salt, $CDCl_3$) δ9.04 (br s, 1H), 8.96 (d, J = 13.7 Hz, 1H), 8.34 (d, J = 7.8 Hz, 1H), 8.14 (s, 1H), 8.05-7.90 (m, 4H), 7.82 (s, 1H), 7.58 (s, 1H), 7.51 (s, 1H), 7.30 (s, 1H), 7.24-7.16 (m, 2H), 7.07 (t, J = 7.5 Hz, 3H), 3.94 (s, 3H), 2.63 (s, 3H), 1.82 (s, 6H); LC-MS (ESI) m/z: 625 [M + H]$^+$ | B |
| 27 | 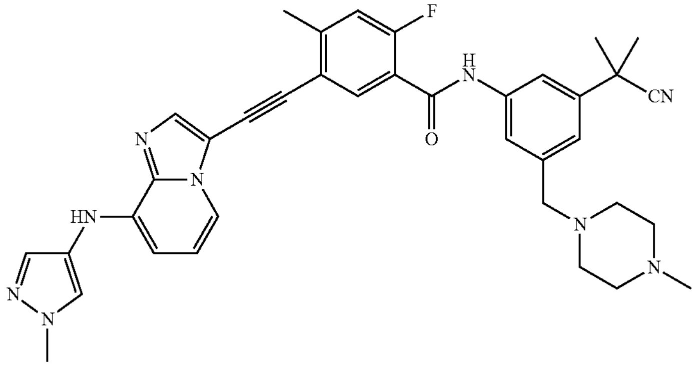 [SMILES: Cc1cc(F)c(C(=O)Nc2cc(CN3CCN(C)CC3)cc(C(C)(C)C#N)c2)cc1C#Cc1cnc2c(Nc3cnn(C)c3)cccn12] N-(3-(2-cyanopropan-2-yl)-5-((4-methylpiperazin-1-yl)methyl)phenyl)-2-fluoro-4-methyl-5-((8-((1-methyl-1H-pyrazol-4-yl) amino)imidazo[1,2-a]pyridin-3-yl)ethynyl)benzamide | $^1$H NMR (400 MHz, TFA salt, MeOD-$d_4$) δ 8.00-7.94 (m, 3H), 7.84 (s, 1H), 7.74 (s, 1H), 7.71 (s, 1H), 7.54 (s, 1H), 7.35 (s, 1H), 7.29 (d, J = 11.24 Hz, 1H), 7.05 (t, J = 6.72 Hz, 1H), 6.73 (d, J = 7.88 Hz, 1H), 3.92 (s, 3H), 3.71 (s, 2H), 3.30-3.12 (m, 8H), 2.89 (s, 3H), 2.64 (s, 3H), 1.75 (s, 6H); LC-MS (ESI) m/z: 644 [M + H]$^+$ | B |
| 28 | 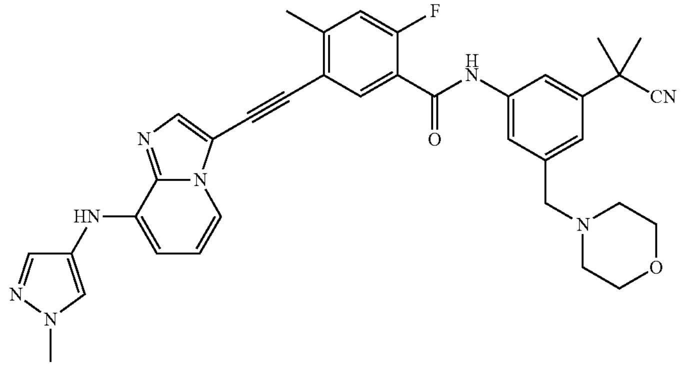 [SMILES: Cc1cc(F)c(C(=O)Nc2cc(CN3CCOCC3)cc(C(C)(C)C#N)c2)cc1C#Cc1cnc2c(Nc3cnn(C)c3)cccn12] N-(3-(2-cyanopropan-2-yl)-5-(morpholinomethyl)phenyl)-2-fluoro-4-methyl-5-((8-((1-methyl-1H-pyrazol-4-yl) amino)imidazo[1,2-a]pyridin-3-yl)ethynyl)benzamide | $^1$H NMR (400 MHz, TFA salt, DMSO-$d_6$) δ10.75 (s, 1H), 10.04 (br s, 1H), 8.20 (s, 1H), 8.10 (s, 1H), 8.01-7.95 (m, 2H), 7.86-7.79 (m, 2H), 7.51 (s, 1H), 7.48-7.36 (m, 2H), 7.03-6.92 (m, 1H), 6.62 (d, J = 7.6 Hz, 1H), 4.41 (s, 2H), 4.08-3.90 (m, 2H), 3.83 (s, 3H), 3.70-3.62 (m, 2H), 3.34-3.25 (m, 2H), 3.22-3.10 (m, 2H), 2.59 (s, 3H), 1.72 (s, 6H); LC-MS (ESI) m/z: 631 [M + H]$^+$ | B |

TABLE 1-continued

| Example | Structure / Name | $^1$H NMR/LC-MS | Purification condition |
|---|---|---|---|
| 29 | 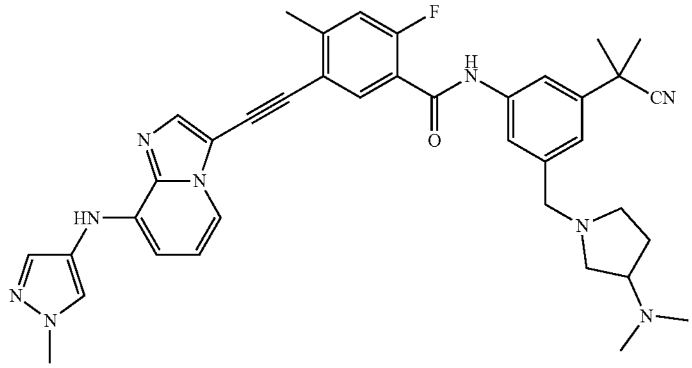 [SMILES: Cc1cc(F)c(C(=O)Nc2cc(CN3CCC(N(C)C)C3)cc(C(C)(C)C#N)c2)cc1C#Cc1cnc2c(Nc3cnn(C)c3)cccn12] N-(3-(2-cyanopropan-2-yl)-5-((3-(dimethylamino)pyrrolidin-1-yl)methyl)phenyl)-2-fluoro-4-methyl-5-((8-((1-methyl-1H-pyrazol-4-yl)amino)imidazo[1,2-a]pyridin-3-yl)ethynyl)benzamide | 1H NMR (400 MHz, TFA salt, MeOD-$d_4$) δ 8.32 (br-s, 1H), 8.20 (d, J = 5.96 Hz, 1H), 8.04-8.02 (m, 2H), 7.86-7.85 (m, 2H), 7.59 (br-s, 1H), 7.50 (t, J = 1.52 Hz, 1H), 7.32 (d, J = 11.24 Hz, 1H), 7.27 (dd, J = 7.78, 6.72 Hz, 1H), 7.02 (d, J = 7.8 Hz, 1H), 4.41 (s, 2H), 4.16-4.12 (m, 1H), 3.97 (s, 3H), 3.76-3.70 (m, 2H), 3.61-3.55 (m, 1H), 3.38-3.34 (m, 1H), 2.95 (s, 6H), 2.65 (sm 3H), 2.61-2.56 (m, 1H), 2.38-2.29 (m, 1H), 1.77 (s, 6H); LC-MS (ESI) m/z: 658 $[M + H]^+$ | B |
| 30 | 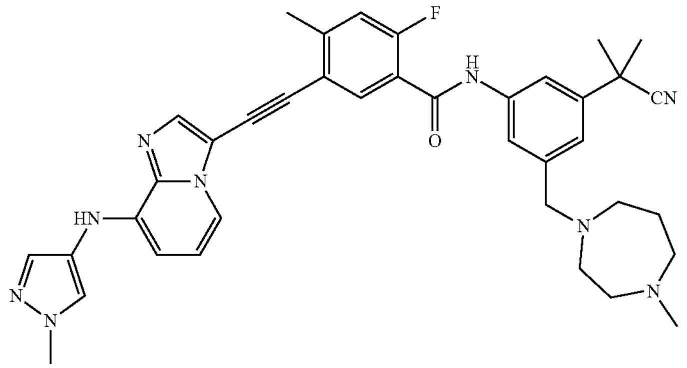 [SMILES: Cc1cc(F)c(C(=O)Nc2cc(CN3CCCN(C)CC3)cc(C(C)(C)C#N)c2)cc1C#Cc1cnc2c(Nc3cnn(C)c3)cccn12] N-(3-(2-cyanopropan-2-yl)-5-((4-methyl-1,4-diazepan-1-yl)methyl)phenyl)-2-fluoro-4-methyl-5-((8-((1-methyl-1H-pyrazol-4-yl)amino)imidazo[1,2-a]pyridin-3-yl)ethynyl)benzamide | $^1$H NMR (400 MHz, TFA salt, MeOD-$d_4$) δ 8.16 (s, 1H), 8.13 (dd, J = 6.56, 0.72 Hz, 1H), 8.02 (d, J = 7.16 Hz, 1H), 8.00 (s, 1H), 7.76 (s, 1H), 7.74 (s, 1H), 7.54 (d, J = 0.68 Hz, 1H), 7.45 (s, 1H), 7.32 (d, J = 11.16 Hz, 1H), 7.22 (dd, J = 7.82 Hz, 6.64 Hz, 1H), 6.95 (d, J = 7.24 Hz, 1H), 4.13 (s, 2H), 3.93 (s, 3H), 3.57-3.56 (m, 2H), 3.51-3.47 (m, 2H), 3.31-3.30 (m, 2H), 3.19-3.18 (m, 2H), 2.96 (s, 3H), 2.65 (s, 3H), 2.21-2.19 (m, 2H), 1.76 (s, 6H); LC-MS (ESI) m/z: 658 $[M + H]^+$ | B |

TABLE 1-continued

| Example | Structure / Name | $^1$H NMR/LC-MS | Purification condition |
|---|---|---|---|
| 31 | 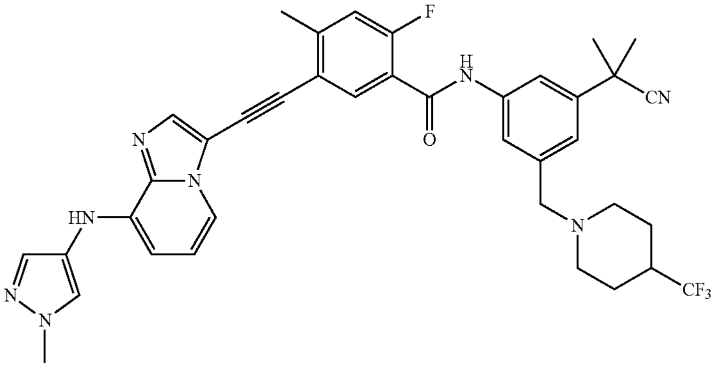 [SMILES: Cc1cc(F)c(C(=O)Nc2cc(CN3CCC(C(F)(F)F)CC3)cc(C(C)(C)C#N)c2)cc1C#Cc1cnc2c(Nc3cnn(C)c3)cccn12] N-(3-(2-cyanopropan-2-yl)-5-((4-(trifluoromethyl)piperidin-1-yl)methyl)phenyl)-2-fluoro-4-methyl-5-((8-((1-methyl-1H-pyrazol-4-yl)amino)imidazo [1,2-a]pyridin-3-yl)ethynyl)benzamide | $^1$H NMR (400 MHz, TFA salt, DMSO-$d_6$) δ10.76 (s, 1H), 9.66 (br s, 1H), 8.20 (s, 1H), 8.09 (s, 1H), 8.01-7.90 (m,3H), 7.86-7.78 (m, 2H), 7.51 (s, 1H), 7.48-7.37 (m, 2H), 7.00-6.91 (m, 1H), 6.60 (d, J = 7.1 Hz, 1H), 4.39 (s, 2H), 3.83 (s, 3H), 3.09-2.97 (m, 2H), 2.60 (s, 3H), 2.55-2.51 (m, 2H), 2.07 (d, J = 11.8 Hz, 2H), 1.82-1.63 (m, 8H); LC-MS (ESI) m/z: 697 $[M + H]^+$ | B |
| 32 | 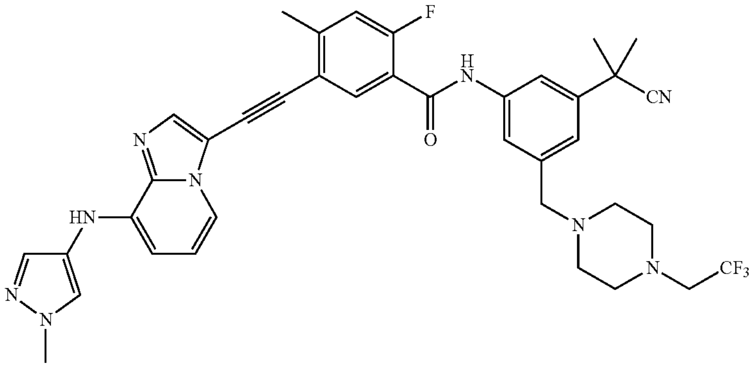 [SMILES: Cc1cc(F)c(C(=O)Nc2cc(CN3CCN(CC(F)(F)F)CC3)cc(C(C)(C)C#N)c2)cc1C#Cc1cnc2c(Nc3cnn(C)c3)cccn12] N-(3-(2-cyanopropan-2-yl)-5-((4-(2,2,2-trifluoroethyl)piperazin-1-yl) methyl)phenyl)-2-fluoro-4-methyl-5-((8-((1-methyl-1H-pyrazol-4-yl)amino)imidazo[1,2-a]pyridin-3-yl)ethynyl)benzamide | $^1$H NMR (400 MHz, TFA salt, DMSO-$d_6$) δ10.75 (s, 1H), 9.76 (br s, 1H), 8.20 (s, 1H), 8.08 (s, 1H), 8.02-7.93 (m, 3H), 7.83 (d, J = 6.4 Hz, 2H), 7.51 (d, J = 0.6 Hz, 1H), 7.45 (d, J = 11.1 Hz, 1H), 7.41 (s, 1H), 7.01-6.93 (m, 1H), 6.61 (d, J = 7.0 Hz, 1H), 4.39 (s, 2H), 3.84 (s, 3H), 3.38-3.28 (m, 4H), 3.17-3.02 (m, 4H), 2.78-2.65 (m, 2H), 2.60 (s, 3H), 1.71 (s, 6H); LC-MS (ESI) m/z: 712 $[M + H]^+$ | B |

TABLE 1-continued

| Example | Structure / Name | $^1$H NMR/LC-MS | Purification condition |
| --- | --- | --- | --- |
| 33 | 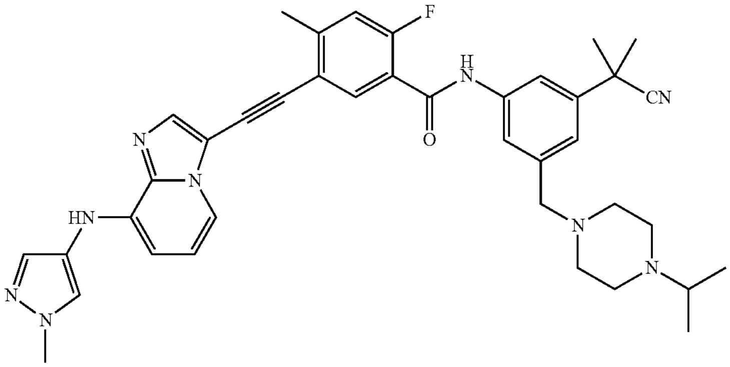 [SMILES: Cc1cc(F)c(C(=O)Nc2cc(CN3CCN(C(C)C)CC3)cc(C(C)(C)C#N)c2)cc1C#Cc1cnc2c(Nc3cnn(C)c3)cccn12] N-(3-(2-cyanopropan-2-yl)-5-((4-isopropylpiperazin-1-yl)methyl)phenyl)-2-fluoro-4-methyl-5-((8-((1-methyl-1H-pyrazol-4-yl)amino)imidazo[1,2-a]pyridin-3-yl)ethynyl)benzamide | $^1$H NMR (400 MHz, TFA salt, MeOD-$d_4$) δ 8.10-8.08 (m, 2H), 8.00 (d, J = 7.16 Hz, 1H), 7.84 (s, 1h), 7.76 (s, 1H), 7.72 (s, 1H), 7.54 (d, J = 0.68 Hz, 1H), 7.35 (s, 1H), 7.31 (d, J = 11.16 Hz, 1H), 7.18 (t, J = 7.0 Hz, 1H), 6.89 (d, J = 7.52 Hz, 1H), 3.93 (s, 3H), 3.72 (s, 2H), 3.47-3.41 (m, 2H), 3.23-3.14 (m, 5H), 2.65 (s, 3H), 2.45-2.41 (m, 2H), 1.75 (s, 6H), 1.38 (s, 3H), 1.36 (s, 3H); LC-MS (ESI) m/z: 672 [M + H]$^+$ | B |
| 34 | 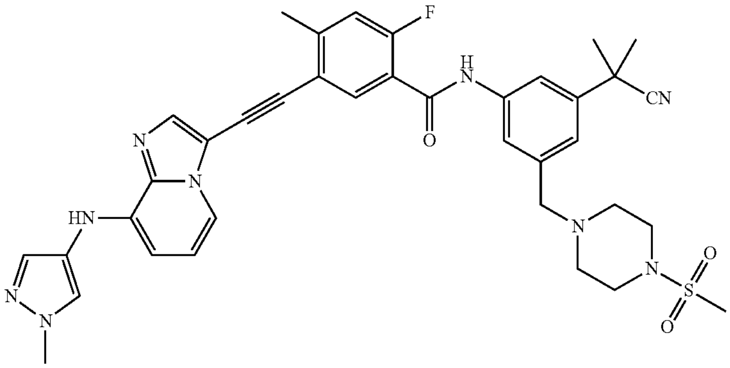 [SMILES: Cc1cc(F)c(C(=O)Nc2cc(CN3CCN(S(C)(=O)=O)CC3)cc(C(C)(C)C#N)c2)cc1C#Cc1cnc2c(Nc3cnn(C)c3)cccn12] N-(3-(2-cyanopropan-2-yl)-5-((4-(methylsulfonyl)piperazin-1-yl)methyl)phenyl)-2-fluoro-4-methyl-5-((8-((1-methyl-1H-pyrazol-4-yl)amino)imidazo[1,2-a]pyridin-3-yl)ethynyl)benzamide | $^1$H NMR (400 MHz, TFA salt, MeOD-$d_4$) δ 8.11 (s, 1H), 8.06-8.05 (m, 2H), 8.01 (d, J = 7.2 Hz, 1H), 7.84 (t, J = 1.8 Hz, 1H), 7.75 (s, 1H), 7.54 (d, J = 0.64 Hz, 1H), 7.50 (t, J = 1.56 Hz, 1H), 7.31 (d, J = 11.12 Hz, 1H), 7.13 (dd, J = 7.74, 6.76 Hz, 1H), 6.84 (d, J = 7.32 Hz, 1H), 4.45 (s, 2H), 3.92 (s, 3H), 2.96 (s, 3H), 2.65 (s, 3H), 1.79 (s, 6H), 1.29 (s, 8H); LC-MS (ESI) m/z: 708 [M + H]$^+$ | B |

TABLE 1-continued

| Example | Structure / Name | $^1$H NMR/LC-MS | Purification condition |
|---|---|---|---|
| 35 | 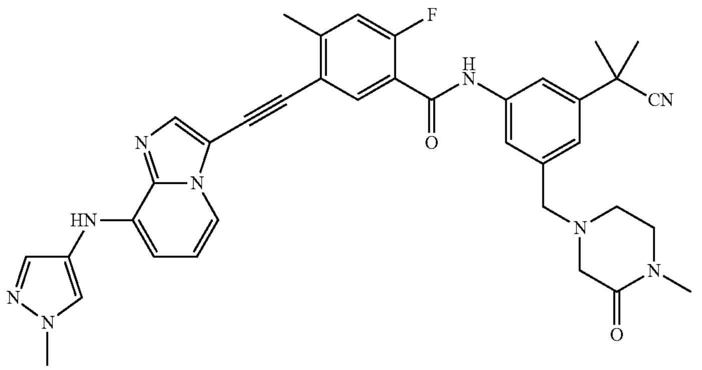 [SMILES: Cc1cc(F)c(C(=O)Nc2cc(CN3CCN(C)C(=O)C3)cc(C(C)(C)C#N)c2)cc1C#Cc1cnc2c(Nc3cnn(C)c3)cccn12] N-(3-(2-cyanopropan-2-yl)-5-((4-methyl-3-oxopiperazin-1-yl)methyl)phenyl)-2-fluoro-4-methyl-5-((8-((1-methyl-1H-pyrazol-4-yl)amino)imidazo[1,2-a]pyridin-3-yl)ethynyl)benzamide | $^1$H NMR (400 MHz, TFA salt, MeOD-$d_4$) δ 8.21 (s, 1H), 8.16 (d, J = 6.6 Hz, 1H), 8.05-8.03 (m, 2H), 7.87 (s, 1H), 7.77 (s, 1H), 7.54 (d, J = 0.6 Hz, 1H), 7.47 (t, J = 1.56 Hz, 1H), 7.32 (d, J = 11.28 Hz, 1H), 7.26 (dd, J = 7.88, 6.64 Hz, 1H), 7.00 (d, J = 7.36 Hz, 1H), 4.32 (s, 2H), 3.93 (s, 3H), 3.71 (s, 2H), 3.60 (t, J = 5.44 Hz, 2H), 3.47-3.46 (m, 2H), 3.00 (s, 3H), 2.66 (s, 3H), 1.78 (s, 6H); LC-MS (ESI) m/z: 658 [M + H]$^+$ | B |
| 36 | 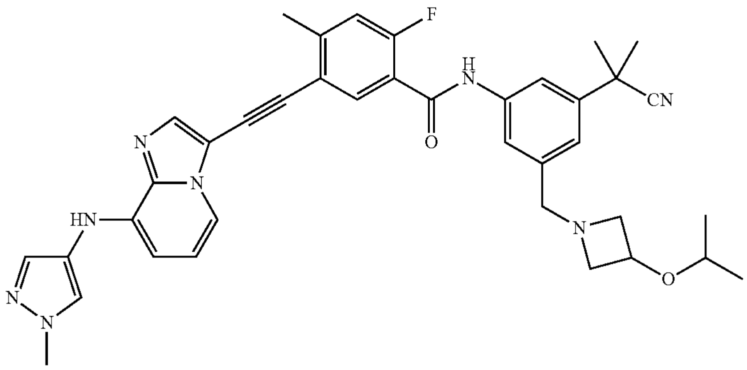 [SMILES: Cc1cc(F)c(C(=O)Nc2cc(CN3CC(OC(C)C)C3)cc(C(C)(C)C#N)c2)cc1C#Cc1cnc2c(Nc3cnn(C)c3)cccn12] N-(3-(2-cyanopropan-2-yl)-5-((3-isopropoxyazetidin-1-yl)methyl)phenyl)-2-fluoro-4-methyl-5-((8-((1-methyl-1H-pyrazol-4-yl)amino)imidazo[1,2-a]pyridin-3-yl)ethynyl)benzamide | 1H NMR (400 MHz, TFA salt, MeOD-$d_4$) δ 8.30 (s, 1H), 8.20 (d, J = 6.48 Hz, 1H), 8.05 (d, J = 7.12 Hz, 1H), 7.99 (s, 1H), 7.88 (br-s, 1H), 7.77 (s, 1H), 7.55 (s, 1H), 7.44 (br-s, 1H), 7.35-7.31 (m, 2H), 7.09 (d, J = 7.92 Hz, 1H), 4.46 (s, 2H), 4.42-4.38 (m, 2H), 4.09-4.05 (m, 2H), 3.71 (quint, J = 6.12 Hz, 1H), 2.65 (s, 3H), 1.77 (s, 6H), 1.17 (s, 3H), 1.15 (s, 3H); LC-MS (ESI) m/z: 659 [M + H]$^+$ | B |

TABLE 1-continued

| Example | Structure / Name | $^1$H NMR/LC-MS | Purification condition |
|---|---|---|---|
| 37 | 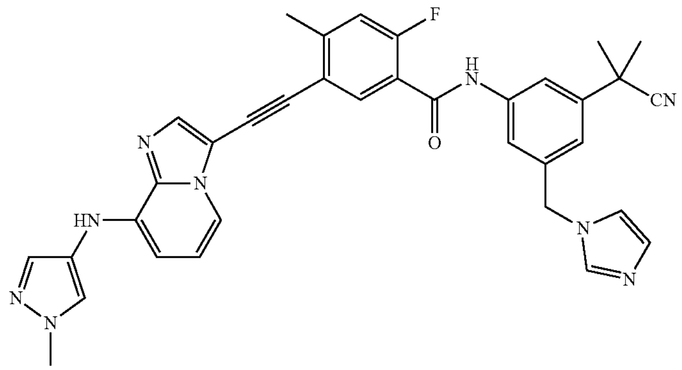 [SMILES: Cc1cc(F)c(C(=O)Nc2cc(Cn3ccnc3)cc(C(C)(C)C#N)c2)cc1C#Cc1cnc2c(Nc3cnn(C)c3)cccn12] N-(3-((1H-imidazol-1-yl)methyl)-5-(2-cyanopropan-2-yl)phenyl)-2-fluoro-4-methyl-5-((8-((1-methyl-1H-pyrazol-4-yl)amino)imidazo[1,2-a]pyridin-3-yl)ethynyl)benzamide | $^1$H NMR (400 MHz, TFA salt, MeOD-$d_4$) δ 9.10 (s, 1H), 8.00-7.95 (m, 3H), 7.90 (s, 1H), 7.80 (s, 1H), 7.74 (s, 1H), 7.69 (t, J = 1.72 Hz, 1H), 7.62 (t, J = 1.64 Hz, 1H), 7.53 (d, J = 0.64 Hz, 1H), 7.39 (s, 1H), 7.29 (d, J = 11.3 Hz, 1H), 7.05 (dd, J = 7.62, 6.72 Hz, 1H), 6.74 (d, J = 7.0 Hz, 1H), 5.53 (s, 2H), 3.92 (s, 3H), 2.64 (s, 3H), 1.76 (s, 6H); LC-MS (ESI) m/z: 612 $[M + H]^+$ | B |
| 38 | 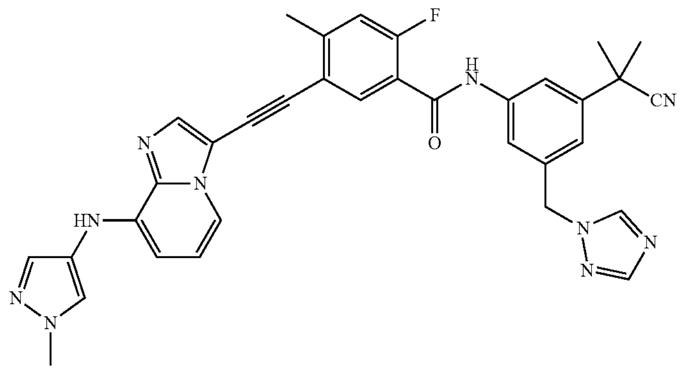 [SMILES: Cc1cc(F)c(C(=O)Nc2cc(Cn3cncn3)cc(C(C)(C)C#N)c2)cc1C#Cc1cnc2c(Nc3cnn(C)c3)cccn12] N-(3-((1H-1,2,4-triazol-1-yl)methyl)-5-(2-cyanopropan-2-yl)phenyl)-2-fluoro-4-methyl-5-((8-((1-methyl-1H-pyrazol-4-yl)amino)imidazo[1,2-a]pyridin-3-yl)ethynyl)benzamide | $^1$H NMR (400 MHz, TFA salt, $CDCl_3$) δ8.49 (d, J = 15.9 Hz, 1H), 8.32 (d, J = 8.0 Hz, 1H), 8.17 (s, 1H), 8.01 (s, 1H), 7.82 (s, 1H), 7.80 (d, J = 6.5 Hz, 1H), 7.77 (s, 1H), 7.61 (s, 1H), 7.54 (s, 1H), 7.44 (s, 1H), 7.21 (s, 1H), 7.14 (d, J = 12.8 Hz, 1H), 6.83 (t, J = 7.1 Hz, 1H), 6.60 (s, 1H), 6.49 (d, J = 7.4 Hz, 1H), 5.40 (s, 2H), 3.94 (s, 3H), 2.62 (s, 3H), 1.74 (s, 6H); LC-MS (ESI) m/z: 613 $[M + H]^+$ | B |

TABLE 1-continued

| Example | Structure / Name | $^1H$ NMR/LC-MS | Purification condition |
|---|---|---|---|
| 39 | 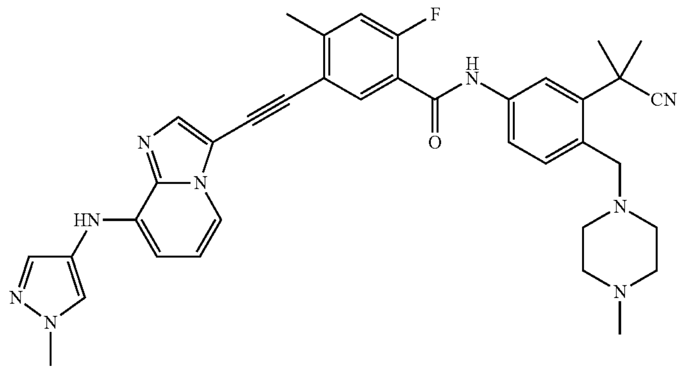 [SMILES: Cc1cc(F)c(C(=O)Nc2ccc(CN3CCN(C)CC3)c(C(C)(C)C#N)c2)cc1C#Cc1cnc2c(Nc3cnn(C)c3)cccn12] N-(3-(2-cyanopropan-2-yl)-4-((4-methylpiperazin-1-yl)methyl)phenyl)-2-fluoro-4-methyl-5-((8-((1-methyl-1H-pyrazol-4-yl)amino)imidazo [1,2-a]pyridin-3-yl)ethynyl)benzamide | $^1H$ NMR (400 MHz, TFA salt, MeOD-$d_4$) δ 8.10-8.08 (m, 2H), 8.00 (d, J = 7.16 Hz, 1H), 7.848-7.843 (m, 1H), 7.76 (s, 1H), 7.73 (dd, J = 8.4, 2.0 Hz, 1H), 7.63 (d, J = 8.44 Hz, 1H), 7.54 (s, 1H), 7.30 (d, J = 11.28 Hz, 1H), 7.15 (dd, J = 7.74, 6.68 Hz, 1H), 6.89 (d, J = 7.32 Hz, 1H), 4.00 (s, 2H), 3.92 (s, 3H), 3.51-3.43 (m, 4H), 3.21-3.08 (m, 4H), 2.91 (s, 3H), 2.65 (s, 3H), 1.85 (s, 6H); LC-MS (ESI) m/z: 644 $[M + H]^+$ | B |
| 40 | 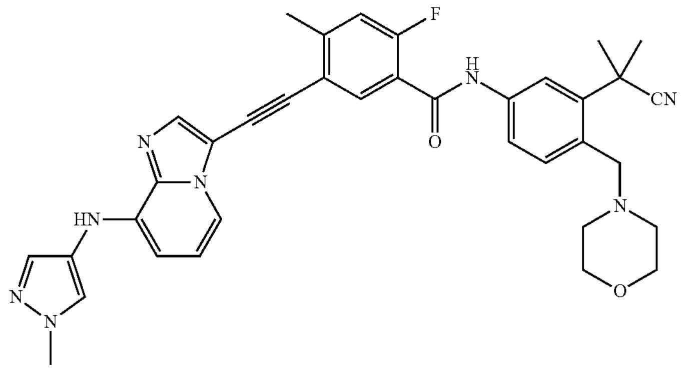 [SMILES: Cc1cc(F)c(C(=O)Nc2ccc(CN3CCOCC3)c(C(C)(C)C#N)c2)cc1C#Cc1cnc2c(Nc3cnn(C)c3)cccn12] N-(3-(2-cyanopropan-2-yl)-4-(morpholinomethyl)phenyl)-2-fluoro-4-methyl-5-((8-((1-methyl-1H-pyrazol-4-yl)amino)imidazo[1,2-a]pyridin-3-yl)ethynyl)benzamide | $^1H$ NMR (400 MHz, $CDCl_3$) δ8.44 (d, J = 15.6 Hz, 1H), 8.34 (d, J = 8.1 Hz, 1H), 7.85 (d, J = 2.0 Hz, 1H), 7.82-7.78 (m, 2H), 7.59 (d, J = 8.4 Hz, 1H), 7.54 (s, 1H), 7.46 (dd, J = 8.4, 2.1 Hz, 1H), 7.44 (s, 1H), 7.13 (d, J = 12.8 Hz, 1H), 6.86-6.79 (m, 1H), 6.64 (s, 1H), 6.49 (d, J = 7.1 Hz, 1H), 3.93 (s, 3H), 3.87 (s, 2H), 3.74-3.67 (m, 4H), 2.62 (s, 3H), 2.57-2.48 (m, 4H), 1.89 (s, 6H); LC-MS (ESI) m/z: 631 $[M + H]^+$ | A |

TABLE 1-continued

| Example | Structure / Name | $^1$H NMR/LC-MS | Purification condition |
|---|---|---|---|
| 41 | 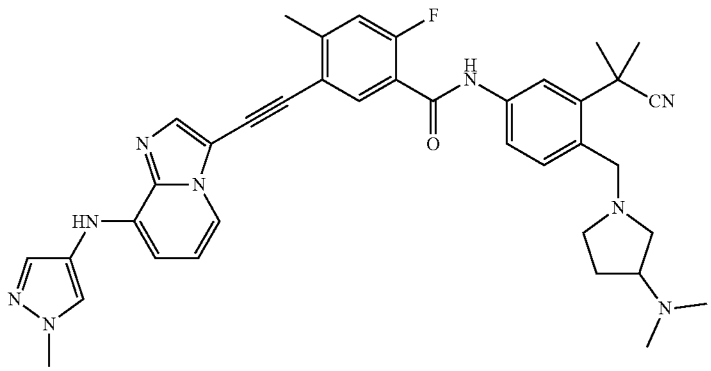 [SMILES: Cc1cc(F)c(C(=O)Nc2ccc(CN3CCC(N(C)C)C3)c(C(C)(C)C#N)c2)cc1C#Cc1cnc2c(Nc3cnn(C)c3)cccn12] N-(3-(2-cyanopropan-2-yl)-4-((3-(dimethylamino)pyrrolidin-1-yl)methyl)phenyl)-2-fluoro-4-methyl-5-((8-((1-methyl-1H-pyrazol-4-yl)amino)imidazo[1,2-a]pyridin-3-yl)ethynyl)benzamide | $^1$H NMR (400 MHz, MeOD-$d_4$) δ8.11-7.95 (m, 3H), 7.87 (s, 1H), 7.82-7.72 (m, 2H), 7.65 (d, J = 8.3 Hz, 1H), 7.54 (s, 1H), 7.29 (d, J = 11.2 Hz, 1H), 7.10 (t, J = 7.2 Hz, 1H), 6.80 (d, J = 7.7 Hz, 1H), 4.45-4.10 (m, 2H), 4.05-3.80 (m, 4H), 3.28-3.03 (m, 3H), 2.98-2.73 (m, 7H), 2.64 (s, 3H), 2.46-2.34 (m, 1H), 2.22-2.09 (m, 1H), 1.84 (s, 6H); LC-MS (ESI) m/z: 658 [M + H]$^+$ | A |
| 42 | 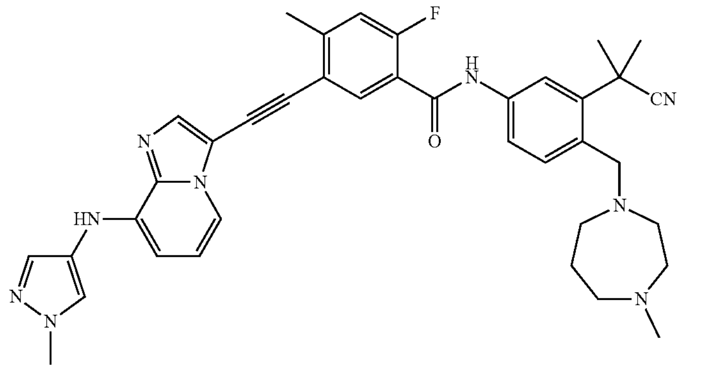 [SMILES: Cc1cc(F)c(C(=O)Nc2ccc(CN3CCCN(C)CC3)c(C(C)(C)C#N)c2)cc1C#Cc1cnc2c(Nc3cnn(C)c3)cccn12] N-(3-(2-cyanopropan-2-yl)-4-((4-methyl-1,4-diazepan-1-yl)methyl)phenyl)-2-fluoro-4-methyl-5-((8-((1-methyl-1H-pyrazol-4-yl) amino)imidazo[1,2-a]pyridin-3-yl)ethynyl)benzamide | $^1$H NMR (400 MHz, $CDCl_3$) δ8.45 (d, J = 15.9 Hz, 1H), 8.34 (d, J = 8.1 Hz, 1H), 7.88 (d, J = 2.0 Hz, 1H), 7.83-7.77 (m, 2H), 7.69 (d, J = 8.4 Hz, 1H), 7.54 (s, 1H), 7.46 (dd, J = 8.4, 2.0 Hz, 1H), 7.44 (s, 1H), 7.13 (d, J = 12.8 Hz, 1H), 6.86-6.79 (m, 1H), 6.61 (s, 1H), 6.49 (d, J = 6.9 Hz, 1H), 4.02 (s, 2H), 3.93 (s, 3H), 3.21-3.01 (m, 4H), 2.98-2.89 (m, 2H), 2.84 (t, J = 6.1 Hz, 2H), 2.67 (s, 3H), 2.62 (s, 3H), 2.14-2.05 (m, 2H), 1.85 (s, 6H), 1.48-1.43 (m, 2H); LC-MS (ESI) m/z: 658 [M + H]$^+$ | B |

TABLE 1-continued

| Example | Structure / Name | $^1$H NMR/LC-MS | Purification condition |
| --- | --- | --- | --- |
| 43 | 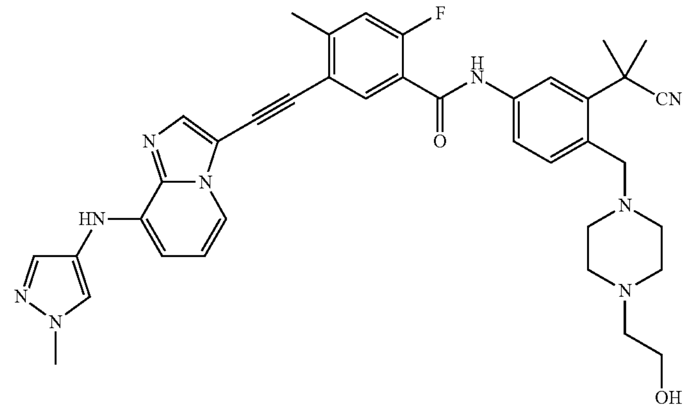 [SMILES: Cc1cc(F)c(C(=O)Nc2ccc(CN3CCN(CCO)CC3)c(C(C)(C)C#N)c2)cc1C#Cc1cnc2c(Nc3cnn(C)c3)cccn12] N-(3-(2-cyanopropan-2-yl)-4-((4-(2-hydroxyethyl)piperazin-1-yl)methyl)phenyl)-2-fluoro-4-methyl-5-((8-((1-methyl-1H-pyrazol-4-yl)amino)imidazo[1,2-a]pyridin-3-yl)ethynyl)benzamide | $^1$H NMR (400 MHz, $CDCl_3$) δ8.43 (d, J = 15.7 Hz, 1H), 8.34 (d, J = 8.1 Hz, 1H), 7.87-7.77 (m, 3H), 7.58 (d, J = 8.4 Hz, 1H), 7.53 (s, 1H), 7.46 (dd, J = 8.3, 2.0 Hz, 1H), 7.44 (s, 1H), 7.13 (d, J = 12.8 Hz, 1H), 6.87-6.79 (m, 1H), 6.60 (s, 1H), 6.49 (d, J = 7.0 Hz, 1H), 4.10-3.96 (m, 2H), 3.93 (s, 3H), 3.87 (s, 2H), 3.61 (t, J = 5.3 Hz, 2H), 2.62 (s, 3H), 2.60-2.41 (m, 8H), 1.88 (s, 6H); LC-MS (ESI) m/z: 674 $[M + H]^+$ | |
| 44 | 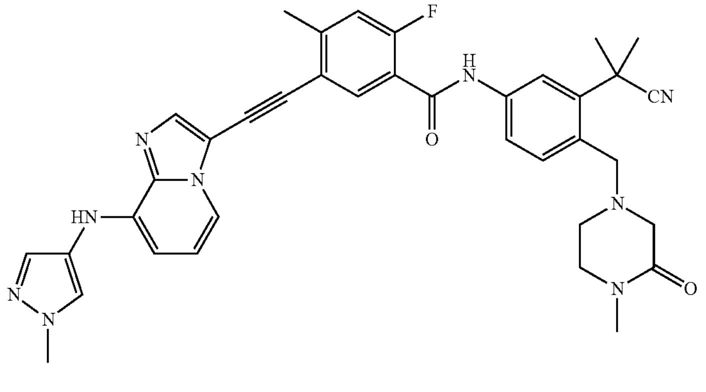 [SMILES: Cc1cc(F)c(C(=O)Nc2ccc(CN3CCN(C)C(=O)C3)c(C(C)(C)C#N)c2)cc1C#Cc1cnc2c(Nc3cnn(C)c3)cccn12] N-(3-(2-cyanopropan-2-yl)-4-((4-methyl-3-oxopiperazin-1-yl)methyl)phenyl)-2-fluoro-4-methyl-5-((8-((1-methyl-1H-pyrazol-4-yl)amino)imidazo[1,2-a]pyridin-3-yl)ethynyl)benzamide | $^1$H NMR (400 MHz, $CDCl_3$) δ8.45 (d, J = 15.9 Hz, 1H), 8.34 (d, J = 8.1 Hz, 1H), 7.89 (d, J = 2.0 Hz, 1H), 7.83-7.77 (m, 2H), 7.58 (d, J = 8.4 Hz, 1H), 7.54 (s, 1H), 7.48-7.41 (m, 2H), 7.13 (d, J = 12.8 Hz, 1H), 6.86-6.79 (m, 1H), 6.63 (s, 1H), 6.49 (d, J = 7.1 Hz, 1H), 3.99-3.86 (m, 5H), 3.37-3.28 (m, 2H), 3.19 (s, 2H), 2.97 (s, 3H), 2.85-2.74 (m, 2H), 2.62 (s, 3H), 1.85 (s, 6H); LC-MS (ESI) m/z: 658 $[M + H]^+$ | A |

TABLE 1-continued

| Example | Structure / Name | $^1$H NMR/LC-MS | Purification condition |
|---|---|---|---|
| 45 | 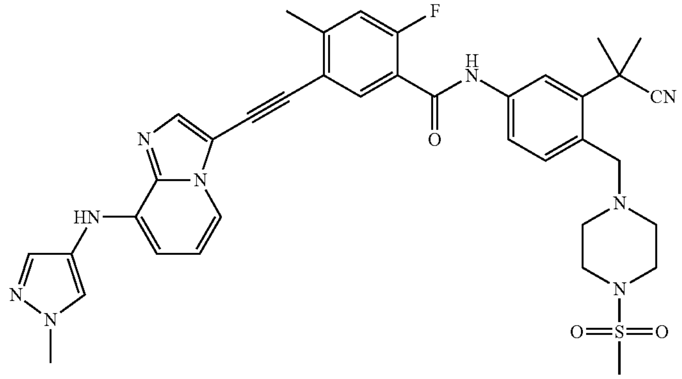 N-(3-(2-cyanopropan-2-yl)-4-((4-(methylsulfonyl)piperazin-1-yl)methyl)phenyl)-2-fluoro-4-methyl-5-((8-((1-methyl-1H-pyrazol-4-yl)amino)imidazo[1,2-a]pyridin-3-yl)ethynyl)benzamide | $^1$H NMR (400 MHz, $CDCl_3$) δ8.44 (d, J = 15.8 Hz, 1H), 8.34 (d, J = 8.0 Hz, 1H), 7.86 (d, J = 1.9 Hz, 1H), 7.83-7.78 (m, 1H), 7.59-7.50 (m, 2H), 7.47 (dd, J = 8.3, 2.0 Hz, 1H), 7.44 (s, 1H), 7.13 (d, J = 12.9 Hz, 1H), 6.86-6.79 (m, 1H), 6.62 (s, 1H), 6.49 (d, J = 7.5 Hz, 1H), 3.97-8.86 (m, 5H), 3.31-3.20 (m, 4H), 2.80 (s, 3H), 2.68-2.56 (m, 5H), 1.87 (s, 6H); LC-MS (ESI) m/z: 708 $[M + H]^+$ | A |
| 46 | 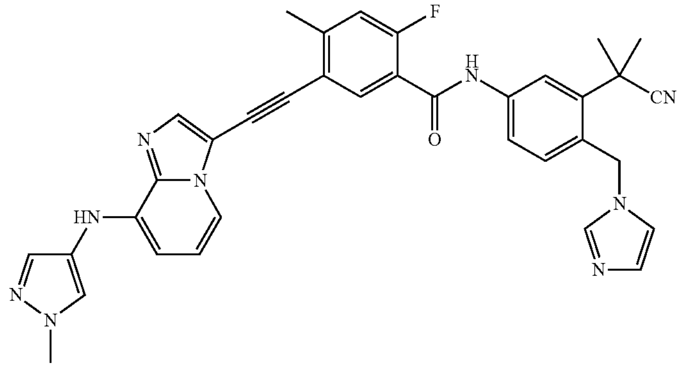 [SMILES: Cc1cc(F)c(C(=O)Nc2ccc(Cn3ccnc3)c(C(C)(C)C#N)c2)cc1C#Cc1cnc2c(Nc3cnn(C)c3)cccn12] N-(4-((1H-imidazol-1-yl)methyl)-3-(2-cyanopropan-2-yl)phenyl)-2-fluoro-4-methyl-5-((8-((1-methyl-1H-pyrazol-4-yl)amino)imidazo [1,2-a]pyridin-3-yl)ethynyl)benzamide | $^1$H NMR (400 MHz, $CDCl_3$) δ8.49 (d, J = 16.0 Hz, 1H), 8.33 (d, J = 8.1 Hz, 1H), 8.05 (d, J = 2.0 Hz, 1H), 7.83-7.75 (m, 2H), 7.60 (s, 1H), 7.53 (s, 1H), 7.44 (s, 1H), 7.39 (dd, J = 8.4, 2.1 Hz, 1H), 7.17-7.09 (m, 2H), 7.00-6.92 (m, 2H), 6.87-6.79 (m, 1H), 6.62 (s, 1H), 6.49 (d, J = 7.5 Hz, 1H), 5.56 (s, 2H), 3.93 (s, 3H), 2.62 (s, 3H), 1.83 (s, 6H); LC-MS (ESI) m/z: 612 $[M + H]^+$ | A |

TABLE 1-continued

| Example | Structure / Name | $^1$H NMR/LC-MS | Purification condition |
|---|---|---|---|
| 47 | 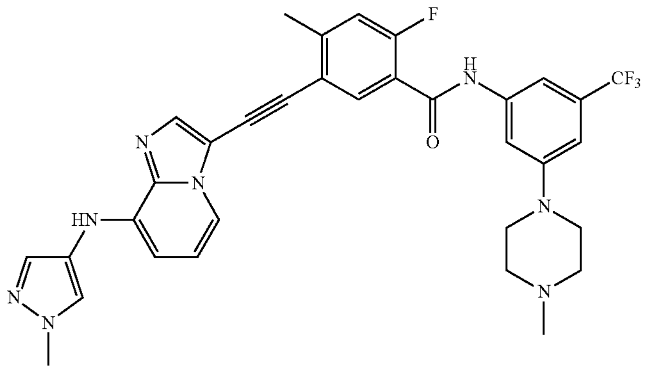 [SMILES: Cc1cc(F)c(C(=O)Nc2cc(N3CCN(C)CC3)cc(C(F)(F)F)c2)cc1C#Cc1cnc2c(Nc3cnn(C)c3)cccn12] 2-fluoro-4-methyl-5-((8-((1-methyl-1H-pyrazol-4-yl)amino)imidazo[1,2-a]pyridin-3-yl)ethynyl)-N-(3-(4-methylpiperazin-1-yl)-5-(trifluoromethyl)phenyl)benzamide | $^1$H NMR (400 MHz, DMSO-$d_6$) δ10.65 (s, 1H), 9.78 (br s, 1H), 8.22 (s, 1H), 8.08-7.89 (m, 3H), 7.82 (s, 1H), 7.63 (d, J = 10.8 Hz, 2H), 7.52 (s, 1H), 7.45 (d, J = 11.1 Hz, 1H), 7.11 (s, 1H), 6.98 (t, J = 7.1 Hz, 1H), 6.62 (d, J = 7.6 Hz, 1H), 3.96-3.89 (m, 2H), 3.84 (s, 3H), 3.56-3.52 (m, 2H), 3.23-3.12 (m, 2H), 3.11-3.00 (m, 2H), 2.88 (s, 3H), 2.59 (s, 3H); LC-MS (ESI) m/z: 631 [M + H]$^+$ | B |
| 48 | 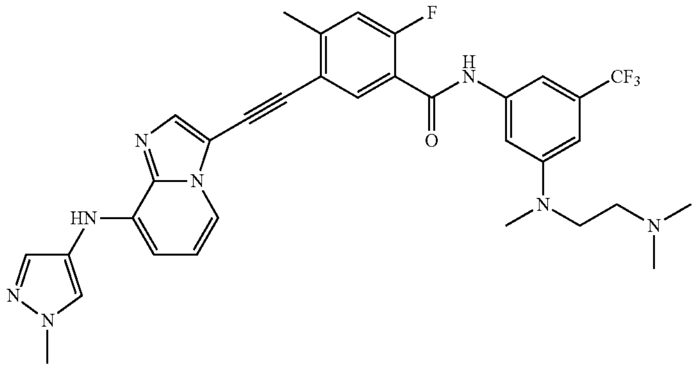 [SMILES: Cc1cc(F)c(C(=O)Nc2cc(N(C)CCN(C)C)cc(C(F)(F)F)c2)cc1C#Cc1cnc2c(Nc3cnn(C)c3)cccn12] N-(3-((2-(dimethylamino)ethyl)(methyl)amino)-5-(trifluoromethyl)phenyl)-2-fluoro-4-methyl-5-((8-((1-methyl-1H-pyrazol-4-yl)amino)imidazo[1,2-a]pyridin-3-yl)ethynyl)benzamide | $^1$H NMR (400 MHz, TFA salt, $CDCl_3$) δ8.46 (d, J = 15.4 Hz, 1H), 8.30 (d, J = 8.0 Hz, 1H), 7.83-7.78 (m, 1H), 7.53 (d, J = 6.1 Hz, 1H), 7.44 (s, 1H), 7.13 (d, J = 12.8 Hz, 1H), 7.07 (s, 1H), 6.86-6.79 (m, 1H), 6.70 (s, 1H), 6.58 (s, 1H), 6.49 (d, J = 7.5 Hz, 1H), 3.94 (s, 3H), 3.67-3.54 (m, 2H), 3.05 (s, 3H), 2.80-2.69 (m, 2H), 2.62 (s, 3H), 2.54 (s, 6H); LC-MS (ESI) m/z: 633 [M + H]$^+$ | B |

TABLE 1-continued

| Example | Structure / Name | $^1$H NMR/LC-MS | Purification condition |
|---|---|---|---|
| 49 | 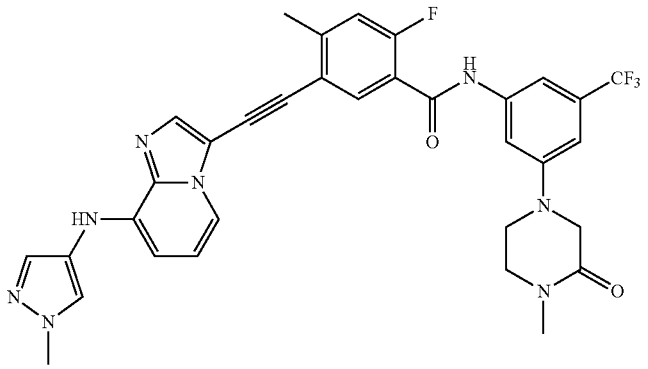 [SMILES: Cc1cc(F)c(C(=O)Nc2cc(N3CCN(C)C(=O)C3)cc(C(F)(F)F)c2)cc1C#Cc1cnc2c(Nc3cnn(C)c3)cccn12] 2-fluoro-4-methyl-5-((8-((1-methyl-1H-pyrazol-4-yl)amino)imidazo[1,2-a]pyridin-3-yl)ethynyl)-N-(3-(4-methyl-3-oxopiperazin-1-yl)-5-(trifluoromethyl)phenyl)benzamide | $^1$H NMR (400 MHz, $CDCl_3$) δ8.48 (d, J = 16.3 Hz, 1H), 8.34 (d, J = 8.1 Hz, 1H), 7.84 (s, 1H), 7.82 (dd, J = 6.6, 0.8 Hz, 1H), 7.66-7.62 (m, 1H), 7.54 (s, 1H), 7.45 (s, 1H), 7.24 (s, 1H), 7.15 (d, J = 12.9 Hz, 1H), 6.94-6.87 (m, 1H), 6.86 (s, 1H), 6.59 (d, J = 7.6 Hz, 1H), 3.97 (s, 2H), 3.94 (s, 3H), 3.64-3.56 (m, 2H), 3.55-3.48 (m, 2H), 3.07 (s, 3H), 2.63 (s, 3H); LC-MS (ESI) m/z: 645 $[M + H]^+$ | A |
| 50 | 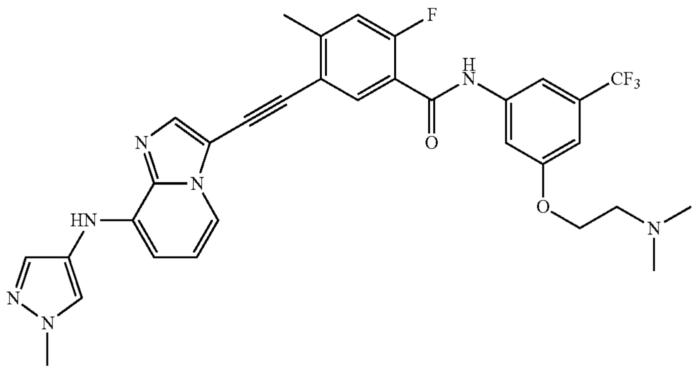 [SMILES: Cc1cc(F)c(C(=O)Nc2cc(OCCN(C)C)cc(C(F)(F)F)c2)cc1C#Cc1cnc2c(Nc3cnn(C)c3)cccn12] N-(3-(2-(dimethylamino)ethoxy)-5-(trifluoromethyl)phenyl)-2-fluoro-4-methyl-5-((8-((1-methyl-1H-pyrazol-4-yl)amino)imidazo[1,2-a]pyridin-3-yl)ethynyl)benzamide | $^1$H NMR (400 MHz, TFA salt, MeOD-$d_4$) δ 7.97 (d, J = 2H), 7.929-7.920 (m, 2H), 7.74 (s, 1H), 7.56 (s, 1H), 7.53 (s, 1H), 7.29 (d, J = 11.4 Hz, 1H), 7.12 (s, 1H), 7.03 (t, J = 6.76 Hz, 1H), 6.70 (d, J = 7.68 Hz, 1H), 4.46 (t, J = 4.72 Hz, 2H), 3.92 (s, 3H), 3.65 (t, J = 5.28 Hz, 2H), 3.01 (s, 3H), 2.64 (s, 3H); LC-MS (ESI) m/z: 620 $[M + H]^+$ | B |

TABLE 1-continued

| Example | Structure / Name | $^1$H NMR/LC-MS | Purification condition |
|---|---|---|---|
| 51 | 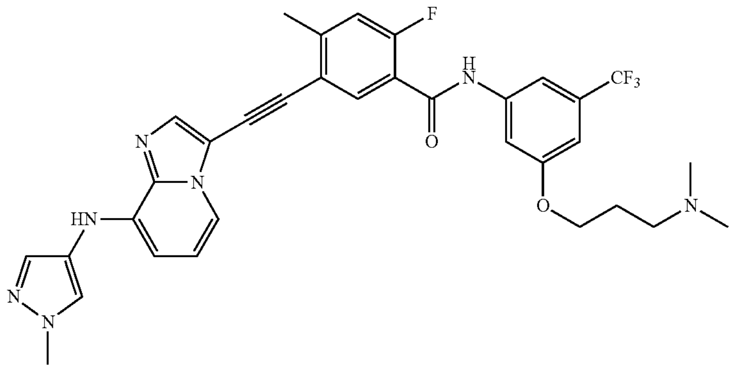 [SMILES: Cc1cc(F)c(C(=O)Nc2cc(OCCCN(C)C)cc(C(F)(F)F)c2)cc1C#Cc1cnc2c(Nc3cnn(C)c3)cccn12] N-(3-(3-(dimethylamino)propoxy)-5-(trifluoromethyl)phenyl)-2-fluoro-4-methyl-5-((8-((1-methyl-1H-pyrazol-4-yl) amino)imidazo[1,2-a]pyridin-3-yl)ethynyl)benzamide | $^1$H NMR (400 MHz, TFA salt, MeOD-$d_4$) δ 8.15 (s, 1H), 8.12 (d, J = 5.96 Hz, 1H), 8.01 (d, J = 7.16 Hz, 1H), 7.79 (s, 1H), 7.76 (s, 1H), 7.55-7.54 (m, 2H), 7.31 (d, J = 11.2 Hz, 1H), 7.21 (dd, J = 7.82, 6.68 Hz, 1H), 7.03 (s, 1H), 6.94 (d, J = 7.28 Hz, 1H), 4.20 (t, J = 5.72 Hz, 2H), 3.93 (s, 3H), 3.38 (t, J = 7.76 Hz, 2H), 2.96 (s, 6H), 2.65 (s, 3H), 2.30-2.23 (m, 2H); LC-MS (ESI) m/z: 634 $[M + H]^+$ | B |
| 52 | 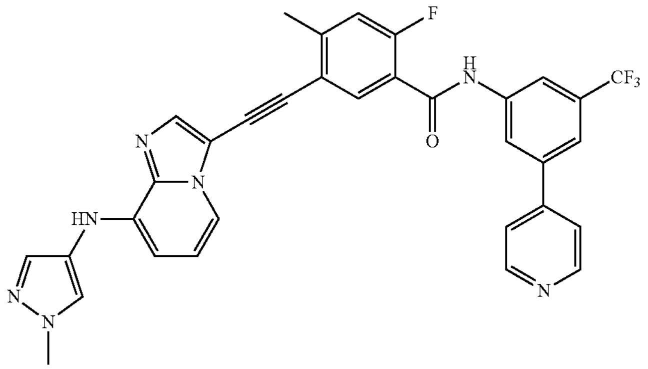 [SMILES: Cc1cc(F)c(C(=O)Nc2cc(-c3ccncc3)cc(C(F)(F)F)c2)cc1C#Cc1cnc2c(Nc3cnn(C)c3)cccn12] 2-fluoro-4-methyl-5-((8-((1-methyl-1H-pyrazol-4-yl)amino)imidazo[1,2-a]pyridin-3-yl)ethynyl)-N-(3-(pyridin-4-yl)-5-(trifluoromethyl)phenyl)benzamide | $^1$H NMR (400 MHz, $CDCl_3$) δ8.75 (dd, J = 4.6, 1.6 Hz, 2H), 8.67 (d, J = 16.3 Hz, 1H), 8.38 (d, J = 8.0 Hz, 1H), 8.29 (s, 1H), 7.97 (s, 1H), 7.88 (s, 1H), 7.85 (d, J = 6.6 Hz, 1H), 7.69 (s, 1H), 7.61 (dd, J = 4.6, 1.6 Hz, 2H), 7.55 (s, 1H), 7.46 (s, 1H), 7.18 (d, J = 12.9 Hz, 1H), 7.01-6.94 (m, 1H), 6.72 (d, J = 7.8 Hz, 1H), 3.93 (s, 3H), 2.64 (s, 3H); LC-MS (ESI) m/z: 610 $[M + H]^+$ | A |

TABLE 1-continued

| Example | Structure / Name | $^1H$ NMR/LC-MS | Purification condition |
|---|---|---|---|
| 53 | 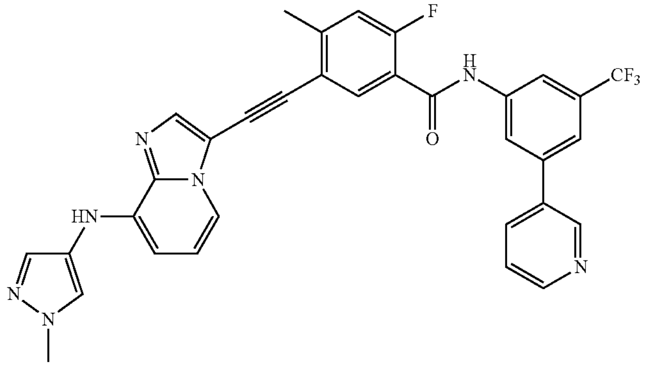 [SMILES: Cc1cc(F)c(C(=O)Nc2cc(-c3cccnc3)cc(C(F)(F)F)c2)cc1C#Cc1cnc2c(Nc3cnn(C)c3)cccn12] 2-fluoro-4-methyl-5-((8-((1-methyl-1H-pyrazol-4-yl)amino)imidazo[1,2-a]pyridin-3-yl)ethynyl)-N-(3-(pyridin-3-yl)-5-(trifluoromethyl)phenyl)benzamide | $^1H$ NMR (400 MHz, $CDCl_3$) δ8.90 (d, J = 1.9 Hz, 1H), 8.72-8.61 (m, 2H), 8.36 (d, J = 8.0 Hz, 1H), 8.18 (s, 1H), 8.01-7.93 (m, 2H), 7.87-7.78 (m, 2H), 7.63 (s, 1H), 7.54 (s, 1H), 7.46-7.40 (m, 2H), 7.16 (d, J = 12.9 Hz, 1H), 6.97-6.83 (m, 2H), 6.57 (d, J = 7.6 Hz, 1H), 3.93 (s, 3H), 2.63 (s, 3H); LC-MS (ESI) m/z: 610 $[M + H]^+$ | A |
| 54 | 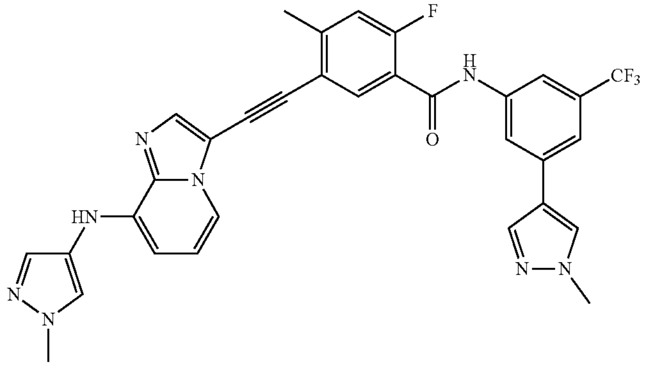 [SMILES: Cc1cc(F)c(C(=O)Nc2cc(-c3cnn(C)c3)cc(C(F)(F)F)c2)cc1C#Cc1cnc2c(Nc3cnn(C)c3)cccn12] 2-fluoro-4-methyl-N-(3-(1-methyl-1H-pyrazol-4-yl)-5-(trifluoromethyl)phenyl)-5-((8-((1-methyl-1H-pyrazol-4-yl)amino)imidazo[1,2-a]pyridin-3-yl)ethynyl)benzamide | $^1H$ NMR (400 MHz, $CDCl_3$) δ8.56 (d, J = 16.0 Hz, 1H), 8.39 (dd, J = 8.0, 3.9 Hz, 1H), 8.15 (br s, 1H), 8.05 (s, 1H), 7.93-7.86 (m, 2H), 7.82 (s, 1H), 7.76-7.71 (m, 2H), 7.56 (s, 1H), 7.49 (d, J = 11.3 Hz, 2H), 7.17 (d, J = 12.6 Hz, 1H), 7.09-7.02 (m, 1H), 6.85 (d, J = 7.8 Hz, 1H), 3.97 (s, 3H), 3.93 (s, 3H), 2.63 (s, 3H); LC-MS (ESI) m/z: 613 $[M + H]^+$ | A |
| 55 | 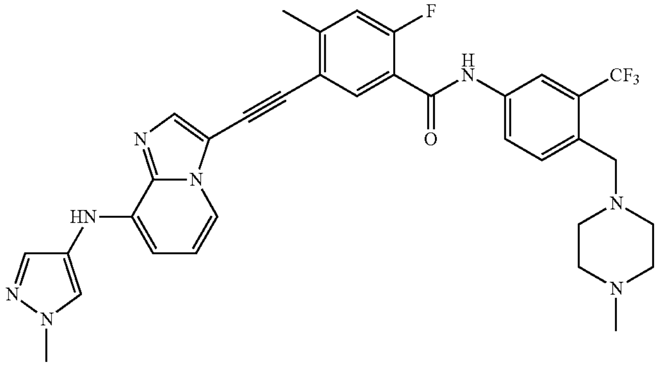 [SMILES: Cc1cc(F)c(C(=O)Nc2ccc(CN3CCN(C)CC3)c(C(F)(F)F)c2)cc1C#Cc1cnc2c(Nc3cnn(C)c3)cccn12] 2-fluoro-4-methyl-5-((8-((1-methyl-1H-pyrazol-4-yl)amino)imidazo[1,2-a]pyridin-3-yl)ethynyl)-N-(4-((4-methylpiperazin-1-yl)methyl)-3-(trifluoromethyl)phenyl)benzamide | $^1H$ NMR (400 MHz, DMSO-$d_6$) δ10.74 (s, 1H), 8.17 (s, 1H), 8.16-8.14 (m, 1H), 8.04-7.90 (m, 4H), 7.81 (s, 1H), 7.72 (d, J = 8.5 Hz, 1H), 7.51 (s, 1H), 7.44 (d, J = 11.2 Hz, 1H), 6.99-6.90 (m, 1H), 6.58 (d, J = 6.9 Hz, 1H), 3.83 (s, 3H), 3.65 (s, 2H), 2.72-2.62 (m, 4H), 2.59 (s, 3H); LC-MS (ESI) m/z: 645 $[M + H]^+$ | A |

TABLE 1-continued

| Example | Structure / Name | $^1$H NMR/LC-MS | Purification condition |
|---|---|---|---|
| 56 | 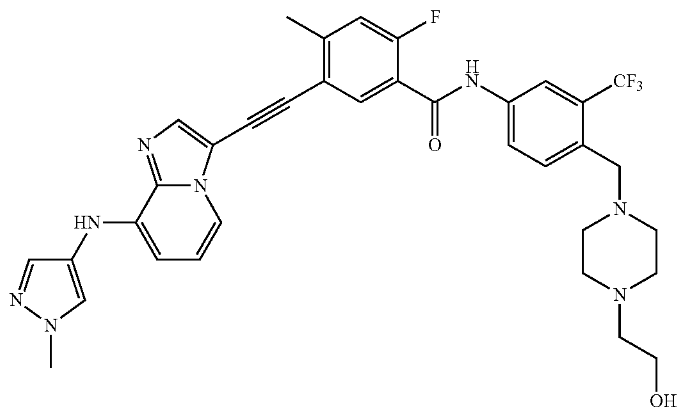 2-fluoro-N-(4-((4-(2-hydroxyethyl)piperazin-1-yl)methyl)-3-(trifluoromethyl)phenyl)-4-methyl-5-((8-((1-methyl-1H-pyrazol-4-yl)amino)imidazo[1,2-a]pyridin-3-yl)ethynyl)benzamide | $^1$H NMR (400 MHz, $CDCl_3$) δ8.50 (d, J = 15.7 Hz, 1H), 8.33 (d, J = 8.0 Hz, 1H), 7.90-7.85 (m, 2H), 7.83-7.74 (m, 3H), 7.53 (s, 1H), 7.43 (s, 1H), 7.12 (d, J = 12.8 Hz, 1H), 6.82 (t, J = 8.0 Hz, 1H), 6.61 (s, 1H), 6.48 (d, J = 8.0 Hz, 1H), 3.93 (s, 3H), 3.66-3.59 (m, 4H), 2.61 (s, 3H), 2.60-2.50 (m, 10H); LC-MS (ESI) m/z: 645 $[M + H]^+$ | A |
| 57 | 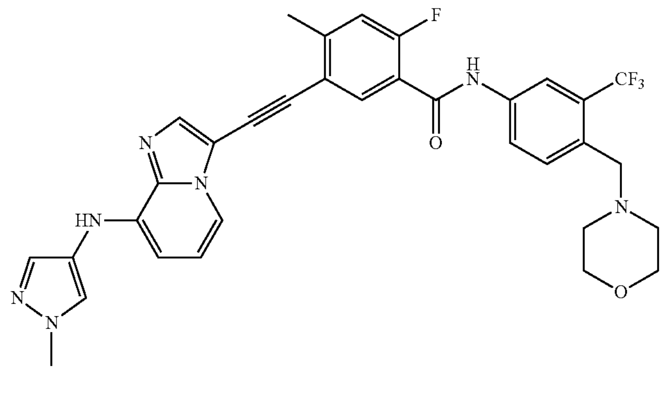 [SMILES: Cc1cc(F)c(C(=O)Nc2ccc(CN3CCOCC3)c(C(F)(F)F)c2)cc1C#Cc1cnc2c(Nc3cnn(C)c3)cccn12] 2-fluoro-4-methyl-5-((8-((1-methyl-1H-pyrazol-4-yl)amino)imidazo [1,2-a]pyridin-3-yl)ethynyl)-N-(4-(morpholinomethyl)-3-(trifluoromethyl)phenyl)benzamide | $^1$H NMR (400 MHz, $CDCl_3$) δ8.52 (d, J = 15.7 Hz, 1H), 8.32 (d, J = 8.1 Hz, 1H), 7.92-7.85 (m, 1H), 7.83-7.75 (m, 3H), 7.52 (s, 1H), 7.43 (s, 1H), 7.11 (d, J = 12.8 Hz, 1H), 6.81 (dd, J = 7.1 Hz, 1H), 6.62 (s, 1H), 6.49 (d, J = 7.1 Hz, 1H), 3.92 (s, 3H), 3.77-3.68 (m, 4H), 3.64 (s, 2H), 2.61 (s, 3H), 2.53-2.40 (m, 4H); LC-MS (ESI) m/z: 632 $[M + H]^+$ | A |

TABLE 1-continued

| Example | Structure / Name | $^1$H NMR/LC-MS | Purification condition |
|---|---|---|---|
| 58 | 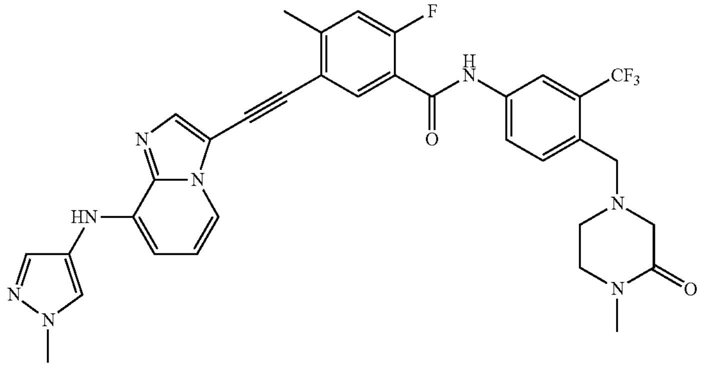 [SMILES: Cc1cc(F)c(C(=O)Nc2ccc(CN3CCN(C)C(=O)C3)c(C(F)(F)F)c2)cc1C#Cc1cnc2c(Nc3cnn(C)c3)cccn12] 2-fluoro-4-methyl-5-((8-((1-methyl-1H-pyrazol-4-yl)amino)imidazo[1,2-a]pyridin-3-yl)ethynyl)-N-(4-((4-methyl-3-oxopiperazin-1-yl)methyl)-3-(trifluoromethyl)phenyl)benzamide | $^1$H NMR (400 MHz, $CDCl_3$) δ8.50 (d, J = 15.9 Hz, 1H), 8.35 (d, J = 8.1 Hz, 1H), 7.94 (s, 1H), 7.88 (d, J = 8.1 Hz, 1H), 7.83-7.79 (m, 2H), 7.75 (d, J = 8.1 Hz, 1H), 7.54 (s, 1H), 7.44 (s, 1H), 7.14 (d, J = 13.0 Hz, 1H), 6.85-6.80 (m, 1H), 6.57 (s, 1H), 6.49 (d, J = 7.5 Hz, 1H), 3.94 (s, 3H), 3.70 (s, 2H), 3.32 (t, J = 5.8 Hz, 2H), 3.21 (s, 2H), 2.97 (s, 3H), 2.70 (t, J = 5.8 Hz, 2H), 2.63 (s, 3H); LC-MS (ESI) m/z: 659 [M + H]$^+$ | A |
| 59 | 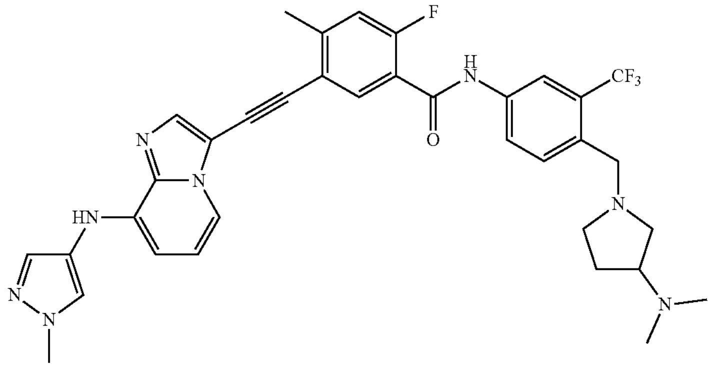 [SMILES: Cc1cc(F)c(C(=O)Nc2ccc(CN3CCC(N(C)C)C3)c(C(F)(F)F)c2)cc1C#Cc1cnc2c(Nc3cnn(C)c3)cccn12] N-(4-((3-(dimethylamino)pyrrolidine-1-yl)methyl)-3-(trifluoromethyl)phenyl)-2-fluoro-4-methyl-5-((8-((1-methyl-1H-pyrazol-4-yl)amino)imidazo[1,2-a]pyridin-3-yl)ethynyl)benzamide | $^1$H NMR (400 MHz, $CDCl_3$) δ8.47 (d, J = 16.0 Hz, 1H), 8.35 (d, J = 8.1 Hz, 1H), 7.92 (s, 1H), 7.89-7.73 (m, 4H), 7.53 (s, 1H), 7.44 (s, 1H), 7.13 (d, J = 12.9 Hz, 1H), 6.86-6.78 (m, 1H), 6.58 (s, 1H), 6.49 (d, J = 6.8 Hz, 1H), 3.94 (s, 3H), 3.78-3.74 (m, 2H), 2.90-2.85 (m, 2H), 2.80-2.71 (m, 1H), 2.71-2.65 (m, 1H), 2.62 (s, 3H), 2.25 (s, 6H), 2.02 (m, 1H), 1.78 (m, 1H); LC-MS (ESI) m/z: 659 [M + H]$^+$ | A |

TABLE 1-continued

| Example | Structure / Name | $^{1}H$ NMR/LC-MS | Purification condition |
|---|---|---|---|
| 60 | 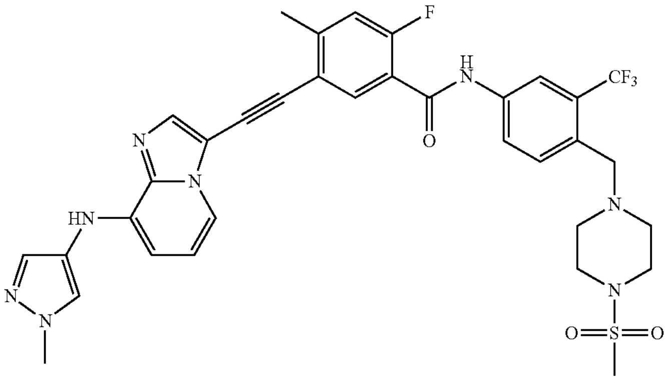 [SMILES: Cc1cc(F)c(C(=O)Nc2ccc(CN3CCN(S(C)(=O)=O)CC3)c(C(F)(F)F)c2)cc1C#Cc1cnc2c(Nc3cnn(C)c3)cccn12] 2-fluoro-4-methyl-5-((8-((1-methyl-1H-pyrazol-4-yl)amino)imidazo[1,2-a]pyridin-3-yl)ethynyl)-N-(4-((4-(methylsulfonyl)piperazin-1-yl)methyl)-3-(trifluoromethyl)phenyl)benzamide | $^{1}H$ NMR (400 MHz, $CDCl_3$) δ8.50 (d, J = 16.0 Hz, 1H), 8.35 (d, J = 8.1 Hz, 1H), 7.96-7.85 (m, 2H), 7.86-7.77 (m, 2H), 7.73 (d, J = 8.3 Hz, 1H), 7.54 (s, 1H), 7.44 (s, 1H), 7.14 (d, J = 12.9 Hz, 1H), 6.88-6.79 (m, 1H), 6.59 (s, 1H), 6.49 (d, J = 6.9 Hz, 1H), 3.94 (s, 3H), 3.70 (s, 2H), 3.30-3.24 (m, 4H), 2.80 (s, 3H), 2.62 (s, 3H), 2.61-2.57 (m, 4H); LC-MS (ESI) m/z: 709 [M + H]$^+$ | A |
| 61 | 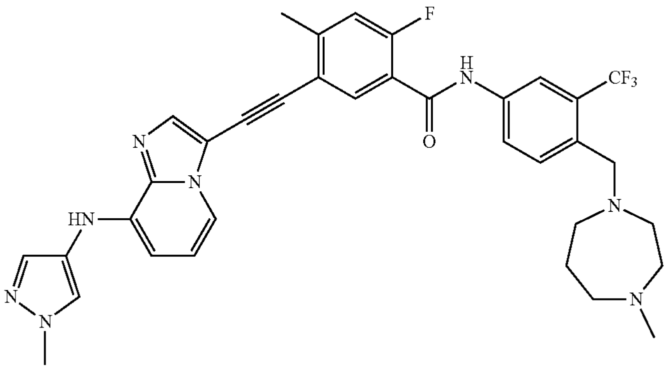 [SMILES: Cc1cc(F)c(C(=O)Nc2ccc(CN3CCCN(C)CC3)c(C(F)(F)F)c2)cc1C#Cc1cnc2c(Nc3cnn(C)c3)cccn12] 2-fluoro-4-methyl-N-(4-((4-methyl-1,4-diazepan-1-yl)methyl)-3-(trifluoromethyl)phenyl)-5-((8-((1-methyl-1H-pyrazol-4-yl) amino)imidazo[1,2-a]pyridin-3-yl)ethynyl)benzamide | $^{1}H$ NMR (400 MHz, $CDCl_3$) δ8.47 (d, J = 16.0 Hz, 1H), 8.35 (d, J = 8.0 Hz, 1H), 7.94-7.78 (m, 4H), 7.54 (s, 1H), 7.44 (s, 1H), 7.13 (d, J = 12.8 Hz, 1H), 6.85-6.79 (m, 1H), 6.59 (s, 1H), 6.49 (d, J = 6.8 Hz, 1H), 3.94 (s, 3H), 3.77 (s, 2H), 2.76-2.65 (m, 6H), 2.64-2.60 (m, 6H), 2.38 (s, 3H), 1.91-1.77 (m, 2H); LC-MS (ESI) m/z: 659 [M + H]$^+$ | A |

TABLE 1-continued

| Example | Structure / Name | $^1H$ NMR/LC-MS | Purification condition |
|---|---|---|---|
| 62 | 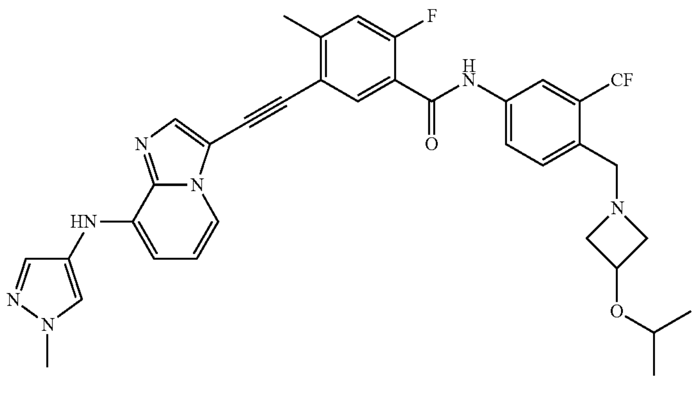 2-fluoro-N-(4-((3-isopropoxyazetidin-1-yl)methyl)-3-(trifluoromethyl)phenyl)-4-methyl-5-((8-((1-methyl-1H-pyrazol-4-yl)amino)imidazo[1,2-a]pyridin-3-yl)ethynyl)benzamide | $^1H$ NMR (400 MHz, $CDCl_3$) δ8.47 (d, J = 16.0 Hz, 1H), 8.35 (d, J = 8.0 Hz, 1H), 7.91 (s, 1H), 7.86 (d, J = 8.0 Hz, 1H), 7.81 (s, 1H), 7.80-7.75 (m, 2H), 7.67 (d, J = 7.9 Hz, 1H), 7.53 (s, 1H), 7.44 (s, 1H), 7.13 (d, J = 13.0 Hz, 1H), 6.85-6.79 (m, 1H), 6.57 (s, 1H), 6.49 (d, J = 7.3 Hz, 1H), 4.24-4.18 (m, 1H), 3.94 (s, 3H), 3.82 (s, 2H), 3.75-3.70 (m, 2H), 3.66-3.49 (m, 1H), 3.01-2.85 (m, 2H), 2.62 (s, 3H), 1.14 (d, J = 6.1 Hz, 6H); LC-MS (ESI) m/z: 660 $[M + H]^+$ | A |
| 63 | 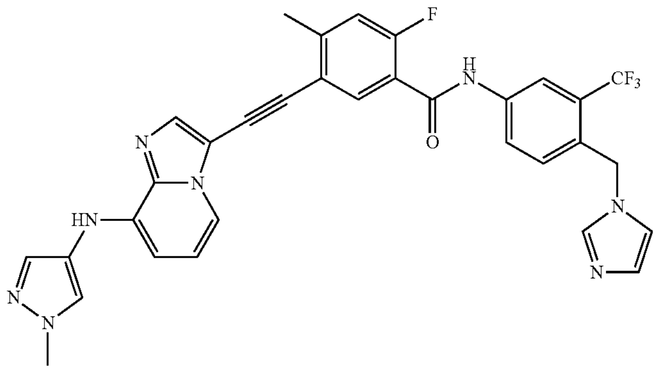 [SMILES: Cc1cc(F)c(C(=O)Nc2ccc(Cn3ccnc3)c(C(F)(F)F)c2)cc1C#Cc1cnc2c(Nc3cnn(C)c3)cccn12] N-(4-((1H-imidazol-1-yl)methyl)-3-(trifluoromethyl)phenyl)-2-fluoro-4-methyl-5-((8-((1-methyl-1H-pyrazol-4-yl)amino)imidazo[1,2-a]pyridin-3-yl)ethynyl)benzamide | $^1H$ NMR (400 MHz, TFA salt, DMSO-$d_6$) δ10.75 (s, 1H), 10.04 (br s, 1H), 8.20 (s, 1H), 8.10 (s, 1H), 8.01-7.95 (m, 2H), 7.86-7.79 (m, 2H), 7.51 (s, 1H), 7.48-7.36 (m, 2H), 7.03-6.92 (m, 1H), 6.62 (d, J = 7.6 Hz, 1H), 4.41 (s, 2H), 4.08-3.90 (m, 2H), 3.83 (s, 3H), 3.70-3.62 (m, 2H), 3.34-3.25 (m, 2H), 3.22-3.10 (m, 2H), 2.59 (s, 3H), 1.72 (s, 6H); LC-MS (ESI) m/z: 613 $[M + H]^+$ | B |

TABLE 1-continued

| Example | Structure / Name | $^1$H NMR/LC-MS | Purification condition |
|---|---|---|---|
| 64 | 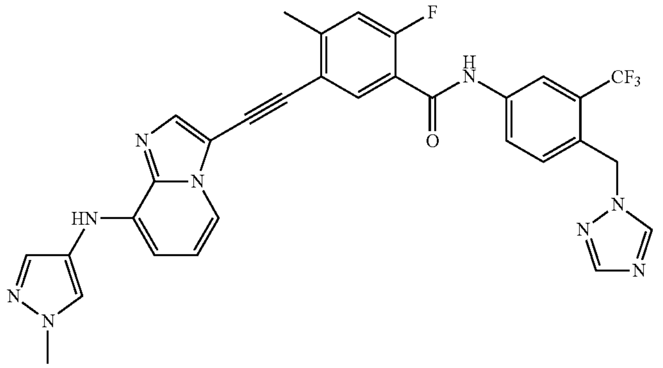 [SMILES: Cc1cc(F)c(C(=O)Nc2ccc(Cn3cncn3)c(C(F)(F)F)c2)cc1C#Cc1cnc2c(Nc3cnn(C)c3)cccn12]<br>N-(4-((1H-1,2,4-triazol-1-yl)methyl)-3-(trifluoromethyl)phenyl)-2-fluoro-4-methyl-5-((8-((1-methyl-1H-pyrazol-4-yl)amino)imidazo[1,2-a]pyridin-3-yl)ethynyl)benzamide | $^1$H NMR (400 MHz, TFA salt, $CDCl_3$) δ8.57 (d, J = 16.4 Hz, 1H), 8.33 (d, J = 8.1 Hz, 1H), 8.15-8.06 (m, 2H), 8.01 (s, 1H), 7.86 (dd, J = 8.5, 2.1 Hz, 1H), 7.82 (s, 1H), 7.80 (d, J = 6.3 Hz, 1H), 7.54 (s, 1H), 7.44 (s, 1H), 7.29 (d, J = 8.5 Hz, 1H), 7.14 (d, J = 12.9 Hz, 1H), 6.83 (t, J = 7.1 Hz, 1H), 6.62 (s, 1H), 6.49 (d, J = 7.4 Hz, 1H), 5.54 (s, 2H), 3.94 (s, 3H), 2.62 (s, 3H); LC-MS (ESI) m/z: 614 $[M + H]^+$ | B |
| 65 | 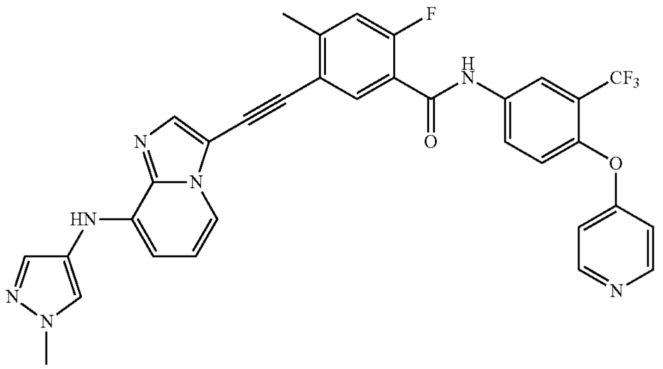 [SMILES: Cc1cc(F)c(C(=O)Nc2ccc(Oc3ccncc3)c(C(F)(F)F)c2)cc1C#Cc1cnc2c(Nc3cnn(C)c3)cccn12]<br>2-fluoro-4-methyl-5-((8-((1-methyl-1H-pyrazol-4-yl)amino)imidazo[1,2-a]pyridin-3-yl)ethynyl)-N-(4-(pyridin-4-yloxy)-3-(trifluoromethyl)phenyl)benzamide | $^1$H NMR (400 MHz, TFA salt, MeOD-$d_4$) δ 8.41 (d, J = 2.32 Hz, 1H), 8.19 (dd, J = 8.66, 2.32 Hz, 1H), 8.12-8.08 (m, 4H), 8.04 (d, J = 7.16 Hz, 1H), 7.76 (s, 1H), 7.70 (d, J = 8.68 Hz, 1H), 7.54 (s, 1H), 7.32 (d, J = 11.28 Hz, 1H), 7.17 (dd, J = 7.78, 6.68 Hz, 1H), 6.89 (d, J = 7.28 Hz, 1H), 6.78 (d, J = 7.56 Hz, 2H), 3.92 (s, 3H), 2.65 (s, 3H); LC-MS (ESI) m/z: 626 $[M + H]^+$ | B |

TABLE 1-continued

| Example | Structure / Name | $^1$H NMR/LC-MS | Purification condition |
|---|---|---|---|
| 66 | 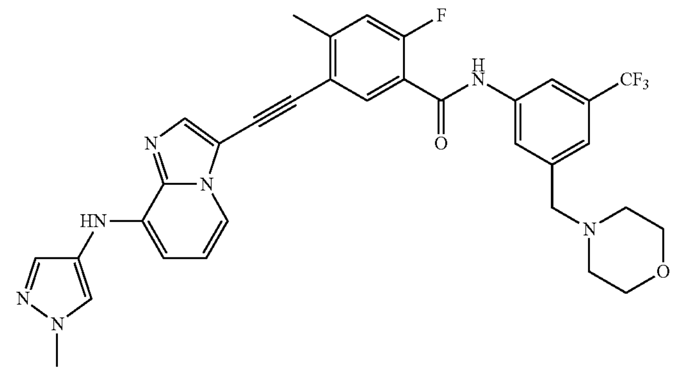 [SMILES: Cc1cc(F)c(C(=O)Nc2cc(CN3CCOCC3)cc(C(F)(F)F)c2)cc1C#Cc1cnc2c(Nc3cnn(C)c3)cccn12] 2-fluoro-4-methyl-5-((8-((1-methyl-1H-pyrazol-4-yl)amino)imidazo[1,2-a]pyridin-3-yl)ethynyl)-N-(3-(morpholinomethyl)-5-(trifluoromethyl)phenyl)benzamide | $^1$H NMR (400 MHz, TFA salt, MeOD-$d_4$) δ 8.30 (s, 1H), 8.25 (s, 1H), 8.18 (d, J = 6.44 Hz, 1H), 8.09 (s, 1H), 8.06 (d, J = 7.16 Hz, 1H), 7.77 (s, 1H), 7.67 (s, 1H), 7.54 (s, 1H), 7.35-7.28 (m, 2H), 7.05 (d, J = 7.76 Hz, 1H), 4.48 (s, 2H), 4.05-3.97 (m, 2H), 3.93 (s, 3H), 3.81-3.75 (m, 2H), 3.36-3.30 (m, 4H), 2.66 (s, 3H); LC-MS (ESI) m/z: 632 $[M + H]^+$ | B |
| 67 | 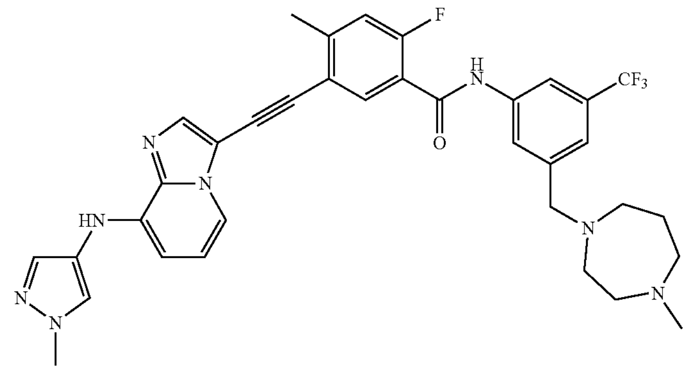 [SMILES: Cc1cc(F)c(C(=O)Nc2cc(CN3CCCN(C)CC3)cc(C(F)(F)F)c2)cc1C#Cc1cnc2c(Nc3cnn(C)c3)cccn12] 2-fluoro-4-methyl-N-(3-((4-methyl-1,4-diazepan-1-yl)methyl)-5-(trifluoromethyl)phenyl)-5-((8-((1-methyl-1H-pyrazol-4-yl)amino)imidazo[1,2-a]pyridin-3-yl)ethynyl)benzamide | $^1$H NMR (400 MHz, TFA salt, MeOD-$d_4$) δ 8.26 (s, 1H), 8.22 (s, 1H), 8.18 (d, J = 6.44 Hz, 1H), 8.06 (d, J = 7.12 Hz, 1H), 8.00 (s, 1H), 7.77 (s, 1H), 7.61 (s, 1H), 7.55 (s, 1H), 7.35-7.28 (m, 2H), 7.05 (d, J =7.84 Hz, 1H), 4.24 (s, 2H), 3.93 (s, 3H), 3.63-3.44 (m, 6H), 3.24 (t, J = 4.6 Hz, 2H), 2.96 (s, 3H), 2.66 (s, 3H), 2.24-2.21 (m, 2H); LC-MS (ESI) m/z: 659 $[M + H]^+$ | B |

TABLE 1-continued

| Example | Structure / Name | $^1$H NMR/LC-MS | Purification condition |
|---|---|---|---|
| 68 | 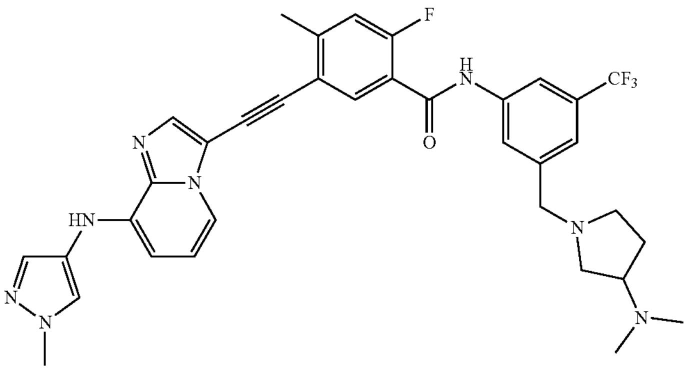 [SMILES: Cc1cc(F)c(C(=O)Nc2cc(CN3CCC(N(C)C)C3)cc(C(F)(F)F)c2)cc1C#Cc1cnc2c(Nc3cnn(C)c3)cccn12] N-(3-((3-(dimethylamino)pyrrolidin-1-yl)methyl)-5-(trifluoromethyl)phenyl)-2-fluoro-4-methyl-5-((8-((1-methyl-1H-pyrazol-4-yl)amino)imidazo[1,2-a]pyridin-3-yl)ethynyl)benzamide | $^1$H NMR (400 MHz, TFA salt, MeOD-$d_4$) δ 8.18 (s, 1H), 8.13 (s, 1H), 8.10 (d, J = 6.52 Hz, 1H), 8.03 (d, J = 7.2 Hz, 1H), 8.00 (s, 1H), 7.76 (s, 1H), 7.58 (s, 1H), 7.54 (s, 1H), 7.32 (d, J = 11.24 Hz, 1H), 7.20 (dd, J = 7.76, 6.76 Hz, 1H), 6.92 (d, J = 7.72 Hz, 1H), 4.18 (dd, J = 17.56, 13.2 Hz, 2H), 4.05-4.02 (m, 1H), 3.92 (s, 3H), 3.48-3.44 (m, 1H), 3.08-3.03 (m, 1H), 2.92 (s, 6H), 2.65 (s, 3H), 2.52-2.46 (m, 1H), 2.28-2.21 (m, 1H), 2.03-2.02 (m, 1H), 1.07-1.05 (m, 1H); LC-MS (ESI) m/z: 659 $[M + H]^+$ | B |
| 69 | 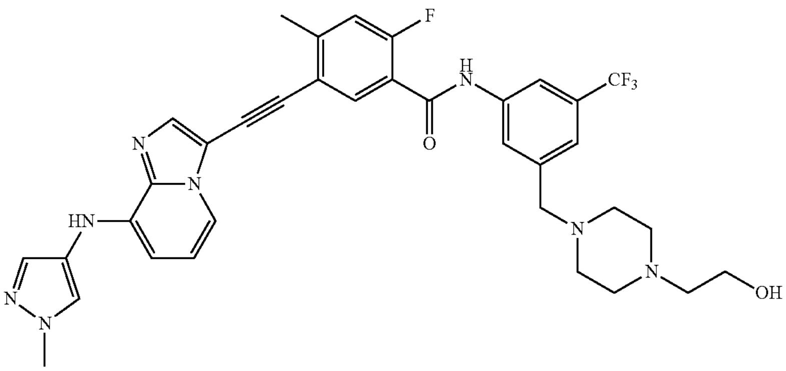 [SMILES: Cc1cc(F)c(C(=O)Nc2cc(CN3CCN(CCO)CC3)cc(C(F)(F)F)c2)cc1C#Cc1cnc2c(Nc3cnn(C)c3)cccn12] 2-fluoro-N-(3-((4-(2-hydroxyethyl)piperazin-1-yl)methyl)-5-(trifluoromethyl)phenyl)-4-methyl-5-((8-((1-methyl-1H-pyrazol-4-yl)amino)imidazo[1,2-a]pyridin-3-yl)ethynyl)benzamide | $^1$H NMR (400 MHz, TFA salt, MeOD-$d_4$) δ 8.34 (s, 1H), 8.23 (t, J = 6.68 Hz, 2H), 7.78 (s, 1H), 7.55 (s, 1H), 7.40-7.34 (m, 1H), 7.28 (d, J = 11.64 Hz, 1H), 7.14 (dd, J = 7.76, 2.56 Hz, 1H), 7.10 (s, 1H), 7.07 (s, 1H), 7.04 (s, 1H), 4.63 (t, J = 4.96 Hz, 2H), 4.04 (s, 2H), 3.98 (s, 1H), 3.93 (s, 3H), 3.13 (br-s, 2H), 2.64 (s, 3H); LC-MS (ESI) m/z: 675 $[M + H]^+$ | B |

TABLE 1-continued

| Example | Structure / Name | $^1$H NMR/LC-MS | Purification condition |
| --- | --- | --- | --- |
| 70 | 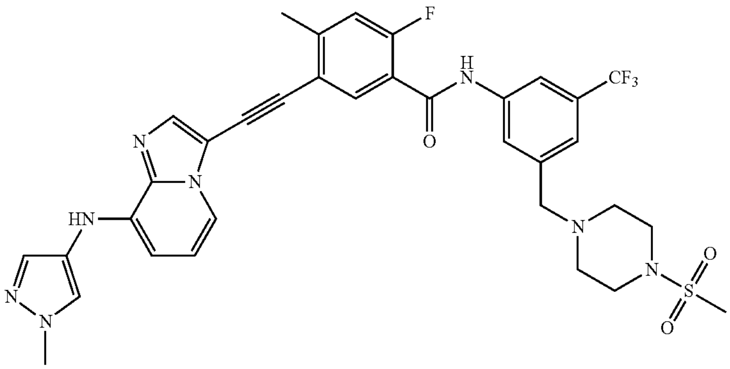 [SMILES: Cc1cc(F)c(C(=O)Nc2cc(CN3CCN(S(C)(=O)=O)CC3)cc(C(F)(F)F)c2)cc1C#Cc1cnc2c(Nc3cnn(C)c3)cccn12] 2-fluoro-4-methyl-5-((8-((1-methyl-1H-pyrazol-4-yl)amino)imidazo[1,2-a]pyridin-3-yl)ethynyl)-N-(3-((4-(methylsulfonyl)piperazin-1-yl)methyl)-5-(trifluoromethyl)phenyl)benzamide | $^1$H NMR (400 MHz, TFA salt, MeOD-$d_4$) δ 8.26 (d, J = 10.36 Hz, 2H), 8.17 (d, J = 6.52 Hz, 1H), 8.10 (s, 1H), 8.06 (d, J = 7.12 Hz, 1H), 7.77 (s, 1H), 7.67 (s, 1H), 7.54 (s, 1H), 7.34-7.28 (m, 2H), 7.04 (d, J = 7.84 Hz, 1H), 4.49 (s, 2H), 3.93 (s, 3H), 3.55 (br-s, 4H), 3.43 (br-s, 4H), 2.96 (s, 3H), 2.66 (s, 3H); LC-MS (ESI) m/z: 709 $[M + H]^+$ | B |
| 71 | 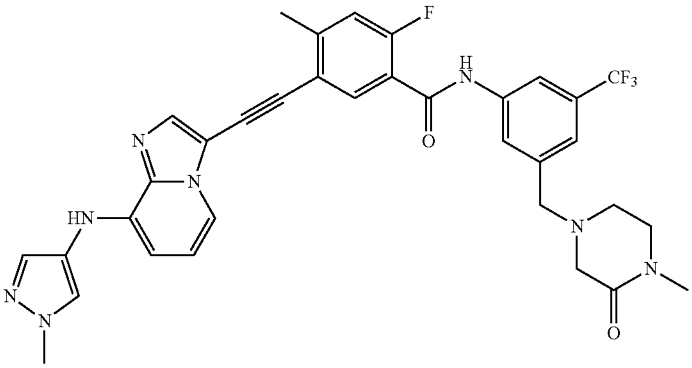 [SMILES: Cc1cc(F)c(C(=O)Nc2cc(CN3CCN(C)C(=O)C3)cc(C(F)(F)F)c2)cc1C#Cc1cnc2c(Nc3cnn(C)c3)cccn12] 2-fluoro-4-methyl-5-((8-((1-methyl-1H-pyrazol-4-yl)amino)imidazo[1,2-a]pyridin-3-yl)ethynyl)-N-(3-((4-methyl-3-oxopiperazin-1-yl)methyl)-5-(trifluoromethyl)phenyl)benzamide | $^1$H NMR (400 MHz, TFA salt, MeOD-$d_4$) δ 8.22 (s, 1H), 8.16-8.14 (m, 2H), 8.08 (s, 1H), 8.05 (d, J = 7.16 Hz, 1H), 7.77 (s, 1H), 7.58 (s, 1H), 7.54 (s, 1H), 7.32 (d, J = 11.16 Hz, 1H), 7.26 (dd, J = 7.8, 6.72 Hz, 1H), 7.01 (d, J = 7.8 Hz, 1H), 4.15 (s, 2H), 3.92 (s, 3H), 3.54-3.52 (m, 4H), 3.24 (t, J = 5.92 Hz, 2H), 2.98 (s, 3H), 2.65 (s, 3H); LC-MS (ESI) m/z: 659 $[M + H]^+$ | B |

TABLE 1-continued

| Example | Structure / Name | $^1H$ NMR/LC-MS | Purification condition |
|---|---|---|---|
| 72 | 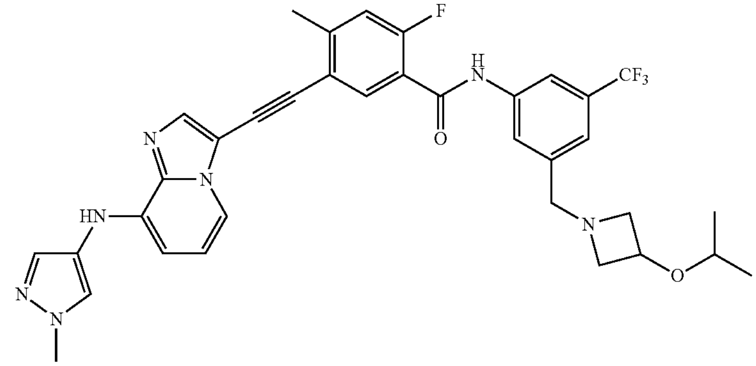 [SMILES: Cc1cc(F)c(C(=O)Nc2cc(CN3CC(OC(C)C)C3)cc(C(F)(F)F)c2)cc1C#Cc1cnc2c(Nc3cnn(C)c3)cccn12] 2-fluoro-N-(3-((3-isopropoxyazetidin-1-yl)methyl)-5-(trifluoromethyl)phenyl)-4-methyl-5-((8-((1-methyl-1H-pyrazol-4-yl)amino)imidazo[1,2-a]pyridin-3-yl)ethynyl)benzamide | $^1H$ NMR (400 MHz, TFA salt, MeOD-$d_4$) δ 8.29 (s, 1H), 8.21-8.19 (m, 2H), 8.08-8.06 (m, 2H), 7.77 (s, 1H), 7.60 (s, 1H), 7.54 (s, 1H), 7.34 (dd, J = 6.26, 1.84 Hz, 1H), 7.31 (s, 1H), 7.09 (d, J = 7.88 Hz, 1H), 4.52 (s, 2H), 4.41 (t, J = 10.56 Hz, 2H), 4.09 (dd, J = 11.26, 5.04 Hz, 2H), 3.93 (s, 3H), 3.71 (quint, J = 6.15 Hz, 1H), 2.66 (s, 3H), 1.17 (s, 3H), 1.15 (s, 3H); LC-MS (ESI) m/z: 660 $[M + H]^+$ | B |
| 73 | 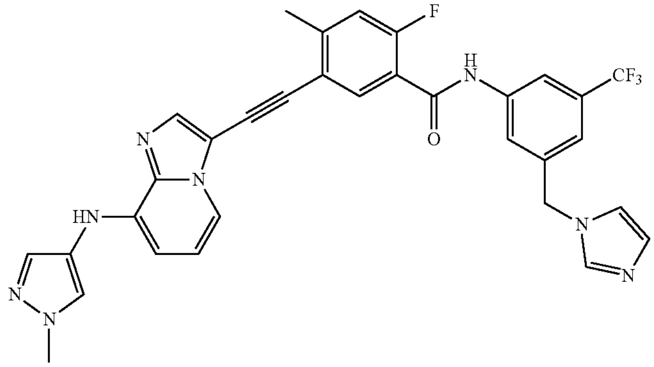 [SMILES: Cc1cc(F)c(C(=O)Nc2cc(Cn3ccnc3)cc(C(F)(F)F)c2)cc1C#Cc1cnc2c(Nc3cnn(C)c3)cccn12] N-(3-((1H-imidazol-1-yl)methyl)-5-(trifluoromethyl)phenyl)-2-fluoro-4-methyl-5-((8-((1-methyl-1H-pyrazol-4-yl) amino)imidazo[1,2-a]pyridin-3-yl)ethynyl)benzamide | $^1H$ NMR (400 MHz, TFA salt, MeOD-$d_4$) δ 9.14 (s, 1H), 8.25 (s, 1H), 8.16 (d, J = 6.44 Hz, 1H), 8.07 (d, J = 6.16 Hz, 2H), 8.03 (d, J = 7.16 Hz, 1H), 7.76 (s, 1H), 7.71 (t, J = 1.56 Hz, 1H), 7.63 (t, J = 1.52 Hz, 1H), 7.54 (s, 2H), 7.32 (s, 1H), 7.29 (dd, J = 6.18, 1.2 Hz, 1H), 7.06 (d, J = 7.8 Hz, 1H), 5.58 (s, 2H), 3.92 (s, 3H), 2.64 (s, 3H); LC-MS (ESI) m/z: 613 $[M + H]^+$ | B |

TABLE 1-continued
| Example | Structure / Name | $^1$H NMR/LC-MS | Purification condition |
|---|---|---|---|
| 74 | 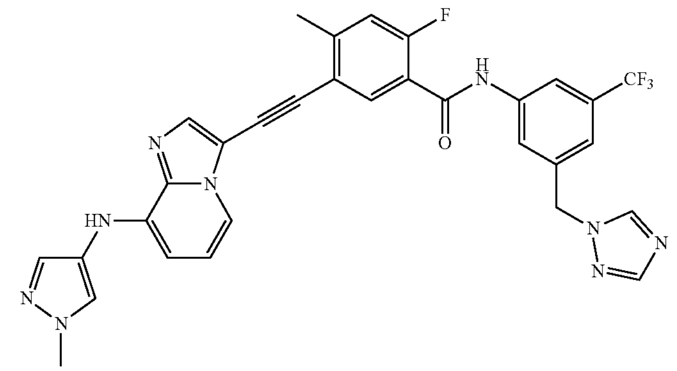 [SMILES: Cc1cc(F)c(C(=O)Nc2cc(Cn3cncn3)cc(C(F)(F)F)c2)cc1C#Cc1cnc2c(Nc3cnn(C)c3)cccn12]<br>N-(3-((1H-1,2,4-triazol-1-yl)methyl)-5-(trifluoromethyl)phenyl)-2-fluoro-4-methyl-5-((8-((1-methyl-1H-pyrazol-4-yl)amino)imidazo[1,2-a]pyridin-3-yl)ethynyl)benzamide | $^1$H NMR (400 MHz, TFA salt, $CDCl_3$) δ8.55 (d, J = 16.5 Hz, 1H), 8.32 (d, J = 8.1 Hz, 1H), 8.19 (s, 1H), 8.03 (s, 1H), 7.90 (d, J = 9.5 Hz, 2H), 7.83 (s, 1H), 7.80 (d, J = 6.0 Hz, 1H), 7.54 (s, 1H), 7.44 (s, 1H), 7.31 (s, 1H), 7.14 (d, J = 12.9 Hz, 1H), 6.86-6.80 (m, 1H), 6.59 (s, 1H), 6.49 (d, J = 7.3 Hz, 1H), 5.44 (s, 2H), 3.94 (s, 3H), 2.63 (s, 3H); LC-MS (ESI) m/z: 614 $[M + H]^+$ | B |
scheme-2
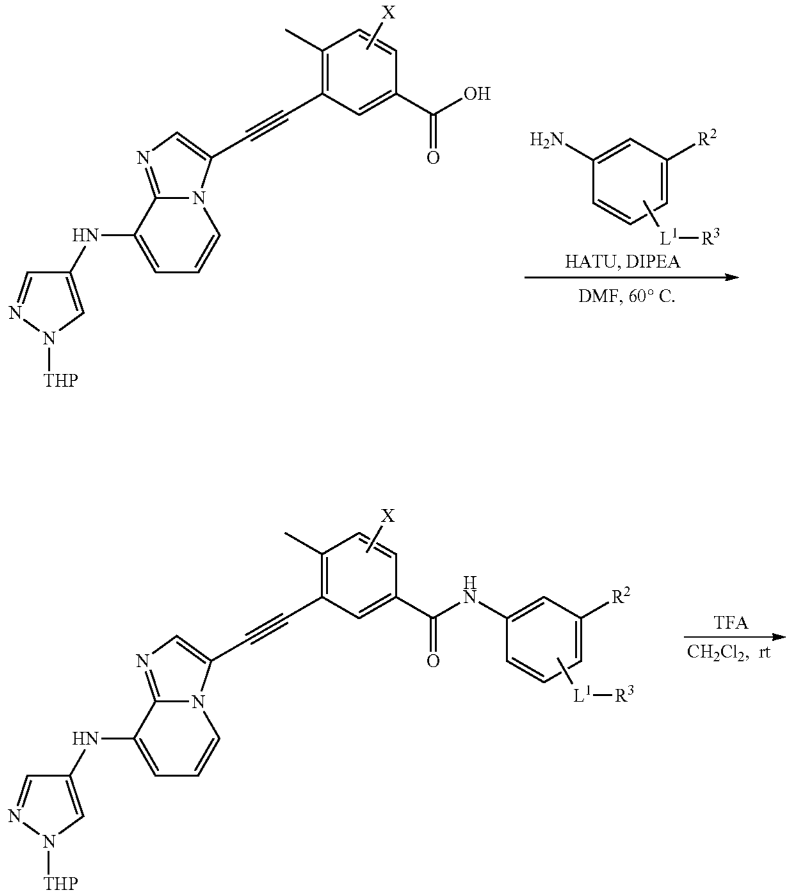

-continued

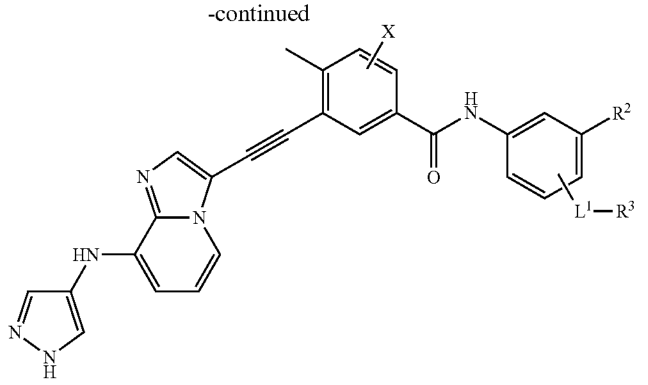

<Example 75> Preparation of 5-((8-((1H-pyrazol-4-yl)amino)imidazo[1,2-a]pyridin-3-yl)ethynyl)-N-(3-(2-cyanopropan-2-yl)-5-(4-methyl-1H-imidazol-1-yl)phenyl)-2-fluoro-4-methylbenzamide

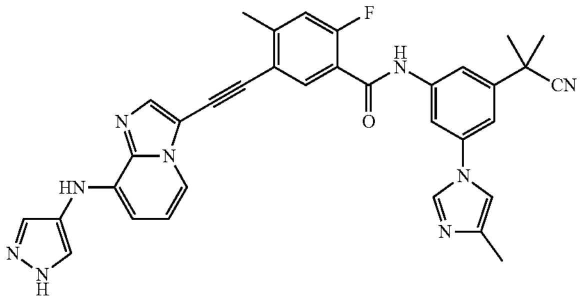 [SMILES: Cc1cn(-c2cc(NC(=O)c3cc(C#Cc4cnc5c(Nc6cn[nH]c6)cccn45)c(C)cc3F)cc(C(C)(C)C#N)c2)cn1]

Step 1: Preparation of N-(3-(2-cyanopropan-2-yl)-5-(4-methyl-1H-imidazol-1-yl)phenyl)-2-fluoro-4-methyl-5-((8-((1-(tetrahydro-2H-pyran-2-yl)-1H-pyrazol-4-yl)amino)imidazo[1,2-a]pyridin-3-yl)ethynyl)benzamide

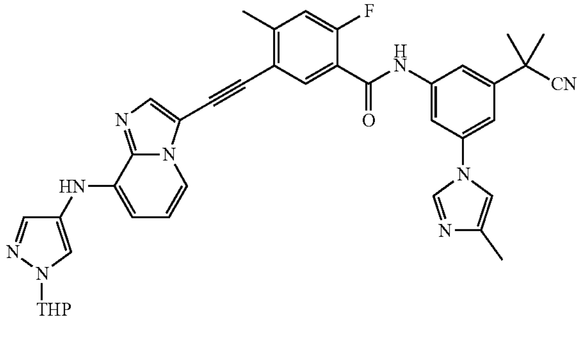

2-Fluoro-4-methyl-5-((8-((1-(tetrahydro-2H-pyran-2-yl)-1H-pyrazol-4-yl)amino)imidazo[1,2-a]pyridin-3-yl)ethynyl)benzoic acid (50 mg, 0.109 mmol) was dissolved in DMF (1 mL), to which HATU (62.1 mg, 0.163 mmol), DIPEA (0.038 mL, 0.218 mmol) and 2-(3-amino-5-(4-methyl-1H-imidazol-1-yl)phenyl)-2-methylpropanenitrile (28.8 mg, 0.120 mmol) were added. The reaction mixture was heated and stirred at 60° C. for 16 hours. Upon completion of the reaction, the mixture was cooled to room temperature, diluted with ethyl acetate, and washed with distilled water and brine. The organic layer was dried over $Na_2SO_4$, filtered and concentrated, and the obtained residue was purified by silica gel chromatography to give a target compound (40 mg, 54%) as a yellow solid.

LC-MS (ESI) m/z: 682[M+H]$^+$

Step 2: Preparation of 5-((8-((1H-pyrazol-4-yl)amino)imidazo[1,2-a]pyridin-3-yl)ethynyl)-N-(3-(2-cyanopropan-2-yl)-5-(4-methyl-1H-imidazol-1-yl)phenyl)-2-fluoro-4-methylbenzamide

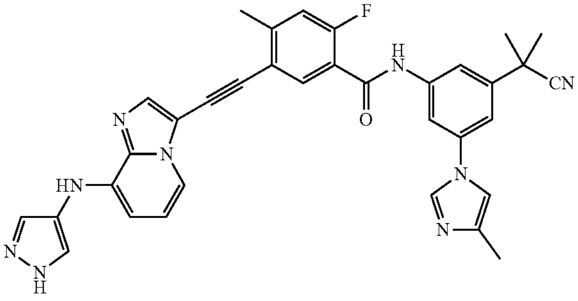 [SMILES: Cc1cn(-c2cc(NC(=O)c3cc(C#Cc4cnc5c(Nc6cn[nH]c6)cccn45)c(C)cc3F)cc(C(C)(C)C#N)c2)cn1]

The N-(3-(2-cyanopropan-2-yl)-5-(4-methyl-1H-imidazol-1-yl)phenyl)-2-fluoro-4-methyl-5-((8-((1-(tetrahydro-2H-pyran-2-yl)-1H-pyrazol-4-yl)amino)imidazo[1,2-a]pyridin-3-yl)ethynyl)benzamide (40 mg, 0.059 mmol) prepared in step 1 was dissolved in $CH_2Cl_2$ (1 mL), and TFA (0.5 mL, 6.53 mmol) was added thereto, followed by stirring at room temperature for 2 hours. Upon completion of the reaction, the mixture was concentrated under reduced pressure, and the obtained residue was purified by preparative HPLC (0.1% TFA in water/acetonitrile). The obtained target compound in the form of TFA salt was neutralized with a supersaturated $NaHCO_3$ aqueous solution, extracted with ethyl acetate, and washed with distilled water. The extracted organic layer was dried over $Na_2SO_4$, filtered, and then concentrated under reduced pressure to give a target compound (33.3 mg, 80%) as a yellow solid.

$^1$H NMR (400 MHz, DMSO-d$_6$) δ 12.7 (br s, 1H), 10.8 (br s, 1H), 8.18 (s, 1H), 8.16 (s, 1H), 8.15-8.12 (m, 1H), 8.04-7.93 (m, 4H), 7.86 (s, 1H), 7.84-7.53 (br s, 2H), 7.48-7.41 (m, 3H), 6.95 (t, J=7.1 Hz, 1H), 6.58 (d, J=7.4 Hz, 1H), 2.60 (s, 3H), 2.18 (s, 3H), 1.75 (s, 6H); LC-MS (ESI) m/z: 598[M+H]$^+$

The compounds of Examples 76 to 114 were prepared in a method similar to the method described in Example 75, and the structures and analysis results of the compounds are summarized in Table 2 below.

TABLE 2

| Example | Structure/Name | $^1$H NMR/LC MS | Purification condition |
|---|---|---|---|
| 76 | 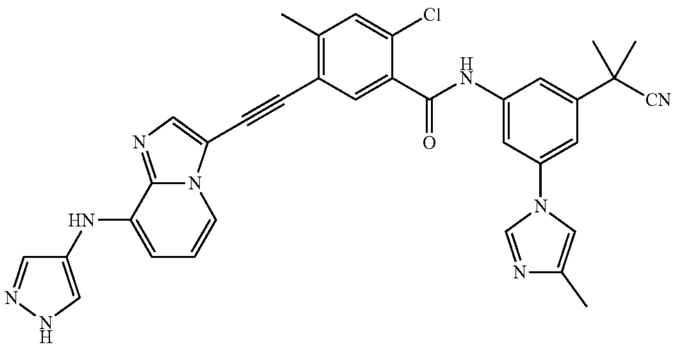 [SMILES: Cc1cn(-c2cc(NC(=O)c3cc(C#Cc4cnc5c(Nc6cn[nH]c6)cccn45)c(C)cc3Cl)cc(C(C)(C)C#N)c2)cn1] 5-((8-((1H-pyrazol-4-yl)amino)imidazo[1,2-a]pyridin-3-yl)ethynyl)-2-chloro-N-(3-(2-cyanopropan-2-yl)-5-(4-methyl-1H-imidazol-1-yl)phenyl)-4-methylbenzamide | LC-MS (ESI) m/z : 614 $[M + H]^+$ | B |
| 77 | 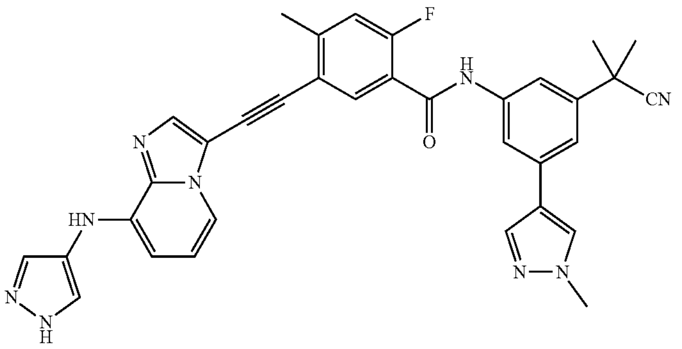 [SMILES: Cc1cc(F)c(C(=O)Nc2cc(-c3cnn(C)c3)cc(C(C)(C)C#N)c2)cc1C#Cc1cnc2c(Nc3cn[nH]c3)cccn12] 5-((8-((1H-pyrazol-4-yl)amino)imidazo[1,2-a]pyridin-3-yl)ethynyl)-N-(3-(2-cyanopropan-2-yl)-5-(1-methyl-1H-pyrazol-4-yl)phenyl)-2-fluoro-4-methylbenzamide | $^1$H NMR (400 MHz, TFA salt, DMSO-$d_6$) δ10.60 (s, 1H), 8.17 (d, J = 5.5 Hz, 2H), 8.05-7.93 (m, 4H), 7.85 (s, 1H), 7.82-7.62 (m, 3H), 7.49-7.39 (m, 2H), 6.95 (t, J = 7.1 Hz, 1H), 6.58 (d, J = 7.5 Hz, 1H), 3.88 (s, 3H), 2.59 (s, 3H), 1.73 (s, 6H); LC-MS (ESI) m/z : 598 $[M + H]^+$ | B |
| 78 | 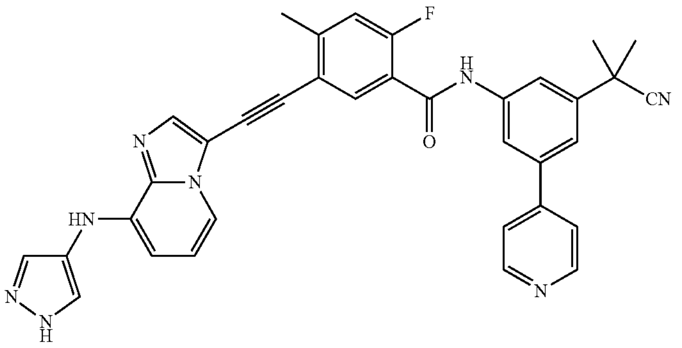 [SMILES: Cc1cc(F)c(C(=O)Nc2cc(-c3ccncc3)cc(C(C)(C)C#N)c2)cc1C#Cc1cnc2c(Nc3cn[nH]c3)cccn12] 5-((8-((1H-pyrazol-4-yl)amino)imidazo [1,2-a]pyridin-3-yl)ethynyl)-N-(3-(2-cyanopropan-2-yl)-5-(pyridin-4-yl)phenyl)-2-fluoro-4-methylbenzamide | $^1$H NMR (400 MHz, TFA salt, MeOD-$d_4$) δ8.78-8.65 (m, 1H), 8.28 (s, 1H), 8.11-7.82 (m, 6H), 7.78 (s, 3H), 7.34-7.28 (m, 1H), 7.02 (t, J = 7.0 Hz, 1H), 6.67 (d, J = 7.7 Hz, 1H), 2.65 (s, 3H), 1.84 (s, 6H); LC-MS (ESI) m/z : 595 $[M + H]^+$ | B |

TABLE 2-continued

| Example | Structure/Name | $^1$H NMR/LC MS | Purification condition |
| --- | --- | --- | --- |
| 79 | 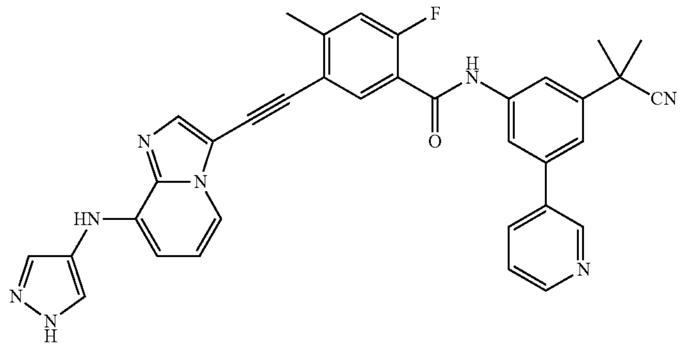 [SMILES: Cc1cc(F)c(C(=O)Nc2cc(-c3cccnc3)cc(C(C)(C)C#N)c2)cc1C#Cc1cnc2c(Nc3cn[nH]c3)cccn12] 5-((8-((1H-pyrazol-4-yl)amino)imidazo[1,2-a]pyridin-3-yl) ethynyl)-N-(3-(2-cyanopropan-2-yl)-5-(pyridin-3-yl)phenyl)-2-fluoro-4-methylbenzamide | $^1$H NMR (400 MHz, TFA salt, DMSO-$d_6$) δ10.74 (s, 1H), 8.91 (d, J = 2.2 Hz, 1H), 8.63 (dd, J = 4.8, 1.5 Hz, 1H), 8.17 (s, 1H), 8.13-8.06 (m, 2H), 8.04-7.99 (m, 2H), 7.99-7.94 (m, 2H), 7.72 (s, 2H), 7.60-7.52 (m, 2H), 7.45 (d, J = 11.1 Hz, 1H), 6.99-6.92 (m, 1H), 6.58 (d, J = 7.5 Hz, 1H), 2.60 (s, 3H), 1.77 (s, 6H); LC-MS (ESI) m/z : 595 $[M + H]^+$ | B |
| 80 | 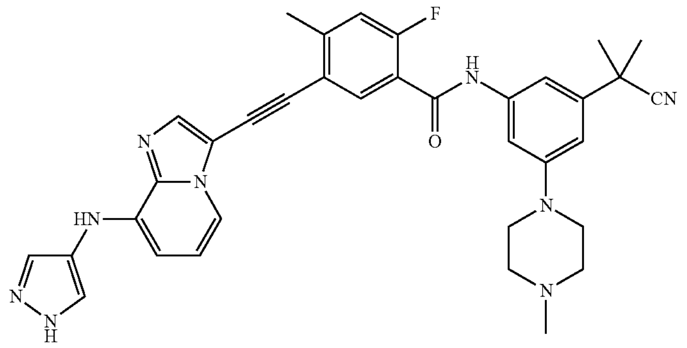 [SMILES: Cc1cc(F)c(C(=O)Nc2cc(N3CCN(C)CC3)cc(C(C)(C)C#N)c2)cc1C#Cc1cnc2c(Nc3cn[nH]c3)cccn12] 5-((8-((1H-pyrazol-4-yl)amino)imidazo[1,2-a]pyridin-3-yl)ethynyl)-N-(3-(2-cyanopropan-2-yl)-5-(4-methylpiperazin-1-yl)phenyl)-2-fluoro-4-methylbenzamide | $^1$H NMR (400 MHz, $CDCl_3$) δ 8.43 (d, J = 15.76 Hz, 1H), 8.32 (d, J = 8.08 Hz, 1H), 7.81-7.79 (m, 2H), 7.66 (s, 2H), 7.37 (s, 1H), 7.13-7.09 (m, 2H), 6.87 (s, 1H), 6.82 (t, J = 7.16 Hz, 1H), 6.72 (s, 1H), 6.49 (d, J = 7.36 Hz, 1H), 3.29 (t, J = 4.8 Hz, 4H), 2.61 (s, 3H), 2.58 (t, J = 5.0 Hz, 4H), 2.36 (s, 3H), 1.74 (s, 6H); LC-MS (ESI) m/z : 616 $[M + H]^+$ | A |
| 81 | 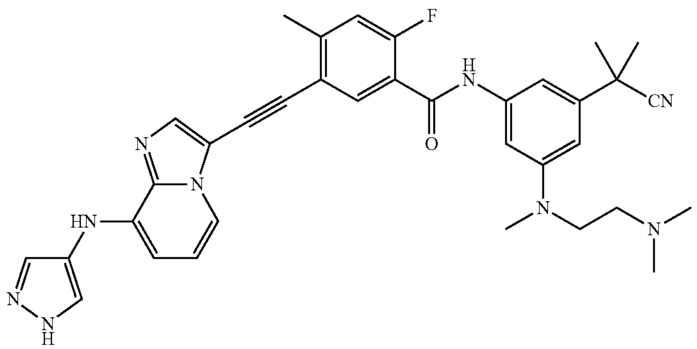 [SMILES: Cc1cc(F)c(C(=O)Nc2cc(N(C)CCN(C)C)cc(C(C)(C)C#N)c2)cc1C#Cc1cnc2c(Nc3cn[nH]c3)cccn12] 5-((8-((1H-pyrazol-4-yl) amino)imidazo[1,2-a]pyridin-3-yl)ethynyl)-N-(3-(2-cyanopropan-2-yl)-5-((2-(dimethylamino)ethyl)(methyl) amino)phenyl)-2-fluoro-4-methylbenzamide | $^1$H NMR (400 MHz, TFA salt, DMSO-$d_6$) δ10.36 (s, 1H), 8.16 (s, 1H), 8.00-7.91 (m, 2H), 7.41 (d, J = 11.0 Hz, 1H), 7.18 (d, J = 13.7 Hz, 2H), 6.98-6.90 (m, 1H), 6.57 (d, J = 7.4 Hz, 1H), 6.52 (s, 1H), 3.49-3.40 (m, 2H), 2.93 (s, 3H), 2.58 (s, 3H), 2.46-2.34 (m, 2H), 2.21 (s, 6H), 1.67 (s, 6H); LC-MS (ESI) m/z : 618 $[M + H]^+$ | B |

TABLE 2-continued

| Example | Structure/Name | $^1$H NMR/LC MS | Purification condition |
|---|---|---|---|
| 82 | 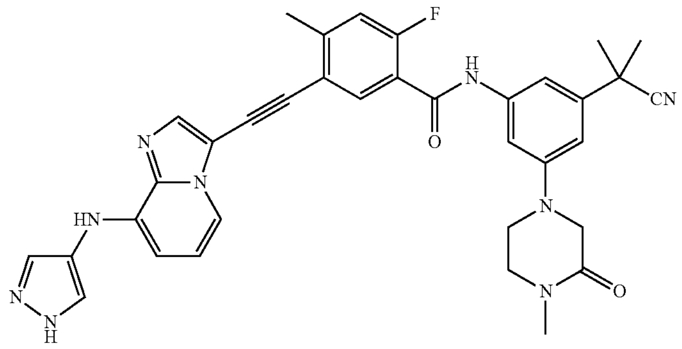 [SMILES: Cc1cc(F)c(C(=O)Nc2cc(N3CCN(C)C(=O)C3)cc(C(C)(C)C#N)c2)cc1C#Cc1cnc2c(Nc3cn[nH]c3)cccn12] 5-((8-((1H-pyrazol-4-yl)amino)imidazo[1,2-a]pyridin-3-yl)ethynyl)-N-(3-(2-cyanopropan-2-yl)-5-(4-methyl-3-oxopiperazin-1-yl)phenyl)-2-fluoro-4-methylbenzamide | $^1$H NMR (400 MHz, TFA salt, DMSO-$d_6$) δ10.46 (s, 1H), 8.16 (s, 1H), 8.02-7.92 (m, 2H), 7.48-7.39 (m, 2H), 7.37 (s, 1H), 7.00-6.90 (m, 1H), 6.81 (s, 1H), 6.58 (d, J = 7.5 Hz, 1H), 3.79 (s, 2H), 3.56-3.49 (m, 2H), 3.49-3.42 (m, 2.91 (s, 3H), 2.58 (s, 3H), 1.69 (s, 6H); LC-MS (ESI) m/z : 630 [M + H]$^+$ | B |
| 83 | 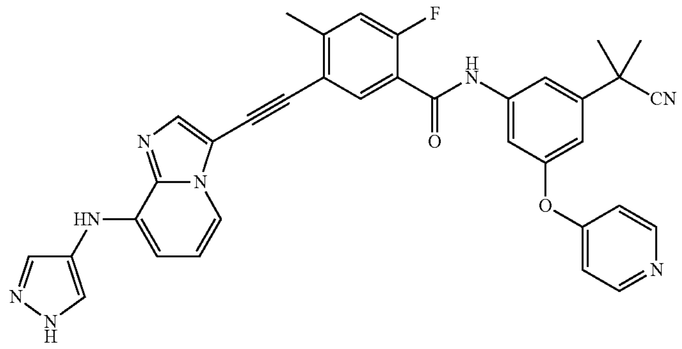 [SMILES: Cc1cc(F)c(C(=O)Nc2cc(Oc3ccncc3)cc(C(C)(C)C#N)c2)cc1C#Cc1cnc2c(Nc3cn[nH]c3)cccn12] 5-((8-((1H-pyrazol-4-yl)amino)imidazo[1,2-a]pyridin-3-yl)ethynyl)-N-(3-(2-cyanopropan-2-yl)-5-(pyridin-4-yloxy)phenyl)-2-fluoro-4-methylbenzamide | $^1$H NMR (400 MHz, TFA salt, DMSO-$d_6$) δ10.89 (s, 1H), 8.17 (s, 1H), 8.08-7.88 (m, 7H), 7.50-7.39 (m, 2H), 6.98-6.92 (m, 1H), 6.58 (d, J = 7.1 Hz, 1H), 6.28 (d, J = 7.8 Hz, 2H), 2.60 (s, 3H), 1.75 (s, 6H); LC-MS (ESI) m/z : 611 [M + H]$^+$ | B |
| 84 | 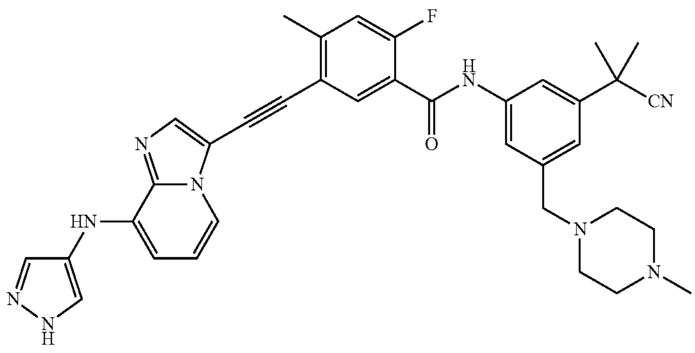 [SMILES: Cc1cc(F)c(C(=O)Nc2cc(CN3CCN(C)CC3)cc(C(C)(C)C#N)c2)cc1C#Cc1cnc2c(Nc3cn[nH]c3)cccn12] 5-((8-((1H-pyrazol-4-yl)amino)imidazo[1,2-a]pyridin-3-yl)ethynyl)-N-(3-(2-cyanopropan-2-yl)-5-((4-methylpiperazin-1-yl)methyl)phenyl)-2-fluoro-4-methylbenzamide | $^1$H NMR (400 MHz, $CDCl_3$) δ 8.49 (d, J = 15.44 Hz, 1H), 8.30 (d, J = 8.0 Hz, 1H), 7.81-7.77 (m, 3H), 7.66 (s, 2H), 7.49 (s, 1H), 7.10 (d, J = 12.72 Hz, 1H), 6.81 (t, J = 7.16 Hz, 1H), 6.76 (s, 1H), 6.78 (d, J = 7.44 Hz, 1H), 3.55 (s, 2H), 2.60 (s, 3H), 2.51 (br-s, 8H), 2.30 (s, 3H), 1.76 (s, 6H); LC-MS (ESI) m/z : 630 [M + H]$^+$ | A |

TABLE 2-continued

| Example | Structure/Name | $^1$H NMR/LC MS | Purification condition |
| --- | --- | --- | --- |
| 85 | 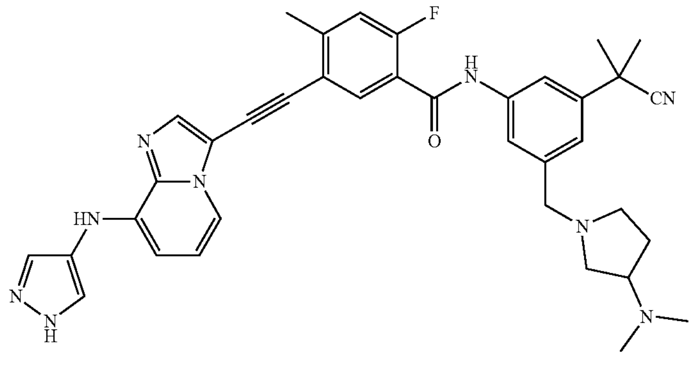 [SMILES: Cc1cc(F)c(C(=O)Nc2cc(CN3CCC(N(C)C)C3)cc(C(C)(C)C#N)c2)cc1C#Cc1cnc2c(Nc3cn[nH]c3)cccn12] 5-((8-((1H-pyrazol-4-yl)amino)imidazo[1,2-a]pyridin-3-yl)ethynyl)-N-(3-(2-cyanopropan-2-yl)-5-((3-(dimethylamino)pyrrolidin-1-yl)methyl)phenyl)-2-fluoro-4-methylbenzamide | $^1$H NMR (400 MHz, $CDCl_3$) δ 8.49 (d, J = 15.36 Hz, 1H), 8.24 (d, J = 8.0 Hz, 1H), 7.87 (s, 1H), 7.78 (s, 1H), 7.74 (d, J = 6.6 Hz, 1H), 7.65 (s, 2H), 7.43 (s, 1H), 7.25 (s, 1H), 7.05 (d, J = 12.76 Hz, 1H), 6.79 (t, J = 7.24 Hz, 1H), 6.74 (s, 1H), 6.46 (d, J = 7.32 Hz, 1H), 3.70 (d, J = 13.24 Hz, 1H), 3.59 (d, J = 13.24 Hz, 1H), 2.83-2.78 (m, 2H), 2.74-2.68 (m, 1H), 2.62-2.57 (m, 4H), 2.47-2.41 (m, 1H), 2.23 (s, 6H), 2.07-1.98 (m, 1H), 1.82-1.75 (m, 7H); LC-MS (ESI) m/z : 644 [M + H]$^+$ | A |
| 86 | 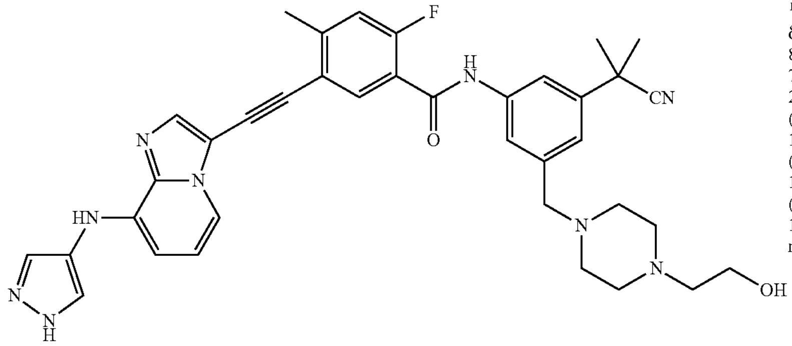 5-((8-((1H-pyrazol-4-yl)amino)imidazo[1,2-a]pyridin-3-yl)ethynyl)-N-(3-(2-cyanopropan-2-yl)-5-((4-(2-hydroxyethyl)piperazin-1-yl) methyl)phenyl)-2-fluoro-4-methylbenzamide | $^1$H NMR (400 MHz, $CDCl_3$) δ8.47 (d, J = 15.6 Hz, 1H), 8.34 (d, J = 8.1 Hz, 1H), 7.88-7.75 (m, 3H), 7.67 (s, 2H), 7.56-7.50 (m, 1H), 7.28 (s, 1H), 7.13 (d, J = 12.8 Hz, 1H), 6.87-6.80 (m, 1H), 6.64 (s, 1H), 6.49 (d, J = 7.4 Hz, 1H), 3.65-3.58 (m, 2H), 3.56 (s, 2H), 2.75-2.39 (m, 13H), 1.77 (s, 6H); LC-MS (ESI) m/z : 614 [M + H]$^+$ | A |
| 87 | 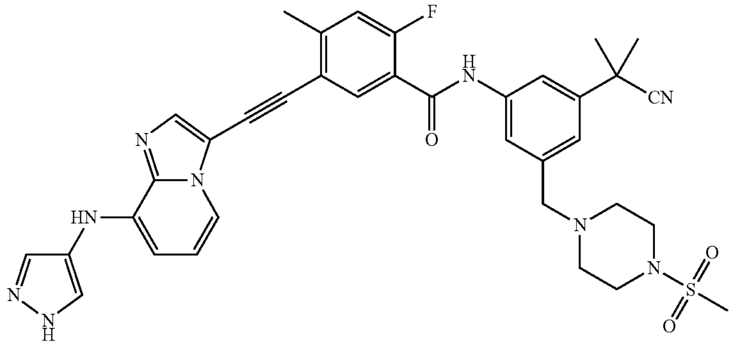 [SMILES: Cc1cc(F)c(C(=O)Nc2cc(CN3CCN(S(C)(=O)=O)CC3)cc(C(C)(C)C#N)c2)cc1C#Cc1cnc2c(Nc3cn[nH]c3)cccn12] 5-((8-((1H-pyrazol-4-yl)amino)imidazo[1,2-a]pyridin-3-yl)ethynyl)-N-(3-(2-cyanopropan-2-yl)-5-((4-(methylsulfonyl)piperazin-1-yl) methyl)phenyl)-2-fluoro-4-methylbenzamide | $^1$H NMR (400 MHz, $CDCl_3$) δ 8.48 (d, J = 15.68 Hz, 1H), 8.33 (d, J = 8.08 Hz, 1H), 7.82-7.79 (m, 2H), 7.70 (s, 1H), 7.67 (s, 2H), 7.60 (s, 1H), 7.28 (s, 1H), 7.13 (d, J = 12.84 Hz, 1H), 6.83 (t, J = 7.16 Hz, 1H), 6.70 (s, 1H), 6.49 (d, J = 7.32 Hz, 1H), 3.59 (s, 2H), 3.27 (br-s, 4H), 2.79 (s, 3H), 2.62 (s, 3H), 2.59 (t, J = 4.52 Hz, 4H), 1.76 (s, 6H); LC-MS (ESI) m/z : 694 [M + H]$^+$ | A |

TABLE 2-continued

| Example | Structure/Name | $^1$H NMR/LC MS | Purification condition |
| --- | --- | --- | --- |
| 88 | 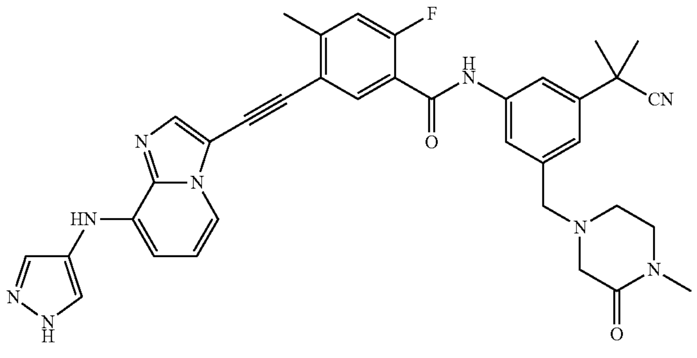 [SMILES: Cc1cc(F)c(C(=O)Nc2cc(CN3CCN(C)C(=O)C3)cc(C(C)(C)C#N)c2)cc1C#Cc1cnc2c(Nc3cn[nH]c3)cccn12] 5-((8-((1H-pyrazol-4-yl)amino)imidazo[1,2-a]pyridin-3-yl)ethynyl)-N-(3-(2-cyanopropan-2-yl)-5-((4-methyl-3-oxopiperazin-1-yl)methyl)phenyl)-2-fluoro-4-methylbenzamide | 1H NMR (400 MHz, $CDCl_3$) δ 8.55 (d, J = 15.04 Hz, 1H), 98.30 (d, J = 7.92 Hz, 1H), 7.86-7.83 (m, 3H), 7.75 (s, 1H), 7.65 (s, 2H), 7.60 (s, 1H), 7.27 (s, 1H), 7.14 (d, J = 12.64 Hz, 1H), 6.99 (t, J = 7.64 Hz, 1H), 6.73 (d, J = 7.72 Hz, 1H), 3.61 (s, 2H), 3.36 (t, J = 5.16 Hz, 2H), 3.17 (s, 2H), 2.96 (s, 3H), 2.75 (t, J = 5.44 Hz, 2H), 2.60 (s, 3H), 1.75 (s, 6H); LC-MS (ESI) m/z : 644 $[M + H]^+$ | A |
| 89 | 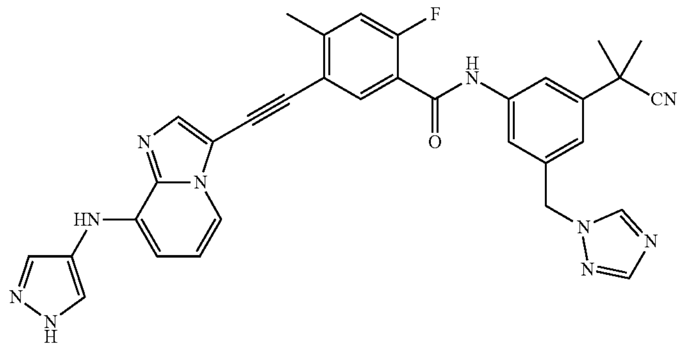 [SMILES: Cc1cc(F)c(C(=O)Nc2cc(Cn3cncn3)cc(C(C)(C)C#N)c2)cc1C#Cc1cnc2c(Nc3cn[nH]c3)cccn12] N-(3-((1H-1,2,4-triazol-1-yl)methyl)-5-(2-cyanopropan-2-yl)phenyl)-5-((8-((1H-pyrazol-4-yl)amino)imidazo[1,2-a]pyridin-3-yl) ethynyl)-2-fluoro-4-methylbenzamide | $^1$H NMR (400 MHz, $CDCl_3$) δ8.50 (d, J = 15.9 Hz, 1H), 8.31 (d, J = 8.0 Hz, 1H), 8.17 (s, 1H), 8.02 (s, 1H), 7.85-7.74 (m, 3H), 7.67 (s, 2H), 7.61 (s, 1H), 7.21 (s, 1H), 7.14 (d, J = 12.8 Hz, 1H), 6.83 (t, J = 7.1 Hz, 1H), 6.65 (s, 1H), 6.50 (d, J = 7.5 Hz, 1H), 5.40 (s, 2H), 2.62 (s, 3H), 1.74 (s, 6H); LC-MS (ESI) m/z : 599 $[M + H]^+$ | A |
| 90 | 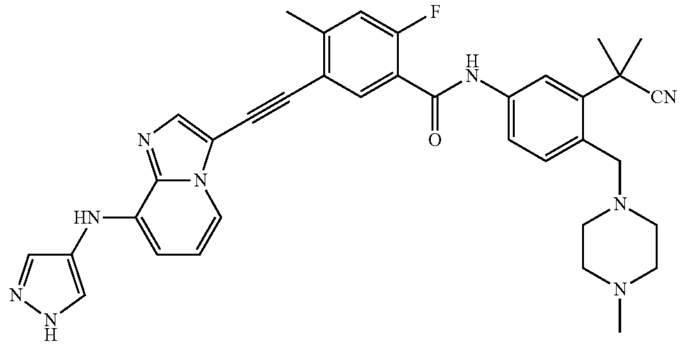 [SMILES: Cc1cc(F)c(C(=O)Nc2ccc(CN3CCN(C)CC3)c(C(C)(C)C#N)c2)cc1C#Cc1cnc2c(Nc3cn[nH]c3)cccn12] 5-((8-((1H-pyrazol-4-yl)amino)imidazo[1,2-a]pyridin-3-yl)ethynyl)-N-(3-(2-cyanopropan-2-yl)-4-((4-methylpiperazin-1-yl) methyl)phenyl)-2-fluoro-4-methylbenzamide | $^1$H NMR (400 MHz, $CDCl_3$) δ 8.45 (d, J = 15.64 Hz, 1H), 8.33 (d, J = 8.08 Hz, 1H), 7.84-7.79 (m, 3H), 7.67 (s, 2H), 7.55 (d, J = 8.36 Hz, 1H), 7.45 (dd, J = 8.34, 2.0 Hz, 1H), 7.12 (d, J = 12.8 Hz, 1H), 6.82 (t, J = 7.24 HZ, 1H), 6.72 (S, 1H), 6.49 (D, J = 7.4 HZ, 1H), 3.85 (S, 2H), 2.61 (S, 3H), 2.57-2.45 (M, 8H), 2.29 (S, 3H), 1.88 (S, 6H); LC-MS (ESI) m/z : 630 $[M + H]^+$ | A |

TABLE 2-continued

| Example | Structure/Name | $^1H$ NMR/LC MS | Purification condition |
|---|---|---|---|
| 91 | 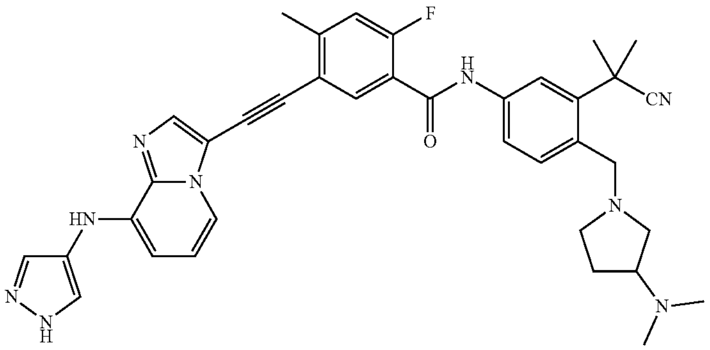 [SMILES: Cc1cc(F)c(C(=O)Nc2ccc(CN3CCC(N(C)C)C3)c(C(C)(C)C#N)c2)cc1C#Cc1cnc2c(Nc3cn[nH]c3)cccn12] 5-((8-((1H-pyrazol-4-yl) amino)imidazo[1,2-a]pyridin-3-yl)ethynyl)-N-(3-(2-cyanopropan-2-yl)-4-((3-(dimethylamino)pyrrolidin-1-yl)methyl)phenyl)-2-fluoro-4-methylbenzamide | $^1H$ NMR (400 MHz, $CDCl_3$) δ8.45 (d, J = 15.7 Hz, 1H), 8.34 (d, J = 8.1 Hz, 1H), 7.88-7.77 (m, 3H), 7.67 (s, 2H), 7.60 (d, J = 8.4 Hz, 1H), 7.46 (dd, J = 8.3, 2.1 Hz, 1H), 7.13 (d, J = 12.8 Hz, 1H), 6.87-6.80 (m, 1H), 6.69-6.63 (m, 1H), 6.50 (d, J = 6.9 Hz, 1H), 3.97 (s, 2H), 2.87-2.65 (m, 4H), 2.65-2.54 (m, 4H), 2.49-2.43 (m, 1H), 2.21 (s, 6H), 2.01-1.93 (m, 1H), 1.86 (s, 6H), 1.76-1.70 (m, 1H); LC-MS (ESI) m/z : 644 $[M + H]^+$ | A |
| 92 | 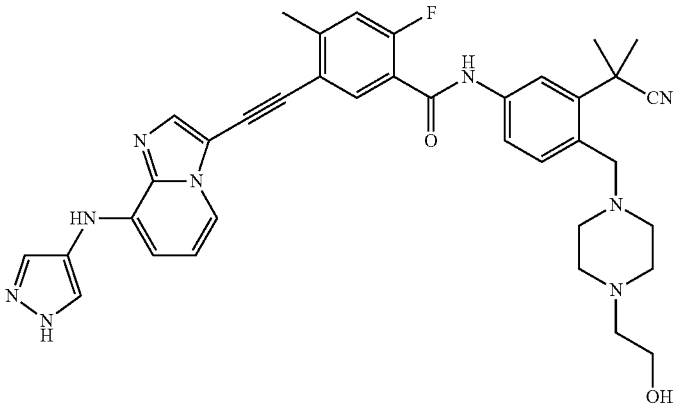 [SMILES: Cc1cc(F)c(C(=O)Nc2ccc(CN3CCN(CCO)CC3)c(C(C)(C)C#N)c2)cc1C#Cc1cnc2c(Nc3cn[nH]c3)cccn12] 5-((8-((1H-pyrazol-4-yl)amino)imidazo[1,2-a]pyridin-3-yl)ethynyl)-N-(3-(2-cyanopropan-2-yl)-4-((4-(2-hydroxyethyl)piperazin-1-yl)methyl)phenyl)-2-fluoro-4-methylbenzamide | $^1H$ NMR (400 MHz, $CDCl_3$) δ8.44 (d, J = 15.6 Hz, 1H), 8.35 (d, J = 8.1 Hz, 1H), 7.86-7.79 (m, 3H), 7.67 (s, 2H), 7.58 (d, J = 8.4 Hz, 1H), 7.46 (dd, J = 8.4, 2.1 Hz, 1H), 7.13 (d, J = 12.8 Hz, 1H), 6.87-6.80 (m, 1H), 16.65 (s, 1H), 6.50 (d, J = 7.1 Hz, 1H), 3.87 (s, 2H), 3.64-3.57 (m, 2H), 2.74-2.31 (m, 13H), 1.88 (s, 6H); LC-MS (ESI) m/z : 660 $[M + H]^+$ | A |

TABLE 2-continued

| Ex-ample | Structure/Name | $^1$H NMR/LC MS | Purifi-cation con-dition |
|---|---|---|---|
| 93 | 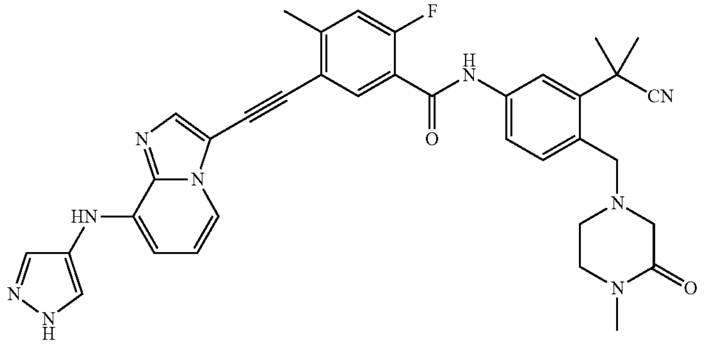 [SMILES: Cc1cc(F)c(C(=O)Nc2ccc(CN3CCN(C)C(=O)C3)c(C(C)(C)C#N)c2)cc1C#Cc1cnc2c(Nc3cn[nH]c3)cccn12] 5-((8-((1H-pyrazol-4-yl)amino)imidazo[1,2-a]pyridin-3-yl)ethynyl)-N-(3-(2-cyanopropan-2-yl)-4-((4-methyl-3-oxopiperazin-1-yl)methyl)phenyl)-2-fluoro-4-methylbenzamide | $^1$H NMR (400 MHz, $CDCl_3$) δ8.46 (d, J = 15.9 Hz, 1H), 8.34 (d, J = 8.1 Hz, 1H), 7.89 (d, J = 1.9 Hz, 1H), 7.85-7.77 (m, 2H), 7.67 (s, 2H), 7.58 (d, J = 8.4 Hz, 1H), 7.44 (dd, J = 8.3, 2.0 Hz, 1H), 7.13 (d, J = 12.8 Hz, 1H), 6.86-6.80 (m, 1H), 6.65 (s, 1H), 6.49 (d, J = 7.3 Hz, 1H), 3.95 (s, 2H), 3.37-3.29 (m, 2H), 3.19 (s, 2H), 2.97 (s, 3H), 2.86-2.78 (m, 2H), 2.62 (s, 3H), 1.85 (s, 6H); LC-MS (ESI) m/z : 644 $[M + H]^+$ | A |
| 94 | 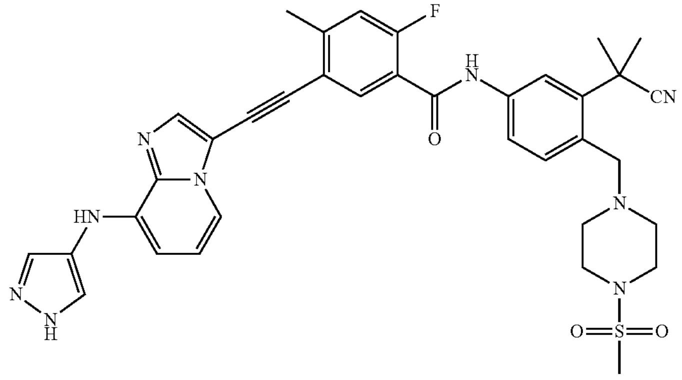 [SMILES: Cc1cc(F)c(C(=O)Nc2ccc(CN3CCN(S(C)(=O)=O)CC3)c(C(C)(C)C#N)c2)cc1C#Cc1cnc2c(Nc3cn[nH]c3)cccn12] 5-((8-((1H-pyrazol-4-yl)amino)imidazo[1,2-a]pyridin-3-yl)ethynyl)-N-(3-(2-cyanopropan-2-yl)-4-((4-(methylsulfonyl)piperazin-1-yl)methyl)phenyl)-2-fluoro-4-methylbenzamide | $^1$H NMR (400 MHz, $CDCl_3$) δ8.45 (d, J = 15.8 Hz, 1H), 8.34 (d, J = 8.1 Hz, 1H), 7.90-7.78 (m, 3H), 7.67 (s, 2H), 7.57 (d, J = 8.4 Hz, 1H), 7.48 (dd, J = 8.4, 2.1 Hz, 1H), 7.14 (d, J = 12.9 Hz, 1H), 6.87-6.80 (m, 1H), 6.65 (s, 1H), 6.50 (d, J = 6.9 Hz, 1H), 3.92 (s, 2H), 3.32-3.18 (m, 4H), 2.80 (s, 3H), 2.72-2.55 (m, 7H), 1.87 (s, 6H); LC-MS (ESI) m/z : 694 $[M + H]^+$ | A |
| 95 | 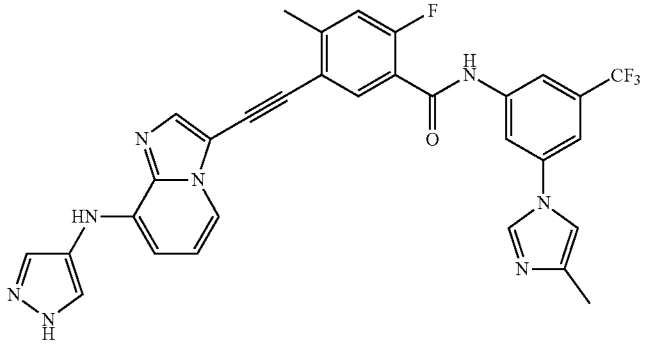 [SMILES: Cc1cn(-c2cc(NC(=O)c3cc(C#Cc4cnc5c(Nc6cn[nH]c6)cccn45)c(C)cc3F)cc(C(F)(F)F)c2)cn1] 5-((8-((1H-pyrazol-4-yl)amino)imidazo[1,2-a]pyridin-3-yl)ethynyl)-2-fluoro-4-methyl-N-(3-(4-methyl-1H-imidazol-1-yl)-5-(trifluoromethyl)phenyl)benzamide | 1H NMR (400 MHz, $CDCl_3$) δ8.68 (d, J = 16.6 Hz, 1H), 8.34 (d, J = 8.0 Hz, 1H), 8.24 (s, 1H), 7.89-7.78 (m, 3H), 7.73-7.65 (m, 3H), 7.40 (s, 1H), 7.17 (d, J = 12.9 Hz, 1H), 7.11 (s, 1H), 6.84 (t, J = 7.1 Hz, 1H), 6.70 (s, 1H), 6.51 (d, J = 7.5 Hz, 1H), 2.64 (s, 3H), 2.31 (s, 3H); LC-MS (ESI) m/z : 599 $[M + H]^+$ | A |

TABLE 2-continued

| Example | Structure/Name | $^1H$ NMR/LC MS | Purification condition |
|---|---|---|---|
| 96 | 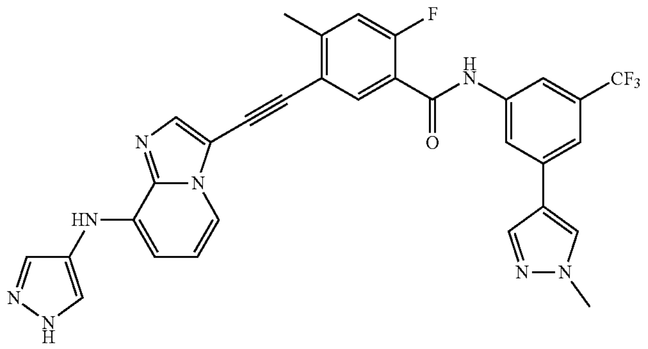 [SMILES: Cc1cc(F)c(C(=O)Nc2cc(-c3cnn(C)c3)cc(C(F)(F)F)c2)cc1C#Cc1cnc2c(Nc3cn[nH]c3)cccn12] 5-((8-((1H-pyrazol-4-yl)amino)imidazo[1,2-a]pyridin-3-yl)ethynyl)-2-fluoro-4-methyl-N-(3-(1-methyl-1H-pyrazol-4-yl)-5-(trifluoromethyl)phenyl)benzamide | $^1H$ NMR (400 MHz, DMSO-$d_6$) δ12.72 (br s, 1H), 10.78 (s, 1H), 8.28 (s, 1H), 8.15 (d, J = 16.0 Hz, 2H), 8.04-7.91 (m, 4H), 7.88-7.52 (m, 3H), 7.46 (d, J = 11.1 Hz, 1H), 6.99-6.91 (m, 1H), 6.58 (d, J = 7.5 Hz, 1H), 3.89 (s, 3H), 2.60 (s, 3H); LC-MS (ESI) m/z : 599 $[M + H]^+$ | A |
| 97 | 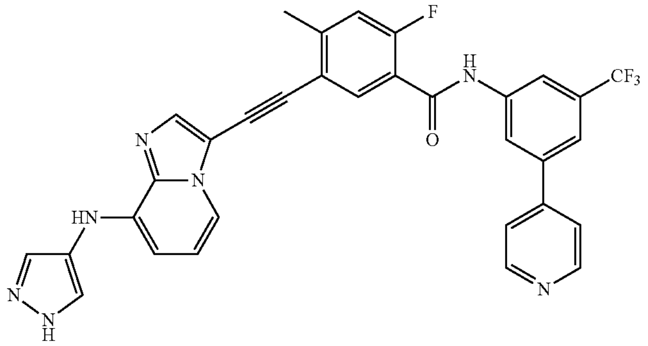 [SMILES: Cc1cc(F)c(C(=O)Nc2cc(-c3ccncc3)cc(C(F)(F)F)c2)cc1C#Cc1cnc2c(Nc3cn[nH]c3)cccn12] 5-((8-((1H-pyrazol-4-yl) amino)imidazo[1,2-a]pyridin-3-yl)ethynyl)-2-fluoro-4-methyl-N-(3-(pyridin-4-yl)-5-(trifluoromethyl)phenyl)benzamide | $^1H$ NMR (400 MHz, DMSO-$d_6$) δ12.71 (br s, 1H), 10.95 (s, 1H), 8.75-8.69 (m, 2H), 8.38 (s, 1H), 8.30 (s, 1H), 8.18 (s, 1H), 8.05 (d, J = 7.2 Hz, 1H), 8.00-7.93 (m, 2H), 7.89 (s, 1H), 7.84-7.58 (m, 4H), 7.48 (d, J = 11.2 Hz, 1H), 6.99-6.91 (m, 1H), 6.58 (d, J = 7.4 Hz, 1H), 2.60 (s, 3H); LC-MS (ESI) m/z : 596 $[M + H]^+$ | A |
| 98 | 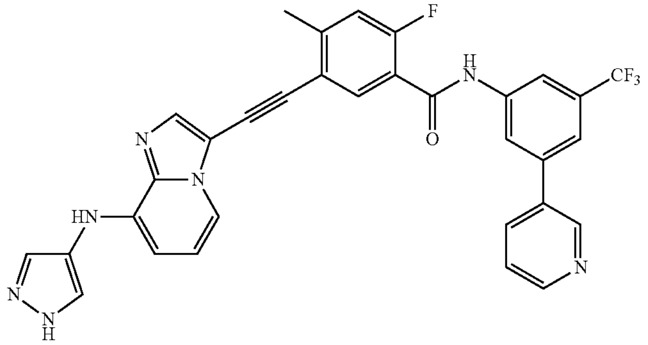 [SMILES: Cc1cc(F)c(C(=O)Nc2cc(-c3cccnc3)cc(C(F)(F)F)c2)cc1C#Cc1cnc2c(Nc3cn[nH]c3)cccn12] 5-((8-((1H-pyrazol-4-yl)amino)imidazo[1,2-a]pyridin-3-yl)ethynyl)-2-fluoro-4-methyl-N-(3-(pyridin-3-yl)-5-(trifluoromethyl)phenyl)benzamide | $^1H$ NMR (400 MHz, DMSO-$d_6$) δ12.72 (br s, 1H), 10.92 (s, 1H), 8.94 (d, J = 2.1 Hz, 1H), 8.65 (dd, J = 4.8, 1.5 Hz, 1H), 8.28 (d, J = 8.2 Hz, 2H), 8.21-8.12 (m, 2H), 8.04 (d, J = 7.2 Hz, 1H), 8.00-7.94 (m, 2H), 7.84 (s, 1H), 7.81-7.61 (m, 2H), 7.59-7.53 (m, 1H), 7.47 (d, J = 11.1 Hz, 1H), 6.99-6.91 (m, 1H), 6.58 (d, J = 7.5 Hz, 1H), 2.60 (s, 3H); LC-MS (ESI) m/z : 596 $[M + H]^+$ | A |

TABLE 2-continued

| Example | Structure/Name | $^1$H NMR/LC MS | Purification condition |
|---|---|---|---|
| 99 | 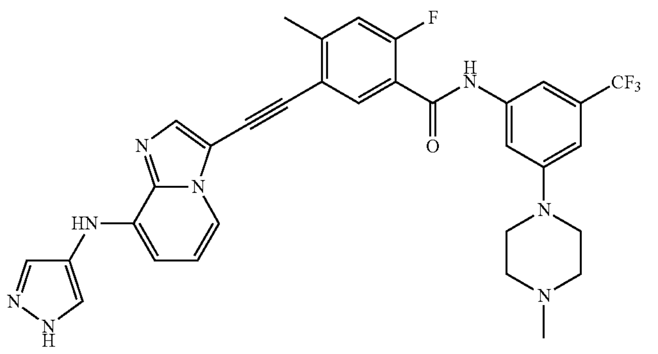 [SMILES: Cc1cc(F)c(C(=O)Nc2cc(N3CCN(C)CC3)cc(C(F)(F)F)c2)cc1C#Cc1cnc2c(Nc3cn[nH]c3)cccn12] 5-((8-((1H-pyrazol-4-yl)amino)imidazo[1,2-a]pyridin-3-yl)ethynyl)-2-fluoro-4-methyl-N-(3-(4-methylpiperazin-1-yl)-5-(trifluoromethyl)phenyl)benzamide | $^1$H NMR (400 MHz, DMSO-$d_6$) δ12.72 (br s, 1H), 10.58 (s, 1H), 8.18 (s, 1H), 8.04-7.92 (m, 3H), 7.88-7.74 (m, 1H), 7.62-7.52 (m, 2H), 7.44 (d, J = 11.1 Hz, 1H), 7.01-6.91 (m, 2H), 6.58 (d, J = 7.3 Hz, 1H), 3.26-3.13 (m, 4H), 2.59 (s, 3H), 2.48-2.41 (m, 4H), 2.22 (s, 3H); LC-MS (ESI) m/z : 617 $[M + H]^+$ | A |
| 100 | 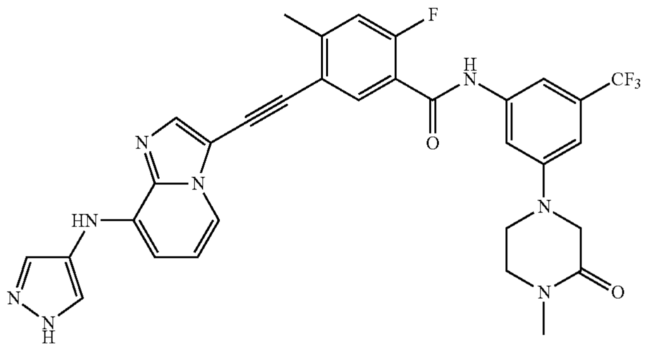 [SMILES: Cc1cc(F)c(C(=O)Nc2cc(N3CCN(C)C(=O)C3)cc(C(F)(F)F)c2)cc1C#Cc1cnc2c(Nc3cn[nH]c3)cccn12] 5-((8-((1H-pyrazol-4-yl) amino)imidazo [1,2-a]pyridin-3-yl)ethynyl)-2-fluoro-4-methyl-N-(3-(4-methyl-3-oxopiperazin-1-yl)-5-(trifluoromethyl)phenyl)benzamide | 1H NMR (400 MHz, DMSO-$d_6$) δ 12.72 (br s, 1H), 10.60 (s, 1H), 8.18 (s, 1H), 8.03-7.90 (m, 3H), 7.88-7.72 (m, 1H), 7.64 (s, 2H), 7.51-7.40 (m, 2H), 7.02 (s, 1H), 6.98-6.91 (m, 1H), 6.58 (d, J = 7.3 Hz, 1H), 3.84 (s, 2H), 3.63-3.53 (m, 2H), 3.49-3.42 (m, 2H), 2.91 (s, 3H), 2.59 (s, 3H); LC-MS (ESI) m/z : 631 $[M + H]^+$ | A |
| 101 | 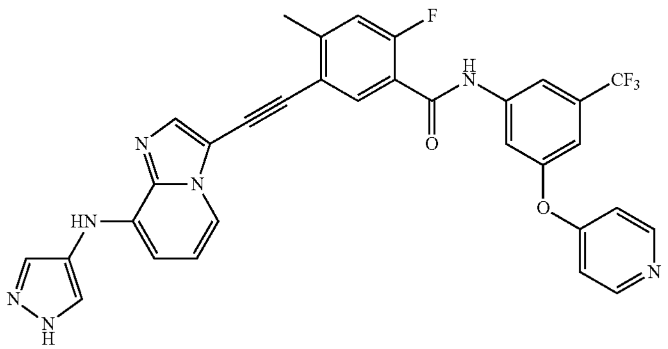 [SMILES: Cc1cc(F)c(C(=O)Nc2cc(Oc3ccncc3)cc(C(F)(F)F)c2)cc1C#Cc1cnc2c(Nc3cn[nH]c3)cccn12] 5-((8-((1H-pyrazol-4-yl)amino)imidazo[1,2-a]pyridin-3-yl)ethynyl)-2-fluoro-4-methyl-N-(3-(pyridin-4-yloxy)-5-(trifluoromethyl)phenyl)benzamide | $^1$H NMR (400 MHz, TFA salt, MeOD-$d_4$) δ8.62 (d, J = 7.48 Hz, 2H), 8.43 (s, 1H), 8.32 (s, 1H), 8.22-8.21 (m, 2H), 8.10 (d, J = 7.16 Hz, 1H), 7.83 (s, 1H), 7.75 (s, 2H), 7.37-7.32 (m, 2H), 7.13 (d, J = 7.52 Hz, 2H), 7.08 (d, J = 7.88 Hz, 1H), 2.67 (s, l3H); LC-MS (ESI) m/z : 612 $[M + H]^+$ | B |

TABLE 2-continued

| Example | Structure/Name | $^1H$ NMR/LC MS | Purification condition |
|---|---|---|---|
| 102 | 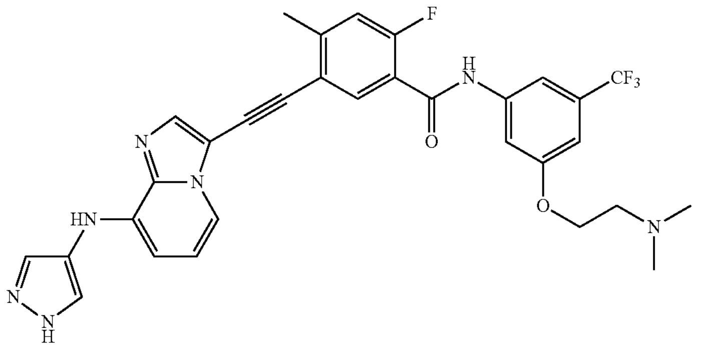 [SMILES: Cc1cc(F)c(C(=O)Nc2cc(OCCN(C)C)cc(C(F)(F)F)c2)cc1C#Cc1cnc2c(Nc3cn[nH]c3)cccn12] 5-((8-((1H-pyrazol-4-yl)amino)imidazo[1,2-a]pyridin-3-yl)ethynyl)-N-(3-(2-(dimethylamino)ethoxy)-5-(trifluoromethyl)phenyl)-2-fluoro-4-methylbenzamide | $^1H$ NMR (400 MHz, TFA salt, MeOD-$d_4$) δ8.27 (s, 1H), 8.18 (d, J = 6.48 Hz, 1H), 8.03 (d, J = 7.16 Hz, 1H), 7.85 (s, 1H), 7.75 (s, 2H), 7.62 (s, 1H), 7.33-7.28 (m, 2H), 7.12 (s, 1H), 7.03 (d, J = 7.92 Hz, 1H), 4.45 (t, J = 4.76 Hz, 2H), 3.64 (t, J = 4.96 Hz, 2H), 3.00 (s, 6H), 2.65 (s, 3H); LC-MS (ESI) m/z : 606 $[M + H]^+$ | B |
| 103 | 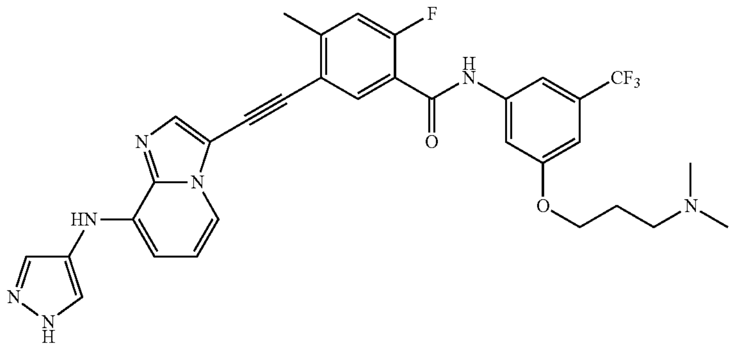 [SMILES: Cc1cc(F)c(C(=O)Nc2cc(OCCCN(C)C)cc(C(F)(F)F)c2)cc1C#Cc1cnc2c(Nc3cn[nH]c3)cccn12] 5-((8-((1H-pyrazol-4-yl)amino)imidazo[1,2-a]pyridin-3-yl)ethynyl)-N-(3-(3-(dimethylamino)propoxy)-5-(trifluoromethyl)phenyl)-2-fluoro-4-methylbenzamide | 1H NMR (400 MHz, TFA salt, MeOD-$d_4$) δ8.24 (s, 1H), 8.16 (d, J = 6.48 Hz, 1H), 8.02 (d, J = 7.12 Hz, 1H), 7.74 (d, J = 7.04 Hz, 3H), 7.59 (s, 1H), 7.32-7.26 (m, 2H), 7.03-7.00 (m, 2H), 4.19 (t, J = 5.64 Hz, 2H), 3.38 (t, J = 7.8 Hz, 2H), 2.95 (s, 6H), 2.64 (s, 3H), 2.30-2.23 (m, 2H); LC-MS (ESI) m/z : 620 $[M + H]^+$ | B |
| 104 | 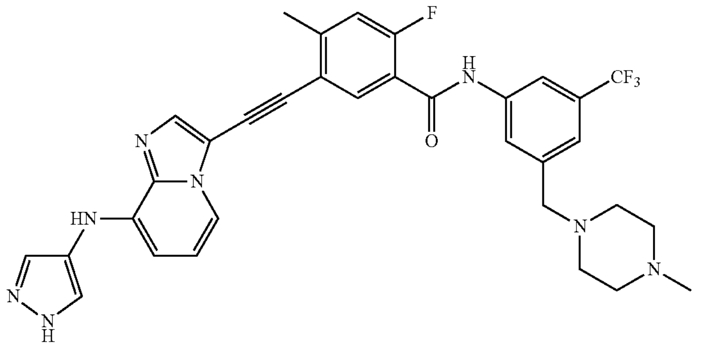 [SMILES: Cc1cc(F)c(C(=O)Nc2cc(CN3CCN(C)CC3)cc(C(F)(F)F)c2)cc1C#Cc1cnc2c(Nc3cn[nH]c3)cccn12] 5-((8-((1H-pyrazol-4-yl) amino)imidazo [1,2-a]pyridin-3-yl)ethynyl)-2-fluoro-4-methyl-N-(3-((4-methylpiperazin-1-yl)methyl)-5-(trifluoromethyl)phenyl)benzamide | $^1H$ NMR (400 MHz, $CDCl_3$) δ 8.54 (d, J = 15.88 Hz, 1H), 8.32 (d, J = 8.08 Hz, 1H), 7.95 (s, 1H), 7.82-7.76 (m, 3H), 7.66 (s, 2H), 7.39 (s, 1H), 7.12 (d, J = 12.88 Hz, 1H), 6.82 (t, J = 7.28 Hz, 1H), 6.71 (s, 1H), 6.49 (d, J = 7.04 Hz, 1H), 3.58 (s, 2H), 2.61 (s, 3H), 2.56 (br-s, 8H), 2.35 (s, 3H); LC-MS (ESI) m/z : 631 $[M + H]^+$ | A |

TABLE 2-continued

| Example | Structure/Name | $^1$H NMR/LC MS | Purification condition |
|---|---|---|---|
| 105 | 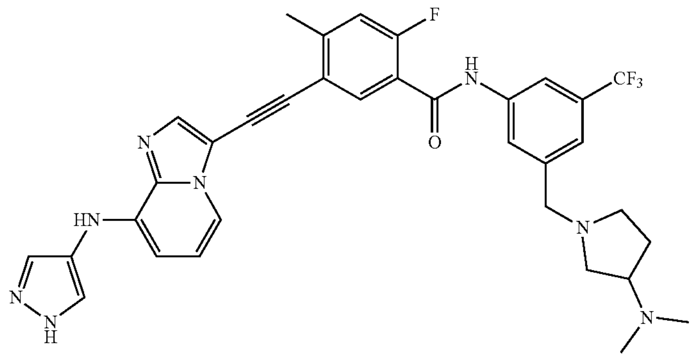 [SMILES: Cc1cc(F)c(C(=O)Nc2cc(CN3CCC(N(C)C)C3)cc(C(F)(F)F)c2)cc1C#Cc1cnc2c(Nc3cn[nH]c3)cccn12] 5-((8-((1H-pyrazol-4-yl)amino)imidazo[1,2-a]pyridin-3-yl)ethynyl)-N-(3-((3-(dimethylamino)pyrrolidin-1-yl)methyl)-5-(trifluoromethyl)phenyl)-2-fluoro-4-methylbenzamide | $^1$H NMR (400 MHz, $CDCl_3$) δ 8.55 (d, J = 15.6 Hz, 1H), 8.25 (d, J = 8.04 Hz, 1H), 8.05 (s, 1H), 7.80 (s, 1H), 7.75 (d, J = 6.04 Hz, 1H), 7.66-7.65 (m, 3H), 7.37 (s, 1H), 7.07 (d, J = 12.84 Hz, 1H), 6.80 (t, J = 7.24 Hz, 1H), 6.73 (s, 1H), 6.46 (d, J = 7.16 Hz, 1H), 3.71 (d, J = 13.36 Hz, 1H), 3.61 (d, J = 13.36 Hz, 1H), 2.81-2.68 (m, 3H), 2.60-2.58 (m, 4H), 2.44-2.39 (m, 1H), 2.23 (s, 6H), 2.05-2.00 (m, 1H), 1.81-1.73 (m, 1H); LC-MS (ESI) m/z : 645 [M + H]$^+$ | A |
| 106 | 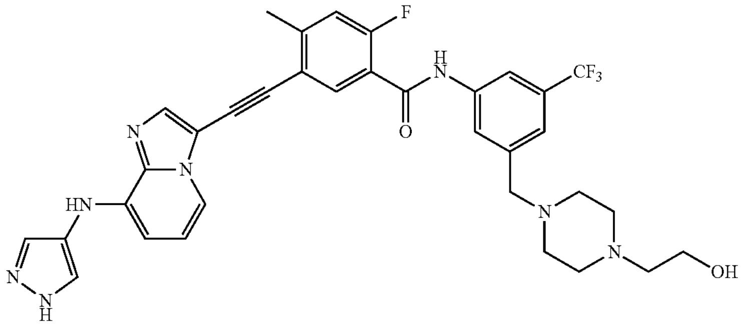 [SMILES: Cc1cc(F)c(C(=O)Nc2cc(CN3CCN(CCO)CC3)cc(C(F)(F)F)c2)cc1C#Cc1cnc2c(Nc3cn[nH]c3)cccn12] 5-((8-((1H-pyrazol-4-yl)amino)imidazo[1,2-a]pyridin-3-yl)ethynyl)-2-fluoro-N-(3-((4-(2-hydroxyethyl)piperazin-1-yl)methyl)-5-(trifluoromethyl)phenyl)-4-methylbenzamide | $^1$H NMR (400 MHz, $CDCl_3$) δ 8.09 (d, J = 7.28 Hz, 1H), 7.81 (s, 1H), 7.79 (d, J = 6.12 Hz, 1H), 7.66 (s, 2H), 7.05 (d, J = 11.24 Hz, 1H), 6.93 (s, 1H), 6.81 (t, J = 7.36 Hz, 2H), 6.77 (s, 1H), 6.68 (s, 1H), 6.48 (d, J = 7.32 Hz, 1H), 4.47 (t, J = 5.92 Hz, 2H), 3.80 (br-s, 1H), 3.43 (s, 2H), 2.80 (t, J = 5.92 Hz, 2H), 2.58 (s, 3H), 2.49 (br-s, 8H); LC-MS (ESI) m/z : 661 [M + H]$^+$ | A |
| 107 | 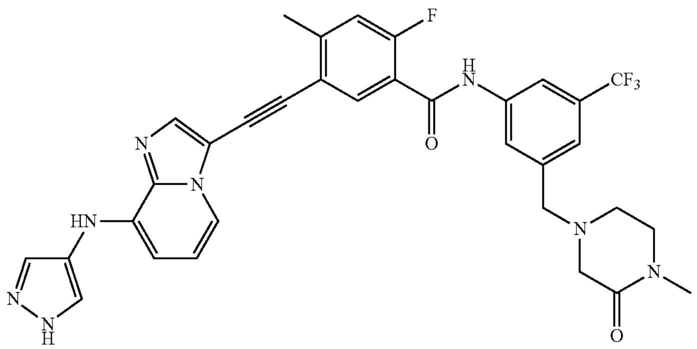 [SMILES: Cc1cc(F)c(C(=O)Nc2cc(CN3CCN(C)C(=O)C3)cc(C(F)(F)F)c2)cc1C#Cc1cnc2c(Nc3cn[nH]c3)cccn12] 5-((8-((1H-pyrazol-4-yl)amino)imidazo[1,2-a]pyridin-3-yl)ethynyl)-2-fluoro-4-methyl-N-(3-((4-methyl-3-oxopiperazin-1-yl)methyl)-5-(trifluoromethyl)phenyl)benzamide | $^1$H NMR (400 MHz, $CDCl_3$) δ 8.59 (d, J = 15.6 Hz, 1H), 8.30 (d, J = 8.04 Hz, 1H), 7.90-7.79 (m, 4H), 7.66 (s, 2H), 7.39 (s, 1H), 7.12 (d, J = 12.8 Hz, 1H), 6.90-6.82 (m, 2H), 6.52 (d, J = 7.16 Hz, 1H), 3.61 (s, 2H), 3.34 (t, J = 5.32 Hz, 2H), 3.17 (s, 2H), 2.96 (s, 3H), 2.72 (t, J = 5.72 Hz, 2H), 2.61 (s, 3H); LC-MS (ESI) m/z : 645 [M + H]$^+$ | A |

TABLE 2-continued

| Example | Structure/Name | $^1$H NMR/LC MS | Purification condition |
|---|---|---|---|
| 108 | 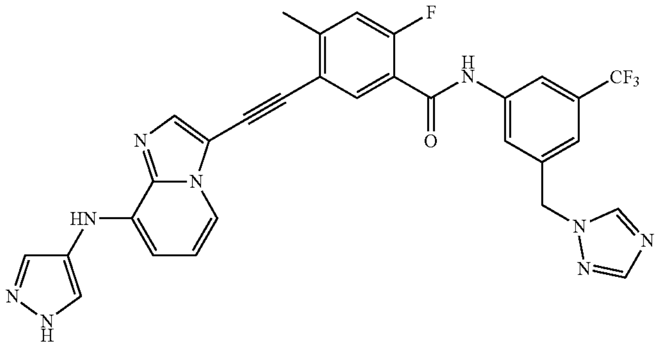 [SMILES: Cc1cc(F)c(C(=O)Nc2cc(Cn3cncn3)cc(C(F)(F)F)c2)cc1C#Cc1cnc2c(Nc3cn[nH]c3)cccn12] N-(3-((1H-1,2,4-triazol-1-yl)methyl)-5-(trifluoromethyl)phenyl)-5-((8-((1H-pyrazol-4-yl)amino)imidazo[1,2-a]pyridin-3-yl)ethynyl)-2-fluoro-4-methylbenzamide | 1H NMR (400 MHz, $CDCl_3$) δ8.56 (d, J = 16.3 Hz, 1H), 8.32 (d, J = 8.1 Hz, 1H), 8.19 (s, 1H), 8.03 (s, 1H), 7.90 (d, J = 13.2 Hz, 2H), 7.85-7.76 (m, 3H), 7.67 (s, 3H), 7.31 (s, 1H), 7.14 (d, J = 12.9 Hz, 1H), 6.84 (t, J = 7.1 Hz, 1H), 6.66 (s, 1H), 6.52-6.48 (m, 1H), 5.44 (s, 2H), 2.63 (s, 3H); LC-MS (ESI) m/z : 600 $[M + H]^+$ | A |
| 109 | 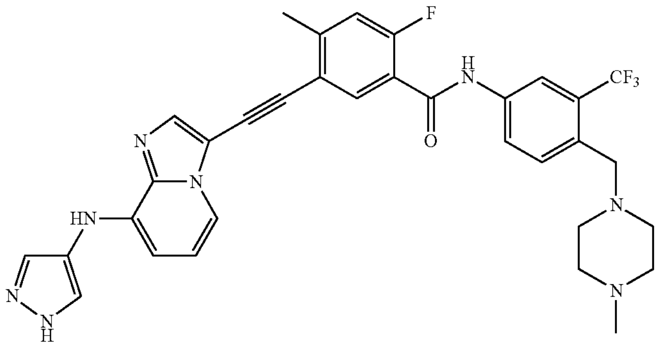 [SMILES: Cc1cc(F)c(C(=O)Nc2ccc(CN3CCN(C)CC3)c(C(F)(F)F)c2)cc1C#Cc1cnc2c(Nc3cn[nH]c3)cccn12] 5-((8-((1H-pyrazol-4-yl)amino)imidazo[1,2-a]pyridin-3-yl)ethynyl)-2-fluoro-4-methyl-N-(4-((4-methylpiperazin-1-yl)methyl)-3-(trifluoromethyl)phenyl)benzamide | $^1$H NMR (400 MHz, $CDCl_3$) δ8.49 (d, J = 16.1 Hz, 1H), 8.35 (d, J = 8.1 Hz, 1H), 7.97-7.75 (m, 5H), 7.67 (s, (2H), 7.14 (d, J = 12.9 Hz, 1H), 6.87-6.81 (m, 1H), 6.65 (s, 1H), 6.50 (d, J = 7.0 Hz, 1H), 3.65 (s, 2H), 2.82-2.33 (m, 11H), 2.30 (s, 3H); LC-MS (ESI) m/z : 631 $[M + H]^+$ | A |
| 110 | 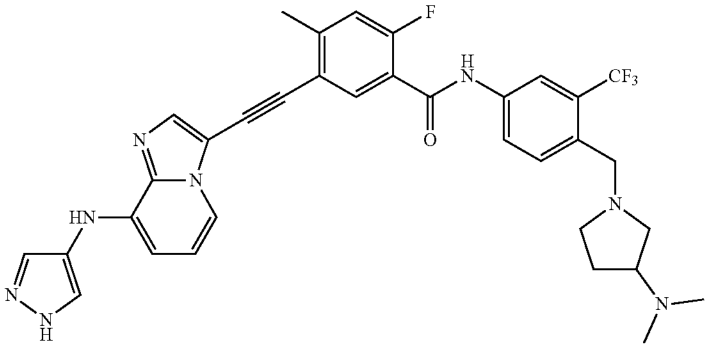 [SMILES: Cc1cc(F)c(C(=O)Nc2ccc(CN3CCC(N(C)C)C3)c(C(F)(F)F)c2)cc1C#Cc1cnc2c(Nc3cn[nH]c3)cccn12] 5-((8-((1H-pyrazol-4-yl) amino)imidazo [1,2-a]pyridin-3-yl)ethynyl)-N-(4-((3-(dimethylamino)pyrrolidin-1-yl)methyl)-3-(trifluoromethyl)phenyl)-2-fluoro-4-methylbenzamide | $^1$H NMR (400 MHz, $CDCl_3$) δ8.48 (d, J = 16.0 Hz, 1H), 8.36 (d, J = 8.1 Hz, 1H), 7.94-7.89 (m, 1H), 7.88-7.75 (m, 3H), 7.67 (s, 2H), 7.13 (d, J = 12.9 Hz, 1H), 6.87-6.81 (m, 1H), 6.63 (s, 1H), 6.50 (d, J = 7.2 Hz, 1H), 3.76 (q, J = 15.0 Hz, 2H), 2.87-2.54 (m, 8H), 2.48-2.43 (m, 1H), 2.22 (s, 6H), 2.03-1.97 (m, 1H), 1.78-1.72 (m, 1H); LC-MS (ESI) m/z : 645 $[M + H]^+$ | A |

TABLE 2-continued

| Example | Structure/Name | $^1H$ NMR/LC MS | Purification condition |
|---|---|---|---|
| 111 | 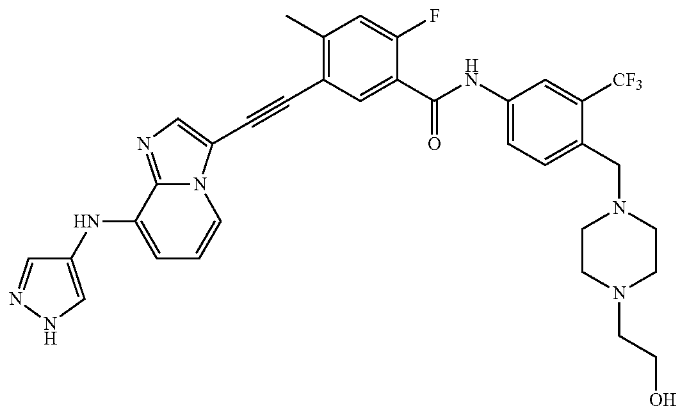 [SMILES: Cc1cc(F)c(C(=O)Nc2ccc(CN3CCN(CCO)CC3)c(C(F)(F)F)c2)cc1C#Cc1cnc2c(Nc3cn[nH]c3)cccn12] 5-((8-((1H-pyrazol-4-yl)amino)imidazo[1,2-a]pyridin-3-yl)ethynyl)-2-fluoro-N-(4-((4-(2-hydroxyethyl)piperazin-1-yl)methyl)-3-(trifluoromethyl)phenyl)-4-methylbenzamide | $^1H$ NMR (400 MHz, $CDCl_3$) δ8.49 (d, J = 16.0 Hz, 1H), 8.35 (d, J = 8.1 Hz, 1H), 7.94-7.77 (m, 4H), 7.67 (s, 2H), 7.14 (d, J = 12.9 Hz, 1H), 6.88-6.81 (m, 1H), 6.64 (s, 1H), 6.50 (d, J = 7.5 Hz, 1H), 3.65 (s, 2H), 3.64-3.56 (m, 2H), 2.76-2.38 (m, 13H); LC-MS (ESI) m/z : 661 $[M + H]^+$ | A |
| 112 | 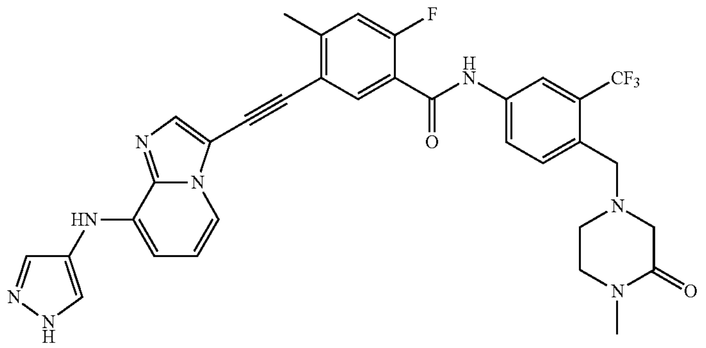 [SMILES: Cc1cc(F)c(C(=O)Nc2ccc(CN3CCN(C)C(=O)C3)c(C(F)(F)F)c2)cc1C#Cc1cnc2c(Nc3cn[nH]c3)cccn12] 5-((8-((1H-pyrazol-4-yl)amino)imidazo[1,2-a]pyridin-3-yl)ethynyl)-2-fluoro-4-methyl-N-(4-((4-methyl-3-oxopiperazin-1-yl)methyl)-3-(trifluoromethyl)phenyl)benzamide | $^1H$ NMR (400 MHz, $CDCl_3$) δ8.52 (d, J = 16.3 Hz, 1H), 8.35 (d, J = 8.1 Hz, 1H), 7.94 (d, J = 2.0 Hz, 1H), 7.92-7.86 (m, 1H), 7.86-7.78 (m, 2H), 7.75 (d, J = 8.5 Hz, 1H), 7.67 (s, 2H), 7.14 (d, J = 12.9 Hz, 1H), 6.87-6.80 (m, 1H), 6.65 (s, 1H), 6.50 (d, J = 7.3 Hz, 1H), 3.69 (s, 2H), 3.36-3.27 (m, 2H), 3.21 (s, 2H), 2.97 (s, 3H), 2.75-2.68 (m, 2H), 2.63 (s, 3H); LC-MS (ESI) m/z : 645 $[M + H]^+$ | A |

TABLE 2-continued

| Example | Structure/Name | $^1$H NMR/LC MS | Purification condition |
|---|---|---|---|
| 113 | 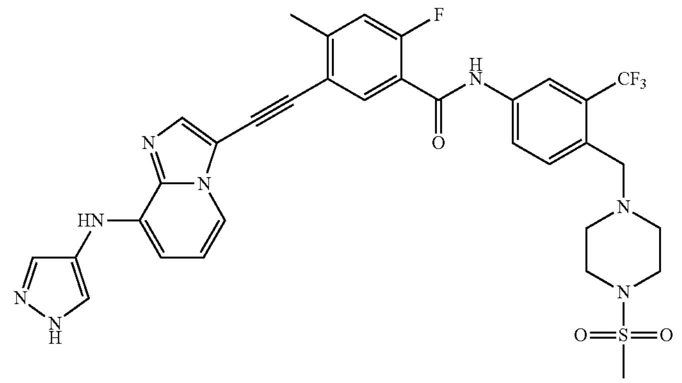 [SMILES: Cc1cc(F)c(C(=O)Nc2ccc(CN3CCN(S(C)(=O)=O)CC3)c(C(F)(F)F)c2)cc1C#Cc1cnc2c(Nc3cn[nH]c3)cccn12] 5-((8-((1H-pyrazol-4-yl)amino)imidazo[1,2-a]pyridin-3-yl)ethynyl)-2-fluoro-4-methyl-N-(4-((4-(methylsulfonyl)piperazin-1-yl)methyl)-3-(trifluoromethyl)phenyl)benzamide | $^1$H NMR (400 MHz, $CDCl_3$) δ8.51 (d, J = 16.1 Hz, 1H), 8.35 (d, J = 8.1 Hz, 1H), 7.97-7.87 (m, 2H), 7.85-7.79 (m, 2H), 7.73 (d, J = 8.3 Hz, 1H), 7.67 (s, 2H), 7.14 (d, J = 12.8 Hz, 1H), 6.87-6.80 (m, 1H), 6.64 (s, 1H), 6.50 (d, J = 7.4 Hz, 1H), 3.69 (s, 2H), 3.32-3.20 (m, 4H), 2.80 (s, 3H), 2.73-2.52 (m, 7H); LC-MS (ESI) m/z : 695 $[M + H]^+$ | A |
| 114 | 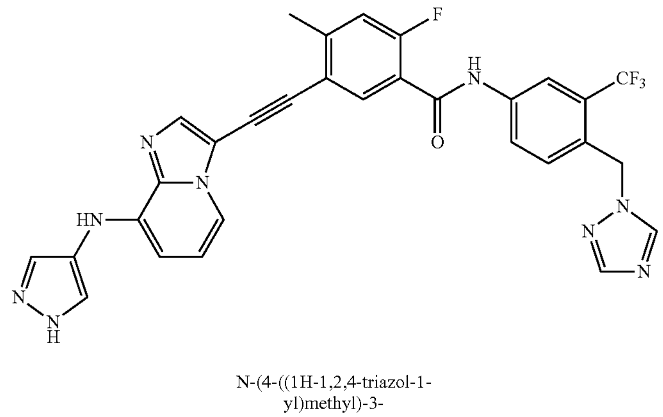 N-(4-((1H-1,2,4-triazol-1-yl)methyl)-3-(trifluoromethyl)phenyl)-5-((8-((1H-pyrazol-4-yl)amino)imidazo[1,2-a]pyridin-3-yl)ethynyl)-2-fluoro-4-methylbenzamide | $^1$H NMR (400 MHz, $CDCl_3$) δ8.56 (d, J = 16.4 Hz, 1H), 8.34 (d, J = 8.1 Hz, 1H), 8.18-8.08 (m, 2H), 8.01 (s, 1H), 7.90-7.76 (m, 3H), 7.67 (s, 2H), 7.30 (d, J = 8.5 Hz, 1H), 7.14 (d, J = 12.9 Hz, 1H), 6.87-6.81(m, 1H), 6.65 (s, 1H), 6.52-6.48 (m, 1H), 5.54 (s, 2H), 2.63 (s, 3H); LC-MS (ESI) m/z : 600 $[M + H]^+$ | A |

<Comparative Example 1> Preparation of 4-methyl-N-(3-(4-methyl-1H-imidazol-1-yl)-5-(trifluoromethyl)phenyl)-3-((8-((1-methyl-1H-pyrazol-4-yl)amino)imidazo[1,2-a]pyridin-3-yl)ethynyl)benzamide

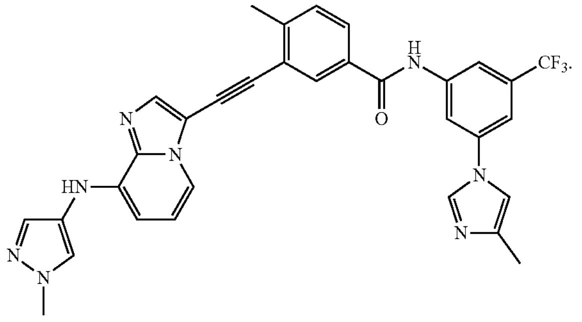 [SMILES: Cc1cn(-c2cc(NC(=O)c3ccc(C)c(C#Cc4cnc5c(Nc6cnn(C)c6)cccn45)c3)cc(C(F)(F)F)c2)cn1]

A target compound was prepared in the same manner as described in Example 12 of Korean Patent No. 10-1931435.

<Comparative Example 2> Preparation of N-(3-(2-cyanopropan-2-yl)-5-((2-(dimethylamino)ethyl)(methyl)amino)phenyl)-4-methyl-3-((8-((1-methyl-1H-pyrazol-4-yl)amino)imidazo[1,2-a]pyridin-3-yl)ethynyl)benzamide

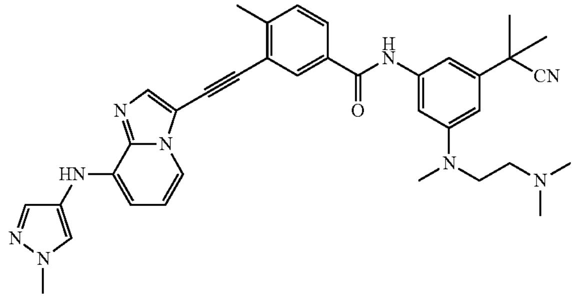 [SMILES: Cc1ccc(C(=O)Nc2cc(N(C)CCN(C)C)cc(C(C)(C)C#N)c2)cc1C#Cc1cnc2c(Nc3cnn(C)c3)cccn12]

A target compound was prepared in the same manner as described in Example 27 of Korean Patent No. 10-1920456.

<Comparative Example 3> Preparation of N-(3-(2-cyanopropan-2-yl)-5-(4-methylpiperazin-1-yl)phenyl)-4-methyl-3-((8-((1-methyl-1H-pyrazol-4-yl)amino)imidazo[1,2-a]pyridin-3-yl)ethynyl)benzamide

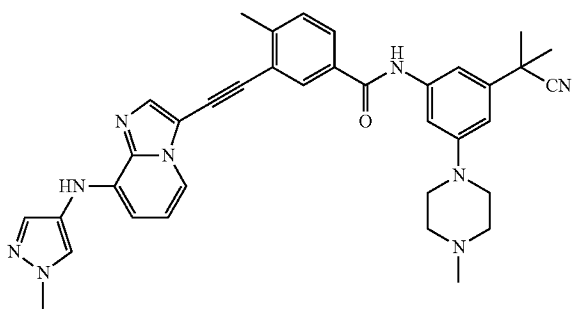 [SMILES: Cc1ccc(C(=O)Nc2cc(N3CCN(C)CC3)cc(C(C)(C)C#N)c2)cc1C#Cc1cnc2c(Nc3cnn(C)c3)cccn12]

A target compound was prepared in the same manner as described in Example 21 of Korean Patent No. 10-1920456.

<Comparative Example 4> Preparation of N-(3-(2-cyanopropan-2-yl)-5-(4-methyl-1H-imidazol-1-yl)phenyl)-4-methyl-3-((8-((1-methyl-1H-pyrazol-4-yl)amino)imidazo[1,2-a]pyridin-3-yl)ethynyl)benzamide

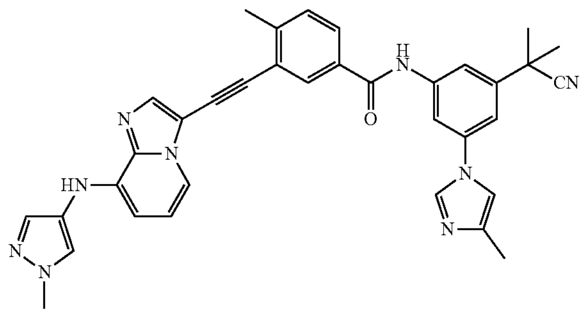 [SMILES: Cc1cn(-c2cc(NC(=O)c3ccc(C)c(C#Cc4cnc5c(Nc6cnn(C)c6)cccn45)c3)cc(C(C)(C)C#N)c2)cn1]

4-Methyl-3-((8-((1-methyl-1H-pyrazol-4-yl)amino)imidazo[1,2-a]pyridin-3-yl)ethynyl)benzoic acid (15 mg, 0.039 mmol) was dissolved in diformamide (1 mL), and EDCI (12 mg, 0.077 mmol), DMAP (9.4 mg, 0.077 mmol) and 2-(3-amino-5-(4-methyl-1H-imidazol-1-yl)phenyl)-2-methylpropanenitrile (9.36 mg, 0.039 mmol) were added thereto at room temperature. The reaction mixture was heated gradually and stirred at 60° C. for 16 hours. Upon completion of the reaction, the mixture was cooled to room temperature, washed with brine, and extracted with dichloromethane. The extracted organic layer was dried over anhydrous sodium sulfate, filtered, and then concentrated under reduced pressure. The obtained residue was purified by preparative HPLC (0.1% TFA in water/acetonitrile) to give the compound of Comparative Example 4 (17.9 mg, 54.4% yield).

$^1$H NMR (400 MHz, TFA salt, MeOD-$d_4$) δ 9.40 (d, J=1.48 Hz, 1H), 8.36 (s, 1H), 8.25 (d, J=1.56 Hz, 1H), 8.09-8.07 (m, 2H), 8.00 (s, 1H), 7.96 (dd, J=8.12, 1.76 Hz, 1H), 7.85 (s, 1H), 7.76 (s, 1H), 7.59 (s, 1H), 7.54-7.53 (m, 2H), 7.16 (t, J=7.64 Hz, 1H), 6.86 (d, J=7.8 Hz, 1H), 3.93 (s, 3H), 2.67 (s, 3H), 2.46 (s, 3H), 1.83 (s, 6H); LC-MS (ESI) m/z: 594 $[M+H]^+$ <Comparative Example 5> Preparation of N-(3-(2-cyanopropan-2-yl)-5-((4-methylpiperazin-1-yl)methyl)phenyl)-4-methyl-3-((8-((1-methyl-1H-pyrazol-4-yl)amino)imidazo[1,2-a]pyridin-3-yl)ethynyl)benzamide

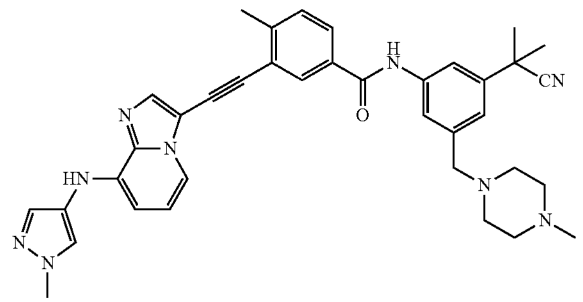 [SMILES: Cc1ccc(C(=O)Nc2cc(CN3CCN(C)CC3)cc(C(C)(C)C#N)c2)cc1C#Cc1cnc2c(Nc3cnn(C)c3)cccn12]

4-Methyl-3-((8-((1-methyl-1H-pyrazol-4-yl)amino)imidazo[1,2-a]pyridin-3-yl)ethynyl)benzoic acid (15 mg, 0.039 mmol) was dissolved in diformamide (1 mL), and EDCI (12 mg, 0.077 mmol), DMAP (9.4 mg, 0.077 mmol) and 2-(3-amino-5-((4-methylpiperazin-1-yl)methyl)phenyl)-2-methylpropanenitrile (9.36 mg, 0.039 mmol) were added thereto at room temperature. The reaction mixture was heated gradually and stirred at 60° C. for 16 hours. Upon completion of the reaction, the mixture was cooled to room temperature, washed with brine, and extracted with dichloromethane. The extracted organic layer was dried over anhydrous sodium sulfate, filtered, and then concentrated under reduced pressure. The obtained residue was purified by preparative HPLC (0.1% TFA in water/acetonitrile) to give the compound of Comparative Example 5 (17.9 mg, 54.4% yield).

$^1$H NMR (400 MHz, TFA salt, MeOD-$d_4$) δ 8.23 (d, J=1.72 Hz, 1H), 8.20 (s, 1H), 8.16 (d, J=6.36 Hz, 1H), 7.95 (dd, J=8.06, 1.76 Hz, 1H), 7.87 (s, 1H), 7.77 (s, 1H), 7.75 (s, 1H), 7.55-7.52 (m, 2H), 7.35 (s, 1H), 7.26 (dd, J=7.8, 6.68 Hz, 1H), 6.99 (d, J=7.76 Hz, 1H), 3.93 (s, 3H), 3.75 (s, 2H), 2.89 (s, 3H), 2.67 (s, 3H), 1.75 (s, 6H); LC-MS (ESI) m/z: 626 $[M+H]^+$

<Experimental Example 1> Evaluation of Inhibitory Activity of the Compound According to the Present Invention to Enzymes In order to evaluate the inhibitory activity of the compound according to the present invention to enzymes, the following experiment was performed.

Specifically, the effect of the compound of Example 1 according to the present invention on the enzymatic activity of ABL1, ABL1 (E255K), ABL1 (E255V), ABL1 (F317I), ABL1 (F317L), ABL1 (G250E), ABL1 (H396P), ABL1 (M351T), ABL1 (Q252H), ABL1 (T315I), ABL1 (V299L), ABL1 (Y253F) and ABL1 (Y253H) was evaluated by requesting Reaction Biology. The results are shown in Table 3 below.

TABLE 3

| Example 1 | |
|---|---|
| enzyme | IC50(nM) |
| ABL1 | 1.57 |
| ABL1 (E255K) | 10.9 |
| ABL1 (E255V) | 7.12 |
| ABL1 (F317I) | 4.15 |
| ABL1 (F317L) | 2.86 |
| ABL1 (G250E) | 6.58 |
| ABL1 (H396P) | 1.97 |
| ABL1 (M351T) | 3.60 |
| ABL1 (Q252H) | 6.35 |
| ABL1 (T315I) | 10.1 |
| ABL1 (V299L) | 0.76 |
| ABL1 (Y253F) | 3.30 |
| ABL1 (Y253H) | 5.36 |

<Experimental Example 2> Evaluation of Inhibitory Activity of the Compound According to the Present Invention to Various Kinases In order to evaluate the inhibitory activity of the compound according to the present invention to more enzymes, the following experiment was performed, and the results are shown in Table 4 below.

Among the example compounds of the present invention, the enzyme (kinase) selectivity of the selected compounds of Examples 1 and 4 was measured by requesting DiscoverX. At this time, the experiment was performed using a panel for scanMAX™ Kinase. The concentration of the drug treated to the enzyme was 1 μM in DMSO, and the percentage control (% control) was determined by the method shown in Equation 1 below. The results are shown in Table 4 below.

(Example Compound−Positive Control)/(Negative Control−Positive control)×100 [Equation 1]

Herein, the positive control refers to a compound exhibiting the percentage control of 0%, and the negative control indicates DMSO exhibiting the percentage control of 100%. In addition, if the enzyme selectivity of the compound of the present invention was less than the percentage control of 35% (<35%) for each enzyme, it was judged to have activity for the enzyme.

TABLE 4

| Kinase | Example 1 (% Cont @ 1 uM) | Example 4 (% Cont @ 1 uM) |
|---|---|---|
| ABL1(E255K)-phosphorylated | 0.9 | 12 |
| ABL1(F317I)-nonphosphorylated | 50 | 2.8 |
| ABL1(F317I)-phosphorylated | 9.2 | 22 |
| ABL1(F317L)-nonphosphorylated | 2.7 | 10 |
| ABL1(F317L)-phosphorylated | 0 | 1.2 |
| ABL1(H396P)-nonphosphorylated | 1.2 | 2.9 |
| ABL1(H396P)-phosphorylated | 0.55 | 9.6 |
| ABL1(M351T)-phosphorylated | 0.25 | 10 |
| ABL1(Q252H)-nonphosphorylated | 15 | 4.1 |
| ABL1(Q252H)-phosphorylated | 1.3 | 14 |
| ABL1(T315I)-nonphosphorylated | 8.9 | 10 |
| ABL1(T315I)-phosphorylated | 2.3 | 16 |
| ABL1(Y253F)-phosphorylated | 0.15 | 5.9 |
| ABL1-nonphosphorylated | 1.9 | 5.6 |
| ABL1-phosphorylated | 0.45 | 8.4 |
| ABL2 | 0.4 | 2.9 |
| AURKB | 26 | 57 |
| AURKC | 27 | 39 |
| AXL | 14.4 | 1.4 |
| BLK | 0.05 | 0.4 |
| BMX | 6.7 | 3.6 |
| BRAF | 13 | 34 |
| BRAF(V600E) | 15 | 48 |
| BRK | 13 | 78 |
| BTK | 2.2 | 38 |
| CDC2L1 | 27 | 79 |
| CDC2L2 | 24 | 83 |
| CDC2L5 | 21 | 60 |
| CDK11 | 14.8 | 55 |
| CDK7 | 4.7 | 71 |
| CDKL2 | 0.7 | 14 |
| CIT | 0.1 | 0.45 |
| CSF1R | 0.2 | 2.5 |
| CSK | 0.3 | 0.8 |
| DDR1 | 0.15 | 0 |
| DDR2 | 2 | 6.5 |
| DLK | 5.9 | 89 |
| EGFR | 29 | 79 |
| EGFR(E746-A750del) | 0 | 56 |
| EGFR(G719C) | 5.2 | 56 |
| EGFR(G719S) | 16 | 65 |
| EGFR(L747-E749del, A750P) | 11 | 24 |
| EGFR(L747-S752del, P753S) | 1.3 | 40 |
| EGFR(L747-T751del, Sins) | 11 | 28 |
| EGFR(L858R) | 5.5 | 57 |
| EGFR(L861Q) | 6.7 | 53 |
| EGFR(S752-I759del) | 5.7 | 30 |
| EPHA1 | 4.1 | 37 |
| EPHA3 | 4 | 8.4 |
| EPHA4 | 26 | 28 |
| EPHA5 | 8.9 | 26 |
| EPHA6 | 16 | 25 |
| EPHA7 | 16 | 63 |
| EPHA8 | 0.1 | 1.6 |

TABLE 4-continued

| Kinase | Example 1 (% Cont @ 1 uM) | Example 4 (% Cont @ 1 uM) |
|---|---|---|
| EPHB1 | 17 | 26 |
| EPHB2 | 6.3 | 32 |
| EPHB6 | 0 | 0 |
| ERBB2 | 34 | 65 |
| ERBB4 | 18 | 46 |
| ERK8 | 19 | 90 |
| FER | 10 | 71 |
| FES | 1.6 | 55 |
| FGFR1 | 1.2 | 27 |
| FGFR2 | 30 | 61 |
| FGFR3 | 23 | 88 |
| FGFR3(G697C) | 7.5 | 90 |
| FGFR4 | 2.8 | 53 |
| FGR | 3.5 | 12 |
| FLT1 | 1.4 | 11 |
| FLT3 | 2 | 1.9 |
| FLT3(D835H) | 0.45 | 4.5 |
| FLT3(D835V) | 0.25 | 25 |
| FLT3(D835Y) | 14 | 22 |
| FLT3(ITD) | 1.1 | 6.6 |
| FLT3(ITD, F691L) | 5.1 | 37 |
| FLT3(K663Q) | 10.8 | 2.8 |
| FLT3(N841I) | 0 | 0 |
| FLT3(R834Q) | 0.9 | 34 |
| FLT4 | 0.35 | 4.4 |
| FRK | 1.6 | 26 |
| FYN | 3 | 32 |
| GAK | 25 | 80 |
| GCN2(Kin.Dom.2, S808G) | 17 | 64 |
| HCK | 0.2 | 0.65 |
| HPK1 | 2 | 41 |
| IKK-alpha | 31 | 35 |
| IKK-beta | 26 | 56 |
| IRAK1 | 27 | 100 |
| IRAK4 | 34 | 89 |
| JNK2 | 12 | 81 |
| KIT | 0 | 1.6 |
| KIT(A829P) | 1.1 | 2 |
| KIT(D816H) | 12 | 53 |
| KIT(D816V) | 13 | 61 |
| KIT(L576P) | 1.4 | 2.8 |
| KIT(V559D) | 0 | 0.25 |
| KIT(V559D, T670I) | 1.2 | 12 |
| KIT(V559D, V654A) | 2.9 | 12 |
| LCK | 0.15 | 0.4 |
| LIMK1 | 33 | 75 |
| LOK | 0.05 | 0.2 |
| LRRK2 | 27 | 92 |
| LTK | 3.4 | 8.7 |
| LYN | 0.5 | 4.7 |
| MAP3K2 | 34 | 87 |
| MAP3K3 | 19 | 82 |
| MAP4K2 | 2.5 | 70 |
| MAP4K3 | 4 | 70 |
| MAP4K4 | 0.75 | 15 |
| MAP4K5 | 0.95 | 38 |
| MEK5 | 0 | 1.2 |
| MERTK | 6.1 | 3.3 |
| MET(Y1235D) | 17 | 87 |
| MINK | 2.4 | 88 |
| MKNK1 | 23 | 78 |
| MKNK2 | 0.7 | 96 |
| MLK1 | 18 | 76 |
| MLK3 | 10 | 57 |
| MST3 | 20 | 70 |
| MUSK | 5 | 46 |
| NEK1 | 34 | 100 |
| NEK4 | 28 | 90 |
| NLK | 0 | 14 |
| p38-alpha | 0.65 | 49 |
| p38-beta | 0.85 | 15 |
| p38-delta | 29 | 92 |
| p38-gamma | 17 | 88 |
| PAK3 | 7.1 | 10 |
| PCTK2 | 23 | 85 |
| PDGFRA | 2 | 11 |
| PDGFRB | 0 | 0.05 |

TABLE 4-continued

| Kinase | Example 1 (% Cont @ 1 uM) | Example 4 (% Cont @ 1 uM) |
|---|---|---|
| PFCDPK1(*P. falciparum*) | 12 | 48 |
| PFTAIRE2 | 4.3 | 76 |
| PFTK1 | 8.3 | 94 |
| RET | 0 | 0.2 |
| RET(M918T) | 0 | 0.95 |
| RET(V804L) | 0.6 | 6 |
| RET(V804M) | 0.35 | 4.3 |
| RIOK3 | 31 | 40 |
| RIPK1 | 1.6 | 44 |
| RIPK2 | 3 | 37 |
| SIK | 2 | 14 |
| SLK | 1.2 | 34 |
| SRC | 0.1 | 1.4 |
| SRMS | 1.2 | 54 |
| STK33 | 12 | 76 |
| STK35 | 10 | 94 |
| STK36 | 20 | 45 |
| TAK1 | 4.3 | 50 |
| TAOK1 | 11 | 96 |
| TAOK2 | 20 | 35 |
| TAOK3 | 1.6 | 12 |
| TEC | 1.3 | 46 |
| TESK1 | 33 | 100 |
| TIE1 | 3.5 | 4.1 |
| TIE2 | 0.4 | 0.7 |
| TNIK | 7.2 | 25 |
| TNK1 | 30 | 31 |
| TNK2 | 31 | 91 |
| TNNI3K | 1.8 | 41 |
| TRKA | 0.6 | 2.6 |
| TRKB | 0.6 | 7.7 |
| TRKC | 0.05 | 1.4 |
| TXK | 1.6 | 11 |
| TYK2(JH1domain-catalytic) | 33 | 72 |
| VEGFR2 | 6.1 | 36 |
| YES | 2.5 | 10 |
| YSK4 | 0.3 | 3 |
| ZAK | 1.5 | 8.1 |

As shown in Table 4, it was confirmed that the compound of Example 1 or Example 4 had less than the percentage control of 35% to one or more protein kinases selected from the group consisting of ABL1(E255K)-phosphorylated, ABL1(F317I)-nonphosphorylated, ABL1(F317I)-phosphorylated, ABL1(F317L)-nonphosphorylated, ABL1(F317L)-phosphorylated, ABL1(H396P)-nonphosphorylated, ABL1 (H396P)-phosphorylated, ABL1(M351T)-phosphorylated, ABL1(Q252H)-nonphosphorylated, ABL1(Q252H)-phosphorylated, ABL1(T315I)-nonphosphorylated, ABL1 (T315I)-phosphorylated, ABL1(Y253F)-phosphorylated, ABL1-nonphosphorylated, ABL1-phosphorylated, ABL2, AURKB, AURKC, AXL, BLK, BMX, BRAF, BRAF (V600E), BRK, BTK, CDC2L1, CDC2L2, CDC2L5, CDK11, CDK7, CDKL2, CIT, CSF1R, CSK, DDR1, DDR2, DLK, EGFR, EGFR(E746-A750del), EGFR(G719C), EGFR(G719S), EGFR(L747-E749del, A750P), EGFR (L747-S752del, P753S), EGFR(L747-T751del,Sins), EGFR (L858R), EGFR(L861Q), EGFR(S752-I759del), EPHA1, EPHA3, EPHA4, EPHA5, EPHA6, EPHA7, EPHA8, EPHB1, EPHB2, EPHB6, ERBB2, ERBB4, ERK8, FER, FES, FGFR1, FGFR2, FGFR3, FGFR3(G697C), FGFR4, FGR, FLT1, FLT3, FLT3(D835H), FLT3(D835V), FLT3 (D835Y), FLT3(ITD), FLT3(ITD,F691L), FLT3(K663Q), FLT3(N841I), FLT3(R834Q), FLT4, FRK, FYN, GAK, GCN2(Kin.Dom.2,S808G), HCK, HPK1, IKK-alpha, IKK-beta, IRAK1, IRAK4, JNK2, KIT, KIT(A829P), KIT (D816H), KIT(D816V), KIT(L576P), KIT(V559D), KIT (V559D,T670I), KIT(V559D, V654A), LCK, LIMK1, LOK, LRRK2, LTK, LYN, MAP3K2, MAP3K3, MAP4K2, MAP4K3, MAP4K4, MAP4K5, MEK5, MERTK, MET (Y1235D), MINK, MKNK1, MKNK2, MLK1, MLK3, MST3, MUSK, NEK1, NEK4, NLK, p38-alpha, p38-beta, p38-delta, p38-gamma, PAK3, PCTK2, PDGFRA, PDGFRB, PFCDPK1(P.falciparum), PFTAIRE2, PFTK1, RET, RET(M918T), RET(V804L), RET(V804M), RIOK3, RIPK1, RIPK2, SIK, SLK, SRC, SRMS, STK33, STK35, STK36, TAK1, TAOK1, TAOK2, TAOK3, TEC, TESK1, TIE1, TIE2, TNIK, TNK1, TNK2, TNNI3K, TRKA, TRKB, TRKC, TXK, TYK2(JH1domain-catalytic), VEGFR2, YES, YSK4 and ZAK, so the compound had inhibitory activity to the enzymes.

<Experimental Example 3> Evaluation of Ba/F3 Cell Proliferation Inhibition

Rat lymphocyte cells, Parental (Ba/F3) and T315I-Bcr-Abl (Ba/F3) were seeded in 96-well plates at the density of $1\times10^4$/90 μL/well. A culture solution containing 9 concentrations (0.015 to 100 μM) of each example compound serially diluted in 3 folds or DMSO (control) were added to the plate (10 L/well) to a final concentration of 0 to 10 μM. The plate was incubated in a 37° C. $CO_2$ incubator for 72 hours.

After incubation for 72 hours, the plate treated with the compound was treated with Cell Counting Kit-8 (Dojindo Molecular Technologies, Inc) solution at the concentration of 10 μL/well, and then mixed well. Then, the plate was incubated in a CO2 incubator at 37° C. for 2 hours, and absorbance at 450 nm was measured with a microplate reader. Data were expressed as percentage compared to vehicle treated cells and $GI_{50}$ values were calculated using GraphPad Prism 5.0 (GraphPad software Inc., San Diego) GraphPad Prism 5.0. The results are shown in Table 5 below.

In the table below, the following designations were used for the evaluation of cancer cell proliferation inhibition.

GI50: A<0.05 μM; 0.05 μM<B<0.5 μM; 0.5 μM<C<5 μM; 5 μM<D

TABLE 5

| Example | Parental Ba/F3 | T315I-Bcr-Abl Ba/F3 |
|---|---|---|
| 1 | D | A |
| 2 | D | A |
| 3 | D | A |
| 4 | D | A |
| 5 | D | A |
| 6 | D | B |
| 7 | D | A |
| 8 | D | A |
| 9 | D | A |
| 10 | C | A |
| 11 | D | A |
| 12 | D | B |
| 13 | D | A |
| 14 | D | A |
| 15 | D | A |
| 16 | D | B |
| 17 | D | B |
| 18 | D | B |
| 19 | D | B |
| 20 | C | B |
| 21 | C | B |
| 22 | C | B |
| 23 | C | B |
| 24 | C | B |
| 25 | C | B |
| 26 | D | A |
| 27 | C | A |
| 28 | D | B |

TABLE 5-continued

| Example | Parental Ba/F3 | T315I-Bcr-Abl Ba/F3 |
|---|---|---|
| 29 | C | B |
| 30 | C | B |
| 31 | D | B |
| 32 | D | B |
| 33 | C | B |
| 34 | D | B |
| 35 | C | B |
| 36 | D | B |
| 37 | D | B |
| 38 | D | A |
| 39 | D | A |
| 40 | D | B |
| 41 | C | B |
| 42 | C | B |
| 43 | C | B |
| 44 | C | B |
| 45 | D | C |
| 46 | D | B |
| 47 | C | B |
| 48 | D | B |
| 49 | C | B |
| 50 | D | B |
| 51 | D | B |
| 52 | D | B |
| 53 | D | B |
| 54 | D | B |
| 55 | C | A |
| 56 | C | A |
| 57 | D | B |
| 58 | D | A |
| 59 | D | B |
| 60 | C | A |
| 61 | C | A |
| 62 | D | C |
| 63 | D | C |
| 64 | D | B |
| 65 | D | B |
| 66 | D | B |
| 67 | C | B |
| 68 | C | A |
| 69 | D | B |
| 70 | D | B |
| 71 | D | B |
| 72 | D | B |
| 73 | D | B |
| 74 | D | A |
| 75 | D | A |
| 76 | D | A |
| 77 | D | B |
| 78 | D | B |
| 79 | D | B |
| 80 | D | B |
| 81 | C | B |
| 82 | C | B |
| 83 | C | A |
| 84 | C | B |
| 85 | C | B |
| 86 | C | A |
| 87 | D | B |
| 88 | C | B |
| 89 | D | A |
| 90 | B | A |
| 91 | C | B |
| 92 | C | A |
| 93 | C | B |
| 94 | D | C |
| 95 | D | A |
| 96 | D | B |
| 97 | D | B |
| 98 | D | B |
| 99 | C | B |
| 100 | D | B |
| 101 | D | A |
| 102 | C | B |
| 103 | D | B |
| 104 | C | B |
| 105 | C | A |

TABLE 5-continued

| Example | Parental Ba/F3 | T315I-Bcr-Abl Ba/F3 |
|---|---|---|
| 106 | D | B |
| 107 | C | B |
| 108 | D | B |
| 109 | C | A |
| 110 | C | A |
| 111 | C | B |
| 112 | C | B |
| 113 | D | C |
| 114 | D | B |

<Experimental Example 4> Evaluation of Human Chronic Myeloid Leukemia (CML) Cell Proliferation Inhibition In order to evaluate the therapeutic effect of the compound according to the present invention on chronic myelogenous leukemia (CML), the following experiment was performed, and the results are shown in Table 6 below. Inhibitory activity to Bcr-Abl kinase was evaluated through the experiment using TCCS and KOPM28 cells, and inhibitory activity to T315I-Bcr-Abl kinase was evaluated through the experiment using T315I-TCCS and T315I-KOPM28 cells.

Human chronic myelogenous leukemia (CML) cells used in the experiment were TCCS, T315I-TCCS, KOPM28 and T315I-KOPM28, and the four types of cells were provided by University of Yamanashi.

Four types of human CML cells were each seeded in 96-well plates at the density of $1\times10^4$/90 μL/well. A culture solution containing 9 concentrations (0.000256 to 100 μM) of each example compound serially diluted in 5 folds or DMSO (control) were added to the plate (10 μL/well) to a final concentration of 0 to 10 μM. The plate was incubated in a 37° C. $CO_2$ incubator for 72 hours.

After incubation for 72 hours, the plate treated with the compound was treated with Cell Counting Kit-8 (Dojindo Molecular Technologies, Inc) solution at the concentration of 10 μL/well, and then mixed well. Then, the plate was incubated in a CO2 incubator at 37° C. for 2 hours, and absorbance at 450 nm was measured with a microplate reader. Data were expressed as percentage compared to vehicle treated cells and $GI_{50}$ values were calculated using GraphPad Prism 8.0 (GraphPad software Inc., San Diego). The results are shown in Table 6 below.

In the table below, the following designations were used for the evaluation of human CML cell inhibitory activity.

GI50: A<10 nM; 100 nM<B<100 nM; 100 nM<C;

TABLE 6

| Example | TCCS | T315I-TCCS | KOPM28 | T315I-KOPM28 |
|---|---|---|---|---|
| 1 | A | A | A | B |
| 2 | A | A | A | B |
| 3 | A | B | A | B |
| 4 | A | B | B | B |
| 5 | B | B | B | B |
| 6 | A | B | B | C |
| 7 | A | A | A | A |
| 8 | A | B | A | B |
| 9 | A | B | A | B |
| 10 | A | B | A | B |
| 11 | A | A | A | B |
| 12 | A | B | A | C |
| 13 | A | A | A | B |
| 14 | A | B | A | B |

TABLE 6-continued

| Example | TCCS | T315I-TCCS | KOPM28 | T315I-KOPM28 |
|---|---|---|---|---|
| 15 | A | A | A | A |
| 16 | A | B | A | B |
| 17 | A | B | A | B |
| 18 | A | B | A | B |
| 19 | A | B | A | C |
| 20 | A | B | A | C |
| 21 | A | B | A | C |
| 22 | A | B | A | B |
| 23 | A | C | A | C |
| 24 | A | B | A | B |
| 25 | A | C | A | B |
| 26 | A | A | A | B |
| 27 | A | B | A | B |
| 28 | A | C | A | C |
| 29 | A | B | A | B |
| 30 | A | B | A | C |
| 31 | A | C | A | C |
| 32 | A | C | A | C |
| 33 | A | B | A | C |
| 34 | A | B | A | C |
| 35 | A | C | A | C |
| 36 | A | B | A | B |
| 37 | A | B | A | B |
| 38 | A | A | A | B |
| 39 | A | B | A | B |
| 40 | A | C | A | C |
| 41 | A | C | A | C |
| 42 | A | B | A | C |
| 43 | A | B | A | C |
| 44 | A | C | A | C |
| 45 | A | C | A | C |
| 46 | A | C | A | C |
| 47 | A | B | A | B |
| 48 | A | B | A | C |
| 49 | A | A | A | B |
| 50 | A | B | A | C |
| 51 | B | B | A | B |
| 52 | A | B | A | B |
| 53 | A | B | A | C |
| 54 | A | B | B | C |
| 55 | A | A | A | A |
| 56 | A | A | A | A |
| 57 | B | B | A | C |
| 58 | A | B | A | B |
| 59 | A | B | A | C |
| 60 | A | B | B | C |
| 61 | A | B | A | A |
| 62 | A | C | A | C |
| 63 | A | C | A | C |
| 64 | A | B | A | C |
| 65 | A | B | A | B |
| 66 | A | C | A | C |
| 67 | A | B | A | B |
| 68 | A | B | A | B |
| 69 | B | C | A | C |
| 70 | A | C | A | C |
| 71 | A | B | A | C |
| 72 | A | C | A | C |
| 73 | A | B | A | B |
| 74 | A | B | A | B |
| 75 | A | B | A | B |
| 76 | A | B | A | B |
| 77 | A | B | A | C |
| 78 | A | C | B | C |
| 79 | A | B | A | C |
| 80 | A | B | A | C |
| 81 | A | B | A | C |
| 82 | A | B | A | C |
| 83 | A | B | A | B |
| 84 | A | B | A | C |
| 85 | A | B | A | C |
| 86 | A | B | A | B |
| 87 | A | B | A | C |
| 88 | A | C | A | C |
| 89 | A | B | A | B |
| 90 | A | B | A | B |
| 91 | A | C | A | C |
| 92 | A | B | A | B |

TABLE 6-continued

| Example | TCCS | T315I-TCCS | KOPM28 | T315I-KOPM28 |
|---|---|---|---|---|
| 93 | A | C | A | C |
| 94 | A | C | A | C |
| 95 | A | B | A | B |
| 96 | B | C | A | C |
| 97 | A | B | A | C |
| 98 | A | B | A | C |
| 99 | A | B | A | C |
| 100 | A | B | A | C |
| 101 | A | A | A | B |
| 102 | A | B | A | C |
| 103 | A | B | A | C |
| 104 | A | B | A | C |
| 105 | A | A | A | B |
| 106 | A | B | A | C |
| 107 | A | B | A | C |
| 108 | A | B | A | C |
| 109 | A | A | A | A |
| 110 | A | B | A | B |
| 111 | A | A | A | A |
| 112 | A | B | A | B |
| 113 | A | C | A | C |
| 114 | A | C | A | C |

<Experimental Example 5> Evaluation of Platelet Aggregation Inhibition

To prepare platelet-rich plasma, human venous blood was collected using sodium citrate (0.32%, final concentration: 10.9 mM) from healthy volunteers who had not received drug treatment and did not have cardiovascular disease, allergies, or lipid metabolism abnormalities. The blood was centrifuged at 1000×g for 10 minutes to separate PRP (platelet rich plasma). Thereafter, PPP (platelet poor plasma) was obtained by centrifugation at 1200×g for 10 minutes.

Platelet aggregation study was performed according to a method previously reported (Arch Pharm Res, 38 (2015) 893-903, BMB Rep, 44 (2011) 140-145.). More specifically, platelet aggregation was induced by treatment with collagen (2 μg/ml) or thrombin (0.1 U/ml) after treating 300 μl of PRP with a compound (in DMSO) at a concentration of 1 μM for 5 minutes. The degree of platelet aggregation was monitored using an aggregation meter (Chronolog, Havertown, PA, USA), and the change in light transmittance was measured at 37° C. The degree of platelet aggregation (%) is shown in Table 7 below.

In the table below, the following designations were used for the evaluation of the degree of inhibition of platelet aggregation.

A<30%; 30%≤B<50%; 50% C≤70%; 70%≤D;

TABLE 7

| Compound | Concentration (μM) | Collagen (2 μg/ml) Percent Aggregation (%) |
|---|---|---|
| Comparative Example 1 | 1 | A |
| Example 4 | 1 | C |
| Comparative Example 2 | 1 | A |
| Example 22 | 1 | D |
| Comparative Example 3 | 1 | A |
| Example 20 | 1 | D |
| Comparative Example 4 | 1 | B |
| Example 1 | 1 | D |
| Comparative Example 5 | 1 | B |
| Example 27 | 1 | C |
| ponatinib | 1 | A |
| imatinib | 1 | C |
| nilotinib | 1 | C |

<Experimental Example 6> In Vivo PK (Oral Administration)

To evaluate the pharmacokinetic properties in vivo, oral pharmacokinetic test was performed with the compounds of Comparative Examples 1 and 4 and Examples 1 and 4 using mice and rats, and the PK parameters are shown in Table 10.

6-1. Oral Pharmacokinetic Test

ICR mice (6-7 weeks old) and SD rats (6-7 weeks old) were used for the test. The fasted group was fasted about 16 hours before oral administration, and the fed group was fasted about 4 hours before oral administration. The test drug for oral administration was used by dissolving the drug in a vehicle at a concentration of 1 mg/mL for use, and blood samples were collected (time point: 0.25, 0.5, 1, 2, 4, 8, 12, 24, 32, n=3) from the heart (mouse, 500 μL/time point) or jugular vein (rat, 120 μL/time point). Blood was centrifuged at 12,000 G at 4° C. for 2 minutes to separate plasma, and stored at −80° C. until analysis.

Vehicle A (NMP:PEG400=5:95)

Vehicle B (0.5% methyl cellulose)

6-2. Sampling and Pretreatment

To 20 μl of plasma, 180 μl of acetonitrile (including internal standard) was added. The mixture was vortexed and centrifuged for 5 minutes at 15,000 rpm at 4° C. The supernatant obtained after centrifugation was analyzed by LC-MS/MS.

TABLE 8

| HPLC conditions | |
|---|---|
| HPLC system | Nexera XR system (Shimadzu, Japan) |
| Column | Kinetex C18 column<br>(2.1 × 100 mm, 2.6 μm, particle size; Phenomenex, USA) |
| Injection volume | 2 μL |
| Mobile phase | (A) 0.1% formic acid in water<br>(B) 0.1% formic acid in acetonitrile |

TABLE 9

| Mass spectrometry conditions | |
|---|---|
| System of Analysis | TSQ vantage triple quadrupole (Thermo, USA) |
| Ion Source type & Ionization mode | Turbo Spray Ionization, positive mode<br>MRM transition (m/z): 613.1 → 132.98<br>CE (V): 49, S-lens: 183 |
| Lower Limit of Quantification(LLOQ) | Plasma: 10 ng/ml |
| Standard Curve Rang | Plasma: 10~1000 ng/ml |

6-3. PK Analysis

PK parameters were calculated with a non-compartmental analysis model using Phoenix WinNonlin 6.4 version (Pharsight, USA) program.

TABLE 10

| | species | Dose (mg/Kg) | Route | $C_{max}$ (ng/mL) | $T_{1/2}$ (hr) | $AUC_{last}$ (hr * ng/mL) | vehicle |
|---|---|---|---|---|---|---|---|
| Comparative Example 1 | mouse | 10 | PO | 810.4 | 3.5 | 7734.8 | A |
| Example 4 | mouse | 10 | PO | 3360.9 | 2.1 | 30445.5 | B |
| Comparative | mouse | 10 | PO | 3835.1 | 3.3 | 12599.4 | A |
| Example 4 | rat | 10 | PO | 168.7 | | 2955.5 | A |
| Example 1 | mouse | 10 | PO | 10020.7 | 2.4 | 80284.9 | B |
| | | 10 | PO | 8572.3 | 2.5 | 138067.9 | A |
| | rat | 10 | PO | 2000 | 3.3 | 15888 | A |

<Experimental Example 7> Evaluation of In Vivo Pharmacological Activity

In Experimental Examples 1 and 2 described above, it was confirmed that the compound of the present invention had an excellent inhibitory effect on Bcr-Abl and T315I-Bcr-Abl enzymes related to blood cancer. In order to evaluate the drug efficacy of the compound of the present invention on actual disease, an in vivo experiment was performed using a disease-induced mouse model as follows.

A total of 50 male 5-week-old nude mice (14-17 g) were obtained from Orient Bio Inc. (322, Galmachi-ro, Jungwon-gu, Seongnam-si, Gyeonggi-do, Korea). After the mice were adapted to an animal facility for 1 week, the Luc_Ba/F3 T315I-Bcr-Abl cell line emitting luciferase was transplanted into the caudal vein at the density of $5\times10^6$/animal. Group separation was performed 3 days after the cell line transplantation. On the day of the group separation, 10 mice were randomly assigned to each group of 5 groups so that the luminescence values were equal after luminescence measurement using IVIS spectrum-CT optical imaging equipment.

5 groups: control (vehicle, 0.5% methylcellulose solution), ponatinib (25 mg/kg), Example 1 (25 mg/kg), Example 1 (50 mg/kg), Example 1 (100 mg/kg).

After the group separation, the compound of Example 1, ponatinib, and a vehicle were orally administered at intervals of once a day for 10 days in order to evaluate the therapeutic efficacy of the drug. The drug effect was confirmed through optical imaging, and the confirmation was carried out before the drug administration (day 0) and on days 4, 11, 18 and 21 after the administration. In addition, the body weight and survival rate of each experimental group were monitored.

Statistical analysis was performed using GraphPad Prism 8, and the statistical significance of the survival rate was confirmed using unpaired t test and log-rank (Mantel-Cox) test.

As shown in FIG. 1, in the optical images taken on days 0, 4, 11 and 18 after the administration of the luminescence signal emitted from the blood cancer cells, strong luminescence signals were confirmed in all subjects in the vehicle group. However, on day 21 after the administration, luminescence images could no longer be obtained because all subjects had died. In all the groups treated with potatinib and the compound of Example 1, weak luminescence values were confirmed compared to the vehicle group.

Figure 2:
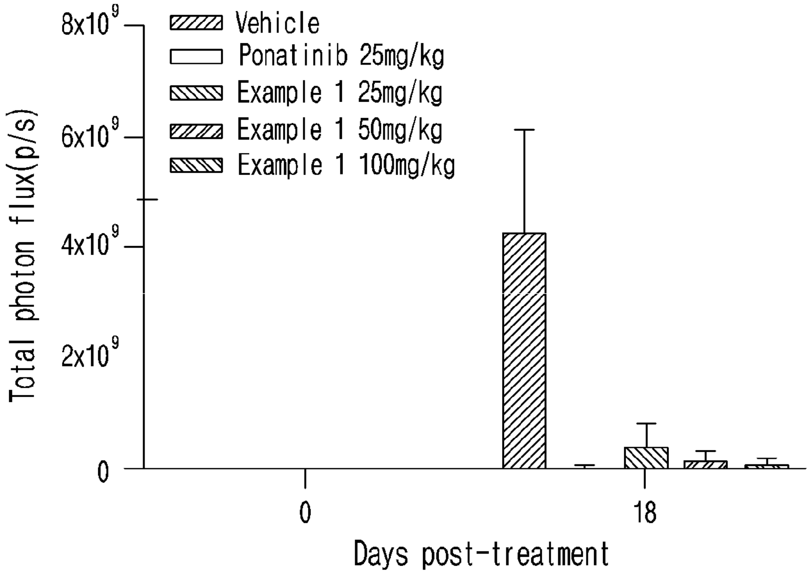
FIG. 2 is a graph showing the luminescent signals emitted from blood cancer cells according to the course of vehicle or drug treatment in each of 5 groups in a blood cancer model.

As shown in FIG. 2, on day 18 after administration, strong luminescence signals emitted from blood cancer cells were confirmed in all subjects in the vehicle group, and weak luminescence signals were observed in the experimental group treated with the compound of Example 1 according to the present invention compared to the vehicle group. In addition, it was confirmed that the luminescence signal was decreased dose-dependently.

Figure 3:
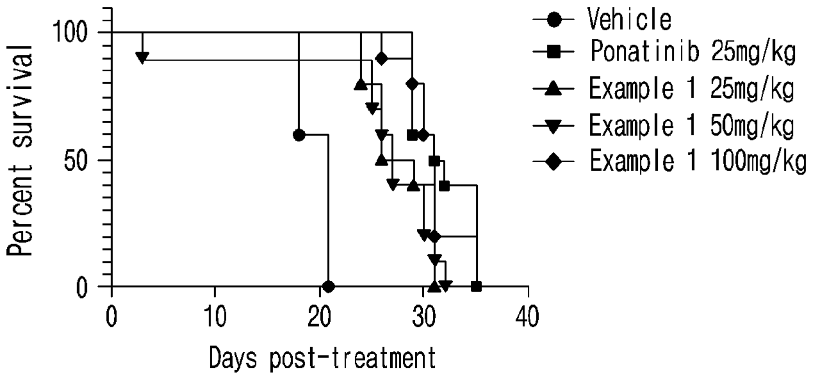
FIG. 3 is a graph showing the survival rate of mice according to the course of vehicle or drug treatment in each of 5 groups in a blood cancer model.

As shown in FIG. 3, as a result of the survival rate analysis, all subjects in the vehicle group died on the $21^{st}$ day after the administration, and all subjects in the group treated with ponatinib (25 mg/kg) died on the $35^{th}$ day after the administration. In the group treated with 25 mg/kg of the compound of Example 1, all subjects died on the $31^{st}$ day after the administration, in the group treated with 50 mg/kg of the compound of Example 1, all subjects died on the $32^{nd}$ day after the administration, and in the group treated with 100 mg/kg of the compound of Example 1, all subjects died on the $35^{th}$ day after the administration. Therefore, it was confirmed that the survival rate was increased in all the groups administered with the drug compared to the vehicle group.

Figure 4:
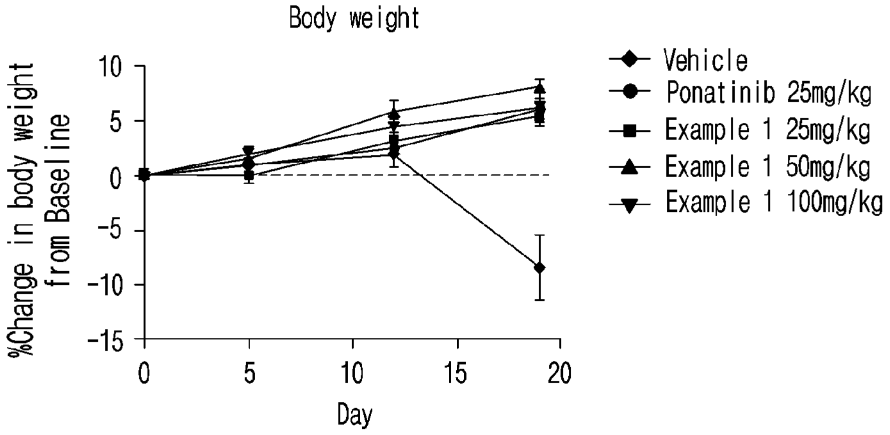
FIG. 4 is a graph showing the change in mouse body weight according to the course of vehicle or drug treatment in each of 5 groups in a blood cancer model.

As shown in FIG. 4, after the $18^{th}$ day after the start of the test, a sharp decrease in body weight was observed in the vehicle group. On the other hand, no significant body weight change was observed in all the groups administered with 25 mg/kg of ponatinib, 25 mg/kg of the compound of Example 1, 50 mg/kg of the compound of Example 1, or 100 mg/kg of the compound of Example 1 during the experimental period.

Therefore, the compound according to the present invention was able to excellently inhibit the proliferation of cancer cells in a hematological cancer model and had an effect of significantly killing cancer cells, so that a pharmaceutical composition comprising the compound of the present invention as an active ingredient can be effectively used for the prevention or treatment of cancer.

What is claimed is:

1. A compound represented by formula 1, a solvate thereof or a pharmaceutically acceptable salt thereof:

[Formula 1]

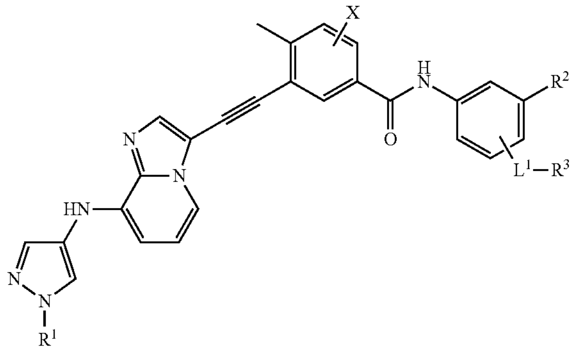

in formula 1, $R^1$ is hydrogen or $C_{1-10}$ alkyl;

X is halogen;

$R_2$ is

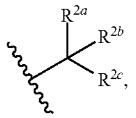

where, $R^{2a}$, $R^{2b}$ and $R^{2c}$ are independently hydrogen, halogen, cyano or $C_{1-10}$ alkyl;

$L^1$ is single bond, —O— or $C_{1-10}$ alkylene;

$R^3$ is 5-8 membered nonsubstituted or substituted heteroaryl containing one or more heteroatoms selected from the group consisting of N, O and S, 4-8 membered nonsubstituted or substituted heterocycloalkyl containing one or more heteroatoms selected from the group consisting of N, O and S, nonsubstituted or substituted $C_{1-10}$ alkyl or $NR^{3a}R^{3b}$, wherein, $R^{3a}$ and $R^{3b}$ are independently hydrogen or nonsubstituted or substituted $C_{1-10}$ alkyl, wherein, the substituted heteroaryl, substituted heterocycloalkyl and substituted alkyl are substituted with one or more substituents selected from the group consisting of $C_{1-10}$ alkyl nonsubstituted or substituted with one or more halogens, $C_{1-10}$ hydroxyalkyl, $C_{1-10}$ alkylsulfonyl, $C_{1-10}$ alkoxy, oxo, $NR^{3c}R^{3d}$ and heterocycloalkyl substituted with 5-8 membered $C_{1-10}$ alkyl containing one or more heteroatoms selected from the group consisting of N, O and S, wherein, $R^{3c}$ and $R^{3d}$ are independently hydrogen or $C_{1-10}$ alkyl.

2. The compound, the solvate thereof or the pharmaceutically acceptable salt thereof according to claim 1, wherein:

$R^1$ is hydrogen or $C_{1-6}$ alkyl;

X is halogen;

$R^2$ is

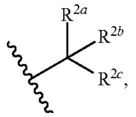

where, $R^{2a}$, $R^{2b}$ and $R^{2c}$ are independently hydrogen, halogen, cyano or $C_{1-6}$ alkyl;

$L^1$ is single bond, —O— or $C_{1-6}$ alkylene;

$R^3$ is 5-6 membered nonsubstituted or substituted heteroaryl containing one or more heteroatoms selected from the group consisting of N and O, 4-7 membered nonsubstituted or substituted heterocycloalkyl containing one or more heteroatoms selected from the group consisting of N and O, nonsubstituted or substituted $C_{1-6}$ alkyl or $NR^{3a}R^{3b}$, wherein, $R^{3a}$ and $R^{3b}$ are independently hydrogen or nonsubstituted or substituted $C_{1-6}$ alkyl, wherein, the substituted heteroaryl, substituted heterocycloalkyl and substituted alkyl are substituted with one or more substituents selected from the group consisting of $C_{1-6}$ alkyl nonsubstituted or substituted with one or more halogens, $C_{1-6}$ hydroxyalkyl, $C_{1-6}$ alkylsulfonyl, $C_{1-6}$ alkoxy, oxo, $NR^{3c}R^{3d}$ and heterocycloalkyl substituted with 5-6 membered $C_{1-6}$ alkyl containing one or more heteroatoms selected from the group consisting of N and O, wherein, $R^{3c}$ and $R^{3d}$ are independently hydrogen or $C_{1-6}$ alkyl.

3. The compound, the solvate thereof or the pharmaceutically acceptable salt thereof according to claim 1, wherein:

$R^1$ is hydrogen or methyl;

X is fluorine or chlorine;

$R^2$ is

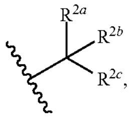

where, $R^{2a}$, $R^{2b}$ and $R^{2c}$ are independently fluorine, cyano or methyl;

$L^1$ is single bond, —O— or methylene;

$R^3$ is nonsubstituted or substituted imidazolyl, pyridinyl, pyrimidinyl, substituted piperazinyl, substituted pyrazolyl, substituted diazepanyl, substituted piperidinyl, morpholinyl, substituted pyrrolidinyl, substituted azetidinyl, triazolyl, substituted ethyl, substituted propyl or $NR^{3a}R^{3b}$, wherein $R^{3a}$ and $R^{3b}$ are independently methyl, substituted ethyl or substituted propyl, wherein the substituted imidazolyl, substituted piperazinyl, substituted pyrazolyl, substituted diazepanyl, substituted piperidinyl, substituted pyrrolidinyl, substituted azetidinyl, substituted ethyl and substituted propyl are substituted with one or more substituents selected from the group consisting of methyl, $CF_3$, $CH_2CF_3$, isopropyl, methylsulfonyl, isopropylalkoxy, hydroxyethyl, piperazine substituted with methyl, piperidine substituted with methyl, oxo and $NR^{3c}R^{3d}$, wherein, $R^{3c}$ and $R^{3d}$ can be methyl.

4. The compound of claim 1, wherein the compound represented by formula 1 is a compound represented by formula 2, a solvate thereof or a pharmaceutically acceptable salt thereof:

[Formula 2]

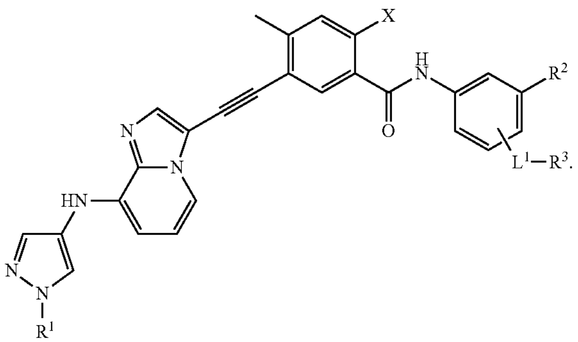

5. The compound, the solvate thereof or the pharmaceutically acceptable salt thereof according to claim 1, wherein:

$R^1$ is hydrogen or methyl;

X is fluorine or chlorine;

$R^2$ is

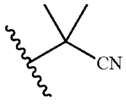 or 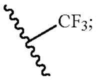

$L^1$-$R^3$ is

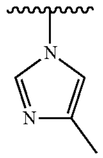 , 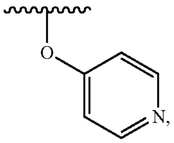 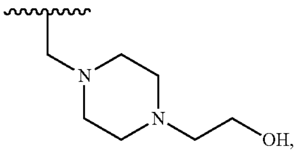 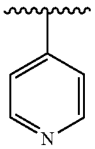 , 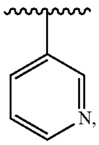 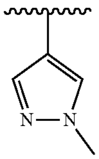 , 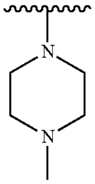 , 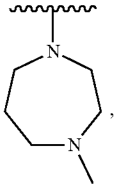 , 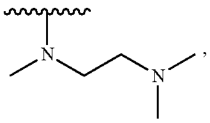 , 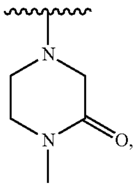 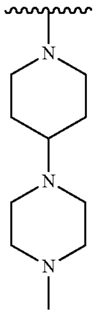 , 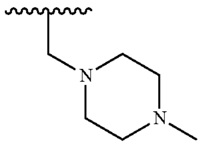 , 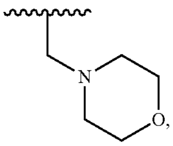 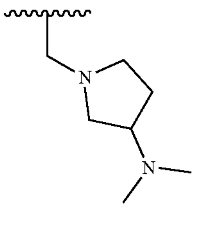 , 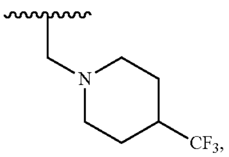

-continued

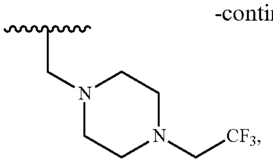 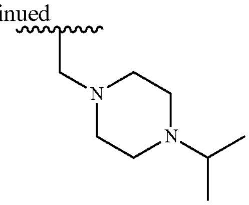 , 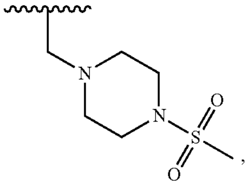 , 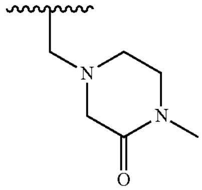 , 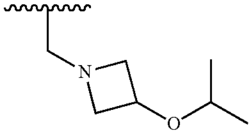 , 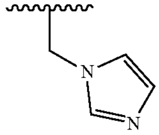 , 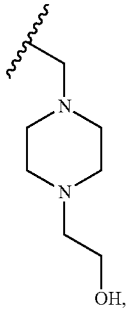 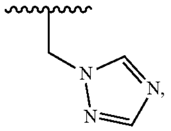 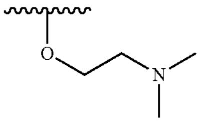 , 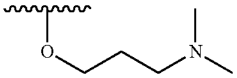 or 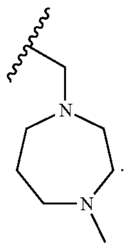 .

6. The compound, the solvate thereof or the pharmaceutically acceptable salt thereof according to claim 1, wherein the compound represented by formula 1 is selected from the group consisting of the following compounds:

1) N-(3-(2-cyanopropan-2-yl)-5-(4-methyl-1H-imidazol-1-yl)phenyl)-2-fluoro-4-methyl-5-((8-((1-methyl-1H-pyrazol-4-yl)amino)imidazo[1,2-a]pyridin-3-yl)ethynyl)benzamide;

2) 3-fluoro-4-methyl-N-(3-(4-methyl-1H-imidazol-1-yl)-5-(trifluoromethyl)phenyl)-5-((8-((1-methyl-1H-pyrazol-4-yl)amino)imidazo[1,2-a]pyridin-3-yl)ethynyl) benzamide;

3) N-(3-(2-cyanopropan-2-yl)-5-(4-methyl-1H-imidazol-1-yl)phenyl)-2-fluoro-4-methyl-3-((8-((1-methyl-1H-pyrazol-4-yl)amino)imidazo[1,2-a]pyridin-3-yl)ethynyl)benzamide;

4) 2-fluoro-4-methyl-N-(3-(4-methyl-1H-imidazol-1-yl)-5-(trifluoromethyl)phenyl)-5-((8-((1-methyl-1H-pyrazol-4-yl)amino)imidazo[1,2-a]pyridin-3-yl)ethynyl) benzamide;

5) 3-fluoro-4-methyl-N-(3-(4-methyl-1H-imidazol-1-yl)-5-(trifluoromethyl)phenyl)-5-((8-((1-methyl-1H-pyrazol-4-yl)amino)imidazo[1,2-a]pyridin-3-yl)ethynyl)benzamide;

6) 2-fluoro-4-methyl-N-(3-(4-methyl-1H-imidazol-1-yl)-5-(trifluoromethyl)phenyl)-3-((8-((1-methyl-1H-pyrazol-4-yl)amino)imidazo[1,2-a]pyridin-3-yl)ethynyl)benzamide;

7) 2-fluoro-4-methyl-5-((8-((1-methyl-1H-pyrazol-4-yl)amino)imidazo[1,2-a]pyridin-3-yl)ethynyl)-N-(3-(pyridin-4-yloxy)-5-(trifluoromethyl)phenyl)benzamide;

8) 3-fluoro-4-methyl-5-((8-((1-methyl-1H-pyrazol-4-yl)amino)imidazo[1,2-a]pyridin-3-yl)ethynyl)-N-(3-(pyridin-4-yloxy)-5-(trifluoromethyl)phenyl)benzamide;

9) 2-fluoro-4-methyl-3-((8-((1-methyl-1H-pyrazol-4-yl)amino)imidazo[1,2-a]pyridin-3-yl)ethynyl)-N-(3-(pyridin-4-yloxy)-5-(trifluoromethyl)phenyl)benzamide;

10) N-(3-(2-cyanopropan-2-yl)-5-((4-(2-hydroxyethyl)piperazin-1-yl)methyl)phenyl)-2-fluoro-4-methyl-5-((8-((1-methyl-1H-pyrazol-4-yl)amino)imidazo[1,2-a]pyridin-3-yl)ethynyl)benzamide;

11) N-(3-(2-cyanopropan-2-yl)-5-((4-(2-hydroxyethyl)piperazin-1-yl)methyl)phenyl)-3-fluoro-4-methyl-5-((8-((1-methyl-1H-pyrazol-4-yl)amino)imidazo[1,2-a]pyridin-3-yl)ethynyl)benzamide;

12) N-(3-(2-cyanopropan-2-yl)-5-((4-(2-hydroxyethyl)piperazin-1-yl)methyl)phenyl)-2-fluoro-4-methyl-3-((8-((1-methyl-1H-pyrazol-4-yl)amino)imidazo[1,2-a]pyridin-3-yl)ethynyl)benzamide;

13) 2-chloro-N-(3-(2-cyanopropan-2-yl)-5-(4-methyl-1H-imidazol-1-yl)phenyl)-4-methyl-5-((8-((1-methyl-1H-pyrazol-4-yl)amino)imidazo[1,2-a]pyridin-3-yl)ethynyl)benzamide;

14) 2-chloro-4-methyl-N-(3-(4-methyl-1H-imidazol-1-yl)-5-(trifluoromethyl)phenyl)-5-((8-((1-methyl-1H-pyrazol-4-yl)amino)imidazo[1,2-a]pyridin-3-yl)ethynyl)benzamide;

15) 2-chloro-4-methyl-5-((8-((1-methyl-1H-pyrazol-4-yl)amino)imidazo[1,2-a]pyridin-3-yl)ethynyl)-N-(3-(pyridin-4-yloxy)-5-(trifluoromethyl)phenyl)benzamide;

16) 2-chloro-N-(3-(2-cyanopropan-2-yl)-5-((4-(2-hydroxyethyl)piperazin-1-yl)methyl)phenyl)-4-methyl-5-((8-((1-methyl-1H-pyrazol-4-yl)amino)imidazo[1,2-a]pyridin-3-yl)ethynyl)benzamide;

17) N-(3-(2-cyanopropan-2-yl)-5-(pyridin-4-yl)phenyl)-2-fluoro-4-methyl-5-((8-((1-methyl-1H-pyrazol-4-yl)amino)imidazo[1,2-a]pyridin-3-yl)ethynyl)benzamide;

18) N-(3-(2-cyanopropan-2-yl)-5-(pyridin-3-yl)phenyl)-2-fluoro-4-methyl-5-((8-((1-methyl-1H-pyrazol-4-yl)amino)imidazo[1,2-a]pyridin-3-yl)ethynyl)benzamide;

19) N-(3-(2-cyanopropan-2-yl)-5-(1-methyl-1H-pyrazol-4-yl)phenyl)-2-fluoro-4-methyl-5-((8-((1-methyl-1H-pyrazol-4-yl)amino)imidazo[1,2-a]pyridin-3-yl)ethynyl)benzamide;

20) N-(3-(2-cyanopropan-2-yl)-5-(4-methylpiperazin-1-yl)phenyl)-2-fluoro-4-methyl-5-((8-((1-methyl-1H-pyrazol-4-yl)amino)imidazo[1,2-a]pyridin-3-yl)ethynyl)benzamide;

21) N-(3-(2-cyanopropan-2-yl)-5-(4-methyl-1,4-diazepan-1-yl)phenyl)-2-fluoro-4-methyl-5-((8-((1-methyl-1H-pyrazol-4-yl)amino)imidazo[1,2-a]pyridin-3-yl)ethynyl)benzamide;

22) N-(3-(2-cyanopropan-2-yl)-5-((2-(dimethylamino)ethyl)(methyl)amino)phenyl)-2-fluoro-4-methyl-5-((8-((1-methyl-1H-pyrazol-4-yl)amino)imidazo[1,2-a]pyridin-3-yl)ethynyl)benzamide;

23) N-(3-(2-cyanopropan-2-yl)-5-((3-(dimethylamino)propyl)(methyl)amino)phenyl)-2-fluoro-4-methyl-5-((8-((1-methyl-1H-pyrazol-4-yl)amino)imidazo[1,2-a]pyridin-3-yl)ethynyl)benzamide;

24) N-(3-(2-cyanopropan-2-yl)-5-(4-methyl-3-oxopiperazin-1-yl)phenyl)-2-fluoro-4-methyl-5-((8-((1-methyl-1H-pyrazol-4-yl)amino)imidazo[1,2-a]pyridin-3-yl)ethynyl)benzamide;

25) N-(3-(2-cyanopropan-2-yl)-5-(4-(4-methylpiperazin-1-yl)piperidin-1-yl)phenyl)-2-fluoro-4-methyl-5-((8-((1-methyl-1H-pyrazol-4-yl)amino)imidazo[1,2-a]pyridin-3-yl)ethynyl)benzamide;

26) N-(3-(2-cyanopropan-2-yl)-5-(pyridin-4-yloxy)phenyl)-2-fluoro-4-methyl-5-((8-((1-methyl-1H-pyrazol-4-yl)amino)imidazo[1,2-a]pyridin-3-yl)ethynyl)benzamide;

27) N-(3-(2-cyanopropan-2-yl)-5-((4-methylpiperazin-1-yl)methyl)phenyl)-2-fluoro-4-methyl-5-((8-((1-methyl-1H-pyrazol-4-yl)amino)imidazo[1,2-a]pyridin-3-yl)ethynyl)benzamide;

28) N-(3-(2-cyanopropan-2-yl)-5-(morpholinomethyl)phenyl)-2-fluoro-4-methyl-5-((8-((1-methyl-1H-pyrazol-4-yl)amino)imidazo[1,2-a]pyridin-3-yl)ethynyl)benzamide;

29) N-(3-(2-cyanopropan-2-yl)-5-((3-(dimethylamino)pyrrolidin-1-yl)methyl)phenyl)-2-fluoro-4-methyl-5-((8-((1-methyl-1H-pyrazol-4-yl)amino)imidazo[1,2-a]pyridin-3-yl)ethynyl)benzamide;

30) N-(3-(2-cyanopropan-2-yl)-5-((4-methyl-1,4-diazepan-1-yl)methyl)phenyl)-2-fluoro-4-methyl-5-((8-((1-methyl-1H-pyrazol-4-yl)amino)imidazo[1,2-a]pyridin-3-yl)ethynyl)benzamide;

31) N-(3-(2-cyanopropan-2-yl)-5-((4-(trifluoromethyl)piperidin-1-yl)methyl)phenyl)-2-fluoro-4-methyl-5-((8-((1-methyl-1H-pyrazol-4-yl)amino)imidazo[1,2-a]pyridin-3-yl)ethynyl)benzamide;

32) N-(3-(2-cyanopropan-2-yl)-5-((4-(2,2,2-trifluoroethyl)piperazin-1-yl)methyl)phenyl)-2-fluoro-4-methyl-5-((8-((1-methyl-1H-pyrazol-4-yl)amino)imidazo[1,2-a]pyridin-3-yl)ethynyl)benzamide;

33) N-(3-(2-cyanopropan-2-yl)-5-((4-isopropylpiperazin-1-yl)methyl)phenyl)-2-fluoro-4-methyl-5-((8-((1-methyl-1H-pyrazol-4-yl)amino)imidazo[1,2-a]pyridin-3-yl)ethynyl)benzamide;

34) N-(3-(2-cyanopropan-2-yl)-5-((4-(methylsulfonyl)piperazin-1-yl)methyl)phenyl)-2-fluoro-4-methyl-5-((8-((1-methyl-1H-pyrazol-4-yl)amino)imidazo[1,2-a]pyridin-3-yl)ethynyl)benzamide;

35) N-(3-(2-cyanopropan-2-yl)-5-((4-methyl-3-oxopiperazin-1-yl)methyl)phenyl)-2-fluoro-4-methyl-5-((8-((1-methyl-1H-pyrazol-4-yl)amino)imidazo[1,2-a]pyridin-3-yl)ethynyl)benzamide;

36) N-(3-(2-cyanopropan-2-yl)-5-((3-isopropoxyazetidin-1-yl)methyl)phenyl)-2-fluoro-4-methyl-5-((8-((1-methyl-1H-pyrazol-4-yl)amino)imidazo[1,2-a]pyridin-3-yl)ethynyl)benzamide;

37) N-(3-((1H-imidazol-1-yl)methyl)-5-(2-cyanopropan-2-yl)phenyl)-2-fluoro-4-methyl-5-((8-((1-methyl-1H-pyrazol-4-yl)amino)imidazo[1,2-a]pyridin-3-yl)ethynyl)benzamide;

38) N-(3-((1H-1,2,4-triazol-1-yl)methyl)-5-(2-cyanopropan-2-yl)phenyl)-2-fluoro-4-methyl-5-((8-((1-methyl-1H-pyrazol-4-yl)amino)imidazo[1,2-a]pyridin-3-yl)ethynyl)benzamide;

39) N-(3-(2-cyanopropan-2-yl)-4-((4-methylpiperazin-1-yl)methyl)phenyl)-2-fluoro-4-methyl-5-((8-((1-methyl-1H-pyrazol-4-yl)amino)imidazo[1,2-a]pyridin-3-yl)ethynyl)benzamide;

40) N-(3-(2-cyanopropan-2-yl)-4-(morpholinomethyl)phenyl)-2-fluoro-4-methyl-5-((8-((1-methyl-1H-pyrazol-4-yl)amino)imidazo[1,2-a]pyridin-3-yl)ethynyl)benzamide;

41) N-(3-(2-cyanopropan-2-yl)-4-((3-(dimethylamino)pyrrolidin-1-yl)methyl)phenyl)-2-fluoro-4-methyl-5-((8-((1-methyl-1H-pyrazol-4-yl)amino)imidazo[1,2-a]pyridin-3-yl)ethynyl)benzamide;

42) N-(3-(2-cyanopropan-2-yl)-4-((4-methyl-1,4-diazepan-1-yl)methyl)phenyl)-2-fluoro-4-methyl-5-((8-((1-methyl-1H-pyrazol-4-yl)amino)imidazo[1,2-a]pyridin-3-yl)ethynyl)benzamide;

43) N-(3-(2-cyanopropan-2-yl)-4-((4-(2-hydroxyethyl)piperazin-1-yl)methyl)phenyl)-2-fluoro-4-methyl-5-((8-((1-methyl-1H-pyrazol-4-yl)amino)imidazo[1,2-a]pyridin-3-yl)ethynyl)benzamide;

44) N-(3-(2-cyanopropan-2-yl)-4-((4-methyl-3-oxopiperazin-1-yl)methyl)phenyl)-2-fluoro-4-methyl-5-((8-((1-methyl-1H-pyrazol-4-yl)amino)imidazo[1,2-a]pyridin-3-yl)ethynyl)benzamide;

45) N-(3-(2-cyanopropan-2-yl)-4-((4-(methylsulfonyl)piperazin-1-yl)methyl)phenyl)-2-fluoro-4-methyl-5-((8-((1-methyl-1H-pyrazol-4-yl)amino)imidazo[1,2-a]pyridin-3-yl)ethynyl)benzamide;

46) N-(4-((1H-imidazol-1-yl)methyl)-3-(2-cyanopropan-2-yl)phenyl)-2-fluoro-4-methyl-5-((8-((1-methyl-1H-pyrazol-4-yl)amino)imidazo[1,2-a]pyridin-3-yl)ethynyl)benzamide;

47) 2-fluoro-4-methyl-5-((8-((1-methyl-1H-pyrazol-4-yl)amino)imidazo[1,2-a]pyridin-3-yl)ethynyl)-N-(3-(4-methylpiperazin-1-yl)-5-(trifluoromethyl)phenyl)benzamide;

48) N-(3-((2-(dimethylamino)ethyl)(methyl)amino)-5-(trifluoromethyl)phenyl)-2-fluoro-4-methyl-5-((8-((1-methyl-1H-pyrazol-4-yl)amino)imidazo[1,2-a]pyridin-3-yl)ethynyl)benzamide;

49) 2-fluoro-4-methyl-5-((8-((1-methyl-1H-pyrazol-4-yl)amino)imidazo[1,2-a]pyridin-3-yl)ethynyl)-N-(3-(4-methyl-3-oxopiperazin-1-yl)-5-(trifluoromethyl)phenyl)benzamide;

50) N-(3-(2-(dimethylamino)ethoxy)-5-(trifluoromethyl)phenyl)-2-fluoro-4-methyl-5-((8-((1-methyl-1H-pyrazol-4-yl)amino)imidazo[1,2-a]pyridin-3-yl)ethynyl)benzamide;

51) N-(3-(3-(dimethylamino)propoxy)-5-(trifluoromethyl)phenyl)-2-fluoro-4-methyl-5-((8-((1-methyl-1H-pyrazol-4-yl)amino)imidazo[1,2-a]pyridin-3-yl)ethynyl)benzamide;

52) 2-fluoro-4-methyl-5-((8-((1-methyl-1H-pyrazol-4-yl)amino)imidazo[1,2-a]pyridin-3-yl)ethynyl)-N-(3-(pyridin-4-yl)-5-(trifluoromethyl)phenyl)benzamide;

53) 2-fluoro-4-methyl-5-((8-((1-methyl-1H-pyrazol-4-yl)amino)imidazo[1,2-a]pyridin-3-yl)ethynyl)-N-(3-(pyridin-3-yl)-5-(trifluoromethyl)phenyl)benzamide;

54) 2-fluoro-4-methyl-N-(3-(1-methyl-1H-pyrazol-4-yl)-5-(trifluoromethyl)phenyl)-5-((8-((1-methyl-1H-pyrazol-4-yl)amino)imidazo[1,2-a]pyridin-3-yl)ethynyl)benzamide;

55) 2-fluoro-4-methyl-5-((8-((1-methyl-1H-pyrazol-4-yl)amino)imidazo[1,2-a]pyridin-3-yl)ethynyl)-N-(4-((4-methylpiperazin-1-yl)methyl)-3-(trifluoromethyl)phenyl)benzamide;

56) 2-fluoro-N-(4-((4-(2-hydroxyethyl)piperazin-1-yl)methyl)-3-(trifluoromethyl)phenyl)-4-methyl-5-((8-((1-methyl-1H-pyrazol-4-yl)amino)imidazo[1,2-a]pyridin-3-yl)ethynyl)benzamide;

57) 2-fluoro-4-methyl-5-((8-((1-methyl-1H-pyrazol-4-yl)amino)imidazo[1,2-a]pyridin-3-yl)ethynyl)-N-(4-(morpholinomethyl)-3-(trifluoromethyl)phenyl)benzamide;

58) 2-fluoro-4-methyl-5-((8-((1-methyl-1H-pyrazol-4-yl)amino)imidazo[1,2-a]pyridin-3-yl)ethynyl)-N-(4-((4-methyl-3-oxopiperazin-1-yl)methyl)-3-(trifluoromethyl)phenyl)benzamide;

59) N-(4-((3-(dimethylamino)pyrrolidine-1-yl)methyl)-3-(trifluoromethyl)phenyl)-2-fluoro-4-methyl-5-((8-((1-methyl-1H-pyrazol-4-yl)amino)imidazo[1,2-a]pyridin-3-yl)ethynyl)benzamide;

60) 2-fluoro-4-methyl-5-((8-((1-methyl-1H-pyrazol-4-yl)amino)imidazo[1,2-a]pyridin-3-yl)ethynyl)-N-(4-((4-(methylsulfonyl)piperazin-1-yl)methyl)-3-(trifluoromethyl)phenyl)benzamide;

61) 2-fluoro-4-methyl-N-(4-((4-methyl-1,4-diazepan-1-yl)methyl)-3-(trifluoromethyl)phenyl)-5-((8-((1-methyl-1H-pyrazol-4-yl)amino)imidazo[1,2-a]pyridin-3-yl)ethynyl)benzamide;

62) 2-fluoro-N-(4-((3-isopropoxyazetidin-1-yl)methyl)-3-(trifluoromethyl)phenyl)-4-methyl-5-((8-((1-methyl-1H-pyrazol-4-yl)amino)imidazo[1,2-a]pyridin-3-yl)ethynyl)benzamide;

63) N-(4-((1H-imidazol-1-yl)methyl)-3-(trifluoromethyl)phenyl)-2-fluoro-4-methyl-5-((8-((1-methyl-1H-pyrazol-4-yl)amino)imidazo[1,2-a]pyridin-3-yl)ethynyl)benzamide;

64) N-(4-((1H-1,2,4-triazol-1-yl)methyl)-3-(trifluoromethyl)phenyl)-2-fluoro-4-methyl-5-((8-((1-methyl-1H-pyrazol-4-yl)amino)imidazo[1,2-a]pyridin-3-yl)ethynyl)benzamide;

65) 2-fluoro-4-methyl-5-((8-((1-methyl-1H-pyrazol-4-yl)amino)imidazo[1,2-a]pyridin-3-yl)ethynyl)-N-(4-(pyridin-4-yloxy)-3-(trifluoromethyl)phenyl)benzamide;

66) 2-fluoro-4-methyl-5-((8-((1-methyl-1H-pyrazol-4-yl)amino)imidazo[1,2-a]pyridin-3-yl)ethynyl)-N-(3-(morpholinomethyl)-5-(trifluoromethyl)phenyl)benzamide;

67) 2-fluoro-4-methyl-N-(3-((4-methyl-1,4-diazepan-1-yl)methyl)-5-(trifluoromethyl)phenyl)-5-((8-((1-methyl-1H-pyrazol-4-yl)amino)imidazo[1,2-a]pyridin-3-yl)ethynyl)benzamide;

68) N-(3-((3-(dimethylamino)pyrrolidin-1-yl)methyl)-5-(trifluoromethyl)phenyl)-2-fluoro-4-methyl-5-((8-((1-methyl-1H-pyrazol-4-yl)amino)imidazo[1,2-a]pyridin-3-yl)ethynyl)benzamide;

69) 2-fluoro-N-(3-((4-(2-hydroxyethyl)piperazin-1-yl)methyl)-5-(trifluoromethyl)phenyl)-4-methyl-5-((8-((1-methyl-1H-pyrazol-4-yl)amino)imidazo[1,2-a]pyridin-3-yl)ethynyl)benzamide;

70) 2-fluoro-4-methyl-5-((8-((1-methyl-1H-pyrazol-4-yl)amino)imidazo[1,2-a]pyridin-3-yl)ethynyl)-N-(3-((4-(methylsulfonyl)piperazin-1-yl)methyl)-5-(trifluoromethyl)phenyl)benzamide;

71) 2-fluoro-4-methyl-5-((8-((1-methyl-1H-pyrazol-4-yl)amino)imidazo[1,2-a]pyridin-3-yl)ethynyl)-N-(3-((4-methyl-3-oxopiperazin-1-yl)methyl)-5-(trifluoromethyl)phenyl)benzamide;

72) 2-fluoro-N-(3-((3-isopropoxyazetidin-1-yl)methyl)-5-(trifluoromethyl)phenyl)-4-methyl-5-((8-((1-methyl-1H-pyrazol-4-yl)amino)imidazo[1,2-a]pyridin-3-yl)ethynyl)benzamide;

73) N-(3-((1H-imidazol-1-yl)methyl)-5-(trifluoromethyl)phenyl)-2-fluoro-4-methyl-5-((8-((1-methyl-1H-pyrazol-4-yl)amino)imidazo[1,2-a]pyridin-3-yl)ethynyl)benzamide;

74) N-(3-((1H-1,2,4-triazol-1-yl)methyl)-5-(trifluoromethyl)phenyl)-2-fluoro-4-methyl-5-((8-((1-methyl-1H-pyrazol-4-yl)amino)imidazo[1,2-a]pyridin-3-yl)ethynyl)benzamide;

75) 5-((8-((1H-pyrazol-4-yl)amino)imidazo[1,2-a]pyridin-3-yl)ethynyl)-N-(3-(2-cyanopropan-2-yl)-5-(4-methyl-1H-imidazol-1-yl)phenyl)-2-fluoro-4-methylbenzamide;

76) 5-((8-((1H-pyrazol-4-yl)amino)imidazo[1,2-a]pyridin-3-yl)ethynyl)-2-chloro-N-(3-(2-cyanopropan-2-yl)-5-(4-methyl-1H-imidazol-1-yl)phenyl)-4-methylbenzamide;

77) 5-((8-((1H-pyrazol-4-yl)amino)imidazo[1,2-a]pyridin-3-yl)ethynyl)-N-(3-(2-cyanopropan-2-yl)-5-(1-methyl-1H-pyrazol-4-yl)phenyl)-2-fluoro-4-methylbenzamide;

78) 5-((8-((1H-pyrazol-4-yl)amino)imidazo[1,2-a]pyridin-3-yl)ethynyl)-N-(3-(2-cyanopropan-2-yl)-5-(pyridin-4-yl)phenyl)-2-fluoro-4-methylbenzamide;

79) 5-((8-((1H-pyrazol-4-yl)amino)imidazo[1,2-a]pyridin-3-yl)ethynyl)-N-(3-(2-cyanopropan-2-yl)-5-(pyridin-3-yl)phenyl)-2-fluoro-4-methylbenzamide;

80) 5-((8-((1H-pyrazol-4-yl)amino)imidazo[1,2-a]pyridin-3-yl)ethynyl)-N-(3-(2-cyanopropan-2-yl)-5-(4-methylpiperazin-1-yl)phenyl)-2-fluoro-4-methylbenzamide;

81) 5-((8-((1H-pyrazol-4-yl)amino)imidazo[1,2-a]pyridin-3-yl)ethynyl)-N-(3-(2-cyanopropan-2-yl)-5-((2-(dimethylamino)ethyl)(methyl)amino)phenyl)-2-fluoro-4-methylbenzamide;

82) 5-((8-((1H-pyrazol-4-yl)amino)imidazo[1,2-a]pyridin-3-yl)ethynyl)-N-(3-(2-cyanopropan-2-yl)-5-(4-methyl-3-oxopiperazin-1-yl)phenyl)-2-fluoro-4-methylbenzamide;

83) 5-((8-((1H-pyrazol-4-yl)amino)imidazo[1,2-a]pyridin-3-yl)ethynyl)-N-(3-(2-cyanopropan-2-yl)-5-(pyridin-4-yloxy)phenyl)-2-fluoro-4-methylbenzamide;

84) 5-((8-((1H-pyrazol-4-yl)amino)imidazo[1,2-a]pyridin-3-yl)ethynyl)-N-(3-(2-cyanopropan-2-yl)-5-((4-methylpiperazin-1-yl)methyl)phenyl)-2-fluoro-4-methylbenzamide;

85) 5-((8-((1H-pyrazol-4-yl)amino)imidazo[1,2-a]pyridin-3-yl)ethynyl)-N-(3-(2-cyanopropan-2-yl)-5-((3-(dimethylamino)pyrrolidin-1-yl)methyl)phenyl)-2-fluoro-4-methylbenzamide;

86) 5-((8-((1H-pyrazol-4-yl)amino)imidazo[1,2-a]pyridin-3-yl)ethynyl)-N-(3-(2-cyanopropan-2-yl)-5-((4-(2-hydroxyethyl)piperazin-1-yl)methyl)phenyl)-2-fluoro-4-methylbenzamide;

87) 5-((8-((1H-pyrazol-4-yl)amino)imidazo[1,2-a]pyridin-3-yl)ethynyl)-N-(3-(2-cyanopropan-2-yl)-5-((4-(methylsulfonyl)piperazin-1-yl)methyl)phenyl)-2-fluoro-4-methylbenzamide;

88) 5-((8-((1H-pyrazol-4-yl)amino)imidazo[1,2-a]pyridin-3-yl)ethynyl)-N-(3-(2-cyanopropan-2-yl)-5-((4-methyl-3-oxopiperazin-1-yl)methyl)phenyl)-2-fluoro-4-methylbenzamide;

89) N-(3-((1H-1,2,4-triazol-1-yl)methyl)-5-(2-cyanopropan-2-yl)phenyl)-5-((8-((1H-pyrazol-4-yl)amino)imidazo[1,2-a]pyridin-3-yl)ethynyl)-2-fluoro-4-methylbenzamide;

90) 5-((8-((1H-pyrazol-4-yl)amino)imidazo[1,2-a]pyridin-3-yl)ethynyl)-N-(3-(2-cyanopropan-2-yl)-4-((4-methylpiperazin-1-yl)methyl)phenyl)-2-fluoro-4-methylbenzamide;

91) 5-((8-((1H-pyrazol-4-yl)amino)imidazo[1,2-a]pyridin-3-yl)ethynyl)-N-(3-(2-cyanopropan-2-yl)-4-((3-(dimethylamino)pyrrolidin-1-yl)methyl)phenyl)-2-fluoro-4-methylbenzamide;

92) 5-((8-((1H-pyrazol-4-yl)amino)imidazo[1,2-a]pyridin-3-yl)ethynyl)-N-(3-(2-cyanopropan-2-yl)-4-((4-(2-hydroxyethyl)piperazin-1-yl)methyl)phenyl)-2-fluoro-4-methylbenzamide;

93) 5-((8-((1H-pyrazol-4-yl)amino)imidazo[1,2-a]pyridin-3-yl)ethynyl)-N-(3-(2-cyanopropan-2-yl)-4-((4-methyl-3-oxopiperazin-1-yl)methyl)phenyl)-2-fluoro-4-methylbenzamide;

94) 5-((8-((1H-pyrazol-4-yl)amino)imidazo[1,2-a]pyridin-3-yl)ethynyl)-N-(3-(2-cyanopropan-2-yl)-4-((4-(methylsulfonyl)piperazin-1-yl)methyl)phenyl)-2-fluoro-4-methylbenzamide;

95) 5-((8-((1H-pyrazol-4-yl)amino)imidazo[1,2-a]pyridin-3-yl)ethynyl)-2-fluoro-4-methyl-N-(3-(4-methyl-1H-imidazol-1-yl)-5-(trifluoromethyl)phenyl)benzamide;

96) 5-((8-((1H-pyrazol-4-yl)amino)imidazo[1,2-a]pyridin-3-yl)ethynyl)-2-fluoro-4-methyl-N-(3-(1-methyl-1H-pyrazol-4-yl)-5-(trifluoromethyl)phenyl)benzamide;

97) 5-((8-((1H-pyrazol-4-yl)amino)imidazo[1,2-a]pyridin-3-yl)ethynyl)-2-fluoro-4-methyl-N-(3-(pyridin-4-yl)-5-(trifluoromethyl)phenyl)benzamide;

98) 5-((8-((1H-pyrazol-4-yl)amino)imidazo[1,2-a]pyridin-3-yl)ethynyl)-2-fluoro-4-methyl-N-(3-(pyridin-3-yl)-5-(trifluoromethyl)phenyl)benzamide;

99) 5-((8-((1H-pyrazol-4-yl)amino)imidazo[1,2-a]pyridin-3-yl)ethynyl)-2-fluoro-4-methyl-N-(3-(4-methylpiperazin-1-yl)-5-(trifluoromethyl)phenyl)benzamide;

100) 5-((8-((1H-pyrazol-4-yl)amino)imidazo[1,2-a]pyridin-3-yl)ethynyl)-2-fluoro-4-methyl-N-(3-(4-methyl-3-oxopiperazin-1-yl)-5-(trifluoromethyl)phenyl)benzamide;

101) 5-((8-((1H-pyrazol-4-yl)amino)imidazo[1,2-a]pyridin-3-yl)ethynyl)-2-fluoro-4-methyl-N-(3-(pyridin-4-yloxy)-5-(trifluoromethyl)phenyl)benzamide;

102) 5-((8-((1H-pyrazol-4-yl)amino)imidazo[1,2-a]pyridin-3-yl)ethynyl)-N-(3-(2-(dimethylamino)ethoxy)-5-(trifluoromethyl)phenyl)-2-fluoro-4-methylbenzamide;

103) 5-((8-((1H-pyrazol-4-yl)amino)imidazo[1,2-a]pyridin-3-yl)ethynyl)-N-(3-(3-(dimethylamino)propoxy)-5-(trifluoromethyl)phenyl)-2-fluoro-4-methylbenzamide;

104) 5-((8-((1H-pyrazol-4-yl)amino)imidazo[1,2-a]pyridin-3-yl)ethynyl)-2-fluoro-4-methyl-N-(3-((4-methylpiperazin-1-yl)methyl)-5-(trifluoromethyl)phenyl)benzamide;

105) 5-((8-((1H-pyrazol-4-yl)amino)imidazo[1,2-a]pyridin-3-yl)ethynyl)-N-(3-((3-(dimethylamino)pyrrolidin-1-yl)methyl)-5-(trifluoromethyl)phenyl)-2-fluoro-4-methylbenzamide;

106) 5-((8-((1H-pyrazol-4-yl)amino)imidazo[1,2-a]pyridin-3-yl)ethynyl)-2-fluoro-N-(3-((4-(2-hydroxyethyl)piperazin-1-yl)methyl)-5-(trifluoromethyl)phenyl)-4-methylbenzamide;

107) 5-((8-((1H-pyrazol-4-yl)amino)imidazo[1,2-a]pyridin-3-yl)ethynyl)-2-fluoro-4-methyl-N-(3-((4-methyl-3-oxopiperazin-1-yl)methyl)-5-(trifluoromethyl)phenyl)benzamide;

108) N-(3-((1H-1,2,4-triazol-1-yl)methyl)-5-(trifluoromethyl)phenyl)-5-((8-((1H-pyrazol-4-yl)amino)imidazo[1,2-a]pyridin-3-yl)ethynyl)-2-fluoro-4-methylbenzamide;

109) 5-((8-((1H-pyrazol-4-yl)amino)imidazo[1,2-a]pyridin-3-yl)ethynyl)-2-fluoro-4-methyl-N-(4-((4-methylpiperazin-1-yl)methyl)-3-(trifluoromethyl)phenyl)benzamide;

110) 5-((8-((1H-pyrazol-4-yl)amino)imidazo[1,2-a]pyridin-3-yl)ethynyl)-N-(4-((3-(dimethylamino)pyrrolidin-1-yl)methyl)-3-(trifluoromethyl)phenyl)-2-fluoro-4-methylbenzamide;

111) 5-((8-((1H-pyrazol-4-yl)amino)imidazo[1,2-a]pyridin-3-yl)ethynyl)-2-fluoro-N-(4-((4-(2-hydroxyethyl)piperazin-1-yl)methyl)-3-(trifluoromethyl)phenyl)-4-methylbenzamide;

112) 5-((8-((1H-pyrazol-4-yl)amino)imidazo[1,2-a]pyridin-3-yl)ethynyl)-2-fluoro-4-methyl-N-(4-((4-methyl-3-oxopiperazin-1-yl)methyl)-3-(trifluoromethyl)phenyl)benzamide;

113) 5-((8-((1H-pyrazol-4-yl)amino)imidazo[1,2-a]pyridin-3-yl)ethynyl)-2-fluoro-4-methyl-N-(4-((4-(methylsulfonyl)piperazin-1-yl)methyl)-3-(trifluoromethyl)phenyl)benzamide;

114) N-(4-((1H-1,2,4-triazol-1-yl)methyl)-3-(trifluoromethyl)phenyl)-5-((8-((1H-pyrazol-4-yl)amino)imidazo[1,2-a]pyridin-3-yl)ethynyl)-2-fluoro-4-methylbenzamide.

7. A method for preparing the compound represented by formula 1 of claim 1, comprising a step of preparing a compound represented by formula 1 by reacting a compound represented by formula 2 with a compound represented by formula 3, as shown in reaction formula 1:

[Reaction Formula 1]

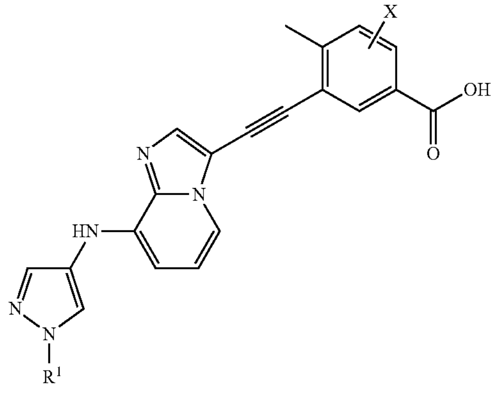

+

2

-continued

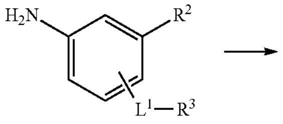

3

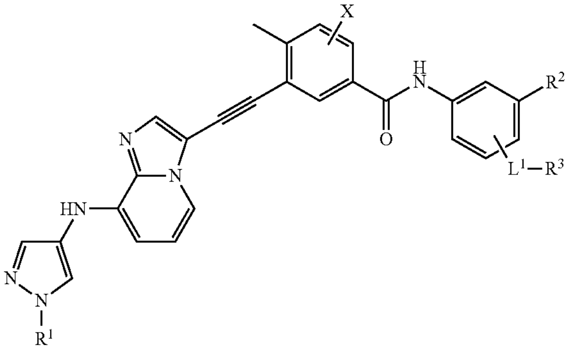

1

8. A pharmaceutical composition containing an effective amount of the compound represented by formula 1 of claim 1, a solvate thereof or a pharmaceutically acceptable salt thereof and a pharmaceutically acceptable excipient.

9. A method of treating cancer comprising administering the compound represented by formula 1 of claim 1, a solvate thereof or a pharmaceutically acceptable salt thereof as an active ingredient to a subject in need thereof, wherein the cancer is liver cancer, prostate cancer, rhabdomyosarcoma, colon cancer, non-small cell lung cancer or colorectal cancer.

10. A method of treating leukemia, comprising administering the compound represented by formula 1 of claim 1, a solvate thereof or a pharmaceutically acceptable salt thereof as an active ingredient to a subject in need thereof, wherein the leukemia is acute myeloid leukemia, acute lymphocytic leukemia, chronic myelogenous leukemia or chronic lymphocytic leukemia.

* * * * *